US009631232B2

(12) United States Patent
Rapier et al.

(10) Patent No.: US 9,631,232 B2
(45) Date of Patent: Apr. 25, 2017

(54) RECOVERY OF GENOMIC DNA FROM REMNANT EXTRACTED SEED SAMPLES

(71) Applicant: Agrigenetics, Inc, Indianapolis, IN (US)

(72) Inventors: Brandon Rapier, Zionsville, IN (US); Carol Powers, Indianapolis, IN (US); Christof Stoll, Emsdetten (DE)

(73) Assignee: Dow AgroSciences LLC, Indianapoils, IN (US)

( * ) Notice: Subject to any disclaimer, the term of this patent is extended or adjusted under 35 U.S.C. 154(b) by 0 days.

(21) Appl. No.: 14/100,713

(22) Filed: Dec. 9, 2013

(65) Prior Publication Data

US 2014/0170651 A1 Jun. 19, 2014

Related U.S. Application Data

(60) Provisional application No. 61/735,485, filed on Dec. 10, 2012.

(51) Int. Cl.
*C12Q 1/68* (2006.01)

(52) U.S. Cl.
CPC .......... *C12Q 1/686* (2013.01); *C12Q 1/6806* (2013.01); *C12Q 1/6895* (2013.01); *C12Q 2563/143* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 5,705,628 A | 1/1998 | Hawkins | |
| 5,773,295 A | 6/1998 | Turyan et al. | |
| 6,100,030 A | 8/2000 | McCasky et al. | |
| 7,832,143 B2 * | 11/2010 | Deppermann | A01H 1/02 47/58.1 R |
| 8,062,840 B2 * | 11/2011 | Anderson et al. | 435/6.11 |
| 2007/0048872 A1 | 3/2007 | Deppermann et al. | |
| 2008/0301831 A1 * | 12/2008 | Mack et al. | 800/265 |
| 2009/0215060 A1 * | 8/2009 | Deppermann | A01H 1/02 435/6.11 |
| 2012/0117865 A1 * | 5/2012 | Deppermann | G01N 1/04 47/14 |
| 2012/0174255 A1 * | 7/2012 | Chen | A23K 1/1813 800/275 |

OTHER PUBLICATIONS

Barkley, Noelle A., Kelly D. Chenault Chamberlin, Ming Li Wang, and Roy N. Pittman. Development of a real-time PCR genotyping assay to identify high oleic acid peanuts (*Arachis hypogaea* L.). Molecular Breeding, 2010, 25(3): 541-548.*
Barkley, Noelle A., Ming Li Wang, and Roy N. Pittman. A real-time PCR genotyping assay to detect FAD2A SNPs in peanuts (*Arachis hypogaea* L.). Electronic Journal of Biotechnology 2011, 14(1):9-10.*
Chen, Zhenbang, Ming Li Wang, Noelle A. Barkley, and Roy N. Pittman. A simple allele-specific PCR assay for detecting FAD2 alleles in both A and B genomes of the cultivated peanut for high-oleate trait selection. Plant Molecular Biology Reporter 2010, 28(3): 542-548.*
Eder K. Gas chromatographic analysis of fatty acid methyl esters. J Chromatogr B Biomed Appl. Sep. 15, 1995; 671(1-2):113-31.*
Frame BR, Paque T, Wang K. Maize (*Zea mays* L.). Methods Mol Biol. 2006; 343:185-99.*
Hahnen, S., Offermann, S., Miedl, B., Rüger, B., & Peterhänsel, C. Automated DNA preparation from maize tissues and food samples suitable for real-time PCR detection of native genes. European Food Research and Technology, 2002. 215(5): 443-446.*
Gao, S., Martinez, C., Skinner, D. J., Krivanek, A. F., Crouch, J. H., & Xu, Y. Development of a seed DNA-based genotyping system for marker-assisted selection in maize. 2008. Molecular Breeding, 22(3): 477-494.*
Grote, Karen Elaine. Genetic basis of maize whole kernel, embryo, and endosperm oil. (2011) Dissertation. Iowa State University.*
Kamalay, Joe C., Raman Tejwani, and G. Keith Rufener. Isolation and analysis of genomic DNA from single seeds. Crop science 1990. 30(5): 1079-1084.*
Luque-Rodriguez JM, Luque de Castro MD, Pérez-Juan P. Extraction of fatty acids from grape seed by superheated hexane. Talanta. Nov. 15, 2005; 68(1):126-30.Epub Jun. 3, 2005.*
McKernan, Kevin J. Automation and Robotics for Genetic Analysis. Current Protocols in Human Genetics: Chapter 16, pp. 16-0.1-16. 0.5.*
Nath, Ujjal Kumar, Mohammed CM Iqbal, and Christian Möllers. Early, non-destructive selection of microspore-derived embryo genotypes in oilseed rape (*Brassica napus* L.) by molecular markers and oil quality analysis. 2007. Molecular Breeding 19(3): 285-289.*
Peterhansel et al. Quantitative detection of transgenic and endogenous DNA sequences in seeds after automated DNA preparation. Biomedical Engineering: Applications, Basis and Communications 2004.16(01): 1-6.*
Sabudak, Temine. Fatty acid composition of seed and leaf oils of pumpkin, walnut, almond, maize, sunflower and melon. Chemistry of Natural Compounds (2007) 43.4: 465-467.*
Sangtong, Varaporn, et al. Serial extraction of endosperm drillings (seed)—A method for detecting transgenes and proteins in single viable maize kernels. Plant Molecular Biology Reporter 2001.19(2): 151-158.*
Springer NM, Stupar RM. Allelic variation and heterosis in maize: how do two halves make more than a whole? Genome Res. Mar. 2007;17(3):264-75. Epub Jan. 25, 2007.*
Wang, J., Zhong, G. Y., Chin, E. C. L., Register Iii, J. C., Riley, R. D., Niebur, W. S., & Smith, J. S. C. Identification of parents of F1 hybrids through SSR profiling of maternal and hybrid tissue. 2002. Euphytica, 124(1): 29-34.*

(Continued)

*Primary Examiner* — Samuel Woolwine
*Assistant Examiner* — Olayinka Oyeyemi
(74) *Attorney, Agent, or Firm* — Marcia I. Rosenfeld; Magleby Cataxinos & Greenwood

(57) ABSTRACT

This disclosure concerns the isolation of nucleic acids (e.g., genomic DNA) from plant seed material that has been defatted. In some embodiments, such nucleic acids are of sufficient quality and abundance that they may be used in an amplification-based genetic analysis technique; for example and without limitation, to make selections in a plant breeding program.

7 Claims, 65 Drawing Sheets

(56) References Cited

OTHER PUBLICATIONS

Wilson IG. Inhibition and facilitation of nucleic acid amplification. Appl Environ Microbiol. Oct. 1997; 63(10):3741-51.*
Yan, J., Yang, X., Shah, T., Sanchez-Villeda, H., Li, J., Warburton, M., & Xu, Y. (2010). High-throughput SNP genotyping with the GoldenGate assay in maize. Molecular Breeding, 2009. 25(3) 441-451.*
Sadia M, Rabbani MA, Hameed S, Pearce SR, Malik SA. Isolation of genomic DNA from defatted oil seed residue of rapeseed (*Brassica napus*). Genet Mol Res. Feb. 8, 2011; 10(1):197-202.*
Sangwan, R. S., Yadav, U., Sangwan, N. S., Isolation of genomic DNA from defatted oil seed residue of opium poppy (*Papaver sominiferum*). Plant Mol. Biol. Rep. 2000, 18, 265-270.*
ThermoFisher Application Note: 51692 (2009). The Effect of Spectral Bandwidth on the Determination of Nucleic Acid Quantity and Purity: pp. 1-3.*
Chunwongse et al., "Pre-germination genotypic screening using PCR amplifications of half seeds," Theoretical and Applied Genetics, 1996, pp. 694-698, vol. 86, No. 6.
International Search Report and Written Opinion for PCT/US2013/073826, dated Aug. 26, 2014.
Vandeynze, A., et al., "High-throughput DNA extraction from seeds," Seed Science and Technology, 2006 pp. 741-745, vol. 34, No. 3.
Vandeynze, A., et al., Seed extraction supplement (from High-throughput DNA extraction from seeds) Seed Science and Technology, 2006, p. 6.

* cited by examiner

| Box | Well | Geno_Id | Rec ID | Source ID | Gen | RowId | C18:1 | C18:2 | C18:3 |
|---|---|---|---|---|---|---|---|---|---|
| 5 | A1 | 231757 | 1005893 | BG11XG380009.0001.001 | F2 | 1007885 | 67.82 | 17.78 | 5.39 |
| 5 | A2 | 231757 | 1005901 | BG11XG380009.0001.001 | F2 | 1007893 | 70.48 | 16.04 | 4.46 |
| 5 | A3 | 231757 | 1005909 | BG11XG380009.0001.001 | F2 | 1007901 | 67.97 | 20.84 | 2.28 |
| 5 | A4 | 231757 | 1005917 | BG11XG380009.0001.001 | F2 | 1007909 | 63.03 | 25.79 | 2.45 |
| 5 | A5 | 231757 | 1005925 | BG11XG380009.0001.001 | F2 | 1007917 | 68.26 | 17.05 | 6.52 |
| 5 | A6 | 231757 | 1005933 | BG11XG380009.0001.001 | F2 | 1007925 | 64.04 | 21.82 | 5.23 |
| 5 | A7 | 231757 | 1005941 | BG11XG380009.0001.001 | F2 | 1007933 | 66.14 | 18.84 | 6.58 |
| 5 | A8 | 231757 | 1005949 | BG11XG380009.0001.001 | F2 | 1007941 | 71.96 | 15.34 | 5.14 |
| 5 | A9 | 231757 | 1005957 | BG11XG380009.0001.001 | F2 | 1007949 | 65.85 | 21.72 | 4.27 |
| 5 | A10 | 231757 | 1005965 | BG11XG380009.0001.001 | F2 | 1007957 | 72.76 | 10.20 | 7.52 |
| 5 | A11 | 231757 | 1005973 | BG11XG380009.0001.001 | F2 | 1007965 | 67.52 | 17.01 | 6.86 |
| 5 | A12 | 231757 | 1005981 | BG11XG380009.0001.001 | F2 | 1007973 | 65.40 | 22.94 | 3.36 |
| 5 | B1 | 231757 | 1005894 | BG11XG380009.0001.001 | F2 | 1007886 | 69.98 | 14.51 | 7.47 |
| 5 | B2 | 231757 | 1005902 | BG11XG380009.0001.001 | F2 | 1007894 | 70.01 | 15.34 | 5.71 |
| 5 | B3 | 231757 | 1005910 | BG11XG380009.0001.001 | F2 | 1007902 | 66.61 | 17.67 | 6.87 |
| 5 | B4 | 231757 | 1005918 | BG11XG380009.0001.001 | F2 | 1007910 | 75.06 | 11.77 | 5.67 |
| 5 | B5 | 231757 | 1005926 | BG11XG380009.0001.001 | F2 | 1007918 | 68.60 | 16.24 | 6.95 |
| 5 | B6 | 231757 | 1005934 | BG11XG380009.0001.001 | F2 | 1007926 | 64.89 | 20.55 | 6.49 |
| 5 | B7 | 231757 | 1005942 | BG11XG380009.0001.001 | F2 | 1007934 | 69.50 | 15.65 | 6.53 |
| 5 | B8 | 231757 | 1005950 | BG11XG380009.0001.001 | F2 | 1007942 | 76.53 | 12.27 | 2.63 |
| 5 | B9 | 231757 | 1005958 | BG11XG380009.0001.001 | F2 | 1007950 | 72.64 | 10.38 | 9.04 |
| 5 | B10 | 231757 | 1005966 | BG11XG380009.0001.001 | F2 | 1007958 | 64.12 | 23.10 | 4.49 |
| 5 | B11 | 231757 | 1005974 | BG11XG380009.0001.001 | F2 | 1007966 | 68.34 | 16.16 | 6.85 |
| 5 | B12 | 231757 | 1005982 | BG11XG380009.0001.001 | F2 | 1007974 | 66.77 | 19.75 | 4.08 |
| 5 | C1 | 231757 | 1005895 | BG11XG380009.0001.001 | F2 | 1007887 | 77.31 | 10.22 | 4.67 |
| 5 | C2 | 231757 | 1005903 | BG11XG380009.0001.001 | F2 | 1007895 | 74.58 | 12.11 | 5.52 |
| 5 | C3 | 231757 | 1005911 | BG11XG380009.0001.001 | F2 | 1007903 | 72.03 | 13.69 | 5.73 |
| 5 | C4 | 231757 | 1005919 | BG11XG380009.0001.001 | F2 | 1007911 | 69.49 | 16.84 | 5.07 |
| 5 | C5 | 231757 | 1005927 | BG11XG380009.0001.001 | F2 | 1007919 | 65.60 | 21.51 | 4.57 |
| 5 | C6 | 231757 | 1005935 | BG11XG380009.0001.001 | F2 | 1007927 | 64.01 | 23.38 | 3.98 |
| 5 | C7 | 231757 | 1005943 | BG11XG380009.0001.001 | F2 | 1007935 | 68.56 | 18.01 | 4.51 |
| 5 | C8 | 231757 | 1005951 | BG11XG380009.0001.001 | F2 | 1007943 | 64.25 | 22.85 | 3.77 |
| 5 | C9 | 231757 | 1005959 | BG11XG380009.0001.001 | F2 | 1007951 | 68.96 | 17.66 | 6.50 |
| 5 | C10 | 231757 | 1005967 | BG11XG380009.0001.001 | F2 | 1007959 | 75.29 | 11.61 | 4.77 |
| 5 | C11 | 231757 | 1005975 | BG11XG380009.0001.001 | F2 | 1007967 | 77.15 | 10.00 | 4.54 |
| 5 | C12 | 231757 | 1005983 | BG11XG380009.0001.001 | F2 | 1007975 | 72.92 | 12.07 | 6.73 |
| 5 | D1 | 231757 | 1005896 | BG11XG380009.0001.001 | F2 | 1007888 | 72.94 | 11.07 | 7.67 |
| 5 | D2 | 231757 | 1005904 | BG11XG380009.0001.001 | F2 | 1007896 | 71.33 | 13.68 | 6.75 |
| 5 | D3 | 231757 | 1005912 | BG11XG380009.0001.001 | F2 | 1007904 | 70.61 | 15.36 | 5.71 |
| 5 | D4 | 231757 | 1005920 | BG11XG380009.0001.001 | F2 | 1007912 | 69.68 | 16.59 | 5.03 |
| 5 | D5 | 231757 | 1005928 | BG11XG380009.0001.001 | F2 | 1007920 | 67.93 | 18.68 | 7.25 |
| 5 | D6 | 231757 | 1005936 | BG11XG380009.0001.001 | F2 | 1007928 | 71.87 | 15.74 | 4.19 |
| 5 | D7 | 231757 | 1005944 | BG11XG380009.0001.001 | F2 | 1007936 | 76.53 | 9.07 | 6.63 |
| 5 | D8 | 231757 | 1005952 | BG11XG380009.0001.001 | F2 | 1007944 | 66.45 | 20.93 | 4.42 |
| 5 | D9 | 231757 | 1005960 | BG11XG380009.0001.001 | F2 | 1007952 | 73.67 | 15.95 | 2.22 |
| 5 | D10 | 231757 | 1005968 | BG11XG380009.0001.001 | F2 | 1007960 | 72.81 | 16.33 | 3.30 |
| 5 | D11 | 231757 | 1005976 | BG11XG380009.0001.001 | F2 | 1007968 | 62.94 | 23.60 | 4.77 |
| 5 | D12 | 231757 | 1005984 | BG11XG380009.0001.001 | F2 | 1007976 | 74.43 | 14.86 | 2.89 |

*FIG. 1a*

| | | | | | | | | | |
|---|---|---|---|---|---|---|---|---|---|
| 5 | E1 | 231757 | 1005897 | BG11XG380009.0001.001 | F2 | 1007889 | 70.77 | 14.59 | 6.98 |
| 5 | E2 | 231757 | 1005905 | BG11XG380009.0001.001 | F2 | 1007897 | 68.78 | 17.43 | 4.71 |
| 5 | E3 | 231757 | 1005913 | BG11XG380009.0001.001 | F2 | 1007905 | 77.63 | 9.04 | 5.20 |
| 5 | E4 | 231757 | 1005921 | BG11XG380009.0001.001 | F2 | 1007913 | 73.44 | 14.49 | 3.80 |
| 5 | E5 | 231757 | 1005929 | BG11XG380009.0001.001 | F2 | 1007921 | 65.24 | 22.64 | 3.84 |
| 5 | E6 | 231757 | 1005937 | BG11XG380009.0001.001 | F2 | 1007929 | 71.21 | 16.48 | 4.06 |
| 5 | E7 | 231757 | 1005945 | BG11XG380009.0001.001 | F2 | 1007937 | 77.91 | 8.51 | 5.86 |
| 5 | E8 | 231757 | 1005953 | BG11XG380009.0001.001 | F2 | 1007945 | 75.33 | 11.43 | 5.21 |
| 5 | E9 | 231757 | 1005961 | BG11XG380009.0001.001 | F2 | 1007953 | 70.92 | 17.17 | 3.57 |
| 5 | E10 | 231757 | 1005969 | BG11XG380009.0001.001 | F2 | 1007961 | 68.85 | 19.55 | 3.05 |
| 5 | E11 | 231757 | 1005977 | BG11XG380009.0001.001 | F2 | 1007969 | 64.49 | 21.69 | 5.58 |
| 5 | E12 | 231757 | 1005985 | BG11XG380009.0001.001 | F2 | 1007977 | 69.31 | 19.70 | 3.04 |
| 5 | F1 | 231757 | 1005898 | BG11XG380009.0001.001 | F2 | 1007890 | 70.13 | 17.59 | 3.76 |
| 5 | F2 | 231757 | 1005906 | BG11XG380009.0001.001 | F2 | 1007898 | 71.21 | 16.30 | 3.92 |
| 5 | F3 | 231757 | 1005914 | BG11XG380009.0001.001 | F2 | 1007906 | 78.30 | 10.84 | 5.00 |
| 5 | F4 | 231757 | 1005922 | BG11XG380009.0001.001 | F2 | 1007914 | 71.43 | 12.95 | 7.42 |
| 5 | F5 | 231757 | 1005930 | BG11XG380009.0001.001 | F2 | 1007922 | 63.05 | 20.20 | 8.61 |
| 5 | F6 | 231757 | 1005938 | BG11XG380009.0001.001 | F2 | 1007930 | 64.94 | 23.01 | 3.72 |
| 5 | F7 | 231757 | 1005946 | BG11XG380009.0001.001 | F2 | 1007938 | 78.31 | 9.67 | 4.55 |
| 5 | F8 | 231757 | 1005954 | BG11XG380009.0001.001 | F2 | 1007946 | 69.21 | 19.73 | 2.57 |
| 5 | F9 | 231757 | 1005962 | BG11XG380009.0001.001 | F2 | 1007954 | 65.39 | 19.77 | 6.65 |
| 5 | F10 | 231757 | 1005970 | BG11XG380009.0001.001 | F2 | 1007962 | 77.17 | 9.21 | 5.45 |
| 5 | F11 | 231757 | 1005978 | BG11XG380009.0001.001 | F2 | 1007970 | 74.06 | 11.20 | 6.85 |
| 5 | F12 | 231757 | 1005986 | BG11XG380009.0001.001 | F2 | 1007978 | 60.81 | 24.65 | 6.50 |
| 5 | G1 | 231757 | 1005899 | BG11XG380009.0001.001 | F2 | 1007891 | 69.91 | 16.29 | 5.09 |
| 5 | G2 | 231757 | 1005907 | BG11XG380009.0001.001 | F2 | 1007899 | 69.03 | 17.24 | 5.37 |
| 5 | G3 | 231757 | 1005915 | BG11XG380009.0001.001 | F2 | 1007907 | 74.24 | 12.44 | 5.55 |
| 5 | G4 | 231757 | 1005923 | BG11XG380009.0001.001 | F2 | 1007915 | 69.53 | 18.11 | 3.75 |
| 5 | G5 | 231757 | 1005931 | BG11XG380009.0001.001 | F2 | 1007923 | 77.44 | 9.71 | 4.80 |
| 5 | G6 | 231757 | 1005939 | BG11XG380009.0001.001 | F2 | 1007931 | 76.04 | 8.17 | 7.20 |
| 5 | G7 | 231757 | 1005947 | BG11XG380009.0001.001 | F2 | 1007939 | 70.37 | 17.68 | 3.81 |
| 5 | G8 | 231757 | 1005955 | BG11XG380009.0001.001 | F2 | 1007947 | 78.18 | 8.50 | 5.57 |
| 5 | G9 | 231757 | 1005963 | BG11XG380009.0001.001 | F2 | 1007955 | 69.65 | 15.84 | 6.96 |
| 5 | G10 | 231757 | 1005971 | BG11XG380009.0001.001 | F2 | 1007963 | 71.88 | 15.67 | 4.48 |
| 5 | G11 | 231757 | 1005979 | BG11XG380009.0001.001 | F2 | 1007971 | 59.49 | 26.82 | 3.87 |
| 5 | G12 | 231757 | 1005987 | BG11XG380009.0001.001 | F2 | 1007979 | 73.37 | 11.93 | 5.59 |
| 5 | H1 | 231757 | 1005900 | BG11XG380009.0001.001 | F2 | 1007892 | 71.17 | 17.21 | 3.40 |
| 5 | H2 | 231757 | 1005908 | BG11XG380009.0001.001 | F2 | 1007900 | 76.98 | 8.95 | 5.67 |
| 5 | H3 | 231757 | 1005916 | BG11XG380009.0001.001 | F2 | 1007908 | 72.90 | 14.47 | 4.78 |
| 5 | H4 | 231757 | 1005924 | BG11XG380009.0001.001 | F2 | 1007916 | 67.68 | 16.90 | 6.34 |
| 5 | H5 | 231757 | 1005932 | BG11XG380009.0001.001 | F2 | 1007924 | 67.69 | 20.92 | 3.31 |
| 5 | H6 | 231757 | 1005940 | BG11XG380009.0001.001 | F2 | 1007932 | 68.81 | 15.43 | 7.32 |
| 5 | H7 | 231757 | 1005948 | BG11XG380009.0001.001 | F2 | 1007940 | 72.32 | 11.90 | 7.84 |
| 5 | H8 | 231757 | 1005956 | BG11XG380009.0001.001 | F2 | 1007948 | 77.90 | 8.92 | 5.45 |
| 5 | H9 | 231757 | 1005964 | BG11XG380009.0001.001 | F2 | 1007956 | 77.64 | 10.14 | 4.79 |
| 5 | H10 | 231757 | 1005972 | BG11XG380009.0001.001 | F2 | 1007964 | 68.65 | 18.41 | 4.47 |
| 5 | H11 | 231757 | 1005980 | BG11XG380009.0001.001 | F2 | 1007972 | 70.33 | 15.84 | 5.67 |
| 5 | H12 | 231757 | 1005988 | BG11XG380009.0001.001 | F2 | 1007980 | 68.99 | 18.17 | 3.79 |

*FIG. 1b*

| Box | Well | Geno_Id | Rec ID | Source ID | Gen | RowId | C18:1 | C18:2 | C18:3 |
|---|---|---|---|---|---|---|---|---|---|
| 6 | A7 | 200278 | 1006037 | BG11XG380010.0001.001 | F2 | 1008029 | 74.65 | 11.05 | 6.59 |
| 6 | A8 | 200278 | 1006045 | BG11XG380010.0001.001 | F2 | 1008037 | 68.57 | 17.91 | 5.28 |
| 6 | A9 | 200278 | 1006053 | BG11XG380010.0001.001 | F2 | 1008045 | 65.60 | 24.04 | 2.68 |
| 6 | A10 | 200278 | 1006061 | BG11XG380010.0001.001 | F2 | 1008053 | 72.78 | 13.68 | 5.19 |
| 6 | A11 | 200278 | 1006069 | BG11XG380010.0001.001 | F2 | 1008061 | 72.28 | 13.68 | 5.49 |
| 6 | A12 | 200278 | 1006077 | BG11XG380010.0001.001 | F2 | 1008069 | 76.76 | 8.88 | 6.55 |
| 6 | B1 | 200278 | 1005990 | BG11XG380010.0001.001 | F2 | 1007982 | 71.44 | 13.46 | 5.41 |
| 6 | B2 | 200278 | 1005998 | BG11XG380010.0001.001 | F2 | 1007990 | 72.97 | 12.64 | 5.86 |
| 6 | B3 | 200278 | 1006006 | BG11XG380010.0001.001 | F2 | 1007998 | 67.24 | 18.79 | 5.58 |
| 6 | B4 | 200278 | 1006014 | BG11XG380010.0001.001 | F2 | 1008006 | 67.53 | 19.72 | 4.42 |
| 6 | B5 | 200278 | 1006022 | BG11XG380010.0001.001 | F2 | 1008014 | 73.58 | 12.06 | 5.99 |
| 6 | B6 | 200278 | 1006030 | BG11XG380010.0001.001 | F2 | 1008022 | 74.75 | 10.97 | 5.90 |
| 6 | B7 | 200278 | 1006038 | BG11XG380010.0001.001 | F2 | 1008030 | 68.02 | 21.44 | 3.20 |
| 6 | B8 | 200278 | 1006046 | BG11XG380010.0001.001 | F2 | 1008038 | 63.56 | 21.64 | 6.26 |
| 6 | B9 | 200278 | 1006054 | BG11XG380010.0001.001 | F2 | 1008046 | 69.57 | 18.26 | 3.61 |
| 6 | B10 | 200278 | 1006062 | BG11XG380010.0001.001 | F2 | 1008054 | 78.70 | 8.89 | 4.50 |
| 6 | B11 | 200278 | 1006070 | BG11XG380010.0001.001 | F2 | 1008062 | 74.62 | 13.17 | 4.40 |
| 6 | B12 | 200278 | 1006078 | BG11XG380010.0001.001 | F2 | 1008070 | 72.06 | 14.83 | 4.72 |
| 6 | C1 | 200278 | 1005991 | BG11XG380010.0001.001 | F2 | 1007983 | 72.71 | 12.73 | 6.05 |
| 6 | C2 | 200278 | 1005999 | BG11XG380010.0001.001 | F2 | 1007991 | 72.64 | 12.38 | 7.02 |
| 6 | C3 | 200278 | 1006007 | BG11XG380010.0001.001 | F2 | 1007999 | 73.09 | 14.99 | 3.46 |
| 6 | C4 | 200278 | 1006015 | BG11XG380010.0001.001 | F2 | 1008007 | 73.95 | 15.05 | 2.70 |
| 6 | C5 | 200278 | 1006023 | BG11XG380010.0001.001 | F2 | 1008015 | 74.14 | 13.68 | 4.24 |
| 6 | C6 | 200278 | 1006031 | BG11XG380010.0001.001 | F2 | 1008023 | 71.36 | 14.21 | 6.18 |
| 6 | C7 | 200278 | 1006039 | BG11XG380010.0001.001 | F2 | 1008031 | 77.45 | 10.11 | 4.65 |
| 6 | C8 | 200278 | 1006047 | BG11XG380010.0001.001 | F2 | 1008039 | 77.91 | 8.87 | 5.23 |
| 6 | C9 | 200278 | 1006055 | BG11XG380010.0001.001 | F2 | 1008047 | 70.51 | 15.67 | 5.70 |
| 6 | C10 | 200278 | 1006063 | BG11XG380010.0001.001 | F2 | 1008055 | 75.67 | 11.21 | 4.55 |
| 6 | C11 | 200278 | 1006071 | BG11XG380010.0001.001 | F2 | 1008063 | 73.45 | 12.62 | 6.17 |
| 6 | C12 | 200278 | 1006079 | BG11XG380010.0001.001 | F2 | 1008071 | 74.58 | 13.93 | 3.77 |
| 6 | D1 | 200278 | 1005992 | BG11XG380010.0001.001 | F2 | 1007984 | 69.08 | 14.71 | 7.86 |
| 6 | D2 | 200278 | 1006000 | BG11XG380010.0001.001 | F2 | 1007992 | 68.03 | 19.22 | 4.26 |
| 6 | D3 | 200278 | 1006008 | BG11XG380010.0001.001 | F2 | 1008000 | 79.60 | 7.83 | 4.35 |
| 6 | D4 | 200278 | 1006016 | BG11XG380010.0001.001 | F2 | 1008008 | 72.07 | 13.97 | 6.22 |
| 6 | D5 | 200278 | 1006024 | BG11XG380010.0001.001 | F2 | 1008016 | 70.76 | 18.79 | 2.14 |
| 6 | D6 | 200278 | 1006032 | BG11XG380010.0001.001 | F2 | 1008024 | 73.58 | 12.12 | 6.21 |
| 6 | D7 | 200278 | 1006040 | BG11XG380010.0001.001 | F2 | 1008032 | 69.93 | 17.58 | 4.08 |
| 6 | D8 | 200278 | 1006048 | BG11XG380010.0001.001 | F2 | 1008040 | 77.42 | 8.30 | 5.89 |
| 6 | D9 | 200278 | 1006056 | BG11XG380010.0001.001 | F2 | 1008048 | 74.06 | 11.12 | 6.92 |
| 6 | D10 | 200278 | 1006064 | BG11XG380010.0001.001 | F2 | 1008056 | 74.55 | 9.79 | 7.02 |
| 6 | D11 | 200278 | 1006072 | BG11XG380010.0001.001 | F2 | 1008064 | 70.61 | 13.26 | 7.94 |
| 6 | D12 | 200278 | 1006080 | BG11XG380010.0001.001 | F2 | 1008072 | 70.03 | 18.11 | 3.88 |

*FIG. 1c*

| | | | | | | | | | |
|---|---|---|---|---|---|---|---|---|---|
| 6 | E1 | 200278 | 1005993 | BG11XG380010.0001.001 | F2 | 1007985 | 72.45 | 11.27 | 7.55 |
| 6 | E2 | 200278 | 1006001 | BG11XG380010.0001.001 | F2 | 1007993 | 70.70 | 17.90 | 3.24 |
| 6 | E3 | 200278 | 1006009 | BG11XG380010.0001.001 | F2 | 1008001 | 73.75 | 14.03 | 3.45 |
| 6 | E4 | 200278 | 1006017 | BG11XG380010.0001.001 | F2 | 1008009 | 73.84 | 12.50 | 5.98 |
| 6 | E5 | 200278 | 1006025 | BG11XG380010.0001.001 | F2 | 1008017 | 70.41 | 16.37 | 4.94 |
| 6 | E6 | 200278 | 1006033 | BG11XG380010.0001.001 | F2 | 1008025 | 69.95 | 15.49 | 5.74 |
| 6 | E7 | 200278 | 1006041 | BG11XG380010.0001.001 | F2 | 1008033 | 72.78 | 10.37 | 9.19 |
| 6 | E8 | 200278 | 1006049 | BG11XG380010.0001.001 | F2 | 1008041 | 67.51 | 21.27 | 2.53 |
| 6 | E9 | 200278 | 1006057 | BG11XG380010.0001.001 | F2 | 1008049 | 75.77 | 10.22 | 5.92 |
| 6 | E10 | 200278 | 1006065 | BG11XG380010.0001.001 | F2 | 1008057 | 74.11 | 10.78 | 6.60 |
| 6 | E11 | 200278 | 1006073 | BG11XG380010.0001.001 | F2 | 1008065 | 68.94 | 20.14 | 3.06 |
| 6 | E12 | 200278 | 1006081 | BG11XG380010.0001.001 | F2 | 1008073 | 66.96 | 19.56 | 4.35 |
| 6 | F1 | 200278 | 1005994 | BG11XG380010.0001.001 | F2 | 1007986 | 79.58 | 6.74 | 6.00 |
| 6 | F2 | 200278 | 1006002 | BG11XG380010.0001.001 | F2 | 1007994 | 72.93 | 14.23 | 4.50 |
| 6 | F3 | 200278 | 1006010 | BG11XG380010.0001.001 | F2 | 1008002 | 72.37 | 13.62 | 8.08 |
| 6 | F4 | 200278 | 1006018 | BG11XG380010.0001.001 | F2 | 1008010 | 69.83 | 17.19 | 4.48 |
| 6 | F5 | 200278 | 1006026 | BG11XG380010.0001.001 | F2 | 1008018 | 70.83 | 14.27 | 6.45 |
| 6 | F6 | 200278 | 1006034 | BG11XG380010.0001.001 | F2 | 1008026 | 77.84 | 8.24 | 8.54 |
| 6 | F7 | 200278 | 1006042 | BG11XG380010.0001.001 | F2 | 1008034 | 74.09 | 13.49 | 4.51 |
| 6 | F8 | 200278 | 1006050 | BG11XG380010.0001.001 | F2 | 1008042 | 66.53 | 19.39 | 6.38 |
| 6 | F9 | 200278 | 1006058 | BG11XG380010.0001.001 | F2 | 1008050 | 74.65 | 14.11 | 2.91 |
| 6 | F10 | 200278 | 1006066 | BG11XG380010.0001.001 | F2 | 1008058 | 67.09 | 17.72 | 6.72 |
| 6 | F11 | 200278 | 1006074 | BG11XG380010.0001.001 | F2 | 1008066 | 75.05 | 11.23 | 5.81 |
| 6 | F12 | 200278 | 1006082 | BG11XG380010.0001.001 | F2 | 1008074 | 79.53 | 7.59 | 5.80 |
| 6 | G1 | 200278 | 1005995 | BG11XG380010.0001.001 | F2 | 1007987 | 74.21 | 12.24 | 6.20 |
| 6 | G2 | 200278 | 1006003 | BG11XG380010.0001.001 | F2 | 1007995 | 79.27 | 7.94 | 5.09 |
| 6 | G3 | 200278 | 1006011 | BG11XG380010.0001.001 | F2 | 1008003 | 69.88 | 18.97 | 5.55 |
| 6 | G4 | 200278 | 1006019 | BG11XG380010.0001.001 | F2 | 1008011 | 77.37 | 8.12 | 8.98 |
| 6 | G5 | 200278 | 1006027 | BG11XG380010.0001.001 | F2 | 1008019 | 71.03 | 13.42 | 7.54 |
| 6 | G6 | 200278 | 1006035 | BG11XG380010.0001.001 | F2 | 1008027 | 70.71 | 15.91 | 5.00 |
| 6 | G7 | 200278 | 1006043 | BG11XG380010.0001.001 | F2 | 1008035 | 79.85 | 9.64 | 3.15 |
| 6 | G8 | 200278 | 1006051 | BG11XG380010.0001.001 | F2 | 1008043 | 73.00 | 12.58 | 6.65 |
| 6 | G9 | 200278 | 1006059 | BG11XG380010.0001.001 | F2 | 1008051 | 67.88 | 21.31 | 2.98 |
| 6 | G10 | 200278 | 1006067 | BG11XG380010.0001.001 | F2 | 1008059 | 71.88 | 12.86 | 6.28 |
| 6 | G11 | 200278 | 1006075 | BG11XG380010.0001.001 | F2 | 1008067 | 80.93 | 7.65 | 3.76 |
| 6 | G12 | 200278 | 1006083 | BG11XG380010.0001.001 | F2 | 1008075 | 61.03 | 6.62 | 4.17 |
| 6 | H1 | 200278 | 1005996 | BG11XG380010.0001.001 | F2 | 1007988 | 66.92 | 17.52 | 7.55 |
| 6 | H2 | 200278 | 1006004 | BG11XG380010.0001.001 | F2 | 1007996 | 69.92 | 18.22 | 3.45 |
| 6 | H3 | 200278 | 1006012 | BG11XG380010.0001.001 | F2 | 1008004 | 78.76 | 8.43 | 5.10 |
| 6 | H4 | 200278 | 1006020 | BG11XG380010.0001.001 | F2 | 1008012 | 72.55 | 15.37 | 3.82 |
| 6 | H5 | 200278 | 1006028 | BG11XG380010.0001.001 | F2 | 1008020 | 68.97 | 17.89 | 4.81 |
| 6 | H6 | 200278 | 1006036 | BG11XG380010.0001.001 | F2 | 1008028 | 66.84 | 21.59 | 3.34 |
| 6 | H7 | 200278 | 1006044 | BG11XG380010.0001.001 | F2 | 1008036 | 72.72 | 14.88 | 4.64 |
| 6 | H8 | 200278 | 1006052 | BG11XG380010.0001.001 | F2 | 1008044 | 68.80 | 15.36 | 7.76 |
| 6 | H9 | 200278 | 1006060 | BG11XG380010.0001.001 | F2 | 1008052 | 74.95 | 12.23 | 5.12 |
| 6 | H10 | 200278 | 1006068 | BG11XG380010.0001.001 | F2 | 1008060 | 74.52 | 11.82 | 6.44 |
| 6 | H11 | 200278 | 1006076 | BG11XG380010.0001.001 | F2 | 1008068 | 79.29 | 8.86 | 4.13 |
| 6 | H12 | 200278 | 1006084 | BG11XG380010.0001.001 | F2 | 1008076 | 69.34 | 19.89 | 2.61 |

*FIG. 1d*

| Box | Well | Geno_Id | Rec ID | Source ID | Gen | RowId | C18:1 | C18:2 | C18:3 |
|---|---|---|---|---|---|---|---|---|---|
| 7 | A7 | 231755 | 1006133 | BG11XG380008.0001.001 | F2 | 1008125 | 70.75 | 10.30 | 10.67 |
| 7 | A8 | 231755 | 1006141 | BG11XG380008.0001.001 | F2 | 1008133 | 77.88 | 9.11 | 5.27 |
| 7 | A9 | 231755 | 1006149 | BG11XG380008.0001.001 | F2 | 1008141 | 73.73 | 15.09 | 3.17 |
| 7 | A10 | 231755 | 1006157 | BG11XG380008.0001.001 | F2 | 1008149 | 71.58 | 12.64 | 6.26 |
| 7 | A11 | 231755 | 1006165 | BG11XG380008.0001.001 | F2 | 1008157 | 74.11 | 9.87 | 7.97 |
| 7 | A12 | 231755 | 1006173 | BG11XG380008.0001.001 | F2 | 1008165 | 76.20 | 10.58 | 5.64 |
| 7 | B1 | 231755 | 1006086 | BG11XG380008.0001.001 | F2 | 1008078 | 77.59 | 8.76 | 7.66 |
| 7 | B2 | 231755 | 1006094 | BG11XG380008.0001.001 | F2 | 1008086 | 75.28 | 11.25 | 4.87 |
| 7 | B3 | 231755 | 1006102 | BG11XG380008.0001.001 | F2 | 1008094 | 76.03 | 12.13 | 4.00 |
| 7 | B4 | 231755 | 1006110 | BG11XG380008.0001.001 | F2 | 1008102 | 71.87 | 12.81 | 7.70 |
| 7 | B5 | 231755 | 1006118 | BG11XG380008.0001.001 | F2 | 1008110 | 70.45 | 15.89 | 4.81 |
| 7 | B6 | 231755 | 1006126 | BG11XG380008.0001.001 | F2 | 1008118 | 75.94 | 10.09 | 6.58 |
| 7 | B7 | 231755 | 1006134 | BG11XG380008.0001.001 | F2 | 1008126 | 77.16 | 9.43 | 5.06 |
| 7 | B8 | 231755 | 1006142 | BG11XG380008.0001.001 | F2 | 1008134 | 71.88 | 11.90 | 8.03 |
| 7 | B9 | 231755 | 1006150 | BG11XG380008.0001.001 | F2 | 1008142 | 74.26 | 9.34 | 7.94 |
| 7 | B10 | 231755 | 1006158 | BG11XG380008.0001.001 | F2 | 1008150 | 74.19 | 10.63 | 7.58 |
| 7 | B11 | 231755 | 1006166 | BG11XG380008.0001.001 | F2 | 1008158 | 72.08 | 9.78 | 10.18 |
| 7 | B12 | 231755 | 1006174 | BG11XG380008.0001.001 | F2 | 1008166 | 72.06 | 12.94 | 6.76 |
| 7 | C1 | 231755 | 1006087 | BG11XG380008.0001.001 | F2 | 1008079 | 76.00 | 9.11 | 7.10 |
| 7 | C2 | 231755 | 1006095 | BG11XG380008.0001.001 | F2 | 1008087 | 73.71 | 9.05 | 9.51 |
| 7 | C3 | 231755 | 1006103 | BG11XG380008.0001.001 | F2 | 1008095 | 74.42 | 9.18 | 8.32 |
| 7 | C4 | 231755 | 1006111 | BG11XG380008.0001.001 | F2 | 1008103 | 73.37 | 10.98 | 7.90 |
| 7 | C5 | 231755 | 1006119 | BG11XG380008.0001.001 | F2 | 1008111 | 72.96 | 13.20 | 5.50 |
| 7 | C6 | 231755 | 1006127 | BG11XG380008.0001.001 | F2 | 1008119 | 74.01 | 10.25 | 7.93 |
| 7 | C7 | 231755 | 1006135 | BG11XG380008.0001.001 | F2 | 1008127 | 72.07 | 11.60 | 7.81 |
| 7 | C8 | 231755 | 1006143 | BG11XG380008.0001.001 | F2 | 1008135 | 73.47 | 10.71 | 7.85 |
| 7 | C9 | 231755 | 1006151 | BG11XG380008.0001.001 | F2 | 1008143 | 73.86 | 13.62 | 4.21 |
| 7 | C10 | 231755 | 1006159 | BG11XG380008.0001.001 | F2 | 1008151 | 72.14 | 13.49 | 6.28 |
| 7 | C11 | 231755 | 1006167 | BG11XG380008.0001.001 | F2 | 1008159 | 70.32 | 11.06 | 10.16 |
| 7 | C12 | 231755 | 1006175 | BG11XG380008.0001.001 | F2 | 1008167 | 70.31 | 13.57 | 7.38 |
| 7 | D1 | 231755 | 1006088 | BG11XG380008.0001.001 | F2 | 1008080 | 74.97 | 7.83 | 8.98 |
| 7 | D2 | 231755 | 1006096 | BG11XG380008.0001.001 | F2 | 1008088 | 72.58 | 11.41 | 7.86 |
| 7 | D3 | 231755 | 1006104 | BG11XG380008.0001.001 | F2 | 1008096 | 73.56 | 11.84 | 6.64 |
| 7 | D4 | 231755 | 1006112 | BG11XG380008.0001.001 | F2 | 1008104 | 75.30 | 10.43 | 6.35 |
| 7 | D5 | 231755 | 1006120 | BG11XG380008.0001.001 | F2 | 1008112 | 77.68 | 7.81 | 6.45 |
| 7 | D6 | 231755 | 1006128 | BG11XG380008.0001.001 | F2 | 1008120 | 73.92 | 11.03 | 8.81 |
| 7 | D7 | 231755 | 1006136 | BG11XG380008.0001.001 | F2 | 1008128 | 75.18 | 9.43 | 7.44 |
| 7 | D8 | 231755 | 1006144 | BG11XG380008.0001.001 | F2 | 1008136 | 73.65 | 10.74 | 7.41 |
| 7 | D9 | 231755 | 1006152 | BG11XG380008.0001.001 | F2 | 1008144 | 74.89 | 8.59 | 9.31 |
| 7 | D10 | 231755 | 1006160 | BG11XG380008.0001.001 | F2 | 1008152 | 72.98 | 11.13 | 7.17 |
| 7 | D11 | 231755 | 1006168 | BG11XG380008.0001.001 | F2 | 1008160 | 75.38 | 10.93 | 6.23 |
| 7 | D12 | 231755 | 1006176 | BG11XG380008.0001.001 | F2 | 1008168 | 75.76 | 9.72 | 7.32 |

*FIG. 1e*

| 7 | E1 | 231755 | 1006089 | BG11XG380008.0001.001 | F2 | 1008081 | 70.22 | 10.89 | 9.98 |
| 7 | E2 | 231755 | 1006097 | BG11XG380008.0001.001 | F2 | 1008089 | 78.06 | 7.03 | 7.07 |
| 7 | E3 | 231755 | 1006105 | BG11XG380008.0001.001 | F2 | 1008097 | 76.42 | 10.91 | 4.57 |
| 7 | E4 | 231755 | 1006113 | BG11XG380008.0001.001 | F2 | 1008105 | 72.98 | 12.77 | 5.56 |
| 7 | E5 | 231755 | 1006121 | BG11XG380008.0001.001 | F2 | 1008113 | 74.78 | 9.83 | 7.03 |
| 7 | E6 | 231755 | 1006129 | BG11XG380008.0001.001 | F2 | 1008121 | 74.68 | 8.20 | 9.85 |
| 7 | E7 | 231755 | 1006137 | BG11XG380008.0001.001 | F2 | 1008129 | 73.50 | 9.54 | 8.62 |
| 7 | E8 | 231755 | 1006145 | BG11XG380008.0001.001 | F2 | 1008137 | 74.63 | 9.40 | 8.54 |
| 7 | E9 | 231755 | 1006153 | BG11XG380008.0001.001 | F2 | 1008145 | 77.26 | 8.18 | 7.01 |
| 7 | E10 | 231755 | 1006161 | BG11XG380008.0001.001 | F2 | 1008153 | 73.22 | 9.98 | 9.18 |
| 7 | E11 | 231755 | 1006169 | BG11XG380008.0001.001 | F2 | 1008161 | 71.31 | 11.29 | 6.70 |
| 7 | E12 | 231755 | 1006177 | BG11XG380008.0001.001 | F2 | 1008169 | 72.39 | 13.47 | 5.54 |
| 7 | F1 | 231755 | 1006090 | BG11XG380008.0001.001 | F2 | 1008082 | 66.48 | 12.50 | 10.08 |
| 7 | F2 | 231755 | 1006098 | BG11XG380008.0001.001 | F2 | 1008090 | 73.36 | 11.85 | 7.36 |
| 7 | F3 | 231755 | 1006106 | BG11XG380008.0001.001 | F2 | 1008098 | 70.30 | 11.77 | 8.89 |
| 7 | F4 | 231755 | 1006114 | BG11XG380008.0001.001 | F2 | 1008106 | 72.98 | 10.65 | 8.17 |
| 7 | F5 | 231755 | 1006122 | BG11XG380008.0001.001 | F2 | 1008114 | 70.40 | 9.08 | 11.97 |
| 7 | F6 | 231755 | 1006130 | BG11XG380008.0001.001 | F2 | 1008122 | 73.45 | 11.78 | 6.82 |
| 7 | F7 | 231755 | 1006138 | BG11XG380008.0001.001 | F2 | 1008130 | 73.38 | 11.68 | 7.57 |
| 7 | F8 | 231755 | 1006146 | BG11XG380008.0001.001 | F2 | 1008138 | 76.70 | 8.76 | 6.68 |
| 7 | F9 | 231755 | 1006154 | BG11XG380008.0001.001 | F2 | 1008146 | 75.44 | 11.38 | 6.00 |
| 7 | F10 | 231755 | 1006162 | BG11XG380008.0001.001 | F2 | 1008154 | 73.13 | 11.96 | 6.50 |
| 7 | F11 | 231755 | 1006170 | BG11XG380008.0001.001 | F2 | 1008162 | 72.68 | 9.55 | 9.59 |
| 7 | F12 | 231755 | 1006178 | BG11XG380008.0001.001 | F2 | 1008170 | 74.58 | 12.66 | 4.71 |
| 7 | G1 | 231755 | 1006091 | BG11XG380008.0001.001 | F2 | 1008083 | 76.89 | 8.19 | 6.82 |
| 7 | G2 | 231755 | 1006099 | BG11XG380008.0001.001 | F2 | 1008091 | 72.86 | 13.50 | 5.52 |
| 7 | G3 | 231755 | 1006107 | BG11XG380008.0001.001 | F2 | 1008099 | 73.58 | 11.22 | 7.62 |
| 7 | G4 | 231755 | 1006115 | BG11XG380008.0001.001 | F2 | 1008107 | 71.69 | 12.12 | 8.16 |
| 7 | G5 | 231755 | 1006123 | BG11XG380008.0001.001 | F2 | 1008115 | 76.36 | 9.55 | 6.30 |
| 7 | G6 | 231755 | 1006131 | BG11XG380008.0001.001 | F2 | 1008123 | 74.78 | 11.83 | 5.24 |
| 7 | G7 | 231755 | 1006139 | BG11XG380008.0001.001 | F2 | 1008131 | 77.19 | 7.92 | 7.11 |
| 7 | G8 | 231755 | 1006147 | BG11XG380008.0001.001 | F2 | 1008139 | 75.08 | 9.43 | 7.72 |
| 7 | G9 | 231755 | 1006155 | BG11XG380008.0001.001 | F2 | 1008147 | 75.28 | 12.65 | 4.76 |
| 7 | G10 | 231755 | 1006163 | BG11XG380008.0001.001 | F2 | 1008155 | 74.00 | 12.36 | 5.99 |
| 7 | G11 | 231755 | 1006171 | BG11XG380008.0001.001 | F2 | 1008163 | 66.73 | 16.34 | 7.83 |
| 7 | G12 | 231755 | 1006179 | BG11XG380008.0001.001 | F2 | 1008171 | 74.97 | 9.79 | 7.92 |
| 7 | H1 | 231755 | 1006092 | BG11XG380008.0001.001 | F2 | 1008084 | 75.95 | 9.57 | 6.47 |
| 7 | H2 | 231755 | 1006100 | BG11XG380008.0001.001 | F2 | 1008092 | 74.98 | 10.34 | 6.91 |
| 7 | H3 | 231755 | 1006108 | BG11XG380008.0001.001 | F2 | 1008100 | 74.75 | 12.23 | 5.36 |
| 7 | H4 | 231755 | 1006116 | BG11XG380008.0001.001 | F2 | 1008108 | 75.09 | 10.84 | 5.95 |
| 7 | H5 | 231755 | 1006124 | BG11XG380008.0001.001 | F2 | 1008116 | 77.04 | 7.96 | 7.35 |
| 7 | H6 | 231755 | 1006132 | BG11XG380008.0001.001 | F2 | 1008124 | 74.81 | 12.10 | 5.20 |
| 7 | H7 | 231755 | 1006140 | BG11XG380008.0001.001 | F2 | 1008132 | 74.32 | 10.49 | 6.50 |
| 7 | H8 | 231755 | 1006148 | BG11XG380008.0001.001 | F2 | 1008140 | 74.16 | 12.31 | 5.77 |
| 7 | H9 | 231755 | 1006156 | BG11XG380008.0001.001 | F2 | 1008148 | 75.83 | 8.93 | 7.59 |
| 7 | H10 | 231755 | 1006164 | BG11XG380008.0001.001 | F2 | 1008156 | 73.13 | 15.07 | 4.02 |
| 7 | H11 | 231755 | 1006172 | BG11XG380008.0001.001 | F2 | 1008164 | 72.96 | 9.78 | 8.78 |
| 7 | H12 | 231755 | 1006180 | BG11XG380008.0001.001 | F2 | 1008172 | 75.06 | 9.89 | 6.94 |

*FIG. 1f*

| Box | Well | Geno_Id | Rec ID | Source ID | Gen | RowId | C18:1 | C18:2 | C18:3 |
|---|---|---|---|---|---|---|---|---|---|
| 8 | A7 | 231753 | 1006229 | BG11XG380007.0001.001 | F2 | 1008221 | 69.10 | 17.39 | 6.05 |
| 8 | A8 | 231753 | 1006237 | BG11XG380007.0001.001 | F2 | 1008229 | 74.25 | 11.91 | 5.58 |
| 8 | A9 | 231753 | 1006245 | BG11XG380007.0001.001 | F2 | 1008237 | 72.38 | 14.13 | 4.82 |
| 8 | A10 | 231753 | 1006253 | BG11XG380007.0001.001 | F2 | 1008245 | 73.02 | 14.80 | 4.59 |
| 8 | A11 | 231753 | 1006261 | BG11XG380007.0001.001 | F2 | 1008253 | 66.26 | 16.94 | 6.61 |
| 8 | A12 | 231753 | 1006269 | BG11XG380007.0001.001 | F2 | 1008261 | 78.26 | 8.88 | 5.69 |
| 8 | B1 | 231753 | 1006182 | BG11XG380007.0001.001 | F2 | 1008174 | 69.81 | 17.93 | 4.34 |
| 8 | B2 | 231753 | 1006190 | BG11XG380007.0001.001 | F2 | 1008182 | 76.21 | 9.81 | 6.21 |
| 8 | B3 | 231753 | 1006198 | BG11XG380007.0001.001 | F2 | 1008190 | 71.93 | 14.11 | 6.06 |
| 8 | B4 | 231753 | 1006206 | BG11XG380007.0001.001 | F2 | 1008198 | 72.16 | 13.91 | 6.08 |
| 8 | B5 | 231753 | 1006214 | BG11XG380007.0001.001 | F2 | 1008206 | 72.12 | 12.95 | 7.14 |
| 8 | B6 | 231753 | 1006222 | BG11XG380007.0001.001 | F2 | 1008214 | 72.60 | 14.29 | 5.56 |
| 8 | B7 | 231753 | 1006230 | BG11XG380007.0001.001 | F2 | 1008222 | 70.48 | 12.76 | 8.53 |
| 8 | B8 | 231753 | 1006238 | BG11XG380007.0001.001 | F2 | 1008230 | 72.36 | 14.10 | 6.09 |
| 8 | B9 | 231753 | 1006246 | BG11XG380007.0001.001 | F2 | 1008238 | 71.24 | 12.44 | 7.99 |
| 8 | B10 | 231753 | 1006254 | BG11XG380007.0001.001 | F2 | 1008246 | 71.51 | 10.72 | 9.97 |
| 8 | B11 | 231753 | 1006262 | BG11XG380007.0001.001 | F2 | 1008254 | 70.14 | 14.85 | 6.53 |
| 8 | B12 | 231753 | 1006270 | BG11XG380007.0001.001 | F2 | 1008262 | 78.06 | 11.77 | 2.85 |
| 8 | C1 | 231753 | 1006183 | BG11XG380007.0001.001 | F2 | 1008175 | 77.46 | 7.29 | 7.43 |
| 8 | C2 | 231753 | 1006191 | BG11XG380007.0001.001 | F2 | 1008183 | 66.82 | 13.63 | 11.77 |
| 8 | C3 | 231753 | 1006199 | BG11XG380007.0001.001 | F2 | 1008191 | 76.39 | 9.88 | 6.32 |
| 8 | C4 | 231753 | 1006207 | BG11XG380007.0001.001 | F2 | 1008199 | 67.91 | 16.88 | 7.07 |
| 8 | C5 | 231753 | 1006215 | BG11XG380007.0001.001 | F2 | 1008207 | 65.85 | 21.40 | 4.88 |
| 8 | C6 | 231753 | 1006223 | BG11XG380007.0001.001 | F2 | 1008215 | 76.01 | 7.14 | 8.72 |
| 8 | C7 | 231753 | 1006231 | BG11XG380007.0001.001 | F2 | 1008223 | 68.68 | 17.95 | 4.86 |
| 8 | C8 | 231753 | 1006239 | BG11XG380007.0001.001 | F2 | 1008231 | 70.22 | 13.63 | 7.84 |
| 8 | C9 | 231753 | 1006247 | BG11XG380007.0001.001 | F2 | 1008239 | 69.92 | 15.27 | 6.57 |
| 8 | C10 | 231753 | 1006255 | BG11XG380007.0001.001 | F2 | 1008247 | 65.67 | 23.54 | 3.00 |
| 8 | C11 | 231753 | 1006263 | BG11XG380007.0001.001 | F2 | 1008255 | 69.45 | 17.36 | 5.68 |
| 8 | C12 | 231753 | 1006271 | BG11XG380007.0001.001 | F2 | 1008263 | 72.34 | 18.85 | 3.70 |
| 8 | D1 | 231753 | 1006184 | BG11XG380007.0001.001 | F2 | 1008176 | 68.58 | 15.98 | 7.63 |
| 8 | D2 | 231753 | 1006192 | BG11XG380007.0001.001 | F2 | 1008184 | 71.01 | 14.39 | 6.28 |
| 8 | D3 | 231753 | 1006200 | BG11XG380007.0001.001 | F2 | 1008192 | 66.95 | 19.19 | 5.02 |
| 8 | D4 | 231753 | 1006208 | BG11XG380007.0001.001 | F2 | 1008200 | 73.61 | 15.18 | 3.41 |
| 8 | D5 | 231753 | 1006216 | BG11XG380007.0001.001 | F2 | 1008208 | 69.25 | 16.73 | 5.82 |
| 8 | D6 | 231753 | 1006224 | BG11XG380007.0001.001 | F2 | 1008216 | 70.89 | 14.21 | 7.43 |
| 8 | D7 | 231753 | 1006232 | BG11XG380007.0001.001 | F2 | 1008224 | 67.14 | 15.98 | 8.31 |
| 8 | D8 | 231753 | 1006240 | BG11XG380007.0001.001 | F2 | 1008232 | 65.24 | 19.60 | 7.20 |
| 8 | D9 | 231753 | 1006248 | BG11XG380007.0001.001 | F2 | 1008240 | 71.33 | 14.98 | 5.49 |
| 8 | D10 | 231753 | 1006256 | BG11XG380007.0001.001 | F2 | 1008248 | 69.32 | 16.46 | 6.25 |
| 8 | D11 | 231753 | 1006264 | BG11XG380007.0001.001 | F2 | 1008256 | 71.91 | 12.30 | 8.03 |
| 8 | D12 | 231753 | 1006272 | BG11XG380007.0001.001 | F2 | 1008264 | 78.24 | 10.70 | 3.46 |

*FIG. 1g*

| 8 | E1 | 231753 | 1006185 | BG11XG380007.0001.001 | F2 | 1008177 | 68.28 | 16.40 | 5.47 |
|---|---|---|---|---|---|---|---|---|---|
| 8 | E2 | 231753 | 1006193 | BG11XG380007.0001.001 | F2 | 1008185 | 74.09 | 13.52 | 4.96 |
| 8 | E3 | 231753 | 1006201 | BG11XG380007.0001.001 | F2 | 1008193 | 66.84 | 19.72 | 5.43 |
| 8 | E4 | 231753 | 1006209 | BG11XG380007.0001.001 | F2 | 1008201 | 65.36 | 19.39 | 6.35 |
| 8 | E5 | 231753 | 1006217 | BG11XG380007.0001.001 | F2 | 1008209 | 75.36 | 11.12 | 4.90 |
| 8 | E6 | 231753 | 1006225 | BG11XG380007.0001.001 | F2 | 1008217 | 78.31 | 7.48 | 6.61 |
| 8 | E7 | 231753 | 1006233 | BG11XG380007.0001.001 | F2 | 1008225 | 76.49 | 9.50 | 5.94 |
| 8 | E8 | 231753 | 1006241 | BG11XG380007.0001.001 | F2 | 1008233 | 78.41 | 9.18 | 5.29 |
| 8 | E9 | 231753 | 1006249 | BG11XG380007.0001.001 | F2 | 1008241 | 66.11 | 18.87 | 6.83 |
| 8 | E10 | 231753 | 1006257 | BG11XG380007.0001.001 | F2 | 1008249 | 73.87 | 11.31 | 6.88 |
| 8 | E11 | 231753 | 1006265 | BG11XG380007.0001.001 | F2 | 1008257 | 67.10 | 18.69 | 5.71 |
| 8 | E12 | 231753 | 1006273 | BG11XG380007.0001.001 | F2 | 1008265 | 71.47 | 15.61 | 4.78 |
| 8 | F1 | 231753 | 1006186 | BG11XG380007.0001.001 | F2 | 1008178 | 69.91 | 13.00 | 8.79 |
| 8 | F2 | 231753 | 1006194 | BG11XG380007.0001.001 | F2 | 1008186 | 67.98 | 16.89 | 7.21 |
| 8 | F3 | 231753 | 1006202 | BG11XG380007.0001.001 | F2 | 1008194 | 72.19 | 13.62 | 6.42 |
| 8 | F4 | 231753 | 1006210 | BG11XG380007.0001.001 | F2 | 1008202 | 64.45 | 18.57 | 9.54 |
| 8 | F5 | 231753 | 1006218 | BG11XG380007.0001.001 | F2 | 1008210 | 68.97 | 13.47 | 9.34 |
| 8 | F6 | 231753 | 1006226 | BG11XG380007.0001.001 | F2 | 1008218 | 69.48 | 19.68 | 2.97 |
| 8 | F7 | 231753 | 1006234 | BG11XG380007.0001.001 | F2 | 1008226 | 71.13 | 13.01 | 6.83 |
| 8 | F8 | 231753 | 1006242 | BG11XG380007.0001.001 | F2 | 1008234 | 70.29 | 13.11 | 8.25 |
| 8 | F9 | 231753 | 1006250 | BG11XG380007.0001.001 | F2 | 1008242 | 78.60 | 8.92 | 4.81 |
| 8 | F10 | 231753 | 1006258 | BG11XG380007.0001.001 | F2 | 1008250 | 70.24 | 16.07 | 5.85 |
| 8 | F11 | 231753 | 1006266 | BG11XG380007.0001.001 | F2 | 1008258 | 72.23 | 13.54 | 6.32 |
| 8 | F12 | 231753 | 1006274 | BG11XG380007.0001.001 | F2 | 1008266 | 76.73 | 7.08 | 8.43 |
| 8 | G1 | 231753 | 1006187 | BG11XG380007.0001.001 | F2 | 1008179 | 69.68 | 14.77 | 6.59 |
| 8 | G2 | 231753 | 1006195 | BG11XG380007.0001.001 | F2 | 1008187 | 66.65 | 19.27 | 6.17 |
| 8 | G3 | 231753 | 1006203 | BG11XG380007.0001.001 | F2 | 1008195 | 67.53 | 19.86 | 5.17 |
| 8 | G4 | 231753 | 1006211 | BG11XG380007.0001.001 | F2 | 1008203 | 71.73 | 17.04 | 3.35 |
| 8 | G5 | 231753 | 1006219 | BG11XG380007.0001.001 | F2 | 1008211 | 72.73 | 12.31 | 6.91 |
| 8 | G6 | 231753 | 1006227 | BG11XG380007.0001.001 | F2 | 1008219 | 74.97 | 9.64 | 7.25 |
| 8 | G7 | 231753 | 1006235 | BG11XG380007.0001.001 | F2 | 1008227 | 73.84 | 12.47 | 5.37 |
| 8 | G8 | 231753 | 1006243 | BG11XG380007.0001.001 | F2 | 1008235 | 67.03 | 17.11 | 7.92 |
| 8 | G9 | 231753 | 1006251 | BG11XG380007.0001.001 | F2 | 1008243 | 73.85 | 14.08 | 4.54 |
| 8 | G10 | 231753 | 1006259 | BG11XG380007.0001.001 | F2 | 1008251 | 69.77 | 16.96 | 5.62 |
| 8 | G11 | 231753 | 1006267 | BG11XG380007.0001.001 | F2 | 1008259 | 68.15 | 18.68 | 5.04 |
| 8 | G12 | 231753 | 1006275 | BG11XG380007.0001.001 | F2 | 1008267 | 69.14 | 13.45 | 9.68 |
| 8 | H1 | 231753 | 1006188 | BG11XG380007.0001.001 | F2 | 1008180 | 72.00 | 11.00 | 7.33 |
| 8 | H2 | 231753 | 1006196 | BG11XG380007.0001.001 | F2 | 1008188 | 73.54 | 13.39 | 5.59 |
| 8 | H3 | 231753 | 1006204 | BG11XG380007.0001.001 | F2 | 1008196 | 69.57 | 15.48 | 7.70 |
| 8 | H4 | 231753 | 1006212 | BG11XG380007.0001.001 | F2 | 1008204 | 66.92 | 17.78 | 7.60 |
| 8 | H5 | 231753 | 1006220 | BG11XG380007.0001.001 | F2 | 1008212 | 68.57 | 18.21 | 4.94 |
| 8 | H6 | 231753 | 1006228 | BG11XG380007.0001.001 | F2 | 1008220 | 69.81 | 15.70 | 7.48 |
| 8 | H7 | 231753 | 1006236 | BG11XG380007.0001.001 | F2 | 1008228 | 70.91 | 13.92 | 6.89 |
| 8 | H8 | 231753 | 1006244 | BG11XG380007.0001.001 | F2 | 1008236 | 63.84 | 19.01 | 8.80 |
| 8 | H9 | 231753 | 1006252 | BG11XG380007.0001.001 | F2 | 1008244 | 68.12 | 14.14 | 9.70 |
| 8 | H10 | 231753 | 1006260 | BG11XG380007.0001.001 | F2 | 1008252 | nd | nd | nd |
| 8 | H11 | 231753 | 1006268 | BG11XG380007.0001.001 | F2 | 1008260 | 76.21 | 7.98 | 7.84 |
| 8 | H12 | 231753 | 1006276 | BG11XG380007.0001.001 | F2 | 1008268 | 76.57 | 10.27 | 5.57 |

*FIG. 1h*

| Lab ID | Sample Box | Well Position | Geno_id | Rowid | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0385 | 5 | A1 | 231757 | 1007885 | 1.40 | | 17.78 | | | | |
| 2011-0231-0397 | 5 | B1 | 231757 | 1007886 | 1.10 | | 14.51 | | | | |
| 2011-0231-0409 | 5 | C1 | 231757 | 1007887 | 1.33 | | 10.22 | | | | |
| 2011-0231-0421 | 5 | D1 | 231757 | 1007888 | 1.07 | | 11.07 | | | | |
| 2011-0231-0433 | 5 | E1 | 231757 | 1007889 | 1.15 | | 14.59 | | | | |
| 2011-0231-0445 | 5 | F1 | 231757 | 1007890 | 1.26 | 70.77 | 17.59 | 3.76 | | | |
| 2011-0231-0457 | 5 | G1 | 231757 | 1007891 | 1.29 | 70.13 | 16.29 | | | | |
| 2011-0231-0469 | 5 | H1 | 231757 | 1007892 | 1.22 | 71.17 | 17.21 | | | | |
| 2011-0231-0386 | 5 | A2 | 231757 | 1007893 | 1.54 | 70.48 | 16.04 | | | | |
| 2011-0231-0398 | 5 | B2 | 231757 | 1007894 | 1.46 | 70.01 | 15.34 | | | | |
| 2011-0231-0410 | 5 | C2 | 231757 | 1007895 | 1.04 | | 12.11 | | | | |
| 2011-0231-0422 | 5 | D2 | 231757 | 1007896 | 1.46 | 71.33 | 13.88 | | | | |
| 2011-0231-0434 | 5 | E2 | 231757 | 1007897 | 1.24 | 71.21 | 17.43 | | | | |
| 2011-0231-0446 | 5 | F2 | 231757 | 1007898 | 1.47 | | 16.30 | 3.92 | | | |
| 2011-0231-0458 | 5 | G2 | 231757 | 1007899 | 1.36 | | 17.24 | | | | |
| 2011-0231-0470 | 5 | H2 | 231757 | 1007900 | 1.31 | | 8.95 | | | | |
| 2011-0231-0387 | 5 | A3 | 231757 | 1007901 | 1.76 | | 20.84 | | | | |
| 2011-0231-0399 | 5 | B3 | 231757 | 1007902 | 0.97 | | 17.67 | | | | |
| 2011-0231-0411 | 5 | C3 | 231757 | 1007903 | 1.78 | | 13.69 | | | | |
| 2011-0231-0423 | 5 | D3 | 231757 | 1007904 | 1.15 | 70.81 | 15.36 | | | | |
| 2011-0231-0435 | 5 | E3 | 231757 | 1007905 | 1.46 | | 9.04 | | | | |
| 2011-0231-0447r | 5 | F3 | 231757 | 1007906 | 1.37 | | 10.84 | | | | |

FIG. 7a

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0459 | 5 | G3 | 231757 | 1007907 | 1.40 | | 12.44 | | | | |
| 2011-0231-0471 | 5 | H3 | 231757 | 1007908 | 1.31 | 2.50 | 14.47 | | | | |
| 2011-0231-0388 | 5 | A4 | 231757 | 1007909 | 0.97 | | 25.79 | 2.49 | | | |
| 2011-0231-0400 | 5 | B4 | 231757 | 1007910 | 1.33 | | 11.77 | | | | |
| 2011-0231-0412 | 5 | C4 | 231757 | 1007911 | 1.34 | | 16.24 | | | | |
| 2011-0231-0424 | 5 | D4 | 231757 | 1007912 | 1.67 | | 16.59 | | | | |
| 2011-0231-0436 | 5 | E4 | 231757 | 1007913 | 1.56 | | 14.49 | | | | |
| 2011-0231-0448rr | 5 | F4 | 231757 | 1007914 | 1.30 | 71.43 | 12.95 | 3.60 | | | |
| 2011-0231-0460 | 5 | G4 | 231757 | 1007915 | 1.36 | | 18.11 | 3.75 | | | |
| 2011-0231-0472 | 5 | H4 | 231757 | 1007916 | 1.58 | | 16.90 | | | | |
| 2011-0231-0389 | 5 | A5 | 231757 | 1007917 | 1.37 | | 17.05 | | | | |
| 2011-0231-0401 | 5 | B5 | 231757 | 1007918 | 1.27 | | 16.24 | | | | |
| 2011-0231-0413 | 5 | C5 | 231757 | 1007919 | 1.10 | | 31.51 | | | | |
| 2011-0231-0425 | 5 | D5 | 231757 | 1007920 | 1.22 | | 16.68 | | | | |
| 2011-0231-0437 | 5 | E5 | 231757 | 1007921 | 1.20 | | 22.84 | 3.84 | | | |
| 2011-0231-0449 | 5 | F5 | 231757 | 1007922 | 1.05 | | 20.20 | | | | |
| 2011-0231-0461 | 5 | G5 | 231757 | 1007923 | 1.54 | 71.82 | 9.71 | | | | |
| 2011-0231-0473 | 5 | H5 | 231757 | 1007924 | 1.34 | | 20.92 | | | | |
| 2011-0231-0390 | 5 | A6 | 231757 | 1007925 | 1.31 | | 21.82 | | | | |
| 2011-0231-0402 | 5 | B6 | 231757 | 1007926 | 1.32 | | 20.55 | | | | |
| 2011-0231-0414 | 5 | C6 | 231757 | 1007927 | 1.26 | | 23.38 | 3.98 | | | |
| 2011-0231-0426 | 5 | D6 | 231757 | 1007928 | 1.34 | 71.67 | 15.74 | | | | |
| 2011-0231-0438 | 5 | E6 | 231757 | 1007929 | 1.26 | 71.21 | 16.48 | | | | |
| 2011-0231-0450 | 5 | F6 | 231757 | 1007930 | 0.98 | | 23.01 | 3.72 | | | |
| 2011-0231-0462 | 5 | G6 | 231757 | 1007931 | 1.02 | | 8.17 | | | | |
| 2011-0231-0474 | 5 | H6 | 231757 | 1007932 | 1.18 | | 15.43 | | | | |
| 2011-0231-0391 | 5 | A7 | 231757 | 1007933 | 1.10 | | 18.84 | | | | |

FIG. 7b

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0403 | 5 | B7 | 231757 | 1007934 | 0.99 | | 15.65 | | | | |
| 2011-0231-0415 | 5 | C7 | 231757 | 1007935 | 1.34 | | 18.01 | | | | |
| 2011-0231-0427 | 5 | D7 | 231757 | 1007936 | 1.21 | | 9.07 | | | | |
| 2011-0231-0439 | 5 | E7 | 231757 | 1007937 | 1.40 | | 8.51 | | | | |
| 2011-0231-0451 | 5 | F7 | 231757 | 1007938 | 1.20 | | 9.67 | | | | |
| 2011-0231-0463 | 5 | G7 | 231757 | 1007939 | 1.25 | 70.37 | 17.66 | 3.81 | | | |
| 2011-0231-0475 | 5 | H7 | 231757 | 1007940 | 1.26 | | 11.80 | | | | |
| 2011-0231-0392 | 5 | A8 | 231757 | 1007941 | 1.25 | 71.96 | 15.34 | | | | |
| 2011-0231-0404 | 5 | B8 | 231757 | 1007942 | 1.10 | | 12.27 | 3.63 | | | |
| 2011-0231-0416 | 5 | C8 | 231757 | 1007943 | 1.53 | | 22.65 | 3.77 | | | |
| 2011-0231-0428 | 5 | D8 | 231757 | 1007944 | 1.33 | | 20.93 | | | | |
| 2011-0231-0440 | 5 | E8 | 231757 | 1007945 | 1.56 | | 11.43 | | | | |
| 2011-0231-0452 | 5 | F8 | 231757 | 1007946 | 1.45 | | 19.73 | | | | |
| 2011-0231-0464 | 5 | G8 | 231757 | 1007947 | 1.53 | | 8.50 | | | | |
| 2011-0231-0476 | 5 | H8 | 231757 | 1007948 | 1.22 | | 8.92 | | | | |
| 2011-0231-0393 | 5 | A9 | 231757 | 1007949 | 1.62 | | 21.72 | | | | |
| 2011-0231-0405 | 5 | B9 | 231757 | 1007950 | 1.09 | | 10.38 | | | | |
| 2011-0231-0417 | 5 | C9 | 231757 | 1007951 | 1.39 | | 17.66 | | | | |
| 2011-0231-0429 | 5 | D9 | 231757 | 1007952 | 1.40 | | 15.95 | | | | |
| 2011-0231-0441 | 5 | E9 | 231757 | 1007953 | 1.03 | 70.92 | 17.17 | 3.57 | | | |
| 2011-0231-0453 | 5 | F9 | 231757 | 1007954 | 1.27 | | 19.77 | | | | |
| 2011-0231-0465 | 5 | G9 | 231757 | 1007955 | 1.11 | | 15.84 | | | | |
| 2011-0231-0477 | 5 | H9 | 231757 | 1007956 | 1.25 | | 10.14 | | | | |
| 2011-0231-0394 | 5 | A10 | 231757 | 1007957 | 1.26 | | 10.20 | | | | |

FIG. 7c

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0406 | 5 | B10 | 231757 | 1007958 | 1.15 | | 23.10 | | | | |
| 2011-0231-0418 | 5 | C10 | 231757 | 1007959 | 0.96 | | 11.61 | | | | |
| 2011-0231-0430 | 5 | D10 | 231757 | 1007960 | 1.47 | | 16.33 | | | | |
| 2011-0231-0442 | 5 | E10 | 231757 | 1007961 | 1.29 | | 19.55 | | | | |
| 2011-0231-0454 | 5 | F10 | 231757 | 1007962 | 1.52 | | 9.21 | | | | |
| 2011-0231-0466 | 5 | G10 | 231757 | 1007963 | 1.26 | 71.88 | 15.67 | | | | |
| 2011-0231-0478 | 5 | H10 | 231757 | 1007964 | 1.33 | | 18.41 | | | | |
| 2011-0231-0395 | 5 | A11 | 231757 | 1007965 | 1.15 | | 17.01 | | | | |
| 2011-0231-0407 | 5 | B11 | 231757 | 1007966 | 1.38 | | 16.16 | | | | |
| 2011-0231-0419 | 5 | C11 | 231757 | 1007967 | 1.66 | | 10.00 | | | | |
| 2011-0231-0431 | 5 | D11 | 231757 | 1007968 | 1.16 | | 23.60 | | | | |
| 2011-0231-0443 | 5 | E11 | 231757 | 1007969 | 1.45 | | 21.69 | | | | |
| 2011-0231-0455 | 5 | F11 | 231757 | 1007970 | 1.30 | | 11.20 | | | | |
| 2011-0231-0467 | 5 | G11 | 231757 | 1007971 | 1.03 | | 26.62 | 3.87 | | | |
| 2011-0231-0479 | 5 | H11 | 231757 | 1007972 | 1.09 | 70.33 | 15.84 | | | | |
| 2011-0231-0396 | 5 | A12 | 231757 | 1007973 | 1.29 | | 22.94 | | | | |
| 2011-0231-0408 | 5 | B12 | 231757 | 1007974 | 1.53 | | 19.75 | | | | |
| 2011-0231-0420 | 5 | C12 | 231757 | 1007975 | 1.46 | | 12.07 | | | | |
| 2011-0231-0432 | 5 | D12 | 231757 | 1007976 | 1.32 | | 14.86 | | | | |
| 2011-0231-0444 | 5 | E12 | 231757 | 1007977 | 1.26 | | 19.70 | | | | |
| 2011-0231-0456 | 5 | F12 | 231757 | 1007978 | 1.20 | | 24.65 | | | | |
| 2011-0231-0468 | 5 | G12 | 231757 | 1007979 | 1.15 | | 11.93 | | | | |
| 2011-0231-0480 | 5 | H12 | 231757 | 1007980 | 0.98 | | 18.17 | 3.79 | | | |

*FIG. 7d*

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0577 | | A1 | 231755 | 1008077 | 1.31 | | 8.78 | | | | |
| 2011-0231-0589 | | B1 | 231755 | 1008078 | 1.78 | | 6.76 | | | | |
| 2011-0231-0601 | | C1 | 231755 | 1008079 | 1.19 | | 9.11 | | | | |
| 2011-0231-0613 | | D1 | 231755 | 1008080 | 1.32 | | 7.83 | | | | |
| 2011-0231-0625 | | E1 | 231755 | 1008081 | 1.05 | 70.22 | 10.69 | | | | |
| 2011-0231-0637 | | F1 | 231755 | 1008082 | 0.94 | | 12.50 | | | | |
| 2011-0231-0649 | | G1 | 231755 | 1008083 | 1.53 | | 8.19 | | | | |
| 2011-0231-0661 | | H1 | 231755 | 1008084 | 1.43 | | 9.57 | | | | |
| 2011-0231-0578 | | A2 | 231755 | 1008085 | 1.37 | | 10.25 | | | | |
| 2011-0231-0590 | | B2 | 231755 | 1008086 | 1.22 | | 11.25 | | | | |
| 2011-0231-0602 | | C2 | 231755 | 1008087 | 1.04 | | 9.05 | | | | |
| 2011-0231-0614 | | D2 | 231755 | 1008088 | 0.99 | | 11.41 | | | | |
| 2011-0231-0626 | | E2 | 231755 | 1008089 | 1.26 | | 7.03 | | | | |
| 2011-0231-0638 | | F2 | 231755 | 1008090 | 1.28 | | 11.85 | | | | |
| 2011-0231-0650 | | G2 | 231755 | 1008091 | 0.99 | | 13.50 | | | | |
| 2011-0231-0662 | | H2 | 231755 | 1008092 | 1.23 | | 10.34 | | | | |
| 2011-0231-0579 | | A3 | 231755 | 1008093 | 1.34 | | 7.78 | | | | |
| 2011-0231-0591 | | B3 | 231755 | 1008094 | 1.38 | | 12.13 | 4.00 | | | |
| 2011-0231-0603 | | C3 | 231755 | 1008095 | 1.18 | | 9.18 | | | | |
| 2011-0231-0615 | | D3 | 231755 | 1008096 | 1.13 | | 11.84 | | | | |
| 2011-0231-0627 | | E3 | 231755 | 1008097 | 1.45 | | 10.91 | | | | |
| 2011-0231-0639 | | F3 | 231755 | 1008098 | 1.02 | 70.30 | 11.77 | | | | |

FIG. 7e

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0651 | | G3 | 231755 | 1008099 | 0.98 | | 11.22 | | | | |
| 2011-0231-0663 | | H3 | 231755 | 1008100 | 1.16 | | 12.23 | | | | |
| 2011-0231-0580 | | A4 | 231755 | 1008101 | 1.25 | | 8.73 | | | | |
| 2011-0231-0592 | | B4 | 231755 | 1008102 | 0.96 | 71.67 | 12.61 | | | | |
| 2011-0231-0604 | | C4 | 231755 | 1008103 | 0.84 | | 10.98 | | | | |
| 2011-0231-0616 | | D4 | 231755 | 1008104 | 1.17 | | 10.43 | | | | |
| 2011-0231-0628 | | E4 | 231755 | 1008105 | 1.18 | | 12.77 | | | | |
| 2011-0231-0640 | | F4 | 231755 | 1008106 | 1.39 | | 10.65 | | | | |
| 2011-0231-0652 | | G4 | 231755 | 1008107 | 1.09 | 71.68 | 12.12 | | | | |
| 2011-0231-0664 | | H4 | 231755 | 1008108 | 1.15 | | 10.84 | | | | |
| 2011-0231-0581 | | A5 | 231755 | 1008109 | 1.06 | | 11.04 | | | | |
| 2011-0231-0593 | | B5 | 231755 | 1008110 | 1.04 | 70.45 | 15.89 | | | | |
| 2011-0231-0605 | | C5 | 231755 | 1008111 | 1.35 | | 13.20 | | | | |
| 2011-0231-0617 | | D5 | 231755 | 1008112 | 1.46 | | 7.81 | | | | |
| 2011-0231-0629 | | E5 | 231755 | 1008113 | 1.08 | | 9.63 | | | | |
| 2011-0231-0641 | | F5 | 231755 | 1008114 | 1.00 | 70.40 | 9.06 | | | | |
| 2011-0231-0653 | | G5 | 231755 | 1008115 | 1.11 | | 9.55 | | | | |
| 2011-0231-0665 | | H5 | 231755 | 1008116 | 1.12 | | 7.96 | | | | |
| 2011-0231-0582 | | A6 | 231755 | 1008117 | 1.15 | | 11.50 | | | | |
| 2011-0231-0594 | | B6 | 231755 | 1008118 | 1.16 | | 10.09 | | | | |
| 2011-0231-0606 | | C6 | 231755 | 1008119 | 1.04 | | 10.25 | | | | |
| 2011-0231-0618 | | D6 | 231755 | 1008120 | 1.22 | | 11.83 | | | | |
| 2011-0231-0630 | | E6 | 231755 | 1008121 | 0.98 | | 8.20 | | | | |
| 2011-0231-0642 | | F6 | 231755 | 1008122 | 1.15 | | 11.78 | | | | |
| 2011-0231-0654 | | G6 | 231755 | 1008123 | 1.29 | | 11.83 | | | | |
| 2011-0231-0666 | | H6 | 231755 | 1008124 | 1.16 | | 12.10 | | | | |
| 2011-0231-0583 | | A7 | 231755 | 1008125 | 1.05 | 70.75 | 10.30 | | | | |

*FIG. 7f*

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0595 | | B7 | 231755 | 1008126 | 1.36 | 77.18 | 9.43 | | | | |
| 2011-0231-0607 | | C7 | 231755 | 1008127 | 1.21 | 72.97 | 11.60 | | | | |
| 2011-0231-0619 | | D7 | 231755 | 1008128 | 1.17 | 76.06 | 9.43 | | | | |
| 2011-0231-0631 | | E7 | 231755 | 1008129 | 1.11 | 73.50 | 9.54 | | | | |
| 2011-0231-0643 | | F7 | 231755 | 1008130 | 0.90 | 73.30 | 11.68 | | | | |
| 2011-0231-0655 | | G7 | 231755 | 1008131 | 1.36 | 77.18 | 7.92 | | | | |
| 2011-0231-0667 | | H7 | 231755 | 1008132 | 1.16 | 74.04 | 10.49 | | | | |
| 2011-0231-0584 | | A8 | 231755 | 1008133 | 1.24 | 77.82 | 9.11 | | | | |
| 2011-0231-0596 | | B8 | 231755 | 1008134 | 1.15 | 71.88 | 11.90 | | | | |
| 2011-0231-0608 | | C8 | 231755 | 1008135 | 1.13 | 73.47 | 10.71 | | | | |
| 2011-0231-0620 | | D8 | 231755 | 1008136 | 1.04 | 73.60 | 10.74 | | | | |
| 2011-0231-0632 | | E8 | 231755 | 1008137 | 1.05 | 74.03 | 9.40 | | | | |
| 2011-0231-0644 | | F8 | 231755 | 1008138 | 1.18 | 76.76 | 8.76 | | | | |
| 2011-0231-0656 | | G8 | 231755 | 1008139 | 1.00 | 75.60 | 9.48 | | | | |
| 2011-0231-0668 | | H8 | 231755 | 1008140 | 1.21 | 74.13 | 12.31 | | | | |
| 2011-0231-0585 | | A9 | 231755 | 1008141 | 1.28 | 73.72 | 15.09 | | | | |
| 2011-0231-0597 | | B9 | 231755 | 1008142 | 1.16 | 74.28 | 9.34 | | | | |
| 2011-0231-0609 | | C9 | 231755 | 1008143 | 1.41 | 73.86 | 13.62 | | | | |
| 2011-0231-0621 | | D9 | 231755 | 1008144 | 1.09 | 74.38 | 8.59 | | | | |
| 2011-0231-0633 | | E9 | 231755 | 1008145 | 1.30 | 77.26 | 8.18 | | | | |
| 2011-0231-0645 | | F9 | 231755 | 1008146 | 0.98 | 75.44 | 11.38 | | | | |
| 2011-0231-0657 | | G9 | 231755 | 1008147 | 1.07 | 75.20 | 12.85 | | | | |
| 2011-0231-0669 | | H9 | 231755 | 1008148 | 0.96 | 75.63 | 6.93 | | | | |
| 2011-0231-0586 | | A10 | 231755 | 1008149 | 0.89 | 71.58 | 12.64 | | | | |

FIG. 7g

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0598 | | B10 | 231755 | 1008150 | 1.14 | | 10.63 | | | | |
| 2011-0231-0610 | | C10 | 231755 | 1008151 | 0.94 | 72.14 | 13.49 | | | | |
| 2011-0231-0622 | | D10 | 231755 | 1008152 | 1.48 | | 11.13 | | | | |
| 2011-0231-0634 | | E10 | 231755 | 1008153 | 0.98 | | 9.98 | | | | |
| 2011-0231-0646 | | F10 | 231755 | 1008154 | 1.29 | | 11.96 | | | | |
| 2011-0231-0658 | | G10 | 231755 | 1008155 | 1.26 | | 12.36 | | | | |
| 2011-0231-0670 | | H10 | 231755 | 1008156 | 1.19 | | 15.07 | | | | |
| 2011-0231-0587 | | A11 | 231755 | 1008157 | 0.97 | | 9.87 | | | | |
| 2011-0231-0599 | | B11 | 231755 | 1008158 | 1.16 | | 9.78 | | | | |
| 2011-0231-0611 | | C11 | 231755 | 1008159 | 1.01 | | 11.06 | | | | |
| 2011-0231-0623 | | D11 | 231755 | 1008160 | 1.15 | 70.32 | 10.93 | | | | |
| 2011-0231-0635 | | E11 | 231755 | 1008161 | 1.07 | | 11.29 | | | | |
| 2011-0231-0647 | | F11 | 231755 | 1008162 | 1.18 | 71.31 | 9.55 | | | | |
| 2011-0231-0659 | | G11 | 231755 | 1008163 | 1.15 | | 16.34 | | | | |
| 2011-0231-0671 | | H11 | 231755 | 1008164 | 1.19 | | 9.78 | | | | |
| 2011-0231-0588 | | A12 | 231755 | 1008165 | 1.07 | | 10.58 | | | | |
| 2011-0231-0600 | | B12 | 231755 | 1008166 | 1.30 | | 12.94 | | | | |
| 2011-0231-0612 | | C12 | 231755 | 1008167 | 0.99 | 70.31 | 13.57 | | | | |
| 2011-0231-0624 | | D12 | 231755 | 1008168 | 1.10 | | 9.72 | | | | |
| 2011-0231-0636 | | E12 | 231755 | 1008169 | 1.13 | | 13.47 | | | | |
| 2011-0231-0648 | | F12 | 231755 | 1008170 | 1.23 | | 12.66 | | | | |
| 2011-0231-0660 | | G12 | 231755 | 1008171 | 1.06 | | 9.79 | | | | |
| 2011-0231-0672 | | H12 | 231755 | 1008172 | 1.05 | | 9.69 | | | | |

*FIG. 7h*

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0673 | 8 | A1 | 231753 | 1008173 | 1.29 | | 13.60 | | | | |
| 2011-0231-0685 | 8 | B1 | 231753 | 1008174 | 1.23 | | 17.93 | | | | |
| 2011-0231-0697 | 8 | C1 | 231753 | 1008175 | 1.58 | | 7.29 | | | | |
| 2011-0231-0709 | 8 | D1 | 231753 | 1008176 | 1.46 | | 15.98 | | | | |
| 2011-0231-0721 | 8 | E1 | 231753 | 1008177 | 1.48 | | 18.40 | | | | |
| 2011-0231-0733 | 8 | F1 | 231753 | 1008178 | 1.78 | | 13.08 | | | | |
| 2011-0231-0745 | 8 | G1 | 231753 | 1008179 | 1.71 | | 14.77 | | | | |
| 2011-0231-0757 | 8 | H1 | 231753 | 1008180 | 1.27 | 72.00 | 11.00 | | | | |
| 2011-0231-0674 | 8 | A2 | 231753 | 1008181 | 0.97 | | 13.35 | | | | |
| 2011-0231-0686 | 8 | B2 | 231753 | 1008182 | 1.34 | | 9.81 | | | | |
| 2011-0231-0698 | 8 | C2 | 231753 | 1008183 | 1.28 | | 13.63 | | | | |
| 2011-0231-0710 | 8 | D2 | 231753 | 1008184 | 1.38 | 71.01 | 14.39 | | | | |
| 2011-0231-0722 | 8 | E2 | 231753 | 1008185 | 1.39 | | 13.52 | | | | |
| 2011-0231-0734 | 8 | F2 | 231753 | 1008186 | 1.45 | | 16.69 | | | | |
| 2011-0231-0746 | 8 | G2 | 231753 | 1008187 | 1.23 | | 19.27 | | | | |
| 2011-0231-0758 | 8 | H2 | 231753 | 1008188 | 1.55 | | 13.39 | | | | |
| 2011-0231-0675 | 8 | A3 | 231753 | 1008189 | 1.15 | | 16.40 | | | | |
| 2011-0231-0687 | 8 | B3 | 231753 | 1008190 | 1.54 | 71.93 | 14.11 | | | | |
| 2011-0231-0699 | 8 | C3 | 231753 | 1008191 | 1.35 | | 9.88 | | | | |
| 2011-0231-0711 | 8 | D3 | 231753 | 1008192 | 1.51 | | 19.18 | | | | |
| 2011-0231-0723 | 8 | E3 | 231753 | 1008193 | 1.36 | | 19.72 | | | | |
| 2011-0231-0735 | 8 | F3 | 231753 | 1008194 | 1.42 | | 13.62 | | | | |

FIG. 7i

| Lab ID | Sample Box | Well Position | Geno_Id | RowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0747 | 8 | G3 | 231753 | 1008195 | 1.41 | | 19.66 | | | | |
| 2011-0231-0759 | 8 | H3 | 231753 | 1008196 | 1.25 | | 15.48 | | | | |
| 2011-0231-0676 | 8 | A4 | 231753 | 1008197 | 1.40 | | 19.00 | | | | |
| 2011-0231-0688 | 8 | B4 | 231753 | 1008198 | 1.50 | | 13.91 | | | | |
| 2011-0231-0700 | 8 | C4 | 231753 | 1008199 | 1.64 | | 16.86 | | | | |
| 2011-0231-0712 | 8 | D4 | 231753 | 1008200 | 1.44 | | 15.18 | | | | |
| 2011-0231-0724 | 8 | E4 | 231753 | 1008201 | 1.42 | | 19.39 | | | | |
| 2011-0231-0736 | 8 | F4 | 231753 | 1008202 | 1.19 | | 18.57 | | | | |
| 2011-0231-0748 | 8 | G4 | 231753 | 1008203 | 1.54 | 71.73 | 17.04 | | | | |
| 2011-0231-0760 | 8 | H4 | 231753 | 1008204 | 1.32 | | 17.78 | | | | |
| 2011-0231-0677 | 8 | A5 | 231753 | 1008205 | 1.48 | | 15.41 | | | | |
| 2011-0231-0689 | 8 | B5 | 231753 | 1008206 | 1.37 | | 12.95 | | | | |
| 2011-0231-0701 | 8 | C5 | 231753 | 1008207 | 1.30 | | 21.40 | | | | |
| 2011-0231-0713 | 8 | D5 | 231753 | 1008208 | 1.55 | | 16.73 | | | | |
| 2011-0231-0725 | 8 | E5 | 231753 | 1008209 | 2.26 | | 11.12 | | | | |
| 2011-0231-0737 | 8 | F5 | 231753 | 1008210 | 1.28 | | 13.47 | | | | |
| 2011-0231-0749 | 8 | G5 | 231753 | 1008211 | 1.59 | | 12.31 | | | | |
| 2011-0231-0761 | 8 | H5 | 231753 | 1008212 | 1.39 | | 18.21 | | | | |
| 2011-0231-0678 | 8 | A6 | 231753 | 1008213 | 1.51 | | 9.13 | | | | |
| 2011-0231-0690 | 8 | B6 | 231753 | 1008214 | 1.78 | | 14.29 | | | | |
| 2011-0231-0702 | 8 | C6 | 231753 | 1008215 | 1.30 | | 7.14 | | | | |
| 2011-0231-0714 | 8 | D6 | 231753 | 1008216 | 1.35 | 70.89 | 14.21 | | | | |
| 2011-0231-0726 | 8 | E6 | 231753 | 1008217 | 1.48 | | 7.48 | | | | |
| 2011-0231-0738 | 8 | F6 | 231753 | 1008218 | 1.39 | | 19.68 | | | | |
| 2011-0231-0750 | 8 | G6 | 231753 | 1008219 | 1.33 | | 9.64 | | | | |
| 2011-0231-0762 | 8 | H6 | 231753 | 1008220 | 1.13 | | 15.70 | | | | |
| 2011-0231-0679 | 8 | A7 | 231753 | 1008221 | 1.38 | | 17.39 | | | | |

| Lab ID | Sample Box | Well Position | Geno_Id | BowId | C18:0 | C18:1 | C18:2 | C18:3 | 1/2 Seed FAD2 Call | 1/2 Seed FAD3A Call | 1/2 Seed FAD3C Call |
|---|---|---|---|---|---|---|---|---|---|---|---|
| 2011-0231-0694 | 8 | B10 | 231753 | 1008246 | 1.23 | 71.51 | 10.72 | | | | |
| 2011-0231-0706 | 8 | C10 | 231753 | 1008247 | 1.33 | | 23.54 | | | | |
| 2011-0231-0718 | 8 | D10 | 231753 | 1008248 | 1.68 | | 16.46 | | | | |
| 2011-0231-0730 | 8 | E10 | 231753 | 1008249 | 1.58 | | 11.31 | | | | |
| 2011-0231-0742 | 8 | F10 | 231753 | 1008250 | 1.33 | 70.24 | 16.07 | | | | |
| 2011-0231-0754 | 8 | G10 | 231753 | 1008251 | 1.26 | | 16.96 | | | | |
| | 8 | H10 | | | | | | | | | |
| 2011-0231-0683 | 8 | A11 | 231753 | 1008253 | 1.56 | | 16.94 | | | | |
| 2011-0231-0695 | 8 | B11 | 231753 | 1008254 | 1.56 | 70.14 | 14.85 | | | | |
| 2011-0231-0707 | 8 | C11 | 231753 | 1008255 | 1.18 | | 17.38 | | | | |
| 2011-0231-0719 | 8 | D11 | 231753 | 1008256 | 1.47 | 71.91 | 12.30 | | | | |
| 2011-0231-0731 | 8 | E11 | 231753 | 1008257 | 1.55 | | 18.69 | | | | |
| 2011-0231-0743 | 8 | F11 | 231753 | 1008258 | 1.42 | | 13.54 | | | | |
| 2011-0231-0755 | 8 | G11 | 231753 | 1008259 | 1.27 | | 18.68 | | | | |
| 2011-0231-0767 | 8 | H11 | 231753 | 1008260 | 1.65 | | 7.98 | | | | |
| 2011-0231-0684 | 8 | A12 | 231753 | 1008261 | 1.35 | | 8.85 | | | | |
| 2011-0231-0696 | 8 | B12 | 231753 | 1008262 | 1.33 | | 11.77 | | | | |
| 2011-0231-0708 | 8 | C12 | 231753 | 1008263 | 1.55 | | 16.65 | | | | |
| 2011-0231-0720 | 8 | D12 | 231753 | 1008264 | 1.44 | | 10.70 | 3.70 | | NoCall | |
| 2011-0231-0732 | 8 | E12 | 231753 | 1008265 | 1.26 | 71.47 | 15.61 | | | | |
| 2011-0231-0744 | 8 | F12 | 231753 | 1008266 | 1.43 | | 7.08 | | | | |
| 2011-0231-0756 | 8 | G12 | 231753 | 1008267 | 1.22 | | 13.45 | | | | |
| 2011-0231-0768 | 8 | H12 | 231753 | 1008268 | 1.44 | | 10.27 | | | | |

*FIG. 7I*

| Project Ref.: | | Mag Trim from FAME | | Soybean Half Seed Analysis. Analysis performed by Ted Freeman, Reviewed by Brita McNew | | | | | | | | | | | | | |
|---|---|---|---|---|---|---|---|---|---|---|---|---|---|---|---|---|---|
| Date Reported: | 8/17/12 | Project Description: | | | | | | | | | | | | | | | |
| Study ID | 2012-0008 | Received: | 2/13/2012 | | | | | | | | | | | | | | |
| | | | | FAME ANALYSIS, % of Total Oil | | | | | | | | | | | | | |
| Lab ID | Plate ID | Well | % Sets | C12:0 | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0001 | Y120065 | A01 | 15.52 | | 0.08 | 11.05 | 0.11 | 3.57 | 27.79 | 46.55 | 8.96 | 0.31 | 0.29 | 0.03 | 0.33 | | 0.18 | |
| 2012-0008-0002 | Y120065 | A02 | 15.23 | | 0.08 | 11.07 | 0.11 | 3.28 | 27.78 | 46.34 | 8.91 | 0.29 | 0.30 | 0.03 | 0.32 | | 0.19 | |
| 2012-0008-0003 | Y120065 | A03 | 12.13 | | 0.09 | 8.11 | 0.12 | 3.35 | 37.67 | 39.58 | 7.73 | 0.29 | 0.43 | 0.02 | 0.27 | | 0.07 | |
| 2012-0008-0004 | Y120065 | A04 | 14.75 | | 0.07 | 9.63 | 0.14 | 4.01 | 30.22 | 45.45 | 8.12 | 0.33 | 0.25 | 0.02 | 0.27 | | 0.13 | |
| 2012-0008-0005 | Y120065 | A05 | 15.86 | | 0.11 | 11.63 | 0.12 | 3.36 | 24.08 | 46.53 | 10.38 | 0.30 | 0.24 | 0.03 | 0.35 | | 0.11 | 0.03 |
| 2012-0008-0006 | Y120065 | A06 | 12.58 | | 0.08 | 8.57 | 0.15 | 3.20 | 37.76 | 39.58 | 7.43 | 0.29 | 0.45 | 0.03 | 0.30 | 0.02 | 0.14 | |
| 2012-0008-0007 | Y120065 | A07 | 12.48 | | 0.08 | 8.73 | 0.13 | 2.86 | 36.73 | 40.20 | 9.29 | 0.27 | 0.41 | 0.04 | 0.29 | 0.07 | 0.16 | 0.04 |
| 2012-0008-0008 | Y120065 | A08 | 12.19 | | 0.10 | 8.18 | 0.18 | 3.05 | 41.90 | 34.17 | 7.80 | 0.34 | 0.66 | 0.03 | 0.35 | | 0.17 | |
| 2012-0008-0009 | Y120065 | A09 | 16.17 | | 0.19 | 11.39 | 0.14 | 3.87 | 26.73 | 45.71 | 9.30 | 0.33 | 0.28 | 0.02 | 0.35 | | 0.10 | 0.04 |
| 2012-0008-0010 | Y120065 | A10 | 11.31 | | 0.08 | 7.32 | 0.17 | 3.08 | 45.64 | 32.68 | 6.32 | 0.34 | 0.60 | 0.04 | 0.39 | | 0.20 | |
| 2012-0008-0011 | Y120065 | A11 | 14.92 | | 0.07 | 9.95 | 0.13 | 4.09 | 29.18 | 45.76 | 8.64 | 0.34 | 0.26 | 0.03 | 0.35 | 0.01 | 0.12 | 0.01 |
| 2012-0008-0012 | Y120065 | A12 | 13.89 | | 0.07 | 8.94 | 0.14 | 3.86 | 34.28 | 40.45 | 8.40 | 0.35 | 0.37 | 0.03 | 0.33 | | 0.19 | |
| 2012-0008-0013 | Y120065 | B01 | 14.35 | | 0.08 | 9.46 | 0.12 | 3.95 | 28.89 | 45.41 | 9.86 | 0.33 | 0.25 | 0.03 | 0.37 | | 0.17 | |
| 2012-0008-0014 | Y120065 | B02 | 14.48 | | 0.08 | 9.12 | 0.12 | 4.36 | 31.68 | 43.69 | 8.23 | 0.36 | 0.30 | 0.03 | 0.40 | | 0.17 | |
| 2012-0008-0015 | Y120065 | B03 | 12.62 | | 0.08 | 9.31 | 0.13 | 3.49 | 34.43 | 41.77 | 8.66 | 0.31 | 0.38 | 0.03 | 0.35 | | 0.09 | 0.02 |
| 2012-0008-0016 | Y120065 | B04 | 14.77 | | 0.08 | 10.84 | 0.14 | 3.86 | 34.46 | 40.63 | 8.22 | 0.29 | 0.35 | 0.03 | 0.31 | | 0.14 | 0.01 |
| 2012-0008-0017 | Y120065 | B05 | 13.77 | | 0.08 | 9.01 | 0.14 | 3.86 | 36.13 | 40.09 | 9.19 | 0.34 | 0.36 | 0.04 | 0.35 | | 0.13 | 0.02 |
| 2012-0008-0018 | Y120065 | B06 | 14.74 | | 0.08 | 10.80 | 0.14 | 3.14 | 32.86 | 41.86 | 9.34 | 0.29 | 0.37 | 0.03 | 0.30 | | 0.11 | 0.02 |
| 2012-0008-0019 | Y120065 | B07 | 15.09 | | 0.08 | 10.55 | 0.12 | 3.71 | 29.68 | 48.30 | 8.74 | 0.31 | 0.24 | 0.04 | 0.36 | | 0.08 | 0.02 |
| 2012-0008-0020 | Y120065 | B08 | 14.13 | | 0.08 | 10.11 | 0.15 | 3.21 | 30.98 | 43.80 | 9.10 | 0.33 | 0.35 | 0.03 | 0.32 | | 0.12 | 0.02 |
| 2012-0008-0021 | Y120065 | B09 | 11.03 | | 0.10 | 7.09 | 0.17 | 2.57 | 51.14 | 26.38 | 6.23 | 0.32 | 0.71 | 0.04 | 0.39 | | 0.11 | 0.03 |
| 2012-0008-0022 | Y120065 | B10 | 9.40 | | 0.09 | 6.04 | 0.19 | 3.99 | 59.99 | 23.51 | 4.36 | 0.31 | 0.91 | 0.03 | 0.26 | | 0.08 | 0.01 |
| 2012-0008-0023 | Y120065 | B11 | 13.44 | | 0.08 | 9.39 | 0.12 | 3.27 | 36.45 | 40.01 | 8.03 | 0.31 | 0.43 | 0.03 | 0.31 | | 0.13 | 0.03 |
| 2012-0008-0024 | Y120065 | B12 | 14.41 | | 0.09 | 10.24 | 0.11 | 3.33 | 27.29 | 47.13 | 9.36 | 0.28 | 0.28 | 0.03 | 0.34 | 0.01 | 0.13 | 0.01 |
| 2012-0008-0025 | Y120065 | C01 | 10.98 | | 0.08 | 9.63 | 0.14 | 3.44 | 29.58 | 44.45 | 10.37 | 0.32 | 0.27 | 0.04 | 0.32 | | 0.14 | |
| 2012-0008-0026 | Y120065 | C02 | 11.70 | | 0.08 | 7.32 | 0.16 | 3.51 | 45.17 | 33.36 | 6.61 | 0.33 | 0.58 | 0.03 | 0.29 | | 0.17 | 0.03 |
| 2012-0008-0027 | Y120065 | C03 | 15.45 | | 0.13 | 11.44 | 0.11 | 3.26 | 26.64 | 44.53 | 10.67 | 0.28 | 0.29 | 0.03 | 0.29 | | 0.06 | |
| 2012-0008-0028 | Y120065 | C04 | 14.09 | | 0.08 | 10.02 | 0.15 | 3.19 | 29.73 | 36.74 | 7.99 | 0.33 | 0.40 | 0.03 | 0.34 | | 0.12 | 0.03 |
| 2012-0008-0029 | Y120065 | C05 | 13.76 | | 0.07 | 9.09 | 0.12 | 3.77 | 33.94 | 42.73 | 8.86 | 0.31 | 0.24 | 0.03 | 0.38 | | 0.10 | 0.02 |
| 2012-0008-0030 | Y120065 | C06 | 14.09 | | 0.08 | 10.08 | 0.14 | 3.11 | 29.76 | 43.36 | 9.80 | 0.34 | 0.41 | 0.03 | 0.32 | | 0.14 | 0.04 |
| 2012-0008-0031 | Y120065 | C07 | 13.04 | | 0.10 | 8.99 | 0.15 | 3.27 | 35.75 | 39.80 | 8.23 | 0.36 | 0.46 | 0.03 | 0.32 | | 0.19 | 0.06 |
| 2012-0008-0032 | Y120065 | C08 | 13.41 | | 0.09 | 9.26 | 0.13 | 3.27 | 31.81 | 44.31 | 8.54 | 0.31 | 0.41 | 0.03 | 0.31 | | 0.09 | 0.02 |
| 2012-0008-0033 | Y120065 | C09 | 14.48 | | 0.08 | 9.72 | 0.11 | 3.75 | 33.15 | 41.94 | 8.73 | 0.33 | 0.30 | 0.04 | 0.36 | | 0.24 | 0.02 |

| Project Ref: | | Mag Trim from FAME | | Soybean Half Seed Analysis. Analysis is performed by Ted Freeman. Reviewed by Brita McNew | | | | | | | | | | | | | |
|---|---|---|---|---|---|---|---|---|---|---|---|---|---|---|---|---|---|
| Date Reported: | 02/17/12 | Project Description: | | | | | | | | | | | | | | | |
| Study ID: | 2012-0008 | Received: | 2/13/2012 | | | | | | | | | | | | | | |
| | | | | FAME ANALYSIS - % of Total Oil | | | | | | | | | | | | | |
| Lab ID | Plate ID | Well | % Sats | C12:0 | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0067 | Y120065 | F07 | 14.97 | | 0.10 | 10.46 | 0.13 | 3.60 | 26.34 | 47.38 | 9.83 | 0.31 | 0.28 | 0.03 | 0.38 | | 0.12 | |
| 2012-0008-0068 | Y120065 | F08 | 15.11 | | 0.09 | 10.86 | 0.13 | 3.37 | 29.91 | 44.86 | 8.70 | 0.30 | 0.30 | 0.03 | 0.36 | | 0.12 | |
| 2012-0008-0069 | Y120065 | F09 | 14.79 | | 0.08 | 10.81 | 0.13 | 3.18 | 31.63 | 42.76 | 9.22 | 0.30 | 0.34 | 0.03 | 0.31 | | 0.12 | 0.02 |
| 2012-0008-0070 | Y120065 | F10 | 13.17 | | 0.11 | 9.36 | 0.17 | 2.92 | 38.59 | 36.60 | 9.09 | 0.29 | 0.52 | 0.04 | 0.32 | | 0.18 | 0.02 |
| 2012-0008-0071 | Y120065 | F11 | 11.84 | | 0.09 | 8.38 | 0.15 | 2.73 | 40.59 | 36.57 | 8.36 | 0.27 | 0.55 | 0.04 | 0.28 | | 0.09 | 0.05 |
| 2012-0008-0072 | Y120065 | F12 | 11.97 | | 0.08 | 7.70 | 0.17 | 3.46 | 46.30 | 31.75 | 7.51 | 0.32 | 0.54 | 0.03 | 0.30 | | 0.11 | 0.03 |
| 2012-0008-0073 | Y120065 | G01 | 14.18 | | 0.08 | 9.83 | 0.12 | 3.51 | 25.38 | 47.69 | 10.55 | 0.32 | 0.24 | 0.03 | 0.36 | | 0.09 | |
| 2012-0008-0074 | Y120065 | G02 | 15.64 | | 0.10 | 11.18 | 0.13 | 4.07 | 28.76 | 44.34 | 9.98 | 0.36 | 0.29 | 0.03 | 0.37 | | 0.13 | |
| 2012-0008-0075 | Y120065 | G03 | 14.90 | | 0.09 | 10.02 | 0.13 | 3.96 | 30.95 | 43.91 | 8.24 | 0.35 | 0.35 | 0.02 | 0.36 | | 0.12 | 0.01 |
| 2012-0008-0076 | Y120065 | G04 | 11.14 | | 0.09 | 7.21 | 0.19 | 3.13 | 49.40 | 31.38 | 5.42 | 0.30 | 0.69 | 0.04 | 0.28 | | 0.13 | 0.04 |
| 2012-0008-0077 | Y120065 | G05 | 15.63 | | 0.10 | 10.54 | 0.13 | 4.02 | 27.72 | 46.05 | 9.08 | 0.36 | 0.31 | 0.03 | 0.44 | | 0.16 | 0.01 |
| 2012-0008-0078 | Y120065 | G06 | 12.49 | | 0.08 | 8.42 | 0.13 | 3.21 | 40.67 | 36.93 | 7.50 | 0.30 | 0.47 | 0.04 | 0.30 | | 0.18 | |
| 2012-0008-0079 | Y120065 | G07 | 15.34 | | 0.08 | 10.94 | 0.12 | 3.54 | 30.88 | 43.84 | 8.23 | 0.32 | 0.34 | 0.03 | 0.35 | | 0.11 | 0.01 |
| 2012-0008-0080 | Y120065 | G08 | 13.05 | | 0.09 | 8.77 | 0.19 | 3.42 | 44.84 | 33.10 | 5.60 | 0.29 | 0.46 | 0.02 | 0.28 | | 0.18 | |
| 2012-0008-0081 | Y120065 | G09 | 16.19 | | 0.09 | 11.86 | 0.12 | 3.37 | 28.68 | 44.01 | 6.94 | 0.32 | 0.31 | 0.03 | 0.36 | | 0.20 | 0.02 |
| 2012-0008-0082 | Y120065 | G10 | 13.45 | | 0.08 | 9.42 | 0.14 | 3.16 | 32.20 | 43.76 | 8.38 | 0.29 | 0.39 | 0.04 | 0.34 | 0.01 | 0.17 | 0.02 |
| 2012-0008-0083 | Y120065 | G11 | 12.45 | | 0.10 | 8.86 | 0.15 | 2.80 | 33.90 | 36.24 | 8.52 | 0.28 | 0.53 | 0.04 | 0.29 | | 0.13 | 0.05 |
| 2012-0008-0084 | Y120065 | G12 | 14.12 | | 0.10 | 10.08 | 0.13 | 3.22 | 30.66 | 43.77 | 9.47 | 0.28 | 0.32 | 0.03 | 0.32 | | 0.11 | |
| 2012-0008-0085 | Y120065 | H01 | 14.12 | | 0.10 | 10.20 | 0.12 | 3.06 | 33.03 | 42.14 | 8.43 | 0.30 | 0.40 | 0.02 | 0.32 | | 0.12 | 0.02 |
| 2012-0008-0086 | Y120065 | H02 | 15.53 | | 0.08 | 11.34 | 0.14 | 3.36 | 28.77 | 44.50 | 9.40 | 0.29 | 0.31 | 0.03 | 0.31 | | 0.15 | |
| 2012-0008-0087 | Y120065 | H03 | 13.81 | | 0.09 | 9.83 | 0.15 | 3.13 | 39.01 | 37.39 | 7.43 | 0.31 | 0.51 | 0.03 | 0.20 | | 0.14 | |
| 2012-0008-0088 | Y120065 | H04 | 15.09 | | 0.08 | 10.56 | 0.15 | 3.67 | 33.71 | 41.78 | 7.57 | 0.32 | 0.36 | 0.04 | 0.33 | | 0.13 | 0.02 |
| 2012-0008-0089 | Y120065 | H05 | 14.78 | | 0.09 | 10.81 | 0.13 | 3.19 | 29.65 | 43.83 | 9.42 | 0.28 | 0.32 | 0.03 | 0.30 | | 0.12 | |
| 2012-0008-0090 | Y120065 | H06 | 12.30 | | 0.10 | 8.08 | 0.15 | 2.99 | 35.54 | 39.84 | 9.98 | 0.29 | 0.32 | 0.03 | 0.34 | | 0.30 | |
| 2012-0008-0091 | Y120065 | H07 | 13.01 | | 0.09 | 9.01 | 0.15 | 3.24 | 39.37 | 37.89 | 7.28 | 0.29 | 0.42 | 0.03 | 0.27 | | 0.15 | 0.03 |
| 2012-0008-0092 | Y120065 | H08 | 10.77 | | 0.07 | 7.37 | 0.16 | 2.75 | 45.50 | 35.18 | 6.16 | 0.24 | 0.57 | 0.03 | 0.24 | 0.01 | 0.10 | 0.04 |
| 2012-0008-0093 | Y120065 | H09 | 13.52 | | 0.08 | 9.55 | 0.13 | 3.23 | 31.72 | 44.08 | 6.80 | 0.29 | 0.34 | 0.03 | 0.35 | | 0.11 | 0.02 |
| 2012-0008-0094 | Y120065 | H10 | 11.54 | | 0.08 | 7.09 | 0.16 | 3.59 | 49.97 | 30.01 | 5.89 | 0.32 | 0.59 | 0.03 | 0.30 | | 0.15 | 0.03 |
| 2012-0008-0095 | Y120065 | H11 | 13.29 | | 0.08 | 9.82 | 0.14 | 2.80 | 37.50 | 39.50 | 7.59 | 0.26 | 0.44 | 0.03 | 0.23 | 0.01 | 0.09 | |
| 2012-0008-0096 | Y120065 | H12 | 12.58 | | 0.07 | 8.54 | 0.13 | 3.25 | 38.65 | 38.52 | 7.95 | 0.29 | 0.46 | 0.03 | 0.28 | | 0.15 | |

*FIG. 9c*

| Study ID | Lab ID | 2012-0008 Plate ID | Well | % Sats | C14:0 | C16:0 | C16:1 | C18:0 | C18:1 | C18:2 | C18:3 | C20:0 | C20:1 | C20:2 | C22:0 | C22:1 | C24:0 | C24:1 |
|---|---|---|---|---|---|---|---|---|---|---|---|---|---|---|---|---|---|---|---|
| FAME ANALYSIS - % of Total Oil | | | | | | | | | | | | | | | | | | | |
| 2012-0008-0097 | | Y120066 | A01 | 15.10 | 0.11 | 11.39 | 0.11 | 3.78 | 28.50 | 47.75 | 9.92 | 0.32 | 0.26 | 0.03 | 0.38 | | 0.12 | |
| 2012-0008-0098 | | Y120066 | A02 | 15.41 | 0.09 | 11.49 | 0.14 | 3.08 | 26.01 | 47.67 | 9.24 | 0.28 | 0.28 | 0.04 | 0.33 | 0.01 | 0.14 | 0.02 |
| 2012-0008-0099 | | Y120066 | A03 | 14.62 | 0.09 | 9.64 | 0.11 | 4.10 | 28.83 | 45.59 | 9.39 | 0.34 | 0.31 | 0.03 | 0.36 | | 0.10 | |
| 2012-0008-0100 | | Y120066 | A04 | 14.96 | 0.10 | 10.33 | 0.09 | 3.83 | 17.84 | 51.26 | 14.40 | 0.31 | 0.18 | 0.04 | 0.29 | | 0.12 | |
| 2012-0008-0101 | | Y120066 | A05 | 15.25 | 0.12 | 10.97 | 0.11 | 3.51 | 16.69 | 50.73 | 15.61 | 0.30 | 0.19 | | 0.28 | | 0.08 | |
| 2012-0008-0102 | | Y120066 | A06 | 15.62 | 0.09 | 11.37 | 0.12 | 3.77 | 28.94 | 46.28 | 9.44 | 0.31 | 0.27 | 0.03 | 0.35 | | 0.12 | |
| 2012-0008-0103 | | Y120066 | A07 | 15.60 | 0.10 | 11.80 | 0.11 | 3.26 | 24.61 | 47.43 | 10.57 | 0.27 | 0.25 | 0.03 | 0.29 | | 0.08 | |
| 2012-0008-0104 | | Y120066 | A08 | 14.61 | 0.10 | 10.66 | 0.11 | 3.14 | 22.30 | 46.54 | 14.22 | 0.30 | 0.30 | 0.05 | 0.27 | | 0.13 | |
| 2012-0008-0105 | | Y120066 | A09 | 14.50 | 0.11 | 10.26 | 0.12 | 3.30 | 27.65 | 45.86 | 10.36 | 0.31 | 0.30 | 0.04 | 0.39 | | 0.13 | |
| 2012-0008-0106 | | Y120066 | A10 | 13.20 | 0.09 | 9.32 | 0.15 | 3.08 | 35.09 | 42.09 | 7.73 | 0.29 | 0.42 | 0.04 | 0.31 | | 0.12 | |
| 2012-0008-0107 | | Y120066 | A11 | 15.35 | 0.08 | 11.12 | 0.11 | 3.45 | 22.74 | 49.55 | 10.10 | 0.32 | 0.21 | 0.03 | 0.33 | | 0.07 | |
| 2012-0008-0108 | | Y120066 | A12 | 15.01 | 0.07 | 10.66 | 0.11 | 3.53 | 24.13 | 50.49 | 8.95 | 0.37 | 0.24 | 0.03 | 0.36 | | 0.11 | |
| 2012-0008-0109 | | Y120066 | B01 | 15.42 | 0.08 | 10.22 | 0.10 | 4.29 | 26.40 | 48.01 | 9.69 | 0.35 | 0.27 | 0.03 | 0.30 | | 0.08 | |
| 2012-0008-0110 | | Y120066 | B02 | 15.67 | 0.09 | 11.77 | 0.11 | 3.30 | 24.11 | 49.58 | 9.00 | 0.29 | 0.27 | 0.03 | 0.32 | | 0.11 | 0.04 |
| 2012-0008-0111 | | Y120066 | B03 | 14.35 | 0.08 | 10.04 | 0.14 | 3.43 | 34.51 | 40.23 | 9.25 | 0.32 | 0.40 | 0.03 | 0.36 | | 0.14 | |
| 2012-0008-0112 | | Y120066 | B04 | 14.73 | 0.08 | 10.28 | 0.12 | 4.15 | 32.55 | 41.47 | 8.94 | 0.37 | 0.30 | 0.04 | 0.40 | | 0.15 | |
| 2012-0008-0113 | | Y120066 | B05 | 14.62 | 0.08 | 9.28 | 0.10 | 4.45 | 26.06 | 49.19 | 10.01 | 0.31 | 0.24 | 0.03 | 0.39 | | 0.08 | |
| 2012-0008-0114 | | Y120066 | B06 | 15.22 | 0.09 | 10.98 | 0.11 | 3.70 | 27.89 | 47.22 | 7.95 | 0.29 | 0.32 | 0.03 | 0.31 | | 0.10 | |
| 2012-0008-0115 | | Y120066 | B07 | 15.97 | 0.09 | 11.40 | 0.11 | 3.80 | 27.82 | 46.65 | 8.43 | 0.31 | 0.27 | 0.03 | 0.30 | | 0.07 | 0.01 |
| 2012-0008-0116 | | Y120066 | B08 | 14.88 | 0.09 | 9.67 | 0.14 | 3.49 | 27.47 | 46.98 | 10.12 | 0.30 | 0.29 | 0.04 | 0.35 | | 0.12 | |
| 2012-0008-0117 | | Y120066 | B09 | 15.55 | 0.08 | 11.66 | 0.12 | 3.53 | 24.40 | 48.01 | 10.56 | 0.32 | 0.24 | 0.03 | 0.40 | | 0.11 | 0.01 |
| 2012-0008-0118 | | Y120066 | B10 | 13.58 | 0.08 | 9.54 | 0.12 | 3.19 | 29.61 | 44.98 | 10.06 | 0.29 | 0.33 | 0.04 | 0.31 | | 0.12 | |
| 2012-0008-0119 | | Y120066 | B11 | 14.19 | 0.09 | 10.19 | 0.13 | 3.22 | 21.39 | 43.47 | 8.99 | 0.29 | 0.26 | 0.03 | 0.34 | | 0.11 | 0.01 |
| 2012-0008-0120 | | Y120066 | B12 | 15.82 | 0.09 | 11.75 | 0.12 | 3.25 | 24.18 | 49.14 | 10.26 | 0.29 | 0.33 | 0.03 | 0.33 | | 0.17 | 0.02 |
| 2012-0008-0121 | | Y120066 | C01 | 15.22 | 0.07 | 11.25 | 0.12 | 3.11 | 23.38 | 45.71 | 9.79 | 0.29 | 0.29 | 0.03 | 0.35 | | 0.13 | 0.01 |
| 2012-0008-0122 | | Y120066 | C02 | 15.11 | 0.09 | 10.66 | 0.12 | 3.41 | 27.79 | 46.07 | 7.86 | 0.30 | 0.25 | 0.03 | 0.36 | | 0.10 | |
| 2012-0008-0123 | | Y120066 | C03 | 15.17 | 0.07 | 10.98 | 0.12 | 3.34 | 26.07 | 47.93 | 9.31 | 0.31 | 0.26 | 0.04 | 0.32 | | 0.10 | |
| 2012-0008-0124 | | Y120066 | C04 | 15.66 | 0.10 | 11.56 | 0.12 | 3.43 | 26.30 | 47.12 | 9.26 | 0.30 | 0.28 | 0.04 | 0.35 | | 0.15 | 0.03 |
| 2012-0008-0125 | | Y120066 | C05 | 15.48 | 0.09 | 10.99 | 0.13 | 3.57 | 30.93 | 43.17 | 9.08 | 0.32 | 0.32 | 0.02 | 0.32 | | 0.09 | |
| 2012-0008-0126 | | Y120066 | C06 | 12.40 | 0.08 | 8.88 | 0.11 | 3.53 | 22.83 | 42.67 | 8.60 | 0.33 | 0.37 | 0.03 | 0.36 | 0.01 | 0.14 | 0.01 |
| 2012-0008-0127 | | Y120066 | C07 | 15.26 | 0.09 | 10.55 | 0.11 | 3.81 | 23.31 | 50.28 | 9.74 | 0.30 | 0.21 | 0.03 | 0.39 | | 0.08 | |
| 2012-0008-0128 | | Y120066 | C08 | 14.57 | 0.08 | 9.99 | 0.11 | 3.87 | 22.43 | 51.41 | 9.34 | 0.30 | 0.21 | 0.03 | 0.33 | | 0.08 | |
| 2012-0008-0129 | | Y120066 | C09 | 14.20 | 0.10 | 10.15 | 0.14 | 3.12 | 29.36 | 44.17 | 10.47 | 0.31 | 0.36 | 0.04 | 0.36 | | 0.14 | 0.02 |

| Study ID: | 2012-0008 | | | | | | | | FAME ANALYSIS - % of Total Oil | | | | | | | | |
|---|---|---|---|---|---|---|---|---|---|---|---|---|---|---|---|---|---|
| Lab ID | Plate ID | Well | % Sats | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0163 | Y120066 | F07 | 13.95 | 0.08 | 10.08 | 0.12 | 3.09 | 31.09 | 43.91 | 9.36 | 0.28 | 0.35 | 0.04 | 0.30 | | 0.11 | 0.02 |
| 2012-0008-0164 | Y120066 | F08 | 13.99 | 0.08 | 9.85 | 0.16 | 3.51 | 33.76 | 43.11 | 7.64 | 0.31 | 0.37 | 0.03 | 0.33 | 0.01 | 0.12 | 0.01 |
| 2012-0008-0165 | Y120066 | F09 | 14.78 | 0.08 | 10.80 | 0.14 | 3.19 | 32.81 | 43.17 | 7.85 | 0.29 | 0.33 | 0.03 | 0.31 | | 0.11 | 0.01 |
| 2012-0008-0166 | Y120066 | F10 | 14.41 | 0.06 | 9.18 | 0.13 | 4.24 | 31.80 | 43.86 | 8.37 | 0.36 | 0.31 | 0.03 | 0.41 | 0.01 | 0.13 | 0.01 |
| 2012-0008-0167 | Y120066 | F11 | 13.60 | 0.08 | 9.49 | 0.12 | 3.32 | 30.99 | 44.78 | 9.25 | 0.28 | 0.33 | 0.03 | 0.33 | 0.01 | 0.09 | 0.02 |
| 2012-0008-0168 | Y120066 | F12 | 14.20 | 0.09 | 10.37 | 0.14 | 3.20 | 32.05 | 44.66 | 7.16 | 0.28 | 0.39 | 0.04 | 0.27 | 0.01 | 0.09 | 0.02 |
| 2012-0008-0169 | Y120066 | G01 | 14.15 | 0.07 | 10.06 | 0.11 | 3.27 | 22.56 | 50.23 | 10.52 | 0.27 | 0.24 | 0.03 | 0.34 | | 0.13 | 0.02 |
| 2012-0008-0170 | Y120066 | G02 | 14.74 | 0.10 | 10.52 | 0.14 | 3.42 | 22.01 | 49.48 | 12.22 | 0.28 | 0.21 | 0.03 | 0.34 | | 0.06 | |
| 2012-0008-0171 | Y120066 | G03 | 14.97 | 0.08 | 10.77 | 0.12 | 3.40 | 30.39 | 44.58 | 8.46 | 0.30 | 0.32 | 0.03 | 0.31 | | 0.12 | 0.01 |
| 2012-0008-0172 | Y120066 | G04 | 13.36 | 0.07 | 9.29 | 0.13 | 3.24 | 31.80 | 43.97 | 8.29 | 0.29 | 0.32 | 0.03 | 0.35 | | 0.13 | 0.01 |
| 2012-0008-0173 | Y120066 | G05 | 15.47 | 0.08 | 11.15 | 0.12 | 3.46 | 27.36 | 46.86 | 8.81 | 0.31 | 0.31 | 0.04 | 0.35 | | 0.13 | 0.02 |
| 2012-0008-0174 | Y120066 | G06 | 13.70 | 0.08 | 9.47 | 0.12 | 3.44 | 32.17 | 44.90 | 7.69 | 0.29 | 0.34 | 0.02 | 0.33 | 0.01 | 0.11 | 0.01 |
| 2012-0008-0175 | Y120066 | G07 | 15.24 | 0.08 | 10.86 | 0.14 | 3.80 | 32.70 | 43.40 | 7.43 | 0.32 | 0.30 | 0.03 | 0.32 | | 0.11 | |
| 2012-0008-0176 | Y120066 | G08 | 12.03 | 0.07 | 8.66 | 0.15 | 3.21 | 41.61 | 37.86 | 6.53 | 0.29 | 0.44 | 0.03 | 0.29 | 0.01 | 0.07 | |
| 2012-0008-0177 | Y120066 | G09 | 13.57 | 0.08 | 9.41 | 0.13 | 3.34 | 31.94 | 44.74 | 8.15 | 0.30 | 0.34 | 0.03 | 0.34 | 0.01 | 0.10 | 0.02 |
| 2012-0008-0178 | Y120066 | G10 | 13.80 | 0.09 | 10.03 | 0.16 | 3.02 | 39.17 | 38.37 | 6.62 | 0.29 | 0.49 | 0.03 | 0.28 | 0.02 | 0.10 | 0.02 |
| 2012-0008-0179 | Y120066 | G11 | 13.14 | 0.08 | 8.19 | 0.14 | 4.09 | 39.22 | 39.03 | 6.94 | 0.36 | 0.44 | 0.03 | 0.34 | 0.02 | 0.09 | 0.03 |
| 2012-0008-0180 | Y120066 | G12 | 15.84 | 0.08 | 11.70 | 0.14 | 3.14 | 27.04 | 46.52 | 9.30 | 0.28 | 0.29 | 0.04 | 0.33 | 0.01 | 0.08 | 0.01 |
| 2012-0008-0181 | Y120066 | H01 | 15.31 | 0.08 | 10.67 | 0.13 | 3.58 | 26.18 | 47.46 | 9.88 | 0.31 | 0.28 | 0.04 | 0.35 | | 0.11 | 0.01 |
| 2012-0008-0182 | Y120066 | H02 | 15.04 | 0.07 | 10.54 | 0.14 | 3.67 | 20.32 | 46.63 | 7.00 | 0.29 | 0.36 | 0.03 | 0.32 | | 0.13 | 0.02 |
| 2012-0008-0183 | Y120066 | H03 | 14.31 | 0.08 | 10.49 | 0.11 | 3.06 | 31.15 | 42.33 | 9.33 | 0.28 | 0.38 | 0.04 | 0.28 | | 0.12 | 0.02 |
| 2012-0008-0184 | Y120066 | H04 | 13.13 | 0.06 | 7.91 | 0.15 | 4.24 | 42.05 | 35.26 | 7.74 | 0.30 | 0.43 | 0.03 | 0.35 | | 0.17 | |
| 2012-0008-0185 | Y120066 | H05 | 15.97 | 0.09 | 11.73 | 0.12 | 3.34 | 26.75 | 46.57 | 9.10 | 0.30 | 0.30 | 0.03 | 0.33 | | 0.12 | 0.02 |
| 2012-0008-0186 | Y120066 | H06 | 13.80 | 0.08 | 9.40 | 0.11 | 3.57 | 27.54 | 47.51 | 9.78 | 0.30 | 0.25 | 0.03 | 0.34 | | 0.12 | |
| 2012-0008-0187 | Y120066 | H07 | 13.19 | 0.08 | 9.25 | 0.12 | 3.09 | 33.51 | 42.19 | 9.30 | 0.30 | 0.40 | 0.03 | 0.35 | 0.01 | 0.11 | 0.03 |
| 2012-0008-0188 | Y120066 | H08 | 13.02 | 0.08 | 9.29 | 0.14 | 2.86 | 33.21 | 43.14 | 6.99 | 0.27 | 0.39 | 0.04 | 0.32 | | 0.11 | |
| 2012-0008-0189 | Y120066 | H09 | 13.66 | 0.08 | 9.28 | 0.14 | 3.73 | 35.86 | 37.66 | 7.79 | 0.36 | 0.44 | 0.04 | 0.31 | 0.01 | 0.11 | 0.04 |
| 2012-0008-0190 | Y120066 | H10 | 13.02 | 0.09 | 9.25 | 0.14 | 3.00 | 36.31 | 41.10 | 7.71 | 0.27 | 0.44 | 0.04 | 0.28 | 0.02 | 0.13 | |
| 2012-0008-0191 | Y120066 | H11 | 15.36 | 0.09 | 11.08 | 0.13 | 3.50 | 27.12 | 46.91 | 9.41 | 0.30 | 0.24 | 0.03 | 0.34 | | 0.13 | 0.02 |
| 2012-0008-0192 | Y120066 | H12 | 13.67 | 0.07 | 8.63 | 0.15 | 4.19 | 36.52 | 41.57 | 6.69 | 0.34 | 0.35 | 0.03 | 0.35 | 0.01 | 0.11 | 0.02 |

*FIG. 9f*

| Project Ref: | Mag Trim from FAME | | Soybean Half Seed Analysis. Analysis performed by Ted Freeman. Reviewed by Brita McNew | | | | | | | | | | | | | |
|---|---|---|---|---|---|---|---|---|---|---|---|---|---|---|---|---|
| Date Reported: | 03/07/12 | Project | | | | | | | | | | | | | | |
| Study ID | 2012-0008 | | FAME ANALYSIS - % of Total Oil | | | | | | | | | | | | | |
| Lab ID | Plate ID | Well | % Sats | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0193 | Y120367 | A01 | 16.75 | 0.10 | 11.77 | 0.14 | 4.33 | 21.61 | 51.92 | 8.91 | 0.31 | 0.21 | 0.04 | 0.29 | | 0.09 | |
| 2012-0008-0194 | Y120367 | A02 | 15.51 | 0.10 | 10.41 | 0.14 | 4.34 | 19.66 | 52.69 | 10.61 | 0.31 | 0.23 | 0.03 | 0.31 | | 0.13 | |
| 2012-0008-0195 | Y120367 | A03 | 17.06 | 0.09 | 11.36 | 0.12 | 4.61 | 20.78 | 52.46 | 6.68 | 0.36 | 0.22 | 0.03 | 0.34 | | 0.12 | |
| 2012-0008-0196 | Y120367 | A04 | 15.77 | 0.09 | 10.74 | 0.15 | 4.14 | 21.46 | 51.85 | 9.94 | 0.32 | 0.25 | 0.04 | 0.32 | | 0.15 | |
| 2012-0008-0197 | Y120367 | A05 | 18.54 | 0.15 | 12.87 | 0.16 | 4.73 | 19.80 | 46.82 | 12.36 | 0.35 | 0.20 | | 0.34 | | 0.10 | |
| 2012-0008-0198 | Y120367 | A06 | 17.57 | 0.12 | 12.58 | 0.19 | 4.11 | 19.95 | 50.94 | 10.55 | 0.31 | 0.19 | 0.03 | 0.31 | | 0.15 | |
| 2012-0008-0199 | Y120367 | A07 | 17.88 | 0.10 | 11.80 | 0.11 | 5.17 | 17.44 | 52.36 | 11.79 | 0.36 | 0.19 | | 0.33 | | 0.12 | |
| 2012-0008-0200 | Y120367 | A08 | 16.61 | 0.11 | 11.04 | 0.17 | 4.70 | 21.22 | 50.72 | 10.50 | 0.34 | 0.22 | | 0.30 | | 0.13 | |
| 2012-0008-0201 | Y120367 | A09 | 17.67 | 0.12 | 12.43 | 0.22 | 4.34 | 19.13 | 51.19 | 10.96 | 0.33 | 0.22 | | 0.32 | | 0.12 | |
| 2012-0008-0202 | Y120367 | A10 | 17.91 | 0.11 | 12.41 | 0.14 | 4.55 | 19.51 | 51.59 | 10.23 | 0.35 | 0.21 | 0.04 | 0.34 | | 0.16 | |
| 2012-0008-0203 | Y120367 | A11 | 17.08 | 0.11 | 11.47 | 0.12 | 4.78 | 20.49 | 50.84 | 10.74 | 0.36 | 0.21 | | 0.33 | | 0.12 | |
| 2012-0008-0204 | Y120367 | A12 | 16.66 | 0.11 | 11.62 | 0.15 | 4.06 | 20.95 | 51.92 | 9.57 | 0.28 | 0.22 | | 0.29 | | 0.13 | |
| 2012-0008-0205 | Y120367 | B01 | 17.71 | 0.10 | 12.07 | 0.16 | 4.66 | 22.86 | 49.10 | 9.42 | 0.37 | 0.22 | 0.04 | 0.37 | | 0.14 | |
| 2012-0008-0206 | Y120367 | B02 | 17.49 | 0.11 | 11.90 | 0.13 | 4.67 | 20.48 | 51.95 | 9.26 | 0.34 | 0.22 | 0.03 | 0.32 | | 0.16 | |
| 2012-0008-0207 | Y120367 | B03 | 16.98 | 0.10 | 11.70 | 0.14 | 4.45 | 20.79 | 51.32 | 9.94 | 0.31 | 0.21 | 0.03 | 0.30 | | 0.12 | |
| 2012-0008-0208 | Y120367 | B04 | 17.04 | 0.12 | 11.50 | 0.16 | 4.60 | 17.99 | 51.46 | 11.71 | 0.34 | 0.20 | 0.04 | 0.34 | | 0.14 | |
| 2012-0008-0209 | Y120367 | B05 | 19.18 | 0.14 | 13.77 | 0.15 | 4.34 | 16.21 | 50.41 | 11.45 | 0.32 | 0.18 | | 0.31 | | 0.10 | |
| 2012-0008-0210 | Y120367 | B06 | 16.68 | 0.12 | 11.34 | 0.16 | 4.31 | 21.01 | 50.72 | 10.33 | 0.30 | 0.19 | 0.04 | 0.26 | | 0.15 | |
| 2012-0008-0211 | Y120367 | B07 | 18.23 | 0.14 | 12.65 | 0.16 | 4.53 | 19.03 | 50.28 | 10.68 | 0.32 | 0.19 | | 0.30 | | 0.10 | |
| 2012-0008-0212 | Y120367 | B08 | 17.76 | 0.11 | 12.50 | 0.16 | 4.34 | 21.63 | 50.77 | 8.52 | 0.31 | 0.20 | | 0.29 | | 0.13 | |
| 2012-0008-0213 | Y120367 | B09 | 17.59 | 0.12 | 12.29 | 0.15 | 4.40 | 21.63 | 50.34 | 9.52 | 0.36 | 0.20 | 0.03 | 0.29 | | 0.15 | |
| 2012-0008-0214 | Y120367 | B10 | 17.34 | 0.12 | 12.14 | 0.14 | 4.28 | 18.65 | 51.63 | 11.19 | 0.33 | 0.22 | 0.04 | 0.30 | | 0.16 | |
| 2012-0008-0215 | Y120367 | B11 | 16.18 | 0.12 | 12.74 | 0.14 | 4.57 | 21.78 | 50.44 | 6.63 | 0.35 | 0.19 | 0.04 | 0.32 | | 0.11 | |
| 2012-0008-0216 | Y120367 | B12 | 17.69 | 0.11 | 12.04 | 0.16 | 4.91 | 20.42 | 50.17 | 10.81 | 0.35 | 0.21 | | 0.30 | | 0.11 | |
| 2012-0008-0217 | Y120367 | C01 | 17.40 | 0.10 | 11.91 | 0.12 | 5.14 | 17.86 | 50.96 | 10.24 | 0.36 | 0.20 | | 0.37 | | 0.12 | |
| 2012-0008-0218 | Y120367 | C02 | 17.54 | 0.11 | 11.52 | 0.13 | 5.01 | 18.14 | 52.90 | 10.41 | 0.39 | 0.26 | 0.04 | 0.36 | | 0.15 | |
| 2012-0008-0219 | Y120367 | C03 | 17.43 | 0.10 | 12.08 | 0.14 | 4.48 | 21.10 | 50.27 | 10.30 | 0.34 | 0.21 | 0.04 | 0.31 | | 0.11 | |
| 2012-0008-0220 | Y120367 | C04 | 16.67 | 0.09 | 11.09 | 0.10 | 4.79 | 20.22 | 51.40 | 10.92 | 0.37 | 0.25 | 0.04 | 0.34 | | 0.19 | |
| 2012-0008-0221 | Y120367 | C05 | 17.46 | 0.11 | 11.80 | 0.12 | 5.31 | 19.21 | 53.47 | 9.39 | 0.32 | 0.23 | | 0.31 | | 0.16 | |
| 2012-0008-0222 | Y120367 | C06 | 16.21 | 0.16 | 10.88 | 0.16 | 4.45 | 20.96 | 51.82 | 9.86 | 0.33 | 0.21 | 0.03 | 0.30 | | 0.15 | |
| 2012-0008-0223 | Y120367 | C07 | 17.51 | 0.12 | 12.27 | 0.12 | 4.56 | 19.26 | 52.39 | 9.77 | 0.32 | 0.20 | 0.03 | 0.37 | | 0.11 | |
| 2012-0008-0224 | Y120367 | C08 | 17.41 | 0.11 | 11.81 | 0.14 | 4.66 | 19.26 | 52.08 | 10.49 | 0.33 | 0.22 | 0.03 | 0.34 | | 0.11 | |
| 2012-0008-0225 | Y120367 | C09 | 17.18 | 0.14 | 11.29 | 0.15 | 4.97 | 19.89 | 50.08 | 12.06 | 0.33 | 0.22 | | 0.32 | | 0.13 | |

FIG. 9g

| Project Ref: | Mag Trim from FAME | | Soybean Half Seed Analysis. Analysis performed by Ted Freeman. Reviewed by Brita McNew | | | | | | | | | | | | | | |
|---|---|---|---|---|---|---|---|---|---|---|---|---|---|---|---|---|---|
| Date Reported: | 03/07/12 | Project | | | | | | | | | | | | | | | |
| Study ID: | 2012-0008 | | | | | | FAME ANALYSIS - % of Total Oil | | | | | | | | | | |
| Lab ID | Plate ID | Well | % Sats | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0226 | Y120067 | C10 | 16.50 | 0.12 | 11.17 | 0.16 | 4.46 | 22.82 | 51.81 | 8.40 | 0.33 | 0.22 | 0.04 | 0.32 | | 0.13 | |
| 2012-0008-0227 | Y120067 | C11 | 17.12 | 0.12 | 11.79 | 0.16 | 4.06 | 20.92 | 51.51 | 9.72 | 0.32 | 0.20 | | 0.28 | | 0.11 | |
| 2012-0008-0228 | Y120067 | C12 | 17.23 | 0.11 | 12.07 | 0.13 | 4.89 | 17.86 | 52.56 | 11.23 | 0.31 | 0.20 | 0.04 | 0.28 | | 0.10 | |
| 2012-0008-0229 | Y120067 | D01 | 16.76 | 0.11 | 11.91 | 0.12 | 4.11 | 21.16 | 51.07 | 10.05 | 0.29 | 0.20 | | 0.26 | | 0.09 | |
| 2012-0008-0230 | Y120067 | D02 | 17.29 | 0.11 | 11.98 | 0.15 | 4.11 | 23.96 | 49.16 | 9.52 | 0.34 | 0.23 | 0.03 | 0.34 | | 0.23 | |
| 2012-0008-0231 | Y120067 | D03 | 17.46 | 0.11 | 11.90 | 0.12 | 4.73 | 19.46 | 53.56 | 9.59 | 0.35 | 0.23 | 0.05 | 0.34 | | 0.13 | |
| 2012-0008-0232 | Y120067 | D04 | 18.98 | 0.11 | 12.58 | 0.14 | 4.83 | 19.14 | 53.55 | 11.03 | 0.37 | 0.21 | | 0.34 | | 0.16 | |
| 2012-0008-0233 | Y120067 | D05 | 17.89 | 0.14 | 12.20 | 0.13 | 4.70 | 20.68 | 49.62 | 10.87 | 0.35 | 0.21 | | 0.34 | | 0.12 | |
| 2012-0008-0234 | Y120067 | D06 | 18.94 | 0.13 | 12.72 | 0.15 | 5.20 | 16.54 | 51.38 | 12.36 | 0.39 | 0.19 | 0.04 | 0.37 | | 0.12 | |
| 2012-0008-0235 | Y120067 | D07 | 17.86 | 0.10 | 12.61 | 0.14 | 4.47 | 20.79 | 50.50 | 10.16 | 0.31 | 0.21 | | 0.30 | | 0.10 | |
| 2012-0008-0236 | Y120067 | D08 | 18.82 | 0.15 | 12.77 | 0.14 | 5.04 | 15.85 | 50.92 | 13.82 | 0.37 | 0.20 | 0.03 | 0.35 | | 0.13 | |
| 2012-0008-0237 | Y120067 | D09 | 17.11 | 0.11 | 11.30 | 0.11 | 4.65 | 23.29 | 48.54 | 10.07 | 0.34 | 0.23 | | 0.35 | | 0.12 | |
| 2012-0008-0238 | Y120067 | D10 | 18.85 | 0.09 | 12.57 | 0.11 | 4.86 | 20.33 | 51.98 | 10.09 | 0.35 | 0.21 | 0.04 | 0.33 | | 0.14 | |
| 2012-0008-0239 | Y120067 | D11 | 18.42 | 0.13 | 12.81 | 0.12 | 4.72 | 18.11 | 52.42 | 12.33 | 0.39 | 0.19 | | 0.31 | | 0.09 | |
| 2012-0008-0240 | Y120067 | D12 | 17.73 | 0.12 | 12.27 | 0.14 | 4.55 | 21.33 | 49.83 | 10.20 | 0.35 | 0.22 | 0.04 | 0.33 | | 0.11 | |
| 2012-0008-0241 | Y120067 | E01 | 18.26 | 0.12 | 12.55 | 0.11 | 4.88 | 18.09 | 51.54 | 11.19 | 0.35 | 0.20 | | 0.35 | | 0.10 | |
| 2012-0008-0242 | Y120067 | E02 | 17.70 | 0.14 | 12.57 | 0.18 | 4.36 | 19.07 | 51.96 | 11.12 | 0.34 | 0.18 | 0.02 | 0.33 | | 0.09 | |
| 2012-0008-0243 | Y120067 | E03 | 19.19 | 0.14 | 13.26 | 0.14 | 5.09 | 19.31 | 49.65 | 11.02 | 0.36 | 0.19 | | 0.25 | | 0.10 | |
| 2012-0008-0244 | Y120067 | E04 | 18.63 | 0.15 | 13.03 | 0.12 | 4.81 | 19.54 | 49.82 | 10.88 | 0.36 | 0.19 | 0.03 | 0.31 | | 0.08 | |
| 2012-0008-0245 | Y120067 | E05 | 18.76 | 0.13 | 12.86 | 0.11 | 4.92 | 17.72 | 51.41 | 11.42 | 0.35 | 0.22 | 0.04 | 0.36 | | 0.12 | |
| 2012-0008-0246 | Y120067 | E06 | 18.28 | 0.12 | 12.68 | 0.12 | 4.61 | 19.78 | 52.31 | 10.55 | 0.35 | 0.18 | | 0.33 | | 0.16 | |
| 2012-0008-0247 | Y120067 | E07 | 17.14 | 0.11 | 11.47 | 0.07 | 4.77 | 21.26 | 50.66 | 10.63 | 0.31 | 0.22 | 0.03 | 0.29 | | 0.10 | |
| 2012-0008-0248 | Y120067 | E08 | 18.09 | 0.10 | 11.64 | 0.11 | 4.90 | 24.46 | 44.93 | 11.58 | 0.38 | 0.23 | | 0.37 | | 0.14 | |
| 2012-0008-0249 | Y120067 | E09 | 17.93 | 0.12 | 11.26 | 0.18 | 6.16 | 16.15 | 51.46 | 14.42 | 0.34 | 0.19 | 0.03 | 0.33 | | 0.09 | |
| 2012-0008-0250 | Y120067 | E10 | 16.91 | 0.10 | 11.28 | 0.13 | 4.99 | 22.00 | 49.86 | 10.30 | 0.35 | 0.23 | | 0.33 | | 0.12 | |
| 2012-0008-0251 | Y120067 | E11 | 17.93 | 0.12 | 11.56 | 0.11 | 5.08 | 20.16 | 50.75 | 10.64 | 0.36 | 0.22 | 0.03 | 0.34 | | 0.11 | |
| 2012-0008-0252 | Y120067 | E12 | 18.36 | 0.13 | 12.48 | 0.14 | 4.66 | 22.98 | 50.49 | 8.76 | 0.34 | 0.19 | | 0.34 | | 0.11 | |
| 2012-0008-0253 | Y120067 | F01 | 18.09 | 0.11 | 12.36 | 0.12 | 4.92 | 17.72 | 51.82 | 11.08 | 0.36 | 0.22 | 0.03 | 0.32 | | 0.18 | |
| 2012-0008-0254 | Y120067 | F02 | 17.90 | 0.11 | 12.65 | 0.17 | 5.05 | 19.76 | 61.41 | 10.55 | 0.33 | 0.19 | | 0.37 | | 0.11 | |
| 2012-0008-0255 | Y120067 | F03 | 16.98 | 0.13 | 12.01 | 0.13 | 4.99 | 21.28 | 50.66 | 10.53 | 0.31 | 0.23 | 0.03 | 0.30 | | 0.11 | |
| 2012-0008-0256 | Y120067 | F04 | 17.58 | 0.10 | 11.53 | 0.12 | 5.06 | 20.18 | 50.75 | 10.64 | 0.36 | 0.21 | | 0.33 | | 0.12 | |
| 2012-0008-0257 | Y120067 | F05 | 17.46 | 0.14 | 12.18 | 0.21 | 4.42 | 23.06 | 43.89 | 8.91 | 0.32 | 0.19 | 0.05 | 0.29 | | 0.17 | |
| 2012-0008-0258 | Y120067 | F06 | 16.79 | 0.11 | 11.11 | 0.12 | 4.70 | 19.26 | 52.96 | 10.11 | 0.34 | 0.24 | 0.04 | 0.35 | | 0.17 | |

*FIG. 9h*

| Project Ref: | Mag Trem from FAME | | | | | | | | | | | | | | | | |
|---|---|---|---|---|---|---|---|---|---|---|---|---|---|---|---|---|---|
| Date Reported: | 03/07/12 | Project | | | | | | | | | | | | | | | |
| Study ID | 2012-0008 | | | Soybean Half Seed Analysis. Analysis performed by Ted Freeman, Reviewed by Brita McNew | | | | | | | | | | | | | |
| | | | | FAME ANALYSIS - % of Total Oil | | | | | | | | | | | | | |
| Lab ID | Plate ID | Well | % Sats | C14:0 | C16:0 | C16:1 | C18:0 | C18:1 | C18:2 | C18:3 | C20:0 | C20:1 | C20:2 | C22:0 | C22:1 | C24:0 | C24:1 |
| 2012-0008-0259 | Y120067 | F07 | 17.15 | 0.08 | 11.51 | 0.11 | 4.87 | 17.83 | 51.72 | 12.16 | 0.39 | 0.21 | | 0.36 | | 0.15 | |
| 2012-0008-0260 | Y120067 | F08 | 17.74 | 0.11 | 12.31 | 0.13 | 4.92 | 18.76 | 50.66 | 11.92 | 0.34 | 0.21 | 0.03 | 0.33 | | 0.13 | |
| 2012-0008-0261 | Y120067 | F09 | 19.17 | 0.15 | 13.71 | 0.13 | 4.57 | 17.83 | 49.90 | 13.10 | 0.32 | 0.17 | | 0.32 | | 0.09 | |
| 2012-0008-0262 | Y120067 | F10 | 17.51 | 0.11 | 12.33 | 0.15 | 4.41 | 20.64 | 50.78 | 10.23 | 0.33 | 0.21 | 0.03 | 0.33 | | 0.12 | |
| 2012-0008-0263 | Y120067 | F11 | 17.49 | 0.12 | 11.94 | 0.13 | 4.71 | 18.89 | 52.37 | 10.76 | 0.32 | 0.20 | | 0.31 | | 0.08 | |
| 2012-0008-0264 | Y120067 | F12 | 18.87 | 0.13 | 12.25 | 0.13 | 5.61 | 18.28 | 50.95 | 11.76 | 0.38 | 0.19 | | 0.37 | | 0.14 | |
| 2012-0008-0265 | Y120067 | G01 | 16.63 | 0.12 | 11.17 | 0.10 | 4.61 | 20.42 | 51.52 | 10.63 | 0.33 | 0.21 | | 0.31 | | 0.10 | |
| 2012-0008-0266 | Y120067 | G02 | 16.54 | 0.11 | 11.36 | 0.13 | 4.40 | 17.52 | 55.21 | 9.67 | 0.28 | 0.19 | 0.04 | 0.36 | | 0.12 | |
| 2012-0008-0267 | Y120067 | G03 | 14.74 | 0.13 | 9.04 | 0.13 | 4.69 | 37.75 | 37.34 | 9.50 | 0.32 | 0.35 | | 0.29 | | 0.20 | |
| 2012-0008-0268 | Y120067 | G04 | 18.20 | 0.11 | 12.32 | 0.15 | 4.97 | 20.94 | 49.44 | 10.56 | 0.36 | 0.19 | 0.03 | 0.31 | | 0.12 | |
| 2012-0008-0269 | Y120067 | G05 | 17.36 | 0.11 | 11.53 | 0.14 | 4.92 | 18.25 | 53.22 | 10.02 | 0.33 | 0.21 | | 0.34 | | 0.12 | |
| 2012-0008-0270 | Y120067 | G06 | 17.58 | 0.14 | 12.22 | 0.16 | 4.80 | 19.86 | 50.37 | 12.04 | 0.30 | 0.20 | 0.03 | 0.36 | | 0.09 | |
| 2012-0008-0271 | Y120067 | G07 | 17.51 | 0.11 | 11.29 | 0.14 | 5.21 | 17.41 | 53.65 | 10.67 | 0.35 | 0.23 | | 0.36 | | 0.13 | |
| 2012-0008-0272 | Y120067 | G08 | 17.82 | 0.11 | 11.87 | 0.13 | 5.06 | 18.46 | 51.15 | 11.64 | 0.37 | 0.19 | 0.02 | 0.30 | | 0.16 | |
| 2012-0008-0273 | Y120067 | G09 | 17.62 | 0.13 | 12.06 | 0.12 | 4.72 | 17.75 | 53.07 | 10.88 | 0.32 | 0.21 | 0.04 | 0.30 | | 0.08 | |
| 2012-0008-0274 | Y120067 | G10 | 17.66 | 0.11 | 12.17 | 0.14 | 4.76 | 19.99 | 50.65 | 11.02 | 0.36 | 0.22 | 0.04 | 0.35 | | 0.16 | |
| 2012-0008-0275 | Y120067 | G11 | 17.59 | 0.11 | 11.16 | 0.15 | 5.36 | 19.82 | 49.93 | 11.95 | 0.36 | 0.22 | | 0.39 | | 0.14 | |
| 2012-0008-0276 | Y120067 | G12 | 16.56 | 0.10 | 10.83 | 0.16 | 4.51 | 19.86 | 51.38 | 10.42 | 0.35 | 0.23 | | 0.33 | | 0.15 | |
| 2012-0008-0277 | Y120067 | H01 | 17.75 | 0.10 | 12.45 | 0.12 | 4.42 | 22.60 | 50.39 | 8.38 | 0.36 | 0.24 | 0.03 | 0.32 | | 0.11 | |
| 2012-0008-0278 | Y120067 | H02 | 17.25 | 0.11 | 11.74 | 0.11 | 4.47 | 21.00 | 50.76 | 9.94 | 0.38 | 0.25 | 0.03 | 0.35 | | 0.18 | |
| 2012-0008-0279 | Y120067 | H03 | 16.90 | 0.11 | 11.86 | 0.12 | 4.22 | 19.59 | 52.12 | 10.63 | 0.32 | 0.20 | 0.04 | 0.33 | | 0.10 | |
| 2012-0008-0280 | Y120067 | H04 | 18.08 | 0.13 | 11.41 | 0.13 | 5.52 | 17.80 | 52.05 | 11.07 | 0.44 | 0.27 | 0.04 | 0.41 | | 0.17 | |
| 2012-0008-0281 | Y120067 | H05 | 17.26 | 0.10 | 11.69 | 0.14 | 4.48 | 20.19 | 52.40 | 9.22 | 0.35 | 0.22 | 0.04 | 0.33 | | 0.11 | |
| 2012-0008-0282 | Y120067 | H06 | 17.01 | 0.10 | 12.06 | 0.15 | 4.02 | 22.55 | 50.04 | 8.44 | 0.32 | 0.23 | 0.08 | 0.32 | | 0.17 | |
| 2012-0008-0283 | Y120067 | H07 | 17.34 | 0.13 | 11.91 | 0.11 | 4.55 | 16.61 | 52.66 | 12.49 | 0.35 | 0.19 | 0.04 | 0.31 | | 0.12 | |
| 2012-0008-0284 | Y120067 | H08 | 16.50 | 0.09 | 10.88 | 0.11 | 4.70 | 18.55 | 53.50 | 10.50 | 0.34 | 0.22 | 0.04 | 0.34 | | 0.15 | |
| 2012-0008-0285 | Y120067 | H09 | 17.75 | 0.12 | 12.12 | 0.11 | 4.69 | 21.95 | 48.99 | 10.25 | 0.37 | 0.23 | 0.04 | 0.36 | | 0.13 | |
| 2012-0008-0286 | Y120067 | H10 | 18.78 | 0.13 | 12.86 | 0.12 | 4.99 | 17.38 | 52.15 | 10.69 | 0.38 | 0.25 | 0.03 | 0.36 | | 0.10 | |
| 2012-0008-0287 | Y120067 | H11 | 17.36 | 0.12 | 12.03 | 0.11 | 4.47 | 19.67 | 51.27 | 10.75 | 0.34 | 0.22 | | 0.31 | | 0.10 | |
| 2012-0008-0288 | Y120067 | H12 | 17.34 | 0.09 | 11.06 | 0.11 | 5.25 | 17.81 | 52.22 | 11.72 | 0.38 | 0.21 | | 0.36 | | 0.16 | |

*FIG. 9i*

| Group | Geno ID | Segregating | Additional Information |
|---|---|---|---|
| A1 | 505038 | Downey Mildew | 1/4 portion (not defatted); 3/4 portion (defatted); 24 hrs post-FAME extraction |
| A1 | 505040 | Downey Mildew | 1/4 portion (not defatted); 3/4 portion (defatted); 24 hrs post-FAME extraction |
| A1 | 505180 | Downey Mildew | 1/4 portion (not defatted); 3/4 portion (defatted); 24 hrs post-FAME extraction |
| A1 | 505181 | Downey Mildew | 1/4 portion (not defatted); 3/4 portion (defatted); 24 hrs post-FAME extraction |
| A1 | 505044 | Downey Mildew | 1/4 portion (not defatted); 3/4 portion (defatted); 24 hrs post-FAME extraction |
| A1 | 505172 | Downey Mildew | 1/4 portion (not defatted); 3/4 portion (defatted); 24 hrs post-FAME extraction |
| A1 | 505175 | Downey Mildew | 1/4 portion (not defatted); 3/4 portion (defatted); 24 hrs post-FAME extraction |
| A1 | 505176 | Downey Mildew | 1/4 portion (not defatted); 3/4 portion (defatted); 24 hrs post-FAME extraction |
| A1 | 505177 | Downey Mildew | 1/4 portion (not defatted); 3/4 portion (defatted); 24 hrs post-FAME extraction |
| A1 | 505178 | Downey Mildew | 1/4 portion (not defatted); 3/4 portion (defatted); 24 hrs post-FAME extraction |
| A1 | 505179 | Downey Mildew | 1/4 portion (not defatted); 3/4 portion (defatted); 24 hrs post-FAME extraction |
| A2 | 546368 | Downey Mildew | 1/4 seed portion (defatted); 24 hrs post-FAME extraction (quants indicated larger portion size sent) |
| A2 | 546372 | Downey Mildew | 1/4 seed portion (defatted); 24 hrs post-FAME extraction (quants indicated larger portion size sent) |
| A2 | 546374 | Downey Mildew | 1/4 seed portion (defatted); 24 hrs post-FAME extraction (quants indicated larger portion size sent) |
| A2 | 546378 | Downey Mildew | 1/4 seed portion (defatted); 24 hrs post-FAME extraction (quants indicated larger portion size sent) |
| A2 | 546375 | Downey Mildew | 1/4 seed portion (defatted); 24 hrs post-FAME extraction (quants indicated larger portion size sent) |

*FIG. 14a*

| Group | Gene ID | Segregating | Additional Information |
|---|---|---|---|
| B1 | 547395 | Downey Mildew and/or Reduced Sats | 1/4 portion -11 days post FAME extraction |
| B1 | 547396 | Downey Mildew and/or Reduced Sats | 1/4 portion -11 days post FAME extraction |
| B1 | 547398 | Downey Mildew and/or Reduced Sats | 1/4 portion -11 days post FAME extraction |
| B1 | 547399 | Downey Mildew and/or Reduced Sats | 1/4 portion -11 days post FAME extraction |
| B1 | 547400 | Downey Mildew and/or Reduced Sats | 1/4 portion -11 days post FAME extraction |
| B1 | 547401 | Downey Mildew and/or Reduced Sats | 1/4 portion -11 days post FAME extraction |
| B1 | 547402 | Downey Mildew and/or Reduced Sats | 1/4 portion -11 days post FAME extraction |
| B1 | 547403 | Downey Mildew and/or Reduced Sats | 1/4 portion -11 days post FAME extraction |
| B1 | 547404 | Downey Mildew and/or Reduced Sats | 1/4 portion -11 days post FAME extraction |
| B1 | 547408 | Downey Mildew and/or Reduced Sats | 1/4 portion -11 days post FAME extraction |
| B1 | 512408 | Downey Mildew and/or Reduced Sats | 1/4 portion -11 days post FAME extraction |
| B1 | 512409 | Downey Mildew and/or Reduced Sats | 1/4 portion -11 days post FAME extraction |
| B2 | 548018 | Downey Mildew and/or Reduced Sats | 1/4 portion -5 days post FAME extraction |
| B2 | 548020 | Downey Mildew and/or Reduced Sats | 1/4 portion -5 days post FAME extraction |
| B2 | 548350 | Downey Mildew and/or Reduced Sats | 1/4 portion -5 days post FAME extraction |
| B2 | 549886 | Downey Mildew and/or Reduced Sats | 1/4 portion -5 days post FAME extraction |

*FIG. 14b*

| Study ID: | 2011-0291 | | Received: | 9/26/2011 | | | | | FAME ANALYSIS - % of Total Oil | | | | | | | | |
|---|---|---|---|---|---|---|---|---|---|---|---|---|---|---|---|---|---|
| LabID | Plate # | Well # | %Sats | C12:0 | C14:0 | C16:0 | C16:1 | C18:0 | C18:1 | C18:2 | C18:3 | C20:0 | C20:1 | C20:2 | C22:0 | C22:1 | C24:0 | C24:1 |
| 2011-0291-0001 | 1 | A01 | 8.79 | | 0.04 | 3.34 | 0.05 | 3.55 | 85.50 | 4.49 | 0.11 | 0.33 | 0.27 | | 1.16 | | 0.37 | 0.03 |
| 2011-0291-0002 | 1 | A02 | 7.06 | | 0.03 | 2.73 | 0.10 | 3.14 | 90.25 | 2.04 | 0.10 | 0.23 | 0.21 | | 0.77 | 0.01 | 0.16 | 0.01 |
| 2011-0291-0006 | 1 | A06 | 10.59 | | 0.04 | 3.40 | 0.10 | 5.29 | 86.75 | 1.78 | 0.04 | 0.41 | 0.22 | | 1.20 | 0.01 | 0.26 | 0.02 |
| 2011-0291-0007 | 1 | A07 | 11.46 | | 0.04 | 3.49 | 0.09 | 5.85 | 86.02 | 1.82 | 0.07 | 0.47 | 0.20 | | 1.29 | | 0.32 | 0.02 |
| 2011-0291-0008 | 1 | A08 | 9.26 | | 0.03 | 3.00 | 0.10 | 4.48 | 88.35 | 1.64 | 0.07 | 0.35 | 0.25 | | 1.12 | 0.01 | 0.28 | 0.02 |
| 2011-0291-0009 | 1 | A09 | 11.56 | | 0.04 | 4.26 | 0.13 | 5.45 | 86.00 | 1.66 | 0.09 | 0.41 | 0.15 | | 1.12 | | 0.27 | 0.02 |
| 2011-0291-0010 | 1 | A10 | 11.91 | | 0.03 | 3.70 | 0.11 | 5.96 | 85.40 | 1.75 | 0.06 | 0.42 | 0.17 | | 1.51 | 0.01 | 0.29 | 0.02 |
| 2011-0291-0011 | 1 | A11 | 11.71 | | 0.04 | 4.41 | 0.15 | 5.30 | 85.98 | 1.51 | 0.06 | 0.41 | 0.17 | | 1.24 | 0.01 | 0.31 | 0.04 |
| 2011-0291-0012 | 1 | A12 | 12.66 | | 0.04 | 3.79 | 0.15 | 5.40 | 83.87 | 4.19 | 0.05 | 0.45 | 0.18 | | 1.27 | | 0.30 | 0.02 |
| 2011-0291-0013 | 1 | B01 | 11.21 | | 0.05 | 4.35 | 0.13 | 5.76 | 85.04 | 1.45 | 0.05 | 0.45 | 0.18 | 0.01 | 1.71 | | 0.34 | 0.02 |
| 2011-0291-0014 | 1 | B02 | 11.00 | | 0.05 | 5.54 | 0.13 | 4.12 | 28.52 | 59.61 | 0.12 | 0.26 | 0.16 | | 0.82 | 0.01 | 0.20 | 0.01 |
| 2011-0291-0015 | 1 | B03 | 8.81 | | 0.03 | 3.60 | 0.16 | 3.32 | 28.60 | 1.89 | 0.08 | 0.29 | 0.29 | 0.01 | 1.20 | 0.01 | 0.37 | 0.03 |
| 2011-0291-0016 | 1 | B04 | 11.04 | | 0.06 | 6.00 | 0.10 | 3.70 | 25.72 | 62.43 | 0.09 | 0.24 | 0.15 | | 0.81 | 0.01 | 0.22 | 0.01 |
| 2011-0291-0017 | 1 | B05 | 10.89 | | 0.06 | 5.62 | 0.15 | 3.86 | 23.25 | 64.99 | 0.10 | 0.26 | 0.16 | 0.01 | 0.81 | 0.01 | 0.26 | 0.01 |
| 2011-0291-0018 | 1 | B06 | 10.98 | | 0.03 | 3.86 | 0.15 | 5.20 | 87.23 | 1.17 | 0.05 | 0.38 | 0.19 | | 1.24 | 0.01 | 0.27 | 0.03 |
| 2011-0291-0019 | 1 | B07 | 9.14 | | 0.03 | 3.58 | 0.14 | 3.90 | 88.62 | 1.62 | 0.07 | 0.31 | 0.22 | | 1.05 | 0.01 | 0.28 | 0.03 |
| 2011-0291-0020 | 1 | B08 | 10.19 | | 0.04 | 3.64 | 0.13 | 4.53 | 87.36 | 1.75 | 0.07 | 0.36 | 0.22 | | 1.32 | 0.01 | 0.31 | 0.03 |
| 2011-0291-0021 | 1 | B09 | 10.35 | | 0.03 | 3.58 | 0.15 | 4.80 | 86.23 | 2.83 | 0.06 | 0.35 | 0.22 | | 1.27 | 0.01 | 0.32 | 0.03 |
| 2011-0291-0022 | 1 | B10 | 6.63 | | 0.04 | 3.63 | 0.11 | 1.87 | 90.07 | 2.05 | 0.06 | 0.16 | 0.29 | | 0.73 | 0.02 | 0.20 | 0.03 |
| 2011-0291-0023 | 1 | B11 | 11.00 | | 0.03 | 3.91 | 0.15 | 5.14 | 86.66 | 1.56 | 0.08 | 0.37 | 0.21 | | 1.28 | | 0.26 | 0.02 |
| 2011-0291-0024 | 1 | B12 | 6.57 | | 0.03 | 3.48 | 0.12 | 2.09 | 90.76 | 1.84 | 0.05 | 0.15 | 0.24 | | 0.66 | | 0.17 | 0.03 |

*FIG. 15a*

| Study ID: | 2011-0291 | | Received: | 9/28/2011 | | | | FAME ANALYSIS - % of Total Oil | | | | | | | | | |
|---|---|---|---|---|---|---|---|---|---|---|---|---|---|---|---|---|---|
| LabID | Plate # | Well # | %Sats | C12:0 | C14:0 | C16:0 | C16:1 | C18:0 | C18:1 | C18:2 | C18:3 | C20:0 | C20:1 | C20:2 | C22:0 | C22:1 | C24:0 | C24:1 |
| 2011-0291-0025 | 1 | C01 | 11.52 | | 0.03 | 3.66 | 0.10 | 5.84 | 86.19 | 1.50 | 0.09 | 0.43 | 0.19 | | 1.29 | 0.01 | 0.27 | 0.02 |
| 2011-0291-0026 | 1 | C02 | 6.95 | | 0.04 | 3.35 | 0.19 | 2.25 | 89.14 | 3.10 | 0.07 | 0.20 | 0.29 | | 0.81 | 0.02 | 0.30 | 0.03 |
| 2011-0291-0027 | 1 | C03 | 11.05 | | 0.06 | 6.01 | 0.14 | 3.75 | 18.78 | 69.21 | 0.10 | 0.26 | 0.14 | 0.01 | 0.70 | | 0.25 | 0.01 |
| 2011-0291-0028 | 1 | C04 | 11.53 | | 0.09 | 6.29 | 0.18 | 3.87 | 20.33 | 67.17 | 0.10 | 0.28 | 0.13 | | 0.76 | | 0.25 | 0.01 |
| 2011-0291-0029 | 1 | C05 | 8.49 | | 0.05 | 4.03 | 0.21 | 2.81 | 87.14 | 3.63 | 0.07 | 0.26 | 0.29 | | 0.98 | 0.01 | 0.35 | 0.03 |
| 2011-0291-0030 | 1 | C06 | 9.34 | | 0.04 | 3.87 | 0.17 | 3.61 | 86.61 | 3.07 | 0.06 | 0.28 | 0.22 | | 1.19 | 0.01 | 0.35 | 0.03 |
| 2011-0291-0031 | 1 | C07 | 7.88 | | 0.04 | 3.67 | 0.19 | 2.48 | 88.88 | 2.55 | 0.07 | 0.24 | 0.29 | | 0.89 | 0.01 | 0.36 | 0.03 |
| 2011-0291-0032 | 1 | C08 | 7.42 | | 0.05 | 3.89 | 0.18 | 2.20 | 89.47 | 2.37 | 0.06 | 0.19 | 0.27 | | 0.81 | 0.02 | 0.29 | 0.02 |
| 2011-0291-0033 | 1 | C09 | 7.11 | | 0.03 | 3.47 | 0.17 | 2.14 | 90.75 | 1.43 | 0.06 | 0.19 | 0.31 | | 0.95 | | 0.32 | 0.04 |
| 2011-0291-0034 | 1 | C10 | 7.61 | | 0.04 | 3.65 | 0.16 | 2.40 | 89.29 | 2.32 | 0.06 | 0.23 | 0.31 | | 0.98 | 0.02 | 0.31 | 0.02 |
| 2011-0291-0035 | 1 | C11 | 7.79 | | 0.04 | 3.74 | 0.15 | 2.48 | 89.55 | 1.92 | 0.06 | 0.25 | 0.32 | | 0.92 | | 0.36 | 0.03 |
| 2011-0291-0036 | 1 | C12 | 10.31 | | 0.06 | 6.36 | 0.13 | 3.00 | 19.52 | 69.27 | 0.08 | 0.20 | 0.18 | 0.01 | 0.48 | | 0.20 | 0.01 |
| 2011-0291-0037 | 1 | D01 | 7.96 | | 0.04 | 3.59 | 0.15 | 2.79 | 89.46 | 1.95 | 0.05 | 0.25 | 0.27 | | 0.99 | 0.01 | 0.31 | 0.03 |
| 2011-0291-0038 | 1 | D02 | 11.46 | | 0.05 | 4.77 | 0.10 | 5.12 | 31.13 | 56.49 | 0.10 | 0.30 | 0.15 | | 1.03 | | 0.20 | 0.01 |
| 2011-0291-0039 | 1 | D03 | 10.48 | | 0.04 | 3.72 | 0.11 | 4.77 | 87.17 | 1.69 | 0.07 | 0.35 | 0.20 | | 1.29 | | 0.31 | 0.02 |
| 2011-0291-0040 | 1 | D04 | 8.94 | | 0.03 | 3.37 | 0.11 | 3.85 | 88.90 | 1.53 | 0.06 | 0.29 | 0.22 | | 1.12 | 0.01 | 0.28 | 0.02 |
| 2011-0291-0041 | 1 | D05 | 11.04 | | 0.03 | 3.41 | 0.08 | 5.71 | 87.25 | 1.17 | 0.06 | 0.42 | 0.18 | | 1.20 | | 0.27 | 0.02 |
| 2011-0291-0042 | 1 | D06 | 11.35 | | 0.04 | 3.40 | 0.10 | 5.86 | 85.82 | 1.94 | 0.13 | 0.45 | 0.19 | | 1.30 | 0.01 | 0.29 | 0.02 |
| 2011-0291-0043 | 1 | D07 | 11.78 | | 0.04 | 3.97 | 0.11 | 5.52 | 25.39 | 52.77 | 0.07 | 0.41 | 0.17 | | 1.52 | | 0.32 | 0.02 |
| 2011-0291-0044 | 1 | D08 | 10.01 | | 0.05 | 4.78 | 0.08 | 3.99 | 30.40 | 58.77 | 0.07 | 0.22 | 0.15 | | 0.78 | | 0.19 | 0.01 |
| 2011-0291-0045 | 1 | D09 | 10.43 | | 0.04 | 3.46 | 0.09 | 4.81 | 85.61 | 3.23 | 0.07 | 0.39 | 0.22 | | 1.36 | 0.01 | 0.38 | 0.02 |
| 2011-0291-0046 | 1 | D10 | 10.29 | | 0.04 | 3.59 | 0.11 | 4.86 | 87.78 | 1.29 | 0.07 | 0.35 | 0.19 | | 1.21 | | 0.26 | 0.02 |
| 2011-0291-0047 | 1 | D11 | 14.84 | | 0.05 | 5.36 | 0.10 | 7.02 | 46.93 | 37.55 | 0.07 | 0.50 | 0.13 | | 1.59 | | 0.33 | 0.02 |
| 2011-0291-0048 | 1 | D12 | 10.38 | | 0.04 | 3.77 | 0.11 | 4.87 | 86.92 | 2.01 | 0.09 | 0.34 | 0.17 | | 1.10 | 0.01 | 0.25 | 0.02 |

*FIG. 15b*

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0001 | 2012-089_1 | Tray 01 A | A1 | HE11EE012155.002.01 | 4.31 | 0.03 | 2.16 | 0.09 | 1.06 | 93.38 | 1.44 | 0.10 | 0.12 | 0.55 | 0.60 | 0.01 | 0.24 | |
| 2012-0089-0002 | 2012-089_1 | Tray 01 A | A2 | HE11EE012155.002.02 | 6.23 | 0.02 | 2.55 | 0.08 | 2.33 | 90.88 | 2.00 | 0.15 | 0.24 | 0.48 | 0.61 | 0.01 | 0.28 | |
| 2012-0089-0003 | 2012-089_1 | Tray 01 A | A3 | HE11EE012155.002.03 | 4.95 | 0.03 | 2.84 | 0.09 | 1.14 | 91.52 | 2.30 | 0.19 | 0.15 | 0.54 | 0.53 | 0.01 | 0.26 | |
| 2012-0089-0004 | 2012-089_1 | Tray 01 A | A4 | HE11EE012155.002.04 | 6.26 | 0.03 | 2.90 | 0.08 | 2.05 | 89.79 | 2.83 | 0.16 | 0.22 | 0.37 | 0.82 | | 0.25 | |
| 2012-0089-0005 | 2012-089_1 | Tray 01 A | A5 | HE11EE012155.002.05 | 3.89 | 0.02 | 1.92 | 0.04 | 0.92 | 94.25 | 1.13 | 0.11 | 0.09 | 0.52 | 0.53 | 0.01 | 0.22 | |
| 2012-0089-0006 | 2012-089_1 | Tray 01 A | A6 | HE11EE012155.002.06 | 4.79 | 0.02 | 2.37 | 0.07 | 1.37 | 92.31 | 1.86 | 0.12 | 0.16 | 0.53 | 0.61 | 0.01 | 0.26 | |
| 2012-0089-0007 | 2012-089_1 | Tray 01 A | A7 | HE11EE012155.002.07 | 4.13 | 0.02 | 2.08 | 0.06 | 1.14 | 92.94 | 1.70 | 0.11 | 0.12 | 0.54 | 0.55 | | 0.23 | |
| 2012-0089-0008 | 2012-089_1 | Tray 01 A | A8 | HE11EE012155.002.08 | 5.70 | 0.02 | 2.42 | 0.05 | 1.95 | 91.15 | 2.18 | 0.15 | 0.21 | 0.44 | 0.83 | 0.01 | 0.26 | |
| 2012-0089-0009 | 2012-089_1 | Tray 01 A | A9 | HE11EE012155.002.09 | 4.42 | 0.02 | 2.24 | 0.07 | 1.20 | 92.81 | 1.97 | 0.13 | 0.13 | 0.55 | 0.61 | 0.01 | 0.21 | |
| 2012-0089-0010 | 2012-089_1 | Tray 01 A | A10 | HE11EE012155.002.10 | 4.06 | 0.02 | 1.96 | 0.03 | 1.11 | 93.44 | 1.49 | 0.10 | 0.13 | 0.59 | 0.61 | 0.02 | 0.24 | 0.01 |
| 2012-0089-0011 | 2012-089_1 | Tray 01 A | A11 | HE11EE012155.002.11 | 4.16 | 0.02 | 2.21 | 0.05 | 1.03 | 93.13 | 1.67 | 0.13 | 0.11 | 0.56 | 0.56 | 0.01 | 0.23 | |
| 2012-0089-0012 | 2012-089_1 | Tray 01 A | A12 | HE11EE012155.002.12 | 4.46 | 0.03 | 2.39 | 0.05 | 1.13 | 92.39 | 2.04 | 0.13 | 0.12 | 0.50 | 0.55 | 0.01 | 0.24 | |
| 2012-0089-0013 | 2012-089_1 | Tray 01 A | B1 | HE11EE012155.003.01 | 4.46 | 0.02 | 2.13 | 0.06 | 1.31 | 93.32 | 1.29 | 0.13 | 0.12 | 0.50 | 0.65 | 0.01 | 0.22 | |
| 2012-0089-0014 | 2012-089_1 | Tray 01 A | B2 | HE11EE012155.003.02 | 5.31 | 0.02 | 2.28 | 0.05 | 1.87 | 92.14 | 1.57 | 0.11 | 0.19 | 0.48 | 0.73 | 0.01 | 0.22 | |
| 2012-0089-0015 | 2012-089_1 | Tray 01 A | B3 | HE11EE012155.003.03 | 4.43 | 0.02 | 2.19 | 0.04 | 1.29 | 93.11 | 1.47 | 0.13 | 0.14 | 0.50 | 0.58 | 0.01 | 0.21 | |
| 2012-0089-0016 | 2012-089_1 | Tray 01 A | B4 | HE11EE012155.003.04 | 5.22 | 0.02 | 2.38 | 0.05 | 1.74 | 91.95 | 1.79 | 0.12 | 0.17 | 0.47 | 0.89 | 0.01 | 0.22 | |
| 2012-0089-0017 | 2012-089_1 | Tray 01 A | B5 | HE11EE012155.003.05 | 4.57 | 0.02 | 2.25 | 0.04 | 1.36 | 92.82 | 1.56 | 0.13 | 0.14 | 0.47 | 0.60 | 0.01 | 0.20 | 0.01 |
| 2012-0089-0018 | 2012-089_1 | Tray 01 A | B6 | HE11EE012155.003.06 | 4.34 | 0.02 | 2.12 | 0.05 | 1.25 | 92.85 | 1.79 | 0.12 | 0.12 | 0.54 | 0.62 | 0.01 | 0.20 | |
| 2012-0089-0019 | 2012-089_1 | Tray 01 A | B7 | HE11EE012155.003.07 | 4.25 | 0.02 | 2.13 | 0.04 | 1.20 | 93.53 | 1.22 | 0.12 | 0.12 | 0.55 | 0.57 | 0.01 | 0.21 | |
| 2012-0089-0020 | 2012-089_1 | Tray 01 A | B8 | HE11EE012155.003.08 | 4.06 | 0.02 | 2.19 | 0.04 | 0.96 | 93.32 | 1.56 | 0.14 | 0.10 | 0.53 | 0.58 | 0.01 | 0.22 | |
| 2012-0089-0021 | 2012-089_1 | Tray 01 A | B9 | HE11EE012155.003.09 | 4.17 | 0.02 | 2.22 | 0.04 | 1.10 | 91.45 | 3.44 | 0.12 | 0.10 | 0.46 | 0.54 | 0.01 | 0.19 | |
| 2012-0089-0022 | 2012-089_1 | Tray 01 A | B10 | HE11EE012155.003.10 | 5.08 | 0.02 | 2.29 | 0.04 | 1.67 | 92.23 | 1.83 | 0.13 | 0.17 | 0.48 | 0.69 | 0.01 | 0.23 | 0.01 |
| 2012-0089-0023 | 2012-089_1 | Tray 01 A | B11 | HE11EE012155.003.11 | 4.50 | 0.02 | 2.11 | 0.04 | 1.35 | 92.23 | 1.85 | 0.14 | 0.14 | 0.54 | 0.64 | 0.01 | 0.25 | |
| 2012-0089-0024 | 2012-089_1 | Tray 01 A | B12 | HE11EE012155.003.12 | 6.27 | 0.03 | 3.09 | 0.09 | 2.08 | 90.82 | 2.04 | 0.13 | 0.19 | 0.34 | 0.71 | | 0.18 | |
| 2012-0089-0025 | 2012-089_1 | Tray 01 A | C1 | HE11EE012155.005.01 | 4.73 | 0.02 | 2.10 | 0.05 | 1.55 | 92.83 | 1.52 | 0.12 | 0.13 | 0.48 | 0.71 | 0.01 | 0.22 | 0.01 |
| 2012-0089-0026 | 2012-089_1 | Tray 01 A | C2 | HE11EE012155.005.02 | 4.99 | 0.02 | 2.27 | 0.07 | 1.61 | 92.03 | 2.03 | 0.12 | 0.16 | 0.46 | 0.71 | 0.01 | 0.22 | |
| 2012-0089-0027 | 2012-089_1 | Tray 01 A | C3 | HE11EE012155.005.03 | 4.96 | 0.02 | 2.33 | 0.06 | 1.54 | 92.01 | 2.00 | 0.15 | 0.18 | 0.52 | 0.65 | 0.01 | 0.23 | |
| 2012-0089-0028 | 2012-089_1 | Tray 01 A | C4 | HE11EE012155.005.04 | 4.80 | 0.02 | 2.26 | 0.04 | 1.51 | 92.37 | 1.78 | 0.13 | 0.16 | 0.51 | 0.65 | 0.01 | 0.21 | |
| 2012-0089-0029 | 2012-089_1 | Tray 01 A | C5 | HE11EE012155.005.05 | 4.74 | 0.02 | 2.25 | 0.04 | 1.42 | 92.28 | 1.96 | 0.13 | 0.15 | 0.50 | 0.58 | 0.01 | 0.22 | |
| 2012-0089-0030 | 2012-089_1 | Tray 01 A | C6 | HE11EE012155.005.06 | 4.47 | 0.02 | 2.10 | 0.03 | 1.31 | 92.62 | 1.90 | 0.12 | 0.13 | 0.53 | 0.68 | 0.01 | 0.23 | 0.01 |
| 2012-0089-0031 | 2012-089_1 | Tray 01 A | C7 | HE11EE012155.005.07 | 3.96 | 0.02 | 2.08 | 0.06 | 1.00 | 93.55 | 1.52 | 0.12 | 0.11 | 0.55 | 0.55 | 0.01 | 0.21 | |
| 2012-0089-0032 | 2012-089_1 | Tray 01 A | C8 | HE11EE012155.005.08 | 5.01 | 0.02 | 2.19 | 0.07 | 1.71 | 92.40 | 1.51 | 0.13 | 0.16 | 0.48 | 0.70 | 0.01 | 0.22 | |
| 2012-0089-0033 | 2012-089_1 | Tray 01 A | C9 | HE11EE012155.005.09 | 4.71 | 0.02 | 2.33 | 0.07 | 1.33 | 92.43 | 1.90 | 0.13 | 0.14 | 0.51 | 0.66 | 0.01 | 0.23 | |

FIG. 15c

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0034 | 2012-089_1 | Tray 01 A | C10 | HE11EE012155.005.10 | 5.01 | 0.02 | 2.43 | 0.04 | 1.43 | 92.46 | 1.48 | 0.14 | 0.15 | 0.61 | 0.71 | 0.02 | 0.26 | |
| 2012-0089-0035 | 2012-089_1 | Tray 01 A | C11 | HE11EE012155.005.11 | 5.00 | 0.02 | 2.20 | 0.02 | 1.63 | 92.08 | 1.88 | 0.14 | 0.18 | 0.55 | 0.76 | 0.01 | 0.23 | |
| 2012-0089-0036 | 2012-089_1 | Tray 01 A | C12 | HE11EE012155.005.12 | 4.48 | 0.03 | 2.29 | 0.02 | 1.18 | 92.11 | 2.41 | 0.14 | 0.13 | 0.51 | 0.84 | 0.01 | 0.23 | |
| 2012-0089-0037 | 2012-089_1 | Tray 01 A | D1 | HE11EE012155.006.01 | 5.37 | 0.02 | 2.47 | 0.10 | 1.77 | 91.54 | 1.88 | 0.12 | 0.20 | 0.44 | 0.69 | | 0.22 | |
| 2012-0089-0038 | 2012-089_1 | Tray 01 A | D2 | HE11EE012155.006.02 | 3.89 | 0.02 | 2.02 | 0.04 | 1.00 | 93.43 | 1.56 | 0.11 | 0.11 | 0.56 | 0.54 | 0.01 | 0.21 | |
| 2012-0089-0039 | 2012-089_1 | Tray 01 A | D3 | HE11EE012155.006.03 | 4.22 | 0.04 | 2.25 | 0.10 | 0.99 | 91.82 | 2.41 | 0.18 | 0.11 | 0.63 | 0.57 | 0.02 | 0.20 | |
| 2012-0089-0040 | 2012-089_1 | Tray 01 A | D4 | HE11EE012155.006.04 | 3.66 | 0.02 | 2.03 | 0.04 | 0.86 | 93.74 | 1.51 | 0.12 | 0.10 | 0.57 | 0.48 | 0.01 | 0.27 | |
| 2012-0089-0041 | 2012-089_1 | Tray 01 A | D5 | HE11EE012155.006.05 | 4.15 | 0.02 | 2.03 | 0.04 | 1.10 | 93.39 | 1.49 | 0.12 | 0.12 | 0.53 | 0.48 | 0.01 | 0.17 | 0.01 |
| 2012-0089-0042 | 2012-089_1 | Tray 01 A | D6 | HE11EE012155.006.06 | 4.22 | 0.02 | 2.14 | 0.07 | 1.15 | 93.10 | 1.70 | 0.13 | 0.12 | 0.52 | 0.58 | 0.01 | 0.19 | |
| 2012-0089-0043 | 2012-089_1 | Tray 01 A | D7 | HE11EE012155.006.07 | 4.38 | 0.03 | 2.13 | 0.03 | 1.25 | 92.76 | 1.85 | 0.14 | 0.13 | 0.54 | 0.63 | 0.01 | 0.22 | |
| 2012-0089-0044 | 2012-089_1 | Tray 01 A | D8 | HE11EE012155.006.08 | 5.40 | 0.03 | 2.79 | 0.08 | 1.59 | 90.85 | 2.05 | 0.18 | 0.19 | 0.46 | 0.63 | 0.01 | 0.22 | |
| 2012-0089-0045 | 2012-089_1 | Tray 01 A | D9 | HE11EE012155.006.09 | 4.69 | 0.02 | 2.17 | 0.04 | 1.59 | 92.55 | 1.82 | 0.12 | 0.16 | 0.47 | 0.61 | 0.01 | 0.20 | 0.01 |
| 2012-0089-0046 | 2012-089_1 | Tray 01 A | D10 | HE11EE012155.006.10 | 5.20 | 0.02 | 2.42 | 0.09 | 1.70 | 92.11 | 1.69 | 0.12 | 0.16 | 0.41 | 0.71 | 0.01 | 0.20 | |
| 2012-0089-0047 | 2012-089_1 | Tray 01 A | D11 | HE11EE012155.006.11 | 5.17 | 0.02 | 2.20 | 0.04 | 1.85 | 92.20 | 1.69 | 0.11 | 0.18 | 0.47 | 0.72 | 0.01 | 0.21 | 0.01 |
| 2012-0089-0048 | 2012-089_1 | Tray 01 A | D12 | HE11EE012155.006.12 | 4.50 | 0.02 | 2.20 | 0.08 | 1.34 | 92.78 | 1.78 | 0.14 | 0.14 | 0.45 | 0.61 | 0.01 | 0.20 | |
| 2012-0089-0049 | 2012-089_1 | Tray 01 B | E1 | HE11EE012155.007.01 | 4.86 | 0.02 | 2.29 | 0.04 | 1.48 | 92.11 | 2.01 | 0.15 | 0.16 | 0.47 | 0.67 | 0.01 | 0.23 | |
| 2012-0089-0050 | 2012-089_1 | Tray 01 B | E2 | HE11EE012155.007.02 | 4.74 | 0.02 | 2.14 | 0.04 | 1.50 | 92.64 | 1.70 | 0.13 | 0.15 | 0.45 | 0.69 | 0.01 | 0.24 | 0.05 |
| 2012-0089-0051 | 2012-089_1 | Tray 01 B | E3 | HE11EE012155.007.03 | 4.68 | 0.02 | 2.18 | 0.04 | 1.39 | 92.85 | 1.65 | 0.13 | 0.15 | 0.54 | 0.69 | 0.01 | 0.25 | 0.01 |
| 2012-0089-0052 | 2012-089_1 | Tray 01 B | E4 | HE11EE012155.007.04 | 4.59 | 0.02 | 2.32 | 0.08 | 1.23 | 92.29 | 1.73 | 0.14 | 0.14 | 0.53 | 0.63 | 0.02 | 0.25 | 0.01 |
| 2012-0089-0053 | 2012-089_1 | Tray 01 B | E5 | HE11EE012155.007.05 | 4.07 | 0.02 | 2.17 | 0.04 | 1.01 | 93.27 | 1.64 | 0.14 | 0.11 | 0.56 | 0.55 | 0.01 | 0.21 | 0.01 |
| 2012-0089-0054 | 2012-089_1 | Tray 01 B | E6 | HE11EE012155.007.06 | 4.69 | 0.03 | 2.35 | 0.10 | 1.35 | 92.14 | 2.11 | 0.15 | 0.15 | 0.44 | 0.60 | 0.01 | 0.21 | |
| 2012-0089-0055 | 2012-089_1 | Tray 01 B | E7 | HE11EE012155.007.07 | 4.29 | 0.02 | 2.09 | 0.04 | 1.22 | 93.12 | 1.51 | 0.13 | 0.13 | 0.46 | 0.60 | 0.01 | 0.23 | 0.01 |
| 2012-0089-0056 | 2012-089_1 | Tray 01 B | E8 | HE11EE012155.007.08 | 4.44 | 0.02 | 2.20 | 0.03 | 1.22 | 93.17 | 1.40 | 0.13 | 0.13 | 0.50 | 0.63 | 0.01 | 0.23 | 0.01 |
| 2012-0089-0057 | 2012-089_1 | Tray 01 B | E9 | HE11EE012155.007.09 | 4.34 | 0.02 | 2.06 | 0.07 | 1.23 | 93.35 | 1.33 | 0.10 | 0.10 | 0.53 | 0.67 | 0.02 | 0.24 | 0.01 |
| 2012-0089-0058 | 2012-089_1 | Tray 01 B | E10 | HE11EE012155.007.10 | 3.85 | 0.02 | 1.95 | 0.03 | 1.02 | 93.55 | 1.57 | 0.13 | 0.13 | 0.58 | 0.55 | 0.02 | 0.20 | |
| 2012-0089-0059 | 2012-089_1 | Tray 01 B | E11 | HE11EE012155.007.11 | 4.26 | 0.02 | 2.05 | 0.04 | 1.22 | 93.34 | 1.45 | 0.12 | 0.13 | 0.49 | 0.62 | 0.01 | 0.22 | |
| 2012-0089-0060 | 2012-089_1 | Tray 01 B | E12 | HE11EE012155.007.12 | 5.11 | 0.02 | 2.24 | 0.05 | 1.67 | 93.10 | 1.77 | 0.13 | 0.17 | 0.53 | 0.76 | 0.01 | 0.25 | 0.03 |
| 2012-0089-0061 | 2012-089_1 | Tray 01 B | F1 | HE11EE012155.008.01 | 4.19 | 0.02 | 2.07 | 0.03 | 1.19 | 93.15 | 1.69 | 0.12 | 0.14 | 0.54 | 0.56 | 0.01 | 0.21 | |
| 2012-0089-0062 | 2012-089_1 | Tray 01 B | F2 | HE11EE012155.008.02 | 4.42 | 0.02 | 2.39 | 0.05 | 1.17 | 92.66 | 1.91 | 0.12 | 0.13 | 0.45 | 0.54 | 0.01 | 0.17 | 0.01 |
| 2012-0089-0063 | 2012-089_1 | Tray 01 B | F3 | HE11EE012155.008.03 | 3.90 | 0.02 | 2.08 | 0.07 | 0.95 | 93.66 | 1.45 | 0.14 | 0.12 | 0.58 | 0.51 | 0.01 | 0.21 | 0.01 |
| 2012-0089-0064 | 2012-089_1 | Tray 01 B | F4 | HE11EE012155.008.04 | 4.02 | 0.02 | 2.08 | 0.06 | 1.07 | 93.41 | 1.52 | 0.10 | 0.13 | 0.54 | 0.53 | 0.01 | 0.21 | |
| 2012-0089-0065 | 2012-089_1 | Tray 01 B | F5 | HE11EE012155.008.05 | 4.43 | 0.03 | 2.17 | 0.08 | 1.28 | 93.06 | 1.55 | 0.14 | 0.14 | 0.51 | 0.59 | 0.01 | 0.22 | 0.01 |
| 2012-0089-0066 | 2012-089_1 | Tray 01 B | F6 | HE11EE012155.008.06 | 3.80 | 0.02 | 2.14 | 0.05 | 0.86 | 93.93 | 1.97 | 0.14 | 0.10 | 0.56 | 0.47 | 0.01 | 0.20 | 0.01 |

*FIG. 15d*

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0067 | 2012-089_1 | Tray 01 B | F7 | HE11EE012155.008.07 | 4.20 | 0.02 | 2.21 | 0.08 | 1.08 | 92.84 | 1.88 | 0.15 | 0.13 | 0.54 | 0.58 | | 0.20 | |
| 2012-0089-0068 | 2012-089_1 | Tray 01 B | F8 | HE11EE012155.008.08 | 5.41 | 0.03 | 2.60 | 0.05 | 1.68 | 91.44 | 2.20 | 0.13 | 0.18 | 0.41 | 0.71 | 0.01 | 0.21 | |
| 2012-0089-0069 | 2012-089_1 | Tray 01 B | F9 | HE11EE012155.008.09 | 4.40 | 0.02 | 2.08 | 0.07 | 1.31 | 93.09 | 1.52 | 0.13 | 0.13 | 0.48 | 0.64 | 0.01 | 0.23 | 0.01 |
| 2012-0089-0070 | 2012-089_1 | Tray 01 B | F10 | HE11EE012155.008.10 | 4.30 | 0.02 | 2.18 | 0.06 | 1.19 | 93.04 | 1.65 | 0.12 | 0.11 | 0.54 | 0.58 | 0.01 | 0.22 | |
| 2012-0089-0071 | 2012-089_1 | Tray 01 B | F11 | HE11EE012155.008.11 | 3.96 | 0.02 | 1.99 | 0.08 | 1.08 | 93.57 | 1.52 | 0.11 | 0.11 | 0.52 | 0.54 | 0.01 | 0.21 | |
| 2012-0089-0072 | 2012-089_1 | Tray 01 B | F12 | HE11EE012155.008.12 | 4.56 | 0.03 | 2.49 | 0.10 | 1.20 | 92.78 | 1.89 | 0.11 | 0.13 | 0.46 | 0.53 | 0.01 | 0.19 | |
| 2012-0089-0073 | 2012-089_1 | Tray 01 B | G1 | HE11EE012156.001.01 | 4.49 | 0.03 | 2.16 | 0.08 | 1.32 | 93.02 | 1.55 | 0.12 | 0.14 | 0.50 | 0.62 | 0.01 | 0.24 | |
| 2012-0089-0074 | 2012-089_1 | Tray 01 B | G2 | HE11EE012156.001.02 | 4.48 | 0.02 | 2.12 | 0.05 | 1.32 | 92.78 | 1.72 | 0.12 | 0.15 | 0.54 | 0.61 | 0.01 | 0.25 | |
| 2012-0089-0075 | 2012-089_1 | Tray 01 B | G3 | HE11EE012156.001.03 | 4.20 | 0.02 | 2.00 | 0.09 | 1.26 | 92.77 | 2.02 | 0.13 | 0.14 | 0.53 | 0.55 | 0.01 | 0.23 | |
| 2012-0089-0076 | 2012-089_1 | Tray 01 B | G4 | HE11EE012156.001.04 | 4.47 | 0.02 | 2.16 | 0.04 | 1.31 | 92.70 | 1.81 | 0.12 | 0.14 | 0.54 | 0.61 | 0.01 | 0.23 | |
| 2012-0089-0077 | 2012-089_1 | Tray 01 B | G5 | HE11EE012156.001.05 | 4.26 | 0.02 | 2.09 | 0.07 | 1.17 | 93.03 | 1.71 | 0.12 | 0.12 | 0.53 | 0.62 | 0.01 | 0.24 | |
| 2012-0089-0078 | 2012-089_1 | Tray 01 B | G6 | HE11EE012156.001.06 | 4.67 | 0.02 | 2.23 | 0.05 | 1.41 | 92.57 | 1.74 | 0.12 | 0.15 | 0.52 | 0.63 | 0.01 | 0.23 | |
| 2012-0089-0079 | 2012-089_1 | Tray 01 B | G7 | HE11EE012156.001.07 | 4.31 | 0.03 | 2.09 | 0.10 | 1.23 | 93.10 | 1.53 | 0.13 | 0.15 | 0.54 | 0.58 | 0.01 | 0.23 | |
| 2012-0089-0080 | 2012-089_1 | Tray 01 B | G8 | HE11EE012156.001.08 | 5.24 | 0.03 | 2.30 | 0.04 | 1.87 | 92.60 | 1.76 | 0.11 | 0.18 | 0.50 | 0.77 | 0.01 | 0.29 | 0.01 |
| 2012-0089-0081 | 2012-089_1 | Tray 01 B | G9 | HE11EE012156.001.09 | 5.20 | 0.03 | 2.42 | 0.11 | 1.63 | 91.86 | 1.93 | 0.14 | 0.18 | 0.47 | 0.69 | 0.01 | 0.25 | |
| 2012-0089-0082 | 2012-089_1 | Tray 01 B | G10 | HE11EE012156.001.10 | 4.67 | 0.03 | 2.24 | 0.05 | 1.31 | 92.49 | 1.82 | 0.12 | 0.15 | 0.54 | 0.67 | 0.01 | 0.28 | 0.01 |
| 2012-0089-0083 | 2012-089_1 | Tray 01 B | G11 | HE11EE012156.001.11 | 4.79 | 0.02 | 2.40 | 0.06 | 1.37 | 91.58 | 2.36 | 0.16 | 0.15 | 0.48 | 0.60 | 0.01 | 0.25 | |
| 2012-0089-0084 | 2012-089_1 | Tray 01 B | G12 | HE11EE012156.001.12 | 4.53 | 0.03 | 2.11 | 0.04 | 1.30 | 92.75 | 1.67 | 0.12 | 0.14 | 0.57 | 0.67 | 0.01 | 0.28 | |
| 2012-0089-0085 | 2012-089_1 | Tray 01 B | H1 | HE11EE012156.002.01 | 4.26 | 0.02 | 2.15 | 0.04 | 1.16 | 93.42 | 1.38 | 0.13 | 0.13 | 0.46 | 0.59 | 0.01 | 0.20 | |
| 2012-0089-0086 | 2012-089_1 | Tray 01 B | H2 | HE11EE012156.002.02 | 5.38 | 0.03 | 2.57 | 0.08 | 1.75 | 91.25 | 2.50 | 0.13 | 0.17 | 0.41 | 0.65 | 0.01 | 0.19 | |
| 2012-0089-0087 | 2012-089_1 | Tray 01 B | H3 | HE11EE012156.002.03 | 5.48 | 0.03 | 3.31 | 0.07 | 1.18 | 88.46 | 4.95 | 0.19 | 0.19 | 0.54 | 0.53 | | 0.23 | |
| 2012-0089-0088 | 2012-089_1 | Tray 01 B | H4 | HE11EE012156.002.04 | 5.04 | 0.02 | 2.53 | 0.09 | 1.44 | 91.58 | 2.32 | 0.14 | 0.18 | 0.53 | 0.62 | 0.01 | 0.28 | 0.03 |
| 2012-0089-0089 | 2012-089_1 | Tray 01 B | H5 | HE11EE012156.002.05 | 5.07 | 0.02 | 2.63 | 0.09 | 1.40 | 91.60 | 2.34 | 0.14 | 0.17 | 0.51 | 0.59 | 0.01 | 0.25 | |
| 2012-0089-0090 | 2012-089_1 | Tray 01 B | H6 | HE11EE012156.002.06 | 4.73 | 0.02 | 2.18 | 0.05 | 1.45 | 92.90 | 1.35 | 0.13 | 0.14 | 0.52 | 0.70 | 0.01 | 0.23 | |
| 2012-0089-0091 | 2012-089_1 | Tray 01 B | H7 | HE11EE012156.002.07 | 5.47 | 0.02 | 2.74 | 0.05 | 1.77 | 91.09 | 2.53 | 0.14 | 0.19 | 0.37 | 0.58 | | 0.18 | |
| 2012-0089-0092 | 2012-089_1 | Tray 01 B | H8 | HE11EE012156.002.08 | 5.32 | 0.03 | 2.96 | 0.12 | 1.40 | 90.83 | 2.73 | 0.16 | 0.19 | 0.48 | 0.53 | | 0.21 | |
| 2012-0089-0093 | 2012-089_1 | Tray 01 B | H9 | HE11EE012156.002.09 | 3.52 | 0.02 | 2.28 | 0.08 | 0.85 | 93.31 | 2.10 | 0.19 | 0.09 | 0.55 | 0.32 | 0.01 | 0.15 | 0.02 |
| 2012-0089-0094 | 2012-089_1 | Tray 01 B | H10 | HE11EE012156.002.10 | 4.31 | 0.02 | 2.08 | 0.08 | 1.23 | 93.19 | 1.46 | 0.11 | 0.13 | 0.53 | 0.61 | 0.01 | 0.24 | |
| 2012-0089-0095 | 2012-089_1 | Tray 01 B | H11 | HE11EE012156.002.11 | 4.84 | 0.02 | 2.39 | 0.08 | 1.45 | 92.08 | 2.07 | 0.12 | 0.15 | 0.48 | 0.68 | 0.01 | 0.23 | |
| 2012-0089-0096 | 2012-089_1 | Tray 01 B | H12 | HE11EE012156.002.12 | 4.77 | 0.02 | 2.38 | 0.08 | 1.39 | 91.63 | 2.62 | 0.14 | 0.16 | 0.52 | 0.61 | 0.01 | 0.21 | |

FIG. 15e

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0097 | 2012-08_2 | Tray 02 A | A1 | HE11EE012156.003.01 | 4.34 | 0.02 | 2.20 | 0.08 | 1.22 | 93.11 | 1.57 | 0.14 | 0.15 | 0.51 | 0.54 | 0.01 | 0.21 | |
| 2012-0089-0098 | 2012-08_2 | Tray 02 A | A2 | HE11EE012156.003.02 | 3.83 | 0.03 | 2.29 | 0.05 | 0.66 | 93.24 | 1.68 | 0.19 | 0.10 | 0.66 | 0.38 | 0.03 | 0.19 | |
| 2012-0089-0099 | 2012-08_2 | Tray 02 A | A3 | HE11EE012156.003.03 | 4.24 | 0.02 | 2.14 | 0.08 | 1.27 | 92.98 | 1.77 | 0.14 | 0.14 | 0.52 | 0.52 | 0.01 | 0.20 | |
| 2012-0089-0100 | 2012-08_2 | Tray 02 A | A4 | HE11EE012156.003.04 | 4.43 | 0.02 | 2.60 | 0.11 | 1.08 | 92.39 | 1.95 | 0.19 | 0.15 | 0.50 | 0.43 | 0.01 | 0.15 | |
| 2012-0089-0101 | 2012-08_2 | Tray 02 A | A5 | HE11EE012156.003.05 | 3.99 | 0.02 | 2.26 | 0.08 | 0.97 | 93.19 | 1.48 | 0.16 | 0.12 | 0.55 | 0.45 | 0.01 | 0.19 | |
| 2012-0089-0102 | 2012-08_2 | Tray 02 A | A6 | HE11EE012156.003.06 | 4.15 | 0.02 | 2.29 | 0.05 | 1.07 | 92.61 | 2.15 | 0.16 | 0.13 | 0.53 | 0.47 | 0.01 | 0.17 | |
| 2012-0089-0103 | 2012-08_2 | Tray 02 A | A7 | HE11EE012156.003.07 | 3.77 | 0.02 | 2.16 | 0.07 | 0.89 | 93.19 | 1.54 | 0.17 | 0.11 | 0.58 | 0.43 | | 0.16 | |
| 2012-0089-0104 | 2012-08_2 | Tray 02 A | A8 | HE11EE012156.003.08 | 4.36 | 0.02 | 2.09 | 0.07 | 1.32 | 93.46 | 1.21 | 0.12 | 0.14 | 0.52 | 0.60 | 0.01 | 0.22 | |
| 2012-0089-0105 | 2012-08_2 | Tray 02 A | A9 | HE11EE012156.003.09 | 4.62 | 0.02 | 2.65 | 0.10 | 1.14 | 91.85 | 2.34 | 0.23 | 0.17 | 0.53 | 0.46 | | 0.16 | |
| 2012-0089-0106 | 2012-08_2 | Tray 02 A | A10 | HE11EE012156.003.10 | 4.34 | 0.02 | 2.24 | 0.08 | 1.28 | 92.80 | 1.66 | 0.16 | 0.15 | 0.47 | 0.50 | 0.01 | 0.16 | |
| 2012-0089-0107 | 2012-08_2 | Tray 02 A | A11 | HE11EE012156.003.11 | 4.13 | 0.02 | 2.51 | 0.09 | 0.89 | 93.03 | 1.73 | 0.18 | 0.12 | 0.53 | 0.42 | 0.01 | 0.16 | |
| 2012-0089-0108 | 2012-08_2 | Tray 02 A | A12 | HE11EE012156.003.12 | 4.20 | 0.03 | 2.83 | 0.07 | 0.72 | 92.37 | 2.20 | 0.22 | 0.12 | 0.59 | 0.35 | 0.02 | 0.16 | |
| 2012-0089-0109 | 2012-08_2 | Tray 02 A | B1 | HE11EE012156.007.01 | 4.72 | 0.02 | 2.43 | 0.08 | 1.37 | 91.80 | 2.70 | 0.16 | 0.15 | 0.49 | 0.55 | 0.01 | 0.20 | |
| 2012-0089-0110 | 2012-08_2 | Tray 02 A | B2 | HE11EE012156.007.02 | 4.52 | 0.03 | 2.04 | 0.04 | 1.41 | 92.52 | 1.82 | 0.11 | 0.16 | 0.52 | 0.66 | 0.01 | 0.23 | 0.01 |
| 2012-0089-0111 | 2012-08_2 | Tray 02 A | B3 | HE11EE012156.007.03 | 4.48 | 0.02 | 2.37 | 0.03 | 1.13 | 92.68 | 1.79 | 0.14 | 0.11 | 0.59 | 0.60 | 0.02 | 0.22 | |
| 2012-0089-0112 | 2012-08_2 | Tray 02 A | B4 | HE11EE012156.007.04 | 4.49 | 0.02 | 2.43 | 0.05 | 1.18 | 90.72 | 3.64 | 0.18 | 0.13 | 0.52 | 0.50 | 0.01 | 0.19 | |
| 2012-0089-0113 | 2012-08_2 | Tray 02 A | B5 | HE11EE012156.007.05 | 3.98 | 0.02 | 2.44 | 0.07 | 0.77 | 92.54 | 2.26 | 0.18 | 0.10 | 0.66 | 0.44 | 0.02 | 0.21 | 0.01 |
| 2012-0089-0114 | 2012-08_2 | Tray 02 A | B6 | HE11EE012156.007.06 | 4.02 | 0.02 | 2.23 | 0.08 | 0.95 | 92.19 | 2.73 | 0.13 | 0.11 | 0.54 | 0.52 | 0.02 | 0.20 | |
| 2012-0089-0115 | 2012-08_2 | Tray 02 A | B7 | HE11EE012156.007.07 | 4.24 | 0.02 | 2.34 | 0.08 | 1.04 | 93.02 | 1.86 | 0.14 | 0.11 | 0.44 | 0.53 | 0.01 | 0.21 | |
| 2012-0089-0116 | 2012-08_2 | Tray 02 A | B8 | HE11EE012156.007.08 | 4.47 | 0.02 | 2.15 | 0.04 | 1.30 | 92.50 | 1.88 | 0.14 | 0.13 | 0.50 | 0.64 | 0.01 | 0.22 | |
| 2012-0089-0117 | 2012-08_2 | Tray 02 A | B9 | HE11EE012156.007.09 | 5.12 | 0.02 | 2.51 | 0.08 | 1.57 | 91.39 | 2.58 | 0.11 | 0.13 | 0.40 | 0.63 | 0.01 | 0.21 | |
| 2012-0089-0118 | 2012-08_2 | Tray 02 A | B10 | HE11EE012156.007.10 | 4.35 | 0.02 | 2.02 | 0.08 | 1.33 | 93.01 | 1.61 | 0.10 | 0.17 | 0.49 | 0.63 | 0.01 | 0.21 | 0.01 |
| 2012-0089-0119 | 2012-08_2 | Tray 02 A | B11 | HE11EE012156.007.11 | 3.87 | 0.02 | 2.30 | 0.09 | 0.65 | 93.09 | 1.89 | 0.14 | 0.14 | 0.53 | 0.42 | 0.01 | 0.16 | |
| 2012-0089-0120 | 2012-08_2 | Tray 02 A | B12 | HE11EE012156.007.12 | 4.36 | 0.02 | 2.46 | 0.04 | 0.98 | 92.74 | 1.86 | 0.16 | 0.11 | 0.54 | 0.56 | 0.02 | 0.23 | |
| 2012-0089-0121 | 2012-08_2 | Tray 02 A | C1 | HE11EE012414.003.01 | 2.90 | 0.02 | 2.11 | 0.07 | 0.34 | 94.24 | 1.79 | 0.14 | 0.05 | 0.67 | 0.25 | 0.02 | 0.13 | |
| 2012-0089-0123 | 2012-08_2 | Tray 02 A | C2 | HE11EE012414.003.02 | 2.78 | 0.02 | 1.96 | 0.07 | 0.30 | 93.96 | 2.03 | 0.12 | 0.04 | 0.74 | 0.28 | 0.03 | 0.18 | 0.01 |
| 2012-0089-0123 | 2012-08_2 | Tray 02 A | C3 | HE11EE012414.003.03 | 2.77 | 0.02 | 1.99 | 0.04 | 0.30 | 93.54 | 2.38 | 0.17 | 0.05 | 0.75 | 0.25 | 0.03 | 0.17 | |
| 2012-0089-0124 | 2012-08_2 | Tray 02 A | C4 | HE11EE012414.003.04 | 2.69 | 0.02 | 1.93 | 0.07 | 0.27 | 94.17 | 1.91 | 0.12 | 0.04 | 0.76 | 0.28 | 0.03 | 0.16 | |
| 2012-0089-0125 | 2012-08_2 | Tray 02 A | C5 | HE11EE012414.003.05 | 3.19 | 0.03 | 2.24 | 0.04 | 0.42 | 93.54 | 2.11 | 0.12 | 0.08 | 0.70 | 0.29 | 0.02 | 0.15 | |
| 2012-0089-0126 | 2012-08_2 | Tray 02 A | C6 | HE11EE012414.003.06 | 2.90 | 0.02 | 2.08 | 0.06 | 0.32 | 93.13 | 2.57 | 0.17 | 0.05 | 0.77 | 0.26 | 0.01 | 0.17 | |
| 2012-0089-0127 | 2012-08_2 | Tray 02 A | C7 | HE11EE012414.003.07 | 2.78 | 0.02 | 1.85 | 0.07 | 0.40 | 94.26 | 1.74 | 0.12 | 0.05 | 0.71 | 0.29 | 0.02 | 0.17 | |
| 2012-0089-0128 | 2012-08_2 | Tray 02 A | C8 | HE11EE012414.003.08 | 2.43 | 0.02 | 1.72 | 0.07 | 0.25 | 94.55 | 1.79 | 0.11 | 0.04 | 0.75 | 0.24 | 0.03 | 0.16 | |
| 2012-0089-0129 | 2012-08_2 | Tray 02 A | C9 | HE11EE012414.003.09 | 2.74 | 0.02 | 2.01 | 0.07 | 0.30 | 94.05 | 1.98 | 0.10 | 0.04 | 0.72 | 0.23 | 0.03 | 0.14 | |

FIG. 15f

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0130 | 2012-089_2 | Tray 02 A | C10 | HE11EE012414.003.16 | 2.85 | 0.02 | 2.05 | 0.08 | 0.30 | 93.87 | 2.19 | 0.15 | 0.05 | 0.74 | 0.26 | 0.03 | 0.17 | |
| 2012-0089-0131 | 2012-089_2 | Tray 02 A | C11 | HE11EE012414.003.11 | 2.96 | 0.03 | 2.23 | 0.08 | 0.31 | 94.09 | 1.81 | 0.15 | 0.05 | 0.68 | 0.22 | 0.03 | 0.12 | |
| 2012-0089-0132 | 2012-089_2 | Tray 02 A | C12 | HE11EE012414.003.12 | 2.63 | 0.02 | 1.90 | 0.07 | 0.30 | 94.62 | 1.55 | 0.12 | 0.04 | 0.70 | 0.23 | 0.03 | 0.14 | |
| 2012-0089-0133 | 2012-089_2 | Tray 02 A | D1 | HE11EE012414.003.13 | 3.01 | 0.02 | 2.08 | 0.03 | 0.40 | 93.72 | 2.08 | 0.21 | 0.05 | 0.71 | 0.29 | 0.03 | 0.17 | |
| 2012-0089-0134 | 2012-089_2 | Tray 02 A | D2 | HE11EE012414.003.14 | 2.79 | 0.02 | 1.95 | 0.05 | 0.36 | 93.89 | 2.04 | 0.13 | 0.05 | 0.73 | 0.26 | 0.03 | 0.14 | |
| 2012-0089-0135 | 2012-089_2 | Tray 02 A | D3 | HE11EE012414.003.15 | 2.85 | 0.03 | 2.18 | 0.10 | 0.25 | 92.90 | 2.51 | 0.20 | 0.07 | 0.82 | 0.19 | 0.03 | 0.13 | |
| 2012-0089-0136 | 2012-089_2 | Tray 02 A | D4 | HE11EE012414.003.16 | 2.67 | 0.02 | 1.82 | 0.04 | 0.35 | 94.73 | 1.42 | 0.11 | 0.05 | 0.66 | 0.26 | 0.02 | 0.14 | |
| 2012-0089-0137 | 2012-089_2 | Tray 02 A | D5 | HE11EE012414.003.17 | 2.70 | 0.02 | 1.87 | 0.05 | 0.34 | 94.35 | 1.84 | 0.12 | 0.05 | 0.71 | 0.27 | 0.03 | 0.16 | |
| 2012-0089-0138 | 2012-089_2 | Tray 02 A | D6 | HE11EE012414.003.18 | 2.63 | 0.02 | 1.88 | 0.05 | 0.31 | 93.80 | 2.30 | 0.14 | 0.04 | 0.72 | 0.29 | 0.03 | 0.16 | |
| 2012-0089-0139 | 2012-089_2 | Tray 02 A | D7 | HE11EE012414.003.19 | 2.80 | 0.02 | 2.00 | 0.06 | 0.31 | 93.60 | 2.31 | 0.16 | 0.05 | 0.76 | 0.25 | 0.03 | 0.17 | |
| 2012-0089-0140 | 2012-089_2 | Tray 02 A | D8 | HE11EE012414.003.20 | 2.98 | 0.03 | 2.05 | 0.04 | 0.39 | 93.48 | 2.19 | 0.14 | 0.05 | 0.79 | 0.29 | 0.03 | 0.17 | |
| 2012-0089-0141 | 2012-089_2 | Tray 02 A | D9 | HE11EE012414.003.21 | 2.94 | 0.02 | 2.01 | 0.04 | 0.41 | 94.02 | 1.84 | 0.11 | 0.05 | 0.71 | 0.28 | 0.03 | 0.16 | |
| 2012-0089-0142 | 2012-089_2 | Tray 02 A | D10 | HE11EE012414.003.22 | 2.39 | 0.02 | 1.72 | 0.03 | 0.23 | 94.73 | 1.61 | 0.12 | 0.04 | 0.76 | 0.23 | 0.02 | 0.16 | |
| 2012-0089-0143 | 2012-089_2 | Tray 02 A | D11 | HE11EE012414.003.23 | 3.04 | 0.03 | 2.09 | 0.07 | 0.43 | 93.60 | 2.20 | 0.16 | 0.06 | 0.73 | 0.27 | 0.03 | 0.16 | |
| 2012-0089-0144 | 2012-089_2 | Tray 02 A | D12 | HE11EE012414.003.24 | 2.53 | 0.02 | 1.84 | 0.04 | 0.26 | 94.32 | 1.93 | 0.14 | 0.04 | 0.79 | 0.23 | 0.02 | 0.15 | |
| 2012-0089-0145 | 2012-089_2 | Tray 02 B | E1 | HE11EE012931.001.01 | 2.96 | 0.02 | 1.94 | 0.05 | 0.49 | 94.30 | 1.80 | 0.10 | 0.05 | 0.59 | 0.34 | 0.03 | 0.15 | 0.01 |
| 2012-0089-0146 | 2012-089_2 | Tray 02 B | E2 | HE11EE012931.001.02 | 2.76 | 0.01 | 1.73 | 0.06 | 0.45 | 94.58 | 1.68 | 0.08 | 0.05 | 0.64 | 0.34 | 0.03 | 0.17 | |
| 2012-0089-0147 | 2012-089_2 | Tray 02 B | E3 | HE11EE012931.001.03 | 3.19 | 0.02 | 2.04 | 0.06 | 0.55 | 94.01 | 1.86 | 0.08 | 0.06 | 0.57 | 0.37 | 0.02 | 0.16 | |
| 2012-0089-0148 | 2012-089_2 | Tray 02 B | E4 | HE11EE012931.001.04 | 2.57 | 0.01 | 1.59 | 0.05 | 0.45 | 95.05 | 1.41 | 0.07 | 0.04 | 0.61 | 0.31 | 0.02 | 0.16 | |
| 2012-0089-0149 | 2012-089_2 | Tray 02 B | E5 | HE11EE012931.001.05 | 2.94 | 0.02 | 1.95 | 0.06 | 0.42 | 94.37 | 1.85 | 0.10 | 0.04 | 0.62 | 0.32 | 0.03 | 0.18 | |
| 2012-0089-0150 | 2012-089_2 | Tray 02 B | E6 | HE11EE012931.001.06 | 2.70 | 0.02 | 1.89 | 0.05 | 0.33 | 94.68 | 1.49 | 0.07 | 0.05 | 0.68 | 0.34 | 0.02 | 0.18 | |
| 2012-0089-0151 | 2012-089_2 | Tray 02 B | E7 | HE11EE012931.001.07 | 2.79 | 0.01 | 1.76 | 0.04 | 0.45 | 94.64 | 1.60 | 0.08 | 0.04 | 0.58 | 0.33 | 0.02 | 0.16 | 0.01 |
| 2012-0089-0152 | 2012-089_2 | Tray 02 B | E8 | HE11EE012931.001.08 | 2.59 | 0.01 | 1.66 | 0.06 | 0.41 | 94.95 | 1.44 | 0.08 | 0.04 | 0.65 | 0.30 | 0.03 | 0.18 | |
| 2012-0089-0153 | 2012-089_2 | Tray 02 B | E9 | HE11EE012931.001.09 | 2.72 | 0.01 | 1.71 | 0.05 | 0.44 | 94.30 | 1.78 | 0.12 | 0.04 | 0.59 | 0.34 | 0.03 | 0.17 | 0.01 |
| 2012-0089-0154 | 2012-089_2 | Tray 02 B | E10 | HE11EE012931.001.10 | 2.61 | 0.01 | 1.65 | 0.05 | 0.44 | 94.86 | 1.53 | 0.08 | 0.04 | 0.62 | 0.31 | 0.02 | 0.16 | |
| 2012-0089-0155 | 2012-089_2 | Tray 02 B | E11 | HE11EE012931.001.11 | 2.77 | 0.02 | 1.78 | 0.05 | 0.43 | 94.16 | 2.09 | 0.09 | 0.05 | 0.63 | 0.32 | 0.02 | 0.17 | |
| 2012-0089-0156 | 2012-089_2 | Tray 02 B | E12 | HE11EE012931.001.12 | 2.70 | 0.02 | 1.71 | 0.05 | 0.46 | 94.56 | 1.76 | 0.09 | 0.04 | 0.62 | 0.33 | 0.02 | 0.16 | |
| 2012-0089-0157 | 2012-089_2 | Tray 02 B | F1 | HE11EE012931.001.13 | 2.76 | 0.01 | 1.74 | 0.05 | 0.46 | 94.28 | 2.01 | 0.11 | 0.05 | 0.61 | 0.33 | 0.02 | 0.17 | |
| 2012-0089-0158 | 2012-089_2 | Tray 02 B | F2 | HE11EE012931.001.14 | 2.80 | 0.02 | 1.80 | 0.06 | 0.43 | 94.62 | 1.57 | 0.09 | 0.05 | 0.84 | 0.32 | 0.03 | 0.18 | |
| 2012-0089-0159 | 2012-089_2 | Tray 02 B | F3 | HE11EE012931.001.15 | 2.93 | 0.02 | 1.95 | 0.04 | 0.40 | 94.14 | 1.84 | 0.11 | 0.05 | 0.67 | 0.34 | 0.03 | 0.16 | |
| 2012-0089-0160 | 2012-089_2 | Tray 02 B | F4 | HE11EE012931.001.16 | 2.94 | 0.02 | 1.88 | 0.06 | 0.50 | 94.49 | 1.51 | 0.09 | 0.05 | 0.64 | 0.33 | 0.03 | 0.20 | |
| 2012-0089-0161 | 2012-089_2 | Tray 02 B | F5 | HE11EE012931.001.17 | 2.71 | 0.01 | 1.71 | 0.05 | 0.47 | 94.95 | 1.44 | 0.09 | 0.04 | 0.59 | 0.32 | 0.02 | 0.18 | |
| 2012-0089-0162 | 2012-089_2 | Tray 02 B | F6 | HE11EE012931.001.18 | 2.85 | 0.02 | 1.80 | 0.06 | 0.46 | 94.35 | 1.75 | 0.10 | 0.05 | 0.65 | 0.34 | 0.03 | 0.18 | 0.01 |

FIG. 15g

| Lab ID | Plate | Tray | Pos | Source | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0089-0163 | 2012-089_2 | Tray 02 B | F7 | HE11EE012931.003.19 | 2.87 | 0.02 | 1.84 | 0.04 | 0.47 | 94.22 | 1.87 | 0.08 | 0.05 | 0.63 | 0.33 | 0.03 | 0.17 | |
| 2012-0089-0164 | 2012-089_2 | Tray 02 B | F8 | HE11EE012931.003.20 | 2.88 | 0.02 | 1.84 | 0.05 | 0.46 | 94.47 | 1.65 | 0.08 | 0.05 | 0.64 | 0.35 | 0.02 | 0.17 | |
| 2012-0089-0165 | 2012-089_2 | Tray 02 B | F9 | HE11EE012931.003.21 | 2.82 | 0.01 | 1.88 | 0.05 | 0.41 | 94.97 | 1.46 | 0.08 | 0.04 | 0.60 | 0.31 | 0.02 | 0.16 | |
| 2012-0089-0166 | 2012-089_2 | Tray 02 B | F10 | HE11EE012931.003.21 | 2.82 | 0.02 | 1.75 | 0.05 | 0.46 | 94.78 | 1.48 | 0.09 | 0.05 | 0.63 | 0.31 | 0.02 | 0.15 | |
| 2012-0089-0167 | 2012-089_2 | Tray 02 B | F11 | HE11EE012931.003.22 | 2.74 | 0.02 | 1.84 | 0.05 | 0.45 | 94.55 | 1.54 | 0.09 | 0.05 | 0.63 | 0.35 | 0.03 | 0.19 | |
| 2012-0089-0168 | 2012-089_2 | Tray 02 B | F12 | HE11EE012931.003.23 | 2.89 | 0.01 | 1.89 | 0.06 | 0.43 | 94.56 | 1.83 | 0.08 | 0.04 | 0.59 | 0.32 | 0.02 | 0.16 | 0.01 |
| 2012-0089-0169 | 2012-089_2 | Tray 02 B | G1 | HE11EE012934.003.01 | 2.67 | 0.01 | 1.69 | 0.03 | 0.55 | 94.56 | 1.64 | 0.10 | 0.06 | 0.57 | 0.32 | 0.02 | 0.13 | |
| 2012-0089-0170 | 2012-089_2 | Tray 02 B | G2 | HE11EE012934.003.02 | 2.76 | 0.01 | 1.69 | 0.06 | 0.60 | 94.33 | 1.50 | 0.09 | 0.06 | 0.61 | 0.37 | 0.02 | 0.15 | |
| 2012-0089-0171 | 2012-089_2 | Tray 02 B | G3 | HE11EE012934.003.03 | 2.89 | 0.02 | 1.89 | 0.06 | 0.60 | 94.62 | 2.36 | 0.09 | 0.06 | 0.58 | 0.38 | 0.02 | 0.15 | |
| 2012-0089-0172 | 2012-089_2 | Tray 02 B | G4 | HE11EE012934.003.04 | 3.20 | 0.02 | 1.87 | 0.03 | 0.72 | 93.46 | 1.53 | 0.09 | 0.07 | 0.58 | 0.32 | 0.02 | 0.13 | |
| 2012-0089-0173 | 2012-089_2 | Tray 02 B | G5 | HE11EE012934.003.05 | 2.65 | 0.01 | 1.80 | 0.03 | 0.53 | 94.83 | 1.51 | 0.09 | 0.05 | 0.61 | 0.32 | 0.02 | 0.16 | |
| 2012-0089-0174 | 2012-089_2 | Tray 02 B | G6 | HE11EE012934.003.06 | 2.78 | 0.01 | 1.85 | 0.03 | 0.57 | 94.71 | 1.61 | 0.08 | 0.06 | 0.62 | 0.33 | 0.02 | 0.18 | |
| 2012-0089-0175 | 2012-089_2 | Tray 02 B | G7 | HE11EE012934.003.07 | 2.66 | 0.01 | 1.62 | 0.03 | 0.47 | 94.75 | 1.35 | 0.09 | 0.05 | 0.60 | 0.36 | 0.02 | 0.14 | |
| 2012-0089-0176 | 2012-089_2 | Tray 02 B | G8 | HE11EE012934.003.08 | 2.72 | 0.01 | 1.80 | 0.02 | 0.57 | 94.96 | 2.10 | 0.09 | 0.07 | 0.59 | 0.33 | 0.02 | 0.15 | |
| 2012-0089-0177 | 2012-089_2 | Tray 02 B | G9 | HE11EE012934.003.09 | 3.14 | 0.02 | 1.82 | 0.06 | 0.70 | 93.75 | 1.93 | 0.09 | 0.06 | 0.58 | 0.39 | 0.02 | 0.13 | |
| 2012-0089-0178 | 2012-089_2 | Tray 02 B | G10 | HE11EE012934.003.10 | 2.83 | 0.01 | 1.78 | 0.03 | 0.53 | 94.26 | 1.78 | 0.11 | 0.06 | 0.53 | 0.32 | 0.02 | 0.15 | 0.01 |
| 2012-0089-0179 | 2012-089_2 | Tray 02 B | G11 | HE11EE012934.003.11 | 2.86 | 0.02 | 1.67 | 0.03 | 0.60 | 94.40 | 2.16 | 0.08 | 0.08 | 0.55 | 0.37 | 0.02 | 0.14 | |
| 2012-0089-0180 | 2012-089_2 | Tray 02 B | G12 | HE11EE012934.003.12 | 3.35 | 0.02 | 1.96 | 0.04 | 0.88 | 93.53 | 2.16 | 0.11 | 0.08 | 0.55 | 0.38 | 0.02 | 0.18 | 0.01 |
| 2012-0089-0181 | 2012-089_2 | Tray 02 B | H1 | HE11EE012934.003.13 | 2.77 | 0.01 | 1.64 | 0.04 | 0.54 | 94.83 | 1.59 | 0.08 | 0.05 | 0.61 | 0.38 | 0.02 | 0.16 | |
| 2012-0089-0182 | 2012-089_2 | Tray 02 B | H2 | HE11EE012934.003.14 | 2.78 | 0.01 | 1.80 | 0.04 | 0.59 | 94.75 | 1.53 | 0.08 | 0.06 | 0.59 | 0.35 | 0.02 | 0.16 | |
| 2012-0089-0183 | 2012-089_2 | Tray 02 B | H3 | HE11EE012934.003.15 | 2.97 | 0.01 | 1.72 | 0.03 | 0.64 | 94.74 | 1.31 | 0.07 | 0.06 | 0.59 | 0.36 | 0.02 | 0.16 | |
| 2012-0089-0184 | 2012-089_2 | Tray 02 B | H4 | HE11EE012934.003.16 | 3.42 | 0.02 | 1.95 | 0.03 | 0.78 | 93.29 | 2.30 | 0.10 | 0.08 | 0.58 | 0.42 | 0.02 | 0.17 | |
| 2012-0089-0185 | 2012-089_2 | Tray 02 B | H5 | HE11EE012934.003.16 | 2.58 | 0.02 | 1.50 | 0.03 | 0.49 | 94.83 | 1.80 | 0.08 | 0.05 | 0.62 | 0.34 | 0.02 | 0.16 | |
| 2012-0089-0186 | 2012-089_2 | Tray 02 B | H6 | HE11EE012934.003.17 | 3.27 | 0.01 | 1.86 | 0.03 | 0.60 | 93.70 | 2.07 | 0.10 | 0.07 | 0.58 | 0.38 | 0.02 | 0.16 | |
| 2012-0089-0187 | 2012-089_2 | Tray 02 B | H7 | HE11EE012934.003.18 | 3.25 | 0.02 | 1.83 | 0.04 | 0.82 | 93.87 | 1.90 | 0.09 | 0.06 | 0.56 | 0.37 | 0.02 | 0.14 | |
| 2012-0089-0188 | 2012-089_2 | Tray 02 B | H8 | HE11EE012934.003.19 | 3.07 | 0.02 | 1.78 | 0.03 | 0.69 | 93.98 | 1.95 | 0.10 | 0.07 | 0.60 | 0.36 | 0.02 | 0.16 | |
| 2012-0089-0189 | 2012-089_2 | Tray 02 B | H9 | HE11EE012934.003.20 | 2.97 | 0.02 | 1.71 | 0.03 | 0.66 | 94.07 | 1.90 | 0.10 | 0.08 | 0.62 | 0.36 | 0.02 | 0.16 | |
| 2012-0089-0190 | 2012-089_2 | Tray 02 B | H10 | HE11EE012934.003.21 | 2.59 | 0.01 | 1.54 | 0.05 | 0.49 | 94.94 | 1.53 | 0.09 | 0.05 | 0.60 | 0.34 | 0.02 | 0.16 | |
| 2012-0089-0191 | 2012-089_2 | Tray 02 B | H11 | HE11EE012934.003.22 | 3.11 | 0.01 | 1.73 | 0.03 | 0.77 | 93.99 | 1.89 | 0.09 | 0.07 | 0.59 | 0.37 | 0.02 | 0.15 | |
| 2012-0089-0192 | 2012-089_2 | Tray 02 B | H12 | HE11EE012934.003.23 | 2.83 | 0.01 | 1.62 | 0.03 | 0.63 | 94.42 | 1.78 | 0.09 | 0.08 | 0.58 | 0.36 | 0.02 | 0.16 | |
| 2012-0089-0193 | 2012-089_2 | Tray 02 B | H12 | HE11EE012934.003.24 | 2.95 | 0.01 | 1.67 | 0.06 | 0.68 | 94.39 | 1.69 | 0.08 | 0.06 | 0.59 | 0.37 | 0.02 | 0.15 | |

*FIG. 15h*

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0001 | 2012-092_1 | Tray 01 A | A1 | HE11EE0122246.005.01 | 5.60 | 0.02 | 2.48 | 0.10 | 1.92 | 91.26 | 2.41 | 0.05 | 0.18 | 0.34 | 0.70 | 0.01 | 0.30 | |
| 2012-0092-0002 | 2012-092_1 | Tray 01 A | A2 | HE11EE0122246.005.02 | 4.04 | 0.02 | 2.73 | 0.11 | 0.58 | 92.18 | 2.76 | 0.05 | 0.09 | 0.44 | 0.36 | 0.02 | 0.21 | |
| 2012-0092-0003 | 2012-092_1 | Tray 01 A | A3 | HE11EE0122246.005.03 | 3.62 | 0.02 | 2.15 | 0.08 | 0.75 | 92.96 | 2.47 | 0.05 | 0.09 | 0.55 | 0.38 | 0.02 | 0.22 | |
| 2012-0092-0004 | 2012-092_1 | Tray 01 A | A4 | HE11EE0122246.005.04 | 4.97 | 0.01 | 1.78 | 0.08 | 1.95 | 91.66 | 2.54 | 0.07 | 0.20 | 0.47 | 0.74 | 0.01 | 0.38 | |
| 2012-0092-0005 | 2012-092_1 | Tray 01 A | A5 | HE11EE0122246.005.05 | 5.15 | 0.03 | 3.06 | 0.12 | 1.09 | 90.91 | 2.78 | 0.07 | 0.12 | 0.36 | 0.55 | 0.01 | 0.27 | |
| 2012-0092-0006 | 2012-092_1 | Tray 01 A | A6 | HE11EE0122246.005.06 | 3.45 | 0.02 | 2.30 | 0.07 | 0.57 | 92.91 | 2.57 | 0.06 | 0.05 | 0.57 | 0.31 | 0.03 | 0.20 | |
| 2012-0092-0007 | 2012-092_1 | Tray 01 A | A7 | HE11EE0122246.005.07 | 3.99 | 0.02 | 3.01 | 0.16 | 0.41 | 93.00 | 2.04 | 0.08 | 0.05 | 0.48 | 0.27 | 0.03 | 0.19 | |
| 2012-0092-0008 | 2012-092_1 | Tray 01 A | A8 | HE11EE0122246.005.08 | 4.24 | 0.03 | 2.85 | 0.12 | 0.54 | 91.93 | 2.87 | 0.10 | 0.09 | 0.45 | 0.40 | 0.02 | 0.23 | |
| 2012-0092-0009 | 2012-092_1 | Tray 01 A | A9 | HE11EE0122246.005.09 | 7.02 | 0.02 | 2.88 | 0.09 | 2.79 | 89.66 | 2.61 | 0.06 | 0.26 | 0.29 | 0.91 | | 0.35 | |
| 2012-0092-0010 | 2012-092_1 | Tray 01 A | A10 | HE11EE0122246.005.10 | 5.87 | 0.02 | 2.43 | 0.08 | 2.20 | 90.45 | 2.98 | 0.07 | 0.20 | 0.33 | 0.70 | | 0.31 | |
| 2012-0092-0011 | 2012-092_1 | Tray 01 A | A11 | HE11EE0122246.005.11 | 5.46 | 0.03 | 2.40 | 0.08 | 1.91 | 91.01 | 2.71 | 0.09 | 0.22 | 0.34 | 0.64 | 0.01 | 0.27 | |
| 2012-0092-0012 | 2012-092_1 | Tray 01 A | A12 | HE11EE0122246.005.12 | 5.88 | 0.02 | 2.81 | 0.09 | 1.86 | 90.83 | 2.80 | 0.05 | 0.19 | 0.28 | 0.76 | 0.01 | 0.34 | |
| 2012-0092-0013 | 2012-092_1 | Tray 01 B | B1 | HE11EE0122246.005.13 | 6.27 | 0.03 | 2.42 | 0.08 | 2.45 | 90.62 | 2.42 | 0.05 | 0.23 | 0.32 | 0.82 | 0.01 | 0.31 | |
| 2012-0092-0014 | 2012-092_1 | Tray 01 B | B2 | HE11EE0122246.005.14 | 3.95 | 0.01 | 1.70 | 0.05 | 1.32 | 93.57 | 1.81 | 0.06 | 0.10 | 0.50 | 0.58 | 0.02 | 0.24 | |
| 2012-0092-0015 | 2012-092_1 | Tray 01 B | B3 | HE11EE0122246.005.15 | 3.98 | 0.02 | 3.02 | 0.13 | 0.40 | 92.88 | 2.28 | 0.05 | 0.07 | 0.44 | 0.29 | 0.02 | 0.17 | |
| 2012-0092-0016 | 2012-092_1 | Tray 01 B | B4 | HE11EE0122246.005.16 | 5.44 | 0.01 | 1.82 | 0.06 | 2.19 | 90.92 | 2.53 | 0.19 | 0.34 | 0.48 | 0.78 | 0.01 | 0.30 | |
| 2012-0092-0017 | 2012-092_1 | Tray 01 B | B5 | HE11EE0122246.005.17 | 3.07 | 0.02 | 2.11 | 0.04 | 0.44 | 93.35 | 2.40 | 0.09 | 0.09 | 0.61 | 0.27 | 0.02 | 0.14 | |
| 2012-0092-0018 | 2012-092_1 | Tray 01 B | B6 | HE11EE0122246.005.18 | 3.67 | 0.02 | 1.78 | 0.07 | 1.00 | 93.20 | 2.11 | 0.10 | 0.18 | 0.52 | 0.50 | 0.01 | 0.20 | |
| 2012-0092-0019 | 2012-092_1 | Tray 01 B | B7 | HE11EE0122246.005.19 | 5.40 | 0.02 | 2.39 | 0.10 | 1.88 | 91.00 | 2.81 | 0.08 | 0.18 | 0.35 | 0.68 | 0.01 | 0.28 | |
| 2012-0092-0020 | 2012-092_1 | Tray 01 B | B8 | HE11EE0122246.005.20 | 4.14 | 0.02 | 3.01 | 0.11 | 0.51 | 92.14 | 2.88 | 0.06 | 0.09 | 0.43 | 0.33 | 0.03 | 0.19 | |
| 2012-0092-0021 | 2012-092_1 | Tray 01 B | B9 | HE11EE0122246.005.21 | 4.87 | 0.03 | 3.02 | 0.11 | 0.96 | 90.93 | 3.36 | 0.08 | 0.11 | 0.38 | 0.46 | 0.01 | 0.25 | |
| 2012-0092-0022 | 2012-092_1 | Tray 01 B | B10 | HE11EE0122246.005.22 | 5.89 | 0.03 | 1.77 | 0.05 | 2.74 | 90.94 | 2.29 | 0.08 | 0.26 | 0.46 | 0.83 | 0.02 | 0.28 | |
| 2012-0092-0023 | 2012-092_1 | Tray 01 B | B11 | HE11EE0122246.005.23 | 4.20 | 0.01 | 2.33 | 0.06 | 0.96 | 92.43 | 2.68 | 0.07 | 0.13 | 0.55 | 0.50 | 0.01 | 0.25 | |
| 2012-0092-0024 | 2012-092_1 | Tray 01 B | B12 | HE11EE0122246.005.24 | 5.44 | 0.02 | 2.52 | 0.11 | 1.77 | 90.89 | 2.93 | 0.09 | 0.18 | 0.30 | 0.68 | 0.01 | 0.29 | |
| 2012-0092-0025 | 2012-092_1 | Tray 01 C | C1 | HE11EE0122246.005.25 | 5.54 | 0.02 | 1.71 | 0.03 | 2.36 | 90.56 | 2.47 | 0.13 | 0.28 | 0.56 | 0.84 | 0.03 | 0.32 | |
| 2012-0092-0026 | 2012-092_1 | Tray 01 C | C2 | HE11EE0122246.005.26 | 3.73 | 0.02 | 2.79 | 0.12 | 0.38 | 92.80 | 2.50 | 0.08 | 0.08 | 0.50 | 0.29 | 0.01 | 0.18 | |
| 2012-0092-0027 | 2012-092_1 | Tray 01 C | C3 | HE11EE0122246.005.27 | 5.26 | 0.03 | 2.27 | 0.09 | 1.80 | 91.28 | 2.68 | 0.06 | 0.16 | 0.35 | 0.71 | 0.01 | 0.30 | |
| 2012-0092-0028 | 2012-092_1 | Tray 01 C | C4 | HE11EE0122246.005.28 | 4.53 | 0.03 | 2.75 | 0.13 | 0.94 | 92.50 | 2.16 | 0.08 | 0.10 | 0.37 | 0.47 | 0.02 | 0.24 | |
| 2012-0092-0029 | 2012-092_1 | Tray 01 C | C5 | HE11EE0122246.005.29 | 3.04 | 0.02 | 2.25 | 0.04 | 0.31 | 93.36 | 2.33 | 0.08 | 0.08 | 0.67 | 0.24 | 0.02 | 0.15 | |
| 2012-0092-0030 | 2012-092_1 | Tray 01 C | C6 | HE11EE0122246.005.30 | 5.20 | 0.03 | 2.89 | 0.10 | 1.30 | 91.73 | 2.13 | 0.11 | 0.25 | 0.34 | 0.65 | 0.03 | 0.28 | |
| 2012-0092-0031 | 2012-092_1 | Tray 01 C | C7 | HE11EE0122246.005.31 | 4.62 | 0.04 | 3.25 | 0.13 | 0.67 | 91.28 | 3.24 | 0.06 | 0.06 | 0.39 | 0.38 | | 0.22 | |
| 2012-0092-0032 | 2012-092_1 | Tray 01 C | C8 | HE11EE0122246.005.32 | 3.81 | 0.04 | 2.98 | 0.15 | 0.42 | 90.76 | 4.06 | 0.13 | 0.05 | 0.54 | 0.22 | 0.01 | 0.10 | |
| 2012-0092-0033 | 2012-092_1 | Tray 01 C | C9 | HE11EE0122246.005.33 | 6.00 | 0.01 | 1.78 | 0.03 | 2.85 | 90.61 | 2.54 | 0.06 | 0.26 | 0.45 | 0.82 | | 0.30 | |

FIG. 15i

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0034 | 2012-092_1 | Tray 01 A | C10 | HE11EE012246.005.34 | 4.23 | 0.03 | 2.99 | 0.11 | 0.54 | 92.13 | 2.75 | 0.07 | 0.09 | 0.44 | 0.37 | 0.02 | 0.21 | |
| 2012-0092-0035 | 2012-092_1 | Tray 01 A | C11 | HE11EE012246.005.35 | 5.21 | 0.03 | 3.00 | 0.10 | 1.17 | 90.81 | 3.15 | 0.07 | 0.16 | 0.38 | 0.60 | | 0.26 | |
| 2012-0092-0036 | 2012-092_1 | Tray 01 A | C12 | HE11EE012246.005.36 | 4.54 | 0.03 | 3.31 | 0.19 | 0.52 | 91.66 | 2.80 | 0.08 | 0.14 | 0.42 | 0.34 | 0.02 | 0.21 | |
| 2012-0092-0037 | 2012-092_1 | Tray 01 A | D1 | HE11EE012246.005.37 | 5.15 | 0.02 | 2.44 | 0.09 | 1.48 | 91.91 | 2.17 | 0.05 | 0.17 | 0.37 | 0.69 | 0.01 | 0.33 | |
| 2012-0092-0038 | 2012-092_1 | Tray 01 A | D2 | HE11EE012246.005.38 | 3.28 | 0.02 | 2.03 | 0.06 | 0.55 | 93.31 | 2.34 | 0.07 | 0.11 | 0.62 | 0.39 | 0.01 | 0.19 | |
| 2012-0092-0039 | 2012-092_1 | Tray 01 A | D3 | HE11EE012246.005.39 | 5.93 | 0.02 | 2.35 | 0.06 | 2.25 | 90.76 | 2.52 | 0.08 | 0.21 | 0.36 | 0.78 | 0.03 | 0.31 | |
| 2012-0092-0040 | 2012-092_1 | Tray 01 A | D4 | HE11EE012246.005.40 | 4.77 | 0.03 | 2.87 | 0.13 | 0.97 | 91.89 | 2.50 | 0.05 | 0.12 | 0.38 | 0.51 | 0.02 | 0.27 | |
| 2012-0092-0041 | 2012-092_1 | Tray 01 A | D5 | HE11EE012246.005.41 | 4.24 | 0.02 | 2.37 | 0.04 | 0.96 | 91.67 | 3.08 | 0.06 | 0.14 | 0.57 | 0.50 | 0.02 | 0.25 | |
| 2012-0092-0042 | 2012-092_1 | Tray 01 A | D6 | HE11EE012246.005.42 | 6.71 | 0.03 | 2.78 | 0.09 | 2.48 | 90.52 | 2.08 | 0.05 | 0.24 | 0.27 | 0.83 | 0.01 | 0.34 | |
| 2012-0092-0043 | 2012-092_1 | Tray 01 A | D7 | HE11EE012246.005.43 | 4.21 | 0.03 | 3.25 | 0.14 | 0.37 | 91.63 | 3.19 | 0.06 | 0.07 | 0.47 | 0.30 | 0.02 | 0.20 | |
| 2012-0092-0044 | 2012-092_1 | Tray 01 A | D8 | HE11EE012246.005.44 | 6.45 | 0.03 | 2.53 | 0.09 | 2.56 | 89.83 | 2.95 | 0.07 | 0.24 | 0.29 | 0.76 | | 0.33 | |
| 2012-0092-0045 | 2012-092_1 | Tray 01 A | D9 | HE11EE012246.005.45 | 3.24 | 0.02 | 2.23 | 0.03 | 0.42 | 92.24 | 3.37 | 0.10 | 0.10 | 0.61 | 0.31 | 0.02 | 0.17 | |
| 2012-0092-0046 | 2012-092_1 | Tray 01 A | D10 | HE11EE012246.005.46 | 5.50 | 0.02 | 2.37 | 0.09 | 1.93 | 91.42 | 2.31 | 0.07 | 0.20 | 0.35 | 0.78 | 0.01 | 0.32 | |
| 2012-0092-0047 | 2012-092_1 | Tray 01 A | D11 | HE11EE012246.005.47 | 4.77 | 0.03 | 2.92 | 0.10 | 0.96 | 92.12 | 2.32 | 0.08 | 0.14 | 0.37 | 0.49 | 0.01 | 0.23 | |
| 2012-0092-0048 | 2012-092_1 | Tray 01 A | D12 | HE11EE012246.005.48 | 6.05 | 0.02 | 2.35 | 0.08 | 2.29 | 92.13 | 2.25 | 0.07 | 0.22 | 0.34 | 0.64 | 0.01 | 0.31 | |
| 2012-0092-0049 | 2012-092_1 | Tray 01 B | E1 | HE11EE012246.007.01 | 3.67 | 0.03 | 2.92 | 0.20 | 0.26 | 92.94 | 2.33 | 0.06 | 0.07 | 0.50 | 0.21 | 0.02 | 0.17 | |
| 2012-0092-0050 | 2012-092_1 | Tray 01 B | E2 | HE11EE012246.007.02 | 4.81 | 0.02 | 2.41 | 0.11 | 1.34 | 92.80 | 1.57 | 0.08 | 0.17 | 0.38 | 0.58 | 0.01 | 0.29 | |
| 2012-0092-0051 | 2012-092_1 | Tray 01 B | E3 | HE11EE012246.007.03 | 5.98 | 0.02 | 2.63 | 0.11 | 2.08 | 90.98 | 2.31 | 0.05 | 0.23 | 0.35 | 0.69 | | 0.31 | |
| 2012-0092-0052 | 2012-092_1 | Tray 01 B | E4 | HE11EE012246.007.04 | 5.53 | 0.02 | 2.35 | 0.08 | 1.94 | 91.56 | 2.08 | 0.06 | 0.24 | 0.38 | 0.69 | 0.01 | 0.27 | |
| 2012-0092-0053 | 2012-092_1 | Tray 01 B | E5 | HE11EE012246.007.05 | 4.38 | 0.03 | 2.45 | 0.10 | 1.03 | 93.09 | 1.73 | 0.06 | 0.13 | 0.39 | 0.50 | | 0.25 | |
| 2012-0092-0054 | 2012-092_1 | Tray 01 B | E6 | HE11EE012246.007.06 | 4.24 | 0.03 | 2.98 | 0.15 | 0.50 | 91.79 | 2.69 | 0.11 | 0.15 | 0.54 | 0.38 | 0.01 | 0.22 | |
| 2012-0092-0055 | 2012-092_1 | Tray 01 B | E7 | HE11EE012246.007.07 | 5.18 | 0.01 | 1.89 | 0.09 | 2.07 | 90.94 | 2.82 | 0.09 | 0.29 | 0.51 | 0.65 | 0.02 | 0.28 | |
| 2012-0092-0056 | 2012-092_1 | Tray 01 B | E8 | HE11EE012246.007.08 | 5.55 | 0.03 | 2.66 | 0.11 | 1.72 | 91.00 | 2.68 | 0.06 | 0.19 | 0.32 | 0.65 | 0.01 | 0.30 | |
| 2012-0092-0057 | 2012-092_1 | Tray 01 B | E9 | HE11EE012246.007.09 | 4.03 | 0.03 | 2.96 | 0.15 | 0.45 | 92.73 | 2.26 | 0.07 | 0.07 | 0.45 | 0.30 | 0.03 | 0.19 | |
| 2012-0092-0058 | 2012-092_1 | Tray 01 B | E10 | HE11EE012246.007.10 | 4.00 | 0.03 | 3.01 | 0.14 | 0.38 | 92.48 | 2.44 | 0.07 | 0.10 | 0.51 | 0.30 | | 0.18 | |
| 2012-0092-0059 | 2012-092_1 | Tray 01 B | E11 | HE11EE012246.007.11 | 6.60 | 0.02 | 2.58 | 0.12 | 2.67 | 90.40 | 2.23 | 0.07 | 0.31 | 0.29 | 0.75 | 0.03 | 0.28 | |
| 2012-0092-0060 | 2012-092_1 | Tray 01 B | E12 | HE11EE012246.007.12 | 3.92 | 0.02 | 3.01 | 0.13 | 0.35 | 92.62 | 2.45 | 0.07 | 0.07 | 0.54 | 0.28 | 0.03 | 0.19 | |
| 2012-0092-0061 | 2012-092_1 | Tray 01 B | F1 | HE11EE012246.007.13 | 3.43 | 0.02 | 2.46 | 0.09 | 0.39 | 91.75 | 3.28 | 0.07 | 0.12 | 0.68 | 0.26 | 0.02 | 0.17 | |
| 2012-0092-0062 | 2012-092_1 | Tray 01 B | F2 | HE11EE012246.007.14 | 4.79 | 0.01 | 1.79 | 0.07 | 1.81 | 91.94 | 2.32 | 0.07 | 0.21 | 0.52 | 0.65 | 0.02 | 0.31 | |
| 2012-0092-0063 | 2012-092_1 | Tray 01 B | F3 | HE11EE012246.007.15 | 5.95 | 0.03 | 2.65 | 0.12 | 2.06 | 90.51 | 2.70 | 0.07 | 0.22 | 0.34 | 0.68 | 0.02 | 0.30 | |
| 2012-0092-0064 | 2012-092_1 | Tray 01 B | F4 | HE11EE012246.007.16 | 3.95 | 0.03 | 2.81 | 0.13 | 0.47 | 92.73 | 2.35 | 0.07 | 0.08 | 0.48 | 0.32 | 0.02 | 0.23 | |
| 2012-0092-0065 | 2012-092_1 | Tray 01 B | F5 | HE11EE012246.007.17 | 5.12 | 0.02 | 2.34 | 0.09 | 1.65 | 91.97 | 2.17 | 0.08 | 0.18 | 0.36 | 0.64 | 0.01 | 0.29 | |
| 2012-0092-0066 | 2012-092_1 | Tray 01 B | F6 | HE11EE012246.007.18 | 4.61 | 0.03 | 2.35 | 0.09 | 1.24 | 92.78 | 1.81 | 0.06 | 0.14 | 0.41 | 0.57 | 0.02 | 0.29 | |

FIG. 15j

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0067 | 2012-092_1 | Tray 01 B | F7 | HE11EE012246.007.19 | 3.74 | 0.03 | 2.61 | 0.11 | 0.49 | 93.34 | 2.00 | 0.06 | 0.07 | 0.47 | 0.35 | 0.02 | 0.20 | |
| 2012-0092-0068 | 2012-092_1 | Tray 01 B | F8 | HE11EE012246.007.20 | 5.34 | 0.03 | 2.80 | 0.11 | 1.50 | 91.49 | 2.36 | 0.07 | 0.20 | 0.35 | 0.54 | 0.01 | 0.27 | |
| 2012-0092-0069 | 2012-092_1 | Tray 01 B | F9 | HE11EE012246.007.21 | 5.34 | 0.02 | 2.58 | 0.11 | 1.67 | 91.38 | 2.47 | 0.06 | 0.22 | 0.36 | 0.62 | 0.01 | 0.30 | |
| 2012-0092-0070 | 2012-092_1 | Tray 01 B | F10 | HE11EE012246.007.22 | 4.42 | 0.04 | 3.35 | 0.19 | 0.40 | 91.19 | 3.36 | 0.07 | 0.10 | 0.46 | 0.30 | 0.03 | 0.24 | |
| 2012-0092-0071 | 2012-092_1 | Tray 01 B | F11 | HE11EE012246.007.23 | 4.77 | 0.04 | 3.53 | 0.22 | 0.54 | 90.43 | 2.67 | 0.08 | 0.21 | 0.52 | 0.30 | 0.03 | 0.15 | |
| 2012-0092-0072 | 2012-092_1 | Tray 01 B | F12 | HE11EE012246.007.24 | 5.24 | 0.02 | 2.40 | 0.10 | 1.78 | 92.20 | 1.79 | 0.06 | 0.20 | 0.35 | 0.57 | 0.01 | 0.27 | |
| 2012-0092-0073 | 2012-092_1 | Tray 01 B | G1 | HE11EE012246.007.25 | 5.50 | 0.02 | 2.43 | 0.09 | 1.87 | 91.93 | 1.83 | 0.07 | 0.19 | 0.35 | 0.64 | | 0.29 | |
| 2012-0092-0074 | 2012-092_1 | Tray 01 B | G2 | HE11EE012246.007.26 | 3.20 | 0.03 | 2.28 | 0.09 | 0.37 | 93.51 | 2.21 | 0.07 | 0.08 | 0.66 | 0.27 | 0.03 | 0.18 | |
| 2012-0092-0075 | 2012-092_1 | Tray 01 B | G3 | HE11EE012246.007.27 | 3.76 | 0.03 | 2.98 | 0.14 | 0.33 | 92.21 | 2.97 | 0.08 | 0.07 | 0.52 | 0.23 | 0.02 | 0.14 | |
| 2012-0092-0076 | 2012-092_1 | Tray 01 B | G4 | HE11EE012246.007.28 | 4.30 | 0.02 | 2.14 | 0.07 | 1.18 | 91.17 | 3.47 | 0.08 | 0.14 | 0.58 | 0.55 | 0.02 | 0.28 | |
| 2012-0092-0077 | 2012-092_1 | Tray 01 B | G5 | HE11EE012246.007.29 | 3.80 | | 2.65 | 0.22 | 0.41 | 92.28 | 2.61 | 0.07 | 0.25 | 0.52 | 0.33 | | 0.15 | |
| 2012-0092-0078 | 2012-092_1 | Tray 01 B | G6 | HE11EE012246.007.30 | 4.51 | 0.02 | 2.34 | 0.08 | 1.22 | 92.68 | 1.98 | 0.06 | 0.15 | 0.38 | 0.53 | 0.01 | 0.26 | |
| 2012-0092-0079 | 2012-092_1 | Tray 01 B | G7 | HE11EE012246.007.31 | 3.67 | 0.03 | 2.59 | 0.12 | 0.46 | 93.65 | 1.75 | 0.05 | 0.10 | 0.47 | 0.30 | 0.01 | 0.19 | |
| 2012-0092-0080 | 2012-092_1 | Tray 01 B | G8 | HE11EE012246.007.32 | 3.78 | 0.03 | 2.82 | 0.15 | 0.41 | 92.88 | 2.31 | 0.08 | 0.07 | 0.51 | 0.28 | 0.02 | 0.16 | |
| 2012-0092-0081 | 2012-092_1 | Tray 01 B | G9 | HE11EE012246.007.33 | 3.20 | 0.03 | 2.43 | 0.05 | 0.32 | 92.70 | 2.82 | 0.09 | 0.05 | 0.74 | 0.23 | 0.01 | 0.28 | |
| 2012-0092-0082 | 2012-092_1 | Tray 01 B | G10 | HE11EE012246.007.34 | 4.97 | 0.01 | 1.84 | 0.08 | 1.89 | 92.33 | 1.81 | 0.06 | 0.21 | 0.54 | 0.64 | 0.01 | 0.25 | |
| 2012-0092-0083 | 2012-092_1 | Tray 01 B | G11 | HE11EE012246.007.35 | 5.04 | 0.03 | 2.82 | 0.10 | 1.00 | 90.17 | 3.37 | 0.15 | 0.38 | 0.51 | 0.58 | 0.03 | 0.17 | |
| 2012-0092-0084 | 2012-092_1 | Tray 01 B | G12 | HE11EE012246.007.36 | 2.96 | 0.02 | 2.12 | 0.09 | 0.34 | 93.90 | 1.98 | 0.07 | 0.09 | 0.67 | 0.24 | 0.02 | 0.19 | |
| 2012-0092-0085 | 2012-092_1 | Tray 01 B | H1 | HE11EE012246.007.37 | 3.61 | 0.02 | 2.53 | 0.03 | 0.49 | 90.91 | 4.46 | 0.08 | 0.07 | 0.60 | 0.29 | 0.03 | 0.27 | |
| 2012-0092-0086 | 2012-092_1 | Tray 01 B | H2 | HE11EE012246.007.38 | 4.59 | 0.02 | 2.53 | 0.09 | 1.11 | 92.53 | 2.03 | 0.08 | 0.15 | 0.40 | 0.52 | 0.02 | 0.19 | |
| 2012-0092-0087 | 2012-092_1 | Tray 01 B | H3 | HE11EE012246.007.39 | 3.68 | 0.03 | 2.71 | 0.14 | 0.36 | 93.58 | 1.71 | 0.06 | 0.12 | 0.50 | 0.29 | 0.01 | 0.27 | |
| 2012-0092-0088 | 2012-092_1 | Tray 01 B | H4 | HE11EE012246.007.40 | 5.37 | 0.03 | 2.84 | 0.12 | 1.39 | 91.51 | 2.26 | 0.09 | 0.19 | 0.34 | 0.60 | 0.02 | 0.32 | |
| 2012-0092-0089 | 2012-092_1 | Tray 01 B | H5 | HE11EE012246.007.41 | 3.46 | 0.03 | 2.51 | 0.20 | 0.34 | 93.44 | 1.87 | 0.06 | 0.13 | 0.56 | 0.29 | 0.02 | 0.16 | |
| 2012-0092-0090 | 2012-092_1 | Tray 01 B | H6 | HE11EE012246.007.42 | 3.85 | 0.03 | 2.83 | 0.14 | 0.43 | 93.16 | 2.06 | 0.07 | 0.07 | 0.46 | 0.29 | 0.02 | 0.20 | |
| 2012-0092-0091 | 2012-092_1 | Tray 01 B | H7 | HE11EE012246.007.43 | 5.67 | 0.03 | 2.83 | 0.11 | 1.84 | 90.54 | 3.01 | 0.06 | 0.20 | 0.32 | 0.61 | 0.02 | 0.31 | |
| 2012-0092-0092 | 2012-092_1 | Tray 01 B | H8 | HE11EE012246.007.44 | 6.05 | 0.02 | 2.31 | 0.09 | 2.34 | 90.75 | 2.35 | 0.10 | 0.26 | 0.34 | 0.60 | 0.01 | 0.31 | |
| 2012-0092-0093 | 2012-092_1 | Tray 01 B | H9 | HE11EE012246.007.45 | 5.41 | 0.02 | 2.41 | 0.11 | 1.83 | 91.59 | 2.22 | 0.07 | 0.21 | 0.36 | 0.65 | 0.02 | 0.28 | |
| 2012-0092-0094 | 2012-092_1 | Tray 01 B | H10 | HE11EE012246.007.46 | 5.54 | 0.02 | 2.55 | 0.09 | 1.80 | 90.91 | 2.78 | 0.06 | 0.18 | 0.37 | 0.69 | 0.03 | 0.29 | |
| 2012-0092-0095 | 2012-092_1 | Tray 01 B | H11 | HE11EE012246.007.47 | 4.86 | 0.02 | 2.57 | 0.10 | 1.24 | 92.65 | 1.70 | 0.06 | 0.16 | 0.38 | 0.60 | 0.01 | 0.27 | |
| 2012-0092-0096 | 2012-092_1 | Tray 01 B | H12 | HE11EE012246.007.48 | 4.17 | 0.03 | 2.66 | 0.10 | 0.73 | 92.71 | 2.27 | 0.06 | 0.08 | 0.44 | 0.42 | 0.02 | 0.25 | |

*FIG. 15k*

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0097 | 2012-092_2 | Tray 02 A | A1 | HE11EE012302.005.01 | 5.10 | 0.02 | 1.86 | 0.05 | 2.11 | 91.79 | 2.28 | 0.09 | 0.19 | 0.46 | 0.71 | | 0.22 | |
| 2012-0092-0098 | 2012-092_2 | Tray 02 A | A2 | HE11EE012302.005.02 | 4.53 | 0.03 | 2.73 | 0.08 | 1.01 | 92.30 | 2.22 | 0.09 | 0.09 | 0.38 | 0.47 | | 0.19 | |
| 2012-0092-0099 | 2012-092_2 | Tray 02 A | A3 | HE11EE012302.005.03 | 5.37 | 0.03 | 2.59 | 0.09 | 1.61 | 90.79 | 2.77 | 0.12 | 0.18 | 0.40 | 0.70 | | 0.26 | 0.02 |
| 2012-0092-0100 | 2012-092_2 | Tray 02 A | A4 | HE11EE012302.005.04 | 3.41 | 0.02 | 1.86 | 0.05 | 0.84 | 93.45 | 2.06 | 0.10 | 0.07 | 0.60 | 0.45 | 0.02 | 0.18 | |
| 2012-0092-0101 | 2012-092_2 | Tray 02 A | A5 | HE11EE012302.005.05 | 5.28 | 0.04 | 2.88 | 0.11 | 1.40 | 88.27 | 4.74 | 0.19 | 0.17 | 0.42 | 0.54 | | 0.25 | |
| 2012-0092-0102 | 2012-092_2 | Tray 02 A | A6 | HE11EE012302.005.06 | 4.25 | 0.03 | 2.51 | 0.07 | 0.91 | 92.61 | 2.28 | 0.10 | 0.09 | 0.40 | 0.50 | 0.01 | 0.21 | |
| 2012-0092-0103 | 2012-092_2 | Tray 02 A | A7 | HE11EE012302.005.07 | 5.28 | 0.02 | 1.98 | 0.07 | 2.18 | 91.18 | 2.59 | 0.10 | 0.19 | 0.45 | 0.68 | | 0.23 | |
| 2012-0092-0104 | 2012-092_2 | Tray 02 A | A8 | HE11EE012302.005.08 | 5.07 | 0.02 | 2.02 | 0.04 | 2.01 | 91.09 | 2.90 | 0.12 | 0.19 | 0.44 | 0.62 | | 0.20 | |
| 2012-0092-0105 | 2012-092_2 | Tray 02 A | A9 | HE11EE012302.005.09 | 5.63 | 0.03 | 2.78 | 0.10 | 1.73 | 90.61 | 2.74 | 0.10 | 0.19 | 0.34 | 0.66 | | 0.24 | |
| 2012-0092-0106 | 2012-092_2 | Tray 02 A | A10 | HE11EE012302.005.10 | 5.49 | 0.04 | 2.55 | 0.07 | 1.88 | 91.19 | 2.43 | 0.09 | 0.17 | 0.35 | 0.58 | | 0.27 | |
| 2012-0092-0107 | 2012-092_2 | Tray 02 A | A11 | HE11EE012302.005.11 | 5.77 | 0.03 | 2.57 | 0.03 | 1.99 | 89.65 | 3.59 | 0.09 | 0.20 | 0.36 | 0.72 | | 0.26 | |
| 2012-0092-0108 | 2012-092_2 | Tray 02 A | A12 | HE11EE012302.005.12 | 5.40 | 0.02 | 1.99 | 0.06 | 2.36 | 90.18 | 3.29 | 0.13 | 0.23 | 0.49 | 0.68 | | 0.22 | |
| 2012-0092-0109 | 2012-092_2 | Tray 02 A | B1 | HE11EE012302.005.13 | 4.64 | 0.03 | 2.64 | 0.09 | 1.13 | 92.35 | 2.25 | 0.09 | 0.11 | 0.39 | 0.52 | | 0.20 | |
| 2012-0092-0110 | 2012-092_2 | Tray 02 A | B2 | HE11EE012302.005.14 | 6.00 | 0.03 | 2.77 | 0.08 | 2.10 | 90.14 | 2.78 | 0.10 | 0.20 | 0.33 | 0.69 | | 0.21 | |
| 2012-0092-0111 | 2012-092_2 | Tray 02 A | B3 | HE11EE012302.005.15 | 5.07 | 0.02 | 2.02 | 0.02 | 1.95 | 91.08 | 2.82 | 0.11 | 0.19 | 0.50 | 0.65 | | 0.23 | |
| 2012-0092-0112 | 2012-092_2 | Tray 02 A | B4 | HE11EE012302.005.16 | 5.98 | 0.03 | 2.78 | 0.09 | 2.03 | 90.11 | 3.01 | 0.11 | 0.21 | 0.34 | 0.70 | | 0.23 | |
| 2012-0092-0113 | 2012-092_2 | Tray 02 A | B5 | HE11EE012302.005.17 | 5.19 | 0.03 | 2.73 | 0.10 | 1.46 | 91.03 | 2.82 | 0.11 | 0.16 | 0.36 | 0.59 | | 0.23 | |
| 2012-0092-0114 | 2012-092_2 | Tray 02 A | B6 | HE11EE012302.005.18 | 5.82 | 0.03 | 2.67 | 0.08 | 1.96 | 90.31 | 3.09 | 0.10 | 0.19 | 0.31 | 0.71 | 0.01 | 0.26 | 0.01 |
| 2012-0092-0115 | 2012-092_2 | Tray 02 A | B7 | HE11EE012302.005.19 | 5.45 | 0.02 | 2.14 | 0.03 | 2.17 | 90.87 | 2.72 | 0.10 | 0.20 | 0.44 | 0.70 | | 0.21 | |
| 2012-0092-0116 | 2012-092_2 | Tray 02 A | B8 | HE11EE012302.005.20 | 5.32 | 0.02 | 2.66 | 0.06 | 1.63 | 91.47 | 2.44 | 0.11 | 0.15 | 0.31 | 0.58 | | 0.22 | |
| 2012-0092-0117 | 2012-092_2 | Tray 02 A | B9 | HE11EE012302.005.21 | 6.18 | 0.03 | 2.75 | 0.09 | 2.29 | 89.19 | 3.42 | 0.12 | 0.19 | 0.32 | 0.74 | | 0.24 | |
| 2012-0092-0118 | 2012-092_2 | Tray 02 A | B10 | HE11EE012302.005.22 | 6.51 | 0.03 | 2.94 | 0.08 | 3.09 | 89.29 | 3.41 | 0.10 | 0.14 | 0.33 | 0.57 | 0.01 | 0.24 | |
| 2012-0092-0119 | 2012-092_2 | Tray 02 A | B11 | HE11EE012302.005.23 | 5.36 | 0.03 | 2.69 | 0.08 | 1.64 | 90.85 | 2.97 | 0.10 | 0.15 | 0.35 | 0.63 | | 0.23 | |
| 2012-0092-0120 | 2012-092_2 | Tray 02 A | B12 | HE11EE012302.005.24 | 4.49 | 0.04 | 2.72 | 0.08 | 1.03 | 91.93 | 2.63 | 0.10 | 0.10 | 0.37 | 0.44 | | 0.17 | |
| 2012-0092-0121 | 2012-092_2 | Tray 02 A | C1 | HE11EE012302.005.25 | 5.51 | 0.04 | 3.01 | 0.10 | 1.50 | 90.46 | 3.18 | 0.12 | 0.16 | 0.33 | 0.55 | | 0.25 | |
| 2012-0092-0122 | 2012-092_2 | Tray 02 A | C2 | HE11EE012302.005.26 | 5.40 | 0.03 | 2.62 | 0.06 | 1.75 | 90.74 | 3.02 | 0.11 | 0.15 | 0.33 | 0.62 | | 0.23 | |
| 2012-0092-0123 | 2012-092_2 | Tray 02 A | C3 | HE11EE012302.005.27 | 5.14 | 0.03 | 2.57 | 0.08 | 1.58 | 91.35 | 2.89 | 0.10 | 0.15 | 0.34 | 0.58 | | 0.24 | |
| 2012-0092-0124 | 2012-092_2 | Tray 02 A | C4 | HE11EE012302.005.28 | 5.29 | 0.03 | 2.54 | 0.08 | 1.75 | 91.02 | 2.76 | 0.10 | 0.18 | 0.36 | 0.58 | | 0.21 | |
| 2012-0092-0125 | 2012-092_2 | Tray 02 A | C5 | HE11EE012302.005.29 | 4.65 | 0.02 | 2.04 | 0.05 | 1.84 | 91.88 | 2.37 | 0.12 | 0.18 | 0.48 | 0.57 | | 0.19 | |
| 2012-0092-0126 | 2012-092_2 | Tray 02 A | C6 | HE11EE012302.005.30 | 4.94 | 0.02 | 1.97 | 0.05 | 1.95 | 91.37 | 2.74 | 0.11 | 0.17 | 0.46 | 0.62 | | 0.21 | |
| 2012-0092-0127 | 2012-092_2 | Tray 02 A | C7 | HE11EE012302.005.31 | 5.54 | 0.03 | 2.67 | 0.09 | 1.87 | 90.92 | 2.57 | 0.11 | 0.17 | 0.33 | 0.63 | 0.01 | 0.18 | 0.01 |
| 2012-0092-0128 | 2012-092_2 | Tray 02 A | C8 | HE11EE012302.005.32 | 5.29 | 0.03 | 2.02 | 0.02 | 2.22 | 90.18 | 3.09 | 0.12 | 0.19 | 0.45 | 0.62 | | 0.21 | |
| 2012-0092-0129 | 2012-092_2 | Tray 02 A | C9 | HE11EE012302.005.33 | 5.60 | 0.03 | 2.68 | 0.09 | 1.80 | 90.89 | 2.67 | 0.09 | 0.17 | 0.32 | 0.70 | | 0.22 | |

*FIG. 15I*

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0130 | 2012-092_2 | Tray 02 A | C10 | HE11EE012302.005.34 | 5.32 | 0.03 | 2.67 | 0.09 | 1.63 | 90.62 | 3.15 | 0.10 | 0.15 | 0.35 | 0.60 | | 0.23 | |
| 2012-0092-0131 | 2012-092_2 | Tray 02 A | C11 | HE11EE012302.005.35 | 4.71 | 0.02 | 1.97 | 0.04 | 1.81 | 91.55 | 2.89 | 0.10 | 0.16 | 0.45 | 0.57 | | 0.19 | |
| 2012-0092-0132 | 2012-092_2 | Tray 02 A | C12 | HE11EE012302.005.36 | 5.82 | 0.03 | 2.64 | 0.07 | 2.08 | 90.57 | 2.81 | 0.10 | 0.18 | 0.33 | 0.70 | | 0.21 | |
| 2012-0092-0133 | 2012-092_2 | Tray 02 A | D1 | HE11EE012302.005.37 | 5.69 | 0.02 | 1.89 | 0.03 | 2.62 | 91.06 | 2.36 | 0.12 | 0.21 | 0.42 | 0.73 | | 0.23 | |
| 2012-0092-0134 | 2012-092_2 | Tray 02 A | D2 | HE11EE012302.005.38 | 5.99 | 0.03 | 2.74 | 0.07 | 2.11 | 89.72 | 2.37 | 0.11 | 0.22 | 0.38 | 0.88 | | 0.21 | |
| 2012-0092-0135 | 2012-092_2 | Tray 02 A | D3 | HE11EE012302.005.39 | 5.07 | 0.03 | 2.53 | 0.10 | 1.60 | 91.19 | 2.83 | 0.09 | 0.17 | 0.33 | 0.55 | | 0.19 | |
| 2012-0092-0136 | 2012-092_2 | Tray 02 A | D4 | HE11EE012302.005.40 | 5.62 | 0.04 | 2.74 | 0.08 | 1.88 | 89.98 | 2.44 | 0.11 | 0.19 | 0.35 | 0.57 | | 0.20 | |
| 2012-0092-0137 | 2012-092_2 | Tray 02 A | D5 | HE11EE012302.005.41 | 4.84 | 0.03 | 2.61 | 0.09 | 1.35 | 91.02 | 3.44 | 0.10 | 0.13 | 0.35 | 0.54 | | 0.19 | |
| 2012-0092-0138 | 2012-092_2 | Tray 02 A | D6 | HE11EE012302.005.42 | 4.91 | 0.02 | 2.03 | 0.06 | 1.90 | 92.02 | 2.34 | 0.12 | 0.18 | 0.45 | 0.59 | | 0.18 | |
| 2012-0092-0139 | 2012-092_2 | Tray 02 A | D7 | HE11EE012302.005.43 | 4.94 | 0.02 | 1.99 | 0.03 | 1.91 | 91.61 | 2.47 | 0.11 | 0.17 | 0.45 | 0.65 | | 0.20 | |
| 2012-0092-0140 | 2012-092_2 | Tray 02 A | D8 | HE11EE012302.005.44 | 5.52 | 0.03 | 2.60 | 0.07 | 1.85 | 91.48 | 2.70 | 0.10 | 0.18 | 0.35 | 0.67 | | 0.19 | |
| 2012-0092-0141 | 2012-092_2 | Tray 02 A | D9 | HE11EE012302.005.45 | 5.41 | 0.02 | 1.97 | 0.04 | 2.39 | 90.86 | 2.79 | 0.10 | 0.20 | 0.43 | 0.65 | | 0.18 | |
| 2012-0092-0142 | 2012-092_2 | Tray 02 A | D10 | HE11EE012302.005.46 | 5.24 | 0.03 | 2.71 | 0.07 | 1.82 | 91.26 | 2.44 | 0.09 | 0.16 | 0.32 | 0.54 | | 0.17 | |
| 2012-0092-0143 | 2012-092_2 | Tray 02 A | D11 | HE11EE012302.005.47 | 4.83 | 0.03 | 2.47 | 0.06 | 1.43 | 90.75 | 3.86 | 0.11 | 0.15 | 0.37 | 0.55 | 0.01 | 0.21 | |
| 2012-0092-0144 | 2012-092_2 | Tray 02 A | D12 | HE11EE012302.005.48 | 4.47 | 0.02 | 2.24 | 0.05 | 1.43 | 91.81 | 2.91 | 0.09 | 0.11 | 0.45 | 0.52 | | 0.15 | |
| 2012-0092-0145 | 2012-092_2 | Tray 02 B | E1 | HE11EE012304.009.01 | 6.09 | 0.02 | 3.79 | 0.13 | 1.32 | 88.07 | 3.86 | 0.22 | 0.19 | 0.48 | 0.50 | | 0.24 | |
| 2012-0092-0146 | 2012-092_2 | Tray 02 B | E2 | HE11EE012304.009.02 | 4.95 | 0.05 | 3.10 | 0.09 | 1.01 | 91.94 | 2.19 | 0.11 | 0.13 | 0.37 | 0.47 | | 0.20 | |
| 2012-0092-0147 | 2012-092_2 | Tray 02 B | E3 | HE11EE012304.009.03 | 5.62 | 0.04 | 3.35 | 0.10 | 1.40 | 91.29 | 2.21 | 0.13 | 0.14 | 0.33 | 0.51 | | 0.18 | |
| 2012-0092-0148 | 2012-092_2 | Tray 02 B | E4 | HE11EE012304.009.04 | 5.35 | 0.03 | 3.14 | 0.08 | 1.30 | 91.52 | 2.29 | 0.09 | 0.14 | 0.36 | 0.53 | | 0.19 | |
| 2012-0092-0149 | 2012-092_2 | Tray 02 B | E5 | HE11EE012304.009.05 | 3.95 | 0.04 | 2.26 | 0.08 | 0.97 | 92.98 | 1.77 | 0.09 | 0.10 | 0.61 | 0.42 | 0.01 | 0.18 | |
| 2012-0092-0150 | 2012-092_2 | Tray 02 B | E6 | HE11EE012304.009.06 | 5.09 | 0.04 | 3.10 | 0.10 | 1.17 | 91.85 | 2.12 | 0.12 | 0.13 | 0.34 | 0.46 | | 0.19 | |
| 2012-0092-0151 | 2012-092_2 | Tray 02 B | E7 | HE11EE012304.009.07 | 6.24 | 0.04 | 3.45 | 0.11 | 1.67 | 90.97 | 1.85 | 0.12 | 0.18 | 0.34 | 0.55 | | 0.24 | |
| 2012-0092-0152 | 2012-092_2 | Tray 02 B | E8 | HE11EE012304.009.08 | 5.04 | 0.05 | 3.27 | 0.09 | 0.96 | 91.75 | 2.28 | 0.11 | 0.11 | 0.36 | 0.46 | | 0.19 | |
| 2012-0092-0153 | 2012-092_2 | Tray 02 B | E9 | HE11EE012304.009.09 | 4.80 | 0.04 | 3.01 | 0.08 | 0.95 | 92.58 | 1.76 | 0.08 | 0.16 | 0.37 | 0.46 | | 0.18 | |
| 2012-0092-0154 | 2012-092_2 | Tray 02 B | E10 | HE11EE012304.009.10 | 5.78 | 0.05 | 3.69 | 0.12 | 1.11 | 90.76 | 2.41 | 0.14 | 0.19 | 0.34 | 0.52 | | 0.23 | |
| 2012-0092-0155 | 2012-092_2 | Tray 02 B | E11 | HE11EE012304.009.11 | 5.21 | 0.04 | 3.15 | 0.10 | 1.17 | 91.89 | 2.09 | 0.08 | 0.10 | 0.35 | 0.54 | | 0.21 | |
| 2012-0092-0156 | 2012-092_2 | Tray 02 B | E12 | HE11EE012304.009.12 | 6.24 | 0.04 | 3.31 | 0.09 | 1.75 | 90.12 | 2.81 | 0.14 | 0.17 | 0.34 | 0.75 | | 0.23 | |
| 2012-0092-0157 | 2012-092_2 | Tray 02 B | F1 | HE11EE012304.009.13 | 6.01 | 0.05 | 3.50 | 0.12 | 1.59 | 90.37 | 2.57 | 0.10 | 0.18 | 0.35 | 0.53 | | 0.16 | |
| 2012-0092-0158 | 2012-092_2 | Tray 02 B | F2 | HE11EE012304.009.14 | 5.73 | 0.04 | 2.99 | 0.08 | 1.80 | 91.52 | 2.39 | 0.11 | 0.14 | 0.32 | 0.58 | | 0.18 | |
| 2012-0092-0159 | 2012-092_2 | Tray 02 B | F3 | HE11EE012304.009.15 | 5.59 | 0.04 | 3.11 | 0.10 | 1.46 | 91.54 | 1.99 | 0.09 | 0.15 | 0.38 | 0.61 | | 0.21 | |
| 2012-0092-0160 | 2012-092_2 | Tray 02 B | F4 | HE11EE012304.009.16 | 4.74 | 0.04 | 3.19 | 0.10 | 0.86 | 92.38 | 2.03 | 0.12 | 0.10 | 0.37 | 0.38 | | 0.16 | |
| 2012-0092-0161 | 2012-092_2 | Tray 02 B | F5 | HE11EE012304.009.17 | 5.10 | 0.04 | 3.11 | 0.10 | 1.25 | 92.12 | 1.79 | 0.11 | 0.11 | 0.33 | 0.45 | | 0.14 | |
| 2012-0092-0162 | 2012-092_2 | Tray 02 B | F6 | HE11EE012304.009.18 | 4.73 | 0.02 | 2.17 | 0.05 | 1.68 | 91.83 | 2.46 | 0.12 | 0.14 | 0.51 | 0.53 | | 0.17 | |

*FIG. 15m*

| Lab ID | Plate | Tray | Pos | Source ID | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|
| 2012-0092-0163 | 2012-092_2 | Tray 02 B | F7 | HE11EED12304.009.19 | 5.94 | 0.03 | 3.08 | 0.11 | 1.82 | 91.03 | 2.11 | 0.14 | 0.16 | 0.33 | 0.64 | | 0.21 | |
| 2012-0092-0164 | 2012-092_2 | Tray 02 B | F8 | HE11EED12304.009.20 | 5.88 | 0.04 | 2.94 | 0.07 | 1.89 | 90.69 | 2.71 | 0.13 | 0.15 | 0.35 | 0.66 | | 0.21 | |
| 2012-0092-0165 | 2012-092_2 | Tray 02 B | F9 | HE11EED12304.009.21 | 4.86 | 0.04 | 3.04 | 0.10 | 1.08 | 91.63 | 2.51 | 0.12 | 0.10 | 0.39 | 0.43 | | 0.18 | |
| 2012-0092-0166 | 2012-092_2 | Tray 02 B | F10 | HE11EED12304.009.22 | 6.85 | 0.04 | 3.32 | 0.08 | 2.39 | 89.97 | 2.15 | 0.14 | 0.21 | 0.29 | 0.69 | | 0.20 | |
| 2012-0092-0167 | 2012-092_2 | Tray 02 B | F11 | HE11EED12304.009.23 | 5.22 | 0.04 | 3.08 | 0.09 | 1.32 | 91.89 | 2.12 | 0.10 | 0.12 | 0.36 | 0.51 | | 0.18 | |
| 2012-0092-0168 | 2012-092_2 | Tray 02 B | F12 | HE11EED12304.009.24 | 6.42 | 0.06 | 3.78 | 0.09 | 1.85 | 85.44 | 5.90 | 0.34 | 0.24 | 0.58 | 0.49 | 0.18 | 0.20 | |
| 2012-0092-0169 | 2012-092_2 | Tray 02 B | G1 | HE11EED12304.009.25 | 5.13 | 0.04 | 3.25 | 0.10 | 1.06 | 91.55 | 2.37 | 0.14 | 0.13 | 0.37 | 0.44 | | 0.20 | |
| 2012-0092-0170 | 2012-092_2 | Tray 02 B | G2 | HE11EED12304.009.26 | 5.95 | 0.04 | 3.16 | 0.08 | 1.72 | 90.48 | 2.68 | 0.13 | 0.18 | 0.35 | 0.64 | | 0.22 | |
| 2012-0092-0171 | 2012-092_2 | Tray 02 B | G3 | HE11EED12304.009.27 | 5.53 | 0.04 | 3.30 | 0.09 | 1.33 | 90.92 | 2.65 | 0.12 | 0.12 | 0.36 | 0.54 | | 0.21 | |
| 2012-0092-0172 | 2012-092_2 | Tray 02 B | G4 | HE11EED12304.009.28 | 5.65 | 0.05 | 3.56 | 0.13 | 1.18 | 91.23 | 2.05 | 0.09 | 0.14 | 0.35 | 0.51 | | 0.22 | |
| 2012-0092-0173 | 2012-092_2 | Tray 02 B | G5 | HE11EED12304.009.29 | 6.31 | 0.04 | 3.04 | 0.10 | 2.02 | 90.44 | 2.39 | 0.11 | 0.19 | 0.36 | 0.78 | | 0.25 | |
| 2012-0092-0174 | 2012-092_2 | Tray 02 B | G6 | HE11EED12304.009.30 | 5.85 | 0.03 | 3.18 | 0.09 | 1.68 | 91.04 | 2.29 | 0.11 | 0.14 | 0.32 | 0.61 | | 0.20 | |
| 2012-0092-0175 | 2012-092_2 | Tray 02 B | G7 | HE11EED12304.009.31 | 5.13 | 0.03 | 2.39 | 0.07 | 1.75 | 91.17 | 2.58 | 0.12 | 0.16 | 0.51 | 0.60 | | 0.21 | |
| 2012-0092-0176 | 2012-092_2 | Tray 02 B | G8 | HE11EED12304.009.32 | 5.22 | 0.04 | 3.12 | 0.09 | 1.24 | 91.24 | 2.68 | 0.11 | 0.14 | 0.35 | 0.52 | | 0.19 | |
| 2012-0092-0177 | 2012-092_2 | Tray 02 B | G9 | HE11EED12304.009.33 | 4.63 | 0.04 | 3.10 | 0.12 | 0.77 | 92.73 | 1.64 | 0.11 | 0.10 | 0.41 | 0.41 | | 0.18 | |
| 2012-0092-0178 | 2012-092_2 | Tray 02 B | G10 | HE11EED12304.009.34 | 4.94 | 0.05 | 3.02 | 0.07 | 1.08 | 91.67 | 2.42 | 0.11 | 0.12 | 0.39 | 0.47 | | 0.18 | |
| 2012-0092-0179 | 2012-092_2 | Tray 02 B | G11 | HE11EED12304.009.35 | 5.06 | 0.04 | 3.40 | 0.13 | 0.88 | 92.27 | 1.79 | 0.10 | 0.13 | 0.38 | 0.42 | | 0.18 | |
| 2012-0092-0180 | 2012-092_2 | Tray 02 B | G12 | HE11EED12304.009.36 | 4.16 | 0.04 | 2.86 | 0.10 | 0.67 | 93.14 | 1.74 | 0.10 | 0.11 | 0.41 | 0.35 | | 0.13 | |
| 2012-0092-0181 | 2012-092_2 | Tray 02 B | H1 | HE11EED12304.009.37 | 4.16 | 0.02 | 2.21 | 0.06 | 1.11 | 92.83 | 1.94 | 0.09 | 0.12 | 0.58 | 0.47 | | 0.22 | |
| 2012-0092-0182 | 2012-092_2 | Tray 02 B | H2 | HE11EED12304.009.38 | 4.48 | 0.04 | 3.05 | 0.11 | 0.71 | 93.04 | 1.61 | 0.10 | 0.11 | 0.36 | 0.40 | 0.01 | 0.17 | |
| 2012-0092-0183 | 2012-092_2 | Tray 02 B | H3 | HE11EED12304.009.39 | 4.46 | 0.03 | 2.29 | 0.06 | 1.32 | 92.61 | 2.33 | 0.13 | 0.17 | 0.54 | 0.51 | | 0.15 | |
| 2012-0092-0184 | 2012-092_2 | Tray 02 B | H4 | HE11EED12304.009.40 | 4.94 | 0.05 | 3.34 | 0.11 | 0.87 | 91.73 | 2.28 | 0.10 | 0.09 | 0.40 | 0.41 | | 0.18 | |
| 2012-0092-0185 | 2012-092_2 | Tray 02 B | H5 | HE11EED12304.009.41 | 6.28 | 0.04 | 3.35 | 0.10 | 1.79 | 90.35 | 2.42 | 0.13 | 0.19 | 0.34 | 0.67 | | 0.24 | |
| 2012-0092-0186 | 2012-092_2 | Tray 02 B | H6 | HE11EED12304.009.42 | 4.48 | 0.02 | 3.25 | 0.12 | 0.59 | 93.06 | 1.55 | 0.08 | 0.09 | 0.39 | 0.34 | 0.01 | 0.16 | |
| 2012-0092-0187 | 2012-092_2 | Tray 02 B | H7 | HE11EED12304.009.43 | 5.33 | 0.04 | 3.20 | 0.11 | 1.17 | 91.79 | 1.99 | 0.09 | 0.19 | 0.35 | 0.53 | | 0.20 | |
| 2012-0092-0188 | 2012-092_2 | Tray 02 B | H8 | HE11EED12304.009.44 | 3.30 | 0.02 | 1.96 | 0.08 | 0.75 | 93.91 | 1.65 | 0.10 | 0.09 | 0.70 | 0.34 | 0.01 | 0.13 | |
| 2012-0092-0189 | 2012-092_2 | Tray 02 B | H9 | HE11EED12304.009.45 | 4.96 | 0.04 | 3.04 | 0.10 | 1.01 | 92.29 | 1.92 | 0.08 | 0.12 | 0.38 | 0.53 | | 0.22 | |
| 2012-0092-0190 | 2012-092_2 | Tray 02 B | H10 | HE11EED12304.009.46 | 4.21 | 0.02 | 2.21 | 0.05 | 1.13 | 92.82 | 1.87 | 0.11 | 0.11 | 0.59 | 0.52 | 0.02 | 0.22 | |
| 2012-0092-0191 | 2012-092_2 | Tray 02 B | H11 | HE11EED12304.009.47 | 4.36 | 0.02 | 2.32 | 0.07 | 1.19 | 92.32 | 2.27 | 0.11 | 0.13 | 0.57 | 0.51 | | 0.19 | |
| 2012-0092-0192 | 2012-092_2 | Tray 02 B | H12 | HE11EED12304.009.48 | 4.27 | 0.04 | 3.05 | 0.10 | 0.62 | 93.26 | 1.88 | 0.09 | 0.08 | 0.37 | 0.32 | | 0.15 | |

FIG. 15n

| Lab ID | Entry | Tray | Pos | Source | HA468 DM | CL phus | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|---|---|
| 2012-0053-0001 | 76601 | Tray 07 A | A1 | HE10EE020401.002 | | | 8.17 | 0.03 | 2.97 | 0.09 | 3.40 | 87.89 | 2.89 | 0.13 | 0.35 | 0.31 | 1.06 | | 0.36 | |
| 2012-0053-0002 | 76602 | Tray 07 A | A2 | HE10EE020177.001 | | | 7.90 | 0.02 | 3.21 | 0.11 | 3.17 | 87.70 | 2.86 | 0.26 | 0.37 | 0.39 | 0.81 | | 0.32 | 0.02 |
| 2012-0053-0004 | 76604 | Tray 07 A | A4 | HE10EE020077.004 | | | 9.04 | 0.02 | 3.12 | 0.07 | 4.18 | 88.33 | 1.87 | 0.17 | 0.36 | 0.25 | 1.07 | | 0.28 | |
| 2012-0053-0005 | 76605 | Tray 07 A | A5 | HE11EE010292.0032.001 | yes | yes | 8.76 | 0.04 | 3.14 | 0.09 | 3.86 | 88.52 | 1.94 | 0.16 | 0.34 | 0.26 | 1.08 | | 0.31 | |
| 2012-0053-0006 | 76606 | Tray 07 A | A6 | HE11EE010292.0032.002 | yes | yes | 10.85 | 0.04 | 3.88 | 0.09 | 5.01 | 85.82 | 2.54 | 0.17 | 0.46 | 0.28 | 1.31 | | 0.35 | |
| 2012-0053-0007 | 76607 | Tray 07 A | A7 | HE11EE010292.0032.003 | yes | yes | 9.36 | 0.04 | 3.80 | 0.11 | 3.83 | 87.78 | 2.10 | 0.15 | 0.35 | 0.25 | 1.02 | | 0.31 | |
| 2012-0053-0008 | 76608 | Tray 07 A | A8 | HE11EE010292.0032.003 | yes | yes | 9.08 | 0.04 | 3.59 | 0.11 | 3.66 | 88.14 | 1.85 | 0.18 | 0.37 | 0.25 | 0.93 | | 0.30 | |
| 2012-0053-0009 | 76609 | Tray 07 A | A9 | HE11EE010292.0032.004 | yes | yes | 8.76 | 0.03 | 3.32 | 0.10 | 3.66 | 88.52 | 1.95 | 0.20 | 0.36 | 0.29 | 1.05 | | 0.34 | |
| 2012-0053-0010 | 76610 | Tray 07 A | A10 | HE11EE010292.0032.005 | yes | yes | 8.35 | 0.04 | 3.67 | 0.10 | 3.16 | 87.27 | 2.95 | 0.22 | 0.35 | 0.32 | 0.80 | | 0.33 | |
| 2012-0053-0011 | 76611 | Tray 07 A | A11 | HE11EE010292.0032.006 | yes | yes | 8.90 | 0.04 | 3.51 | 0.11 | 3.84 | 87.44 | 2.78 | 0.22 | 0.39 | 0.27 | 0.87 | | 0.24 | |
| 2012-0053-0012 | 76612 | Tray 07 A | A12 | HE11EE010292.0032.007 | yes | yes | 9.05 | 0.04 | 3.62 | 0.11 | 3.84 | 86.88 | 3.08 | 0.19 | 0.41 | 0.28 | 1.00 | | 0.33 | |
| 2012-0053-0013 | 76613 | Tray 07 A | B1 | HE11EE010292.0032.008 | yes | yes | 8.24 | 0.04 | 2.97 | 0.11 | 2.93 | 88.00 | 2.84 | 0.19 | 0.28 | 0.28 | 0.76 | | 0.27 | |
| 2012-0053-0014 | 76614 | Tray 07 A | B2 | HE11EE010292.0032.009 | yes | yes | 11.59 | 0.04 | 3.52 | 0.09 | 5.98 | 84.95 | 2.46 | 0.27 | 0.52 | 0.25 | 1.23 | | 0.31 | |
| 2012-0053-0015 | 76615 | Tray 07 A | B3 | HE11EE010292.0032.010 | yes | yes | 10.02 | 0.04 | 3.55 | 0.10 | 4.62 | 87.12 | 2.11 | 0.16 | 0.42 | 0.24 | 1.10 | | 0.30 | |
| 2012-0053-0016 | 76616 | Tray 07 A | B4 | HE11EE010292.0032.011 | yes | yes | 9.53 | 0.04 | 3.64 | 0.08 | 4.18 | 87.25 | 2.38 | 0.20 | 0.42 | 0.25 | 1.05 | | 0.32 | |
| 2012-0053-0017 | 76617 | Tray 07 A | B5 | HE11EE010292.0032.012 | yes | yes | 9.07 | 0.03 | 3.33 | 0.09 | 4.06 | 88.22 | 1.91 | 0.20 | 0.38 | 0.25 | 0.98 | | 0.30 | |
| 2012-0053-0018 | 76618 | Tray 07 A | B6 | HE11EE010292.0033.013 | yes | yes | 8.43 | 0.03 | 3.35 | 0.09 | 4.06 | 87.12 | 2.32 | 0.27 | 0.36 | 0.21 | 0.81 | | 0.22 | |
| 2012-0053-0019 | 76619 | Tray 07 A | B7 | HE11EE010292.0033.014 | yes | yes | 9.82 | 0.03 | 4.05 | 0.12 | 3.91 | 86.37 | 2.75 | 0.20 | 0.41 | 0.27 | 1.06 | | 0.32 | |
| 2012-0053-0020 | 76620 | Tray 07 A | B8 | HE11EE010292.0033.015 | yes | yes | 9.92 | 0.07 | 3.47 | 0.10 | 4.54 | 87.31 | 2.05 | 0.14 | 0.41 | 0.24 | 1.17 | | 0.30 | |
| 2012-0053-0021 | 76621 | Tray 07 A | B9 | HE11EE010292.0033.016 | yes | yes | 10.97 | 0.03 | 3.95 | 0.10 | 5.19 | 83.97 | 2.98 | 0.23 | 0.43 | 0.25 | 1.16 | | 0.29 | |
| 2012-0053-0022 | 76622 | Tray 07 A | B10 | HE11EE010292.0033.017 | yes | yes | 9.46 | 0.02 | 3.28 | 0.09 | 4.57 | 88.12 | 1.89 | 0.19 | 0.35 | 0.23 | 1.00 | | 0.23 | |
| 2012-0053-0023 | 76623 | Tray 07 A | B11 | HE11EE010292.0033.018 | yes | yes | 8.63 | 0.05 | 4.12 | 0.12 | 3.00 | 88.38 | 2.25 | 0.17 | 0.31 | 0.28 | 0.87 | | 0.28 | |
| 2012-0053-0024 | 76624 | Tray 07 A | B12 | HE11EE010292.0033.019 | yes | yes | 12.36 | 0.05 | 4.05 | 0.13 | 5.98 | 84.83 | 2.07 | 0.19 | 0.54 | 0.20 | 1.40 | | 0.32 | |
| 2012-0053-0025 | 76625 | Tray 07 A | C1 | HE11EE010292.0033.020 | yes | yes | 10.74 | 0.06 | 4.25 | 0.13 | 4.88 | 84.26 | 4.00 | 0.26 | 0.48 | 0.20 | 0.81 | | 0.28 | |
| 2012-0053-0026 | 76626 | Tray 07 A | C2 | HE11EE010292.0033.021 | yes | yes | 10.60 | 0.03 | 3.45 | 0.07 | 5.08 | 86.53 | 2.07 | 0.19 | 0.45 | 0.26 | 1.24 | | 0.36 | |
| 2012-0053-0027 | 76627 | Tray 07 A | C3 | HE11EE010292.0033.022 | yes | yes | 10.59 | 0.04 | 3.87 | 0.10 | 4.89 | 86.33 | 2.32 | 0.21 | 0.47 | 0.23 | 1.05 | | 0.27 | |
| 2012-0053-0028 | 76628 | Tray 07 A | C4 | HE11EE010292.0033.023 | yes | yes | 9.67 | 0.03 | 3.52 | 0.09 | 4.50 | 87.08 | 2.40 | 0.27 | 0.42 | 0.25 | 0.93 | | 0.21 | |
| 2012-0053-0029 | 76629 | Tray 07 A | C5 | HE10EE020135.003 | | | 10.61 | 0.05 | 5.63 | 0.08 | 3.38 | 18.61 | 70.07 | 0.14 | 0.27 | 0.18 | 0.86 | | 0.21 | |
| 2012-0053-0030 | 76630 | Tray 07 A | C6 | HE11EE010220.0036.001 | yes | yes | 8.61 | 0.02 | 3.17 | 0.09 | 2.06 | 87.80 | 4.36 | 0.18 | 0.21 | 0.36 | 0.86 | | 0.28 | |

FIG. 16a

| Lab ID | Entry | Tray | Pos | Source | HA456 DM | CL plus | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|---|---|
| 2012-0053-0031 | 76631 | Tray 07 A | C7 | HE11EE010320.0030.002 | yes | yes | 6.16 | 0.03 | 2.89 | 0.08 | 2.00 | 89.34 | 3.60 | 0.19 | 0.21 | 0.39 | 0.73 | | 0.26 | |
| 2012-0053-0032 | 76632 | Tray 07 A | C8 | HE11EE010320.0030.003 | yes | yes | 7.31 | 0.02 | 2.89 | 0.07 | 2.88 | 88.35 | 3.60 | 0.14 | 0.25 | 0.37 | 1.00 | | 0.26 | |
| 2012-0053-0033 | 76633 | Tray 07 A | C9 | HE11EE010320.0030.004 | yes | yes | 6.72 | 0.03 | 2.96 | 0.09 | 2.38 | 86.62 | 5.79 | 0.17 | 0.27 | 0.38 | 0.81 | | 0.28 | |
| 2012-0053-0034 | 76634 | Tray 07 A | C10 | HE11EE010320.0030.005 | yes | yes | 7.45 | 0.03 | 3.42 | 0.15 | 2.40 | 82.55 | 7.16 | 0.51 | 0.33 | 0.63 | 0.76 | 0.02 | 0.51 | 0.03 |
| 2012-0053-0035 | 76635 | Tray 07 A | C11 | HE11EE010320.0030.006 | yes | yes | 7.89 | 0.03 | 3.10 | 0.08 | 3.68 | 87.38 | 4.01 | 0.14 | 0.26 | 0.35 | 1.02 | | 0.28 | |
| 2012-0053-0036 | 76636 | Tray 07 A | C12 | HE11EE010320.0030.007 | yes | yes | 6.85 | 0.02 | 3.22 | 0.09 | 3.08 | 86.38 | 3.45 | 0.19 | 0.24 | 0.41 | 0.82 | | 0.32 | |
| 2012-0053-0037 | 76637 | Tray 07 A | D1 | HE11EE010320.0030.008 | yes | yes | 6.12 | 0.03 | 2.78 | 0.09 | 2.24 | 89.28 | 2.86 | 0.13 | 0.20 | 0.41 | 0.82 | | 0.28 | |
| 2012-0053-0038 | 76638 | Tray 07 A | D2 | HE11EE010320.0030.009 | yes | yes | 6.92 | 0.02 | 2.91 | 0.07 | 2.02 | 90.12 | 4.48 | 0.17 | 0.28 | 0.40 | 1.00 | | 0.31 | |
| 2012-0053-0039 | 76639 | Tray 07 A | D3 | HE11EE010320.0030.010 | yes | yes | 5.83 | 0.02 | 2.69 | 0.10 | 2.41 | 87.64 | 2.84 | 0.12 | 0.18 | 0.39 | 0.75 | 0.01 | 0.25 | |
| 2012-0053-0040 | 76640 | Tray 07 A | D4 | HE11EE010320.0030.011 | yes | yes | 7.34 | 0.02 | 2.88 | 0.07 | 1.94 | 88.33 | 3.39 | 0.16 | 0.27 | 0.38 | 1.12 | | 0.31 | |
| 2012-0053-0041 | 76641 | Tray 07 A | D5 | HE11EE010320.0030.012 | yes | yes | 7.94 | 0.03 | 3.24 | 0.11 | 3.08 | 86.44 | 4.68 | 0.17 | 0.28 | 0.38 | 1.03 | 0.02 | 0.36 | |
| 2012-0053-0042 | 76642 | Tray 07 A | D6 | HE11EE010320.0030.013 | yes | yes | 5.84 | 0.03 | 3.75 | 0.08 | 1.91 | 88.57 | 4.98 | 0.16 | 0.14 | 0.43 | 0.49 | 0.02 | 0.23 | |
| 2012-0053-0043 | 76643 | Tray 07 A | D7 | HE11EE010320.0030.014 | yes | yes | 7.17 | 0.05 | 4.51 | 0.23 | 1.49 | 86.11 | 6.39 | 0.28 | 0.19 | 0.51 | 0.69 | | 0.39 | |
| 2012-0053-0044 | 76644 | Tray 07 A | D8 | HE11EE010320.0030.015 | yes | yes | 5.78 | 0.03 | 3.51 | 0.08 | 1.35 | 90.23 | 3.17 | 0.15 | 0.14 | 0.37 | 0.53 | 0.01 | 0.20 | |
| 2012-0053-0045 | 76645 | Tray 07 A | D9 | HE11EE010320.0030.016 | yes | yes | 12.47 | 0.08 | 5.91 | 0.09 | 4.95 | 36.74 | 39.68 | 0.21 | 0.36 | 0.21 | 0.90 | | 0.27 | |
| 2012-0053-0046 | 76646 | Tray 07 A | D10 | HE11EE010320.0030.017 | yes | yes | 5.48 | 0.03 | 3.27 | 0.09 | 1.30 | 90.73 | 2.89 | 0.12 | 0.15 | 0.41 | 0.52 | 0.02 | 0.20 | |
| 2012-0053-0047 | 76647 | Tray 07 A | D11 | HE11EE010320.0030.018 | yes | yes | 6.36 | 0.05 | 4.53 | 0.23 | 0.88 | 87.50 | 4.49 | 0.31 | 0.17 | 0.60 | 0.44 | | 0.28 | |
| 2012-0053-0048 | 76648 | Tray 07 A | D12 | HE11EE010320.0030.019 | yes | yes | 11.33 | 0.05 | 5.01 | 0.10 | 4.67 | 49.42 | 36.87 | 0.36 | 0.37 | 0.38 | 0.66 | 0.04 | 0.38 | 0.02 |
| 2012-0053-0050 | 76650 | Tray 07 B | E2 | HE11EE010320.0032.021 | yes | yes | 7.53 | 0.05 | 4.48 | 0.17 | 1.94 | 84.09 | 7.21 | 0.24 | 0.22 | 0.40 | 0.61 | | 0.23 | |
| 2012-0053-0051 | 76651 | Tray 07 B | E3 | HE11EE010320.0032.022 | yes | yes | 5.89 | 0.04 | 3.07 | 0.08 | 1.89 | 90.30 | 2.85 | 0.14 | 0.18 | 0.41 | 0.66 | | 0.26 | |
| 2012-0053-0052 | 76652 | Tray 07 B | E4 | HE11EE010320.0032.023 | yes | yes | 7.82 | 0.03 | 4.00 | 0.16 | 1.59 | 85.72 | 5.87 | 0.32 | 0.25 | 0.54 | 0.81 | | 0.34 | |
| 2012-0053-0053 | 76653 | Tray 07 B | E5 | HE11EE010320.0032.024 | yes | yes | 6.80 | 0.04 | 3.55 | 0.11 | 1.31 | 87.08 | 5.80 | 0.32 | 0.26 | 0.51 | 0.48 | | 0.35 | |
| 2012-0053-0054 | 76654 | Tray 07 B | E6 | HE11EE010320.0032.025 | yes | yes | 6.63 | 0.03 | 2.98 | 0.08 | 2.27 | 89.57 | 3.01 | 0.14 | 0.24 | 0.34 | 0.81 | | 0.30 | |
| 2012-0053-0055 | 76655 | Tray 07 B | E7 | HE11EE010320.0032.026 | yes | yes | 6.86 | 0.03 | 3.16 | 0.09 | 2.46 | 88.57 | 3.47 | 0.18 | 0.23 | 0.34 | 0.75 | | 0.25 | |
| 2012-0053-0056 | 76656 | Tray 07 B | E8 | HE11EE010320.0032.027 | yes | yes | 6.79 | 0.05 | 3.57 | 0.10 | 1.92 | 87.13 | 5.08 | 0.19 | 0.21 | 0.41 | 0.76 | | 0.29 | |
| 2012-0053-0057 | 76657 | Tray 07 B | E9 | HE11EE010320.0032.028 | yes | yes | 6.54 | 0.05 | 3.38 | 0.10 | 1.95 | 87.25 | 5.23 | 0.23 | 0.30 | 0.37 | 0.62 | | 0.27 | |
| 2012-0053-0058 | 76658 | Tray 07 B | E10 | HE11EE010320.0032.029 | yes | yes | 6.25 | 0.03 | 2.99 | 0.07 | 1.98 | 89.41 | 3.50 | 0.13 | 0.21 | 0.35 | 0.78 | | 0.27 | |
| 2012-0053-0059 | 76659 | Tray 07 B | E11 | HE11EE010320.0032.030 | yes | yes | 7.01 | 0.05 | 3.40 | 0.10 | 2.07 | 87.31 | 4.58 | 0.20 | 0.36 | 0.38 | 0.81 | | 0.32 | |

FIG. 16b

| Lab ID | Entry | Tray | Pos | Source | HA468 DM | CL plus | % Sats | C14:0 | C16:0 | C16:1 | C18:0 | C18:1 | C18:2 | C18:3 | C20:0 | C20:1 | C22:0 | C22:1 | C24:0 | C24:1 |
|---|---|---|---|---|---|---|---|---|---|---|---|---|---|---|---|---|---|---|---|---|
| 2012-0053-0060 | 76660 | Tray 07 B | E12 | HE11EE010320.0033.031 | yes | yes | 7.30 | 0.04 | 3.19 | 0.09 | 2.65 | 87.55 | 3.97 | 0.14 | 0.26 | 0.33 | 0.87 | | 0.29 | |
| 2012-0053-0061 | 76661 | Tray 07 B | F1 | HE11EE010320.0033.032 | yes | yes | 13.59 | 0.06 | 5.73 | 0.08 | 6.27 | 33.32 | 52.08 | 0.10 | 0.46 | 0.19 | 0.86 | | 0.21 | |
| 2012-0053-0062 | 76662 | Tray 07 B | F2 | HE11EE010320.0033.033 | yes | yes | 7.18 | 0.04 | 3.53 | 0.08 | 2.19 | 87.07 | 4.75 | 0.17 | 0.29 | 0.37 | 0.82 | | 0.31 | |
| 2012-0053-0063 | 76663 | Tray 07 B | F3 | HE11EE010320.0033.034 | yes | yes | 6.96 | 0.03 | 3.06 | 0.08 | 2.41 | 89.48 | 2.82 | 0.12 | 0.24 | 0.33 | 0.90 | | 0.33 | |
| 2012-0053-0064 | 76664 | Tray 07 B | F4 | HE11EE010320.0033.035 | yes | yes | 6.65 | 0.03 | 3.03 | 0.09 | 2.20 | 89.31 | 3.22 | 0.16 | 0.24 | 0.34 | 0.83 | | 0.32 | |
| 2012-0053-0065 | 76665 | Tray 07 B | F5 | HE11EE010320.0033.036 | yes | yes | 6.73 | 0.04 | 3.30 | 0.09 | 2.08 | 88.07 | 4.48 | 0.13 | 0.22 | 0.33 | 0.79 | | 0.31 | |
| 2012-0053-0066 | 76666 | Tray 07 B | F6 | HE11EE010320.0036.037 | yes | yes | 8.40 | 0.04 | 4.06 | 0.11 | 2.48 | 81.86 | 8.68 | 0.13 | 0.34 | 0.36 | 1.10 | | 0.36 | |
| 2012-0053-0067 | 76667 | Tray 07 B | F7 | HE11EE010320.0036.038 | yes | yes | 8.44 | 0.05 | 4.22 | 0.17 | 2.41 | 83.41 | 6.97 | 0.26 | 0.34 | 0.36 | 0.96 | | 0.36 | |
| 2012-0053-0068 | 76668 | Tray 07 B | F8 | HE11EE010320.0036.039 | yes | yes | 7.95 | 0.04 | 3.57 | 0.10 | 2.62 | 85.19 | 5.86 | 0.16 | 0.30 | 0.34 | 1.09 | | 0.33 | |
| 2012-0053-0069 | 76669 | Tray 07 B | F9 | HE11EE010320.0036.040 | yes | yes | 8.37 | 0.04 | 3.65 | 0.11 | 2.84 | 84.66 | 5.98 | 0.17 | 0.32 | 0.40 | 1.28 | | 0.44 | |
| 2012-0053-0070 | 76670 | Tray 07 B | F10 | HE11EE010320.0036.041 | yes | yes | 8.07 | 0.03 | 3.57 | 0.11 | 2.64 | 84.05 | 6.81 | 0.17 | 0.30 | 0.37 | 1.15 | | 0.37 | |
| 2012-0053-0071 | 76671 | Tray 07 B | F11 | HE11EE010320.0036.042 | yes | yes | 7.44 | 0.03 | 3.31 | 0.10 | 2.53 | 87.76 | 3.90 | 0.14 | 0.28 | 0.37 | 1.08 | | 0.31 | |
| 2012-0053-0072 | 76672 | Tray 07 B | F12 | HE11EE010320.0036.043 | yes | yes | 6.73 | 0.03 | 2.84 | 0.11 | 1.72 | 85.16 | 51.33 | 0.12 | 0.17 | 0.37 | 0.88 | 0.01 | 0.29 | |
| 2012-0053-0073 | 76673 | Tray 07 B | G1 | HE11EE010320.0036.044 | yes | yes | 7.23 | 0.03 | 3.42 | 0.09 | 2.42 | 87.22 | 7.22 | 0.16 | 0.22 | 0.34 | 0.88 | | 0.28 | |
| 2012-0053-0074 | 76674 | Tray 07 B | G2 | HE11EE010320.0036.045 | yes | yes | 6.83 | 0.03 | 3.32 | 0.10 | 2.06 | 87.23 | 4.77 | 0.13 | 0.21 | 0.36 | 0.91 | 0.02 | 0.30 | 0.01 |
| 2012-0053-0075 | 76675 | Tray 07 B | G3 | HE11EE010320.0036.046 | yes | yes | 7.19 | 0.03 | 3.72 | 0.10 | 1.96 | 85.32 | 5.14 | 0.12 | 0.19 | 0.37 | 0.98 | 0.01 | 0.33 | 0.02 |
| 2012-0053-0076 | 76676 | Tray 07 B | G4 | HE11EE010320.0036.047 | yes | yes | 8.39 | 0.04 | 4.37 | 0.16 | 2.38 | 81.31 | 6.57 | 0.18 | 0.39 | 0.42 | 0.98 | | 0.37 | |
| 2012-0053-0077 | 76677 | Tray 07 B | G5 | HE11EE010320.0036.048 | yes | yes | 7.74 | 0.04 | 3.42 | 0.11 | 2.68 | 86.37 | 9.11 | 0.14 | 0.27 | 0.38 | 1.04 | | 0.30 | |
| 2012-0053-0078 | 76678 | Tray 07 B | G6 | HE11EE010320.0037.049 | yes | yes | 9.03 | 0.06 | 5.14 | 0.07 | 2.66 | 28.75 | 51.33 | 0.12 | 0.28 | 0.28 | 0.70 | | 0.21 | |
| 2012-0053-0079 | 76679 | Tray 07 B | G7 | HE11EE010320.0037.050 | yes | yes | 6.67 | 0.03 | 3.35 | 0.08 | 1.93 | 87.85 | 4.51 | 0.13 | 0.23 | 0.40 | 0.85 | | 0.29 | |
| 2012-0053-0080 | 76680 | Tray 07 B | G8 | HE11EE010320.0037.051 | yes | yes | 7.22 | 0.03 | 3.30 | 0.09 | 2.25 | 84.52 | 7.33 | 0.15 | 0.23 | 0.38 | 1.01 | | 0.35 | |
| 2012-0053-0081 | 76681 | Tray 07 B | G9 | HE11EE010320.0037.052 | yes | yes | 7.61 | 0.04 | 3.27 | 0.08 | 2.79 | 87.84 | 3.97 | 0.14 | 0.28 | 0.34 | 0.95 | | 0.29 | |
| 2012-0053-0082 | 76682 | Tray 07 B | G10 | HE11EE010320.0037.053 | yes | yes | 7.14 | 0.03 | 3.36 | 0.10 | 2.35 | 86.45 | 6.46 | 0.14 | 0.27 | 0.37 | 0.86 | | 0.28 | |
| 2012-0053-0083 | 76683 | Tray 07 B | G11 | HE11EE010320.0037.054 | yes | yes | 8.43 | 0.05 | 4.49 | 0.09 | 2.63 | 73.15 | 17.43 | 0.22 | 0.33 | 0.31 | 0.71 | | 0.22 | |
| 2012-0053-0084 | 76684 | Tray 07 B | G12 | HE11EE010320.0037.055 | yes | yes | 6.66 | 0.03 | 3.06 | 0.08 | 2.21 | 86.70 | 5.72 | 0.11 | 0.23 | 0.36 | 0.86 | | 0.25 | |
| 2012-0053-0087 | 76687 | Tray 07 B | H3 | HE11EE010320.0037.058 | yes | yes | 7.20 | 0.03 | 3.24 | 0.09 | 2.51 | 85.78 | 6.01 | 0.12 | 0.27 | 0.35 | 0.87 | 0.01 | 0.27 | |
| 2012-0053-0088 | 76688 | Tray 07 B | H4 | HE11EE010320.0037.059 | yes | yes | 8.28 | 0.04 | 3.84 | 0.09 | 2.56 | 80.47 | 10.34 | 0.17 | 0.35 | 0.35 | 1.09 | | 0.40 | |
| 2012-0053-0089 | 76689 | Tray 07 B | H5 | HE11EE010320.0037.060 | yes | yes | 6.59 | 0.03 | 3.19 | 0.09 | 1.85 | 87.98 | 4.55 | 0.14 | 0.20 | 0.39 | 0.86 | | 0.34 | |
| 2012-0053-0090 | 76690 | Tray 07 B | H6 | HE11EE010320.0037.061 | yes | yes | 6.93 | 0.03 | 3.35 | 0.09 | 2.11 | 87.80 | 4.10 | 0.13 | 0.24 | 0.39 | 0.90 | 0.01 | 0.31 | |
| 2012-0053-0091 | 76691 | Tray 07 B | H7 | HE11EE010320.0038.062 | yes | yes | 8.27 | 0.04 | 3.63 | 0.11 | 2.61 | 84.69 | 5.54 | 0.15 | 0.29 | 0.39 | 0.99 | 0.01 | 0.44 | 0.01 |
| 2012-0053-0092 | 76692 | Tray 07 B | H8 | HE11EE010320.0038.063 | yes | yes | 8.15 | 0.04 | 3.75 | 0.10 | 2.70 | 81.58 | 9.26 | 0.16 | 0.32 | 0.32 | 1.26 | | 0.32 | |
| 2012-0053-0093 | 76693 | Tray 07 B | H9 | HE11EE010320.0038.064 | yes | yes | 7.78 | 0.04 | 3.58 | 0.10 | 2.35 | 85.02 | 6.07 | 0.18 | 0.33 | 0.40 | 1.01 | | 0.40 | |
| 2012-0053-0094 | 76694 | Tray 07 B | H10 | HE11EE010320.0038.065 | yes | yes | 7.11 | 0.03 | 3.64 | 0.08 | 2.17 | 81.76 | 10.28 | 0.13 | 0.21 | 0.33 | 0.80 | | 0.25 | |
| 2012-0053-0095 | 76695 | Tray 07 B | H11 | HE11EE010320.0038.066 | yes | yes | 6.68 | 0.03 | 3.23 | 0.08 | 2.15 | 86.52 | 5.77 | 0.16 | 0.23 | 0.37 | 0.77 | 0.01 | 0.28 | 0.02 |
| 2012-0053-0096 | 76696 | Tray 07 B | H12 | HE11EE010320.0038.067 | yes | yes | 7.21 | 0.03 | 3.30 | 0.09 | 2.41 | 85.17 | 6.64 | 0.15 | 0.27 | 0.35 | 0.91 | 0.01 | 0.31 | |

*FIG. 16c*

Note: These are actually ¼ seed samples

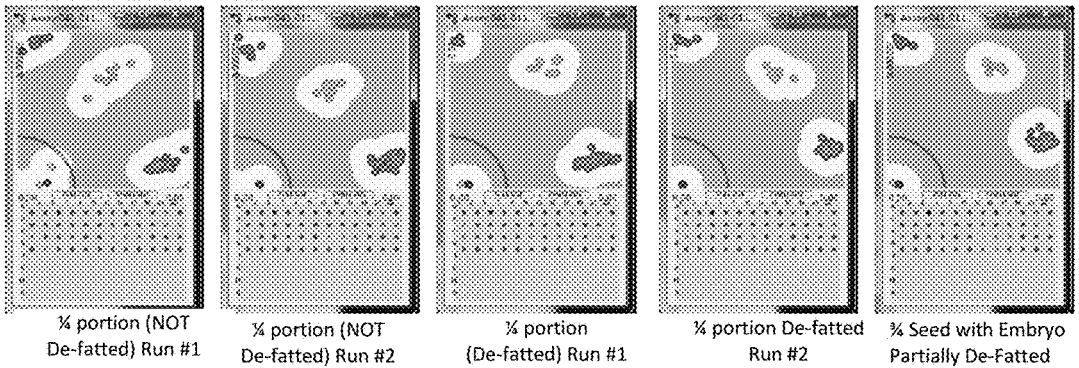
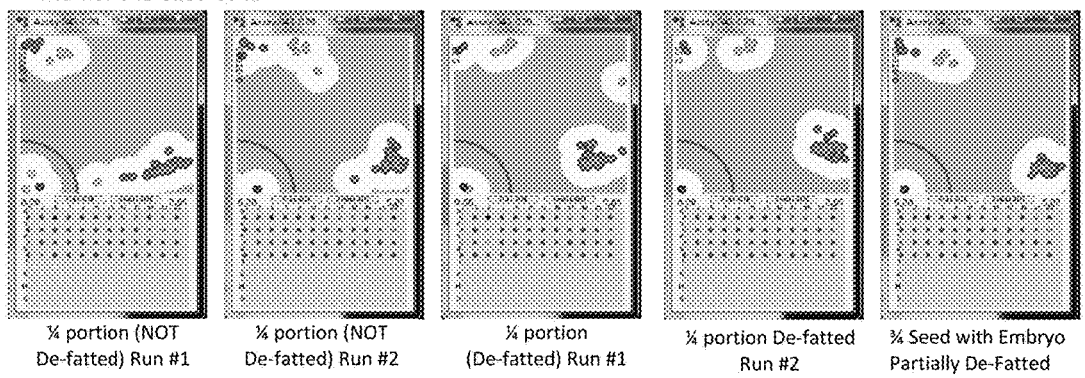
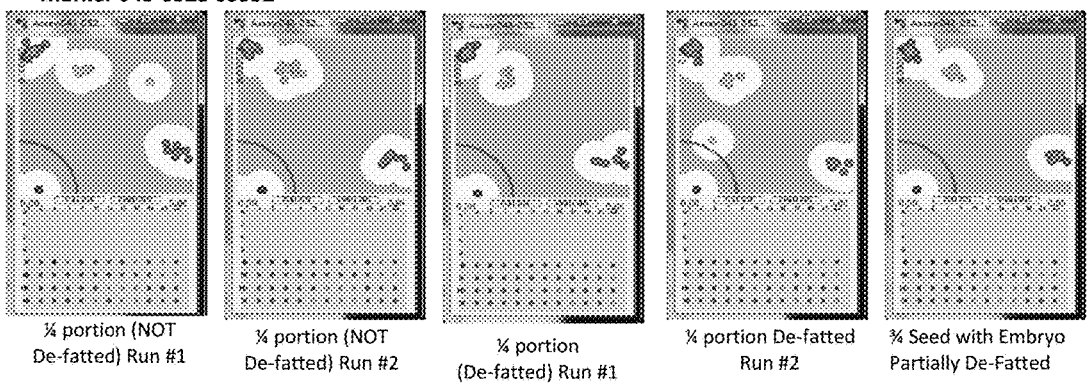
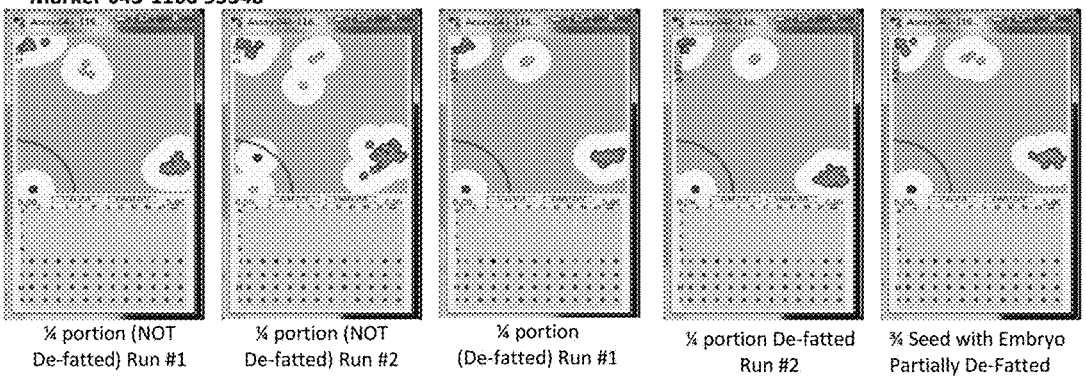
*FIG. 19*

RECOVERY OF GENOMIC DNA FROM REMNANT EXTRACTED SEED SAMPLES

CROSS-REFERENCE TO RELATED APPLICATION

This application claims the benefit of U.S. Provisional Patent Application Ser. No. 61/735,485, filed Dec. 10, 2012, the disclosure of which is hereby incorporated herein in its entirety by this reference.

FIELD OF THE DISCLOSURE

The present disclosure relates to plant biotechnology. Embodiments relate to systems and/or methods for the isolation and analysis of plant genetic information from remnant seed samples, for example, in an automated manner. Such systems and/or methods may be used, for example and without limitation, for efficient plant selection in a plant breeding program.

BACKGROUND

The goal of plant breeding is to develop new, unique, and superior cultivars and hybrids. A breeder initially selects and crosses two or more parental lines, followed by repeated selfing and selection, to eventually produce many new genetic combinations. The breeder can theoretically generate billions of different genetic combinations via crossing, selfing, and mutagenesis. Such a breeder has no direct control of the process at the cellular level. Therefore, two breeders will never develop the same line, or even very similar lines, having the same traits.

There are numerous steps in the development of any novel, desirable plant germplasm. Plant breeding programs combine desirable traits from two or more cultivars or various broad-based sources into breeding pools, from which cultivars are developed by selfing and selection of desired phenotypes. The new cultivars are evaluated to determine which have commercial potential. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

The choice of breeding and selection methods depends on the mode of plant reproduction, the heritability of the trait(s) being improved, and the type of cultivar used commercially (e.g., $F_1$ hybrid cultivar and pureline cultivar). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding and selection methods. For example, backcross breeding may be used to transfer one (or a few) favorable genes for a highly heritable trait into a desirable germplasm. This approach has been used extensively for breeding disease-resistant cultivars. Various recurrent selection techniques may be used to improve quantitatively-inherited traits controlled by numerous genes.

A breeding program typically includes a periodic, objective evaluation of the efficiency of the breeding procedure. Evaluation criteria vary, depending on the goal and objectives, but the criteria may include, for example and without limitation: gain from selection per year (based on comparisons to an appropriate standard); overall value of the advanced breeding lines; and the number of successful cultivars produced per unit of input (e.g., per year and per dollar expended).

Promising advanced breeding lines are then thoroughly tested and compared to appropriate standards in environments representative of the commercial target area(s), typically for three or more years. Candidates for new commercial cultivars are selected from among the best lines; those still deficient in a few traits may be used as parents to produce new populations for further selection. These processes, which lead to the final step of marketing and distribution, usually take from 8 to 12 years from the time the first cross is made. Therefore, development of new cultivars is a time-consuming process that requires precise forward planning, efficient use of resources, and a minimum of changes in direction.

Breeding programs combine desirable traits from two or more inbred lines, or various broad-based sources, into breeding pools from which new inbred lines are developed by selfing and selection of desired phenotypes. A hybrid variety is the cross of two such inbred lines, each of which may have one or more desirable characteristics absent in one line, or complementing the other. The new inbred plants are crossed with other inbred lines, and the hybrids from these crosses are evaluated to determine which are superior, or possess desirable attributes. Hybrid seed is produced by manual crosses between selected male-fertile parents, or by using male sterility systems. These hybrids are selected for certain single gene traits (e.g., pod color, flower color, pubescence color, and herbicide resistance) that indicate that the seed is truly a hybrid. Data on parental lines, as well as the phenotype of the hybrid, influence the breeder's decision regarding whether to continue with the specific hybrid cross.

Accordingly, the development of new cultivars requires the selection of parent varieties, crossing of these varieties, and selection of superior hybrid crosses. The task of identifying genetically superior individuals is particularly difficult. One method of identifying a superior plant is to determine one or more phenotypes in the plant, for example, relative to other experimental plants and to a widely grown standard cultivar. This task is extremely difficult, because (for most traits) the true genotypic value is masked by other confounding plant traits or environmental factors. Thus, it is typically necessary to determine the precise genotype of a particular plant, and its phenotype, in order to adequately evaluate and identify superior cultivars and hybrids.

The composition of a particular plant cultivar developed during selective plant breeding is unpredictable. This unpredictability is due, in part, to the breeder's selection, which occurs in unique environments, and which allows no control at the DNA level (using conventional breeding procedures), with millions of different possible genetic combinations being generated. A breeder of ordinary skill in the art cannot predict the final resulting lines he develops, except possibly in a very gross and general fashion. Similarly, the same breeder cannot produce the same cultivar twice by using the exact same original parents and the same selection techniques. This unpredictability results in the expenditure of large amounts of resources, monetary and otherwise, to develop superior new cultivars.

Pedigree breeding is used commonly for the improvement of self-pollinating crops. In pedigree breeding, two parents that possess favorable, complementary traits are crossed to produce $F_1$ progeny. An $F_2$ population is produced by selling one or several plants from the $F_1$ progeny generation. Selection of the best individuals may begin in the $F_2$ population; then, beginning in the $F_3$, the best individuals in the best families are selected. To improve the effectiveness of selection for traits with low heritability, replicated testing of families can begin in the $F_4$ generation. At an advanced stage of inbreeding (e.g., $F_6$ or $F_7$), the best lines or mixtures of lines with similar phenotypes are tested for potential release as new cultivars.

Mass and recurrent selections can be used to improve populations of either self- or cross-pollinating crops. A genetically variable population of heterozygous individuals may be either identified or created by intercrossing several different parents. The best plants may be selected based on individual superiority, outstanding progeny, or excellent combining ability. The selected plants are intercrossed to produce a new population, in which further cycles of selection may be continued.

Backcross breeding has been used to transfer genes for a simply- and highly-heritable trait into a desirable homozygous cultivar, or inbred line, which is the recurrent parent. The source of the trait to be transferred is the "donor parent." The resulting plant is expected to have the attributes of the recurrent parent (e.g., cultivar), and the desirable trait transferred from the donor parent. After the initial cross, individuals possessing the phenotype of the donor parent are selected, and repeatedly crossed (backcrossed) to the recurrent parent. The resulting plant is expected to have the attributes of the recurrent parent and the desirable trait transferred from the donor parent. During backcross breeding, progeny plants comprising the desired phenotype are typically selected at each generation. Where appropriate, progeny plants may also be selected for the presence of molecular markers; e.g., genetic marker alleles and isozyme markers.

A "single-seed descent procedure" refers to the planting of a segregating population, followed by harvesting a sample of one seed per resulting plant, and using the harvested one-seed sample to plant the next generation. When the population has been advanced from the $F_2$ generation to the desired level of inbreeding, the plants from which lines are derived will each trace to different $F_2$ individuals. The number of plants in a population declines each generation, due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest seeds from each plant in a population and thresh them together to form a bulk. Part of the bulk is used to plant the next generation, and part is put in reserve. This procedure has been referred to as modified single-seed descent. The multiple-seed procedure has been used to save labor involved in the harvest. It is considerably faster to remove seeds with a machine, than to remove one seed from each by hand for the single-seed procedure. The multiple-seed procedure also makes it possible to plant the same number of seeds of a population for each generation of inbreeding. Enough seeds are harvested to compensate for the number of plants that did not germinate or produce seed.

One set of traits that may be of interest to an oilseed plant breeder are oil traits (e.g., yield and composition). This is in large part due to the fact that vegetable-derived oils have gradually replaced animal-derived oils and fats as the major source of dietary fat intake. However, saturated fat intake in most industrialized nations has remained at about 15% to 20% of total caloric consumption. In efforts to promote healthier lifestyles, the United States Department of Agriculture (USDA) has recently recommended that saturated fats make up less than 10% of daily caloric intake. To facilitate consumer awareness, current labeling guidelines issued by the USDA now require total saturated fatty acid levels be less than 1.0 g per 14 g serving to receive the "low-sat" label and less than 0.5 g per 14 g serving to receive the "no-sat" label. This means that the saturated fatty acid content of plant oils needs to be less than 7% and 3.5% to receive the "low-sat" or "no-sat" label, respectively. Since issuance of these guidelines, there has been a surge in consumer demand for "low-sat" and "no-sat" oils. To date, this demand has been met principally with canola oil, and to a much lesser degree with sunflower and safflower oils.

In addition to direct human consumption, vegetable oil has added value for livestock feed, due to its higher energy density and is also increasingly used as a primary source for biodiesel production, particularly in Europe. Vegetable oils with high oleic acid (a monounsaturated fatty acid), and/or low levels of saturate fatty acids, provide considerable health and cooking benefits when compared to saturated and polyunsaturated fatty acids. Kinney et al. (2002) Biochem. Soc. Trans. 30:1099-103; White and Weber (2003) "Lipids of the kernel," in Corn: Chemistry and Technology. $2^{nd}$ Ed., Vol. 10, Eds. White & Johnson, American Association of Cereal Chemists, Inc., St. Paul, Minn., pp. 355-95.

BRIEF SUMMARY OF THE DISCLOSURE

Included herein are systems and methods for isolating high-quality nucleic acids (e.g., genomic DNA) from remnant defatted plant seed material for use in amplification-based genetic analysis. Embodiments thereby allow the determination of both oil and genetic profiles from a single seed tissue source, wherein a separate portion of the seed may be reserved to be planted or discarded according to the determined profiles. In particular examples, high-quality nucleic acids isolated and analyzed utilizing a system and/or method herein may provide zygosity data with greater than 99% data return and greater than about 96% agreement with a leaf reference sample. The identification of both the oil and genetic profile from a single half-seed source may allow a plant breeder to select only those plants (grown from the embryo containing portion of the seed) with desired characteristics for transplantation, thereby reducing sampling workload in the field and increasing breeding efficiency. By obtaining the oil and genetic profiles from a single seed source in a partially non-destructive manner utilizing a system and/or method herein, the number of seed that are planted can be dramatically reduced by selecting only germplasm with advantageous attributes for generation advancement.

In some embodiments, a system for determining the genotype of a plant for at least one gene of interest may comprise, for example and without limitation: a seed sample that has been subjected to oil extraction; solubilization of DNA from the defatted seed matrix, magnetic particles (e.g., magnetic beads) that bind nucleic acids from the seed sample to produce a high-quality nucleic acid sample; means for amplifying the high-quality nucleic acid sample (e.g., polymerase chain reaction (PCR)) to produce amplified nucleic acids; a probe that detects an allele of the gene or locus of interest (e.g., oligonucleotide probes specific for each of two alleles of the gene of interest); and computer-implemented means to determine the genotype of the seed sample from the hybridization or lack thereof of the oligonucleotide probe to the amplified nucleic acids. In particular embodiments, the system for determining the genotype of a plant for at least one gene of interest may be fully automated, for example, by the use of a programmable robot.

Seed samples that may be useful in some embodiments include seed material that has been defatted, for example, by exposure to an organic solvent (e.g., hexane). In particular examples, the seed material has been defatted by heptane extraction. The extracted oil is converted to fatty acid methyl esters (FAME) by transesterification. Individual fatty acids are quantified by gas chromatography. In particular examples, a seed sample may include a sample from seed of an oilseed plant (e.g., a *Brassica* spp., for example, canola; *Glycine max*; and sunflower (*Helianthus annuus*)).

In some embodiments, a method for determining the genotype of a plant for at least one gene of interest may comprise, for example and without limitation: providing from the plant a seed sample that has been subjected to oil extraction; isolating high-quality nucleic acids from the defatted seed sample; amplifying the high-quality nucleic acids; and identifying the allelic composition of the amplified nucleic acids. In particular embodiments, the method is fully-automated, which may provide significant cost savings and throughput in a plant breeding program.

Isolated nucleic acid samples obtained by systems and methods according to particular embodiments of the invention may be sufficiently pure that they may be used in PCR-based genetic analysis techniques. For example, particular systems and methods herein may provide and/or comprise a high-quality nucleic acid sample obtained from a defatted seed material. A high-quality nucleic acid sample may have, for example, an $A_{260}/A_{280}$ absorbance ration between about 1.7 and about 2.0, and it may be capable of amplification by the polymerase chain reaction (PCR).

In some embodiments, a method for using information obtained by genetic analysis of high-quality nucleic acids may comprise the utilization of a PCR-based analysis technique (e.g., KASPar analysis and TAQMAN® analysis). Information thus obtained may be used in particular embodiments in applications including, for example and without limitation: to identify and genotype a cultivar; to make selections in a plant breeding program; to identify markers linked to a trait of interest (e.g., an oil trait of interest); and to describe the relationship of a gene with a trait of interest.

In particular embodiments, information obtained by genetic analysis of extracted nucleic acids may be used to inform and/or direct a plant breeding program. Such information may be used, for example and without limitation, to select seeds for planting and breeding that comprise a desired combination of at least one trait of interest and at least one gene of interest.

The foregoing and other features will become more apparent from the following detailed description of several embodiments, which proceeds with reference to the accompanying figures.

BRIEF DESCRIPTION OF THE FIGURES

FIGS. 1a through 1h inlcude FAME profiles determined from canola half-seed samples by gas chromatography analysis.

Figure 7K:
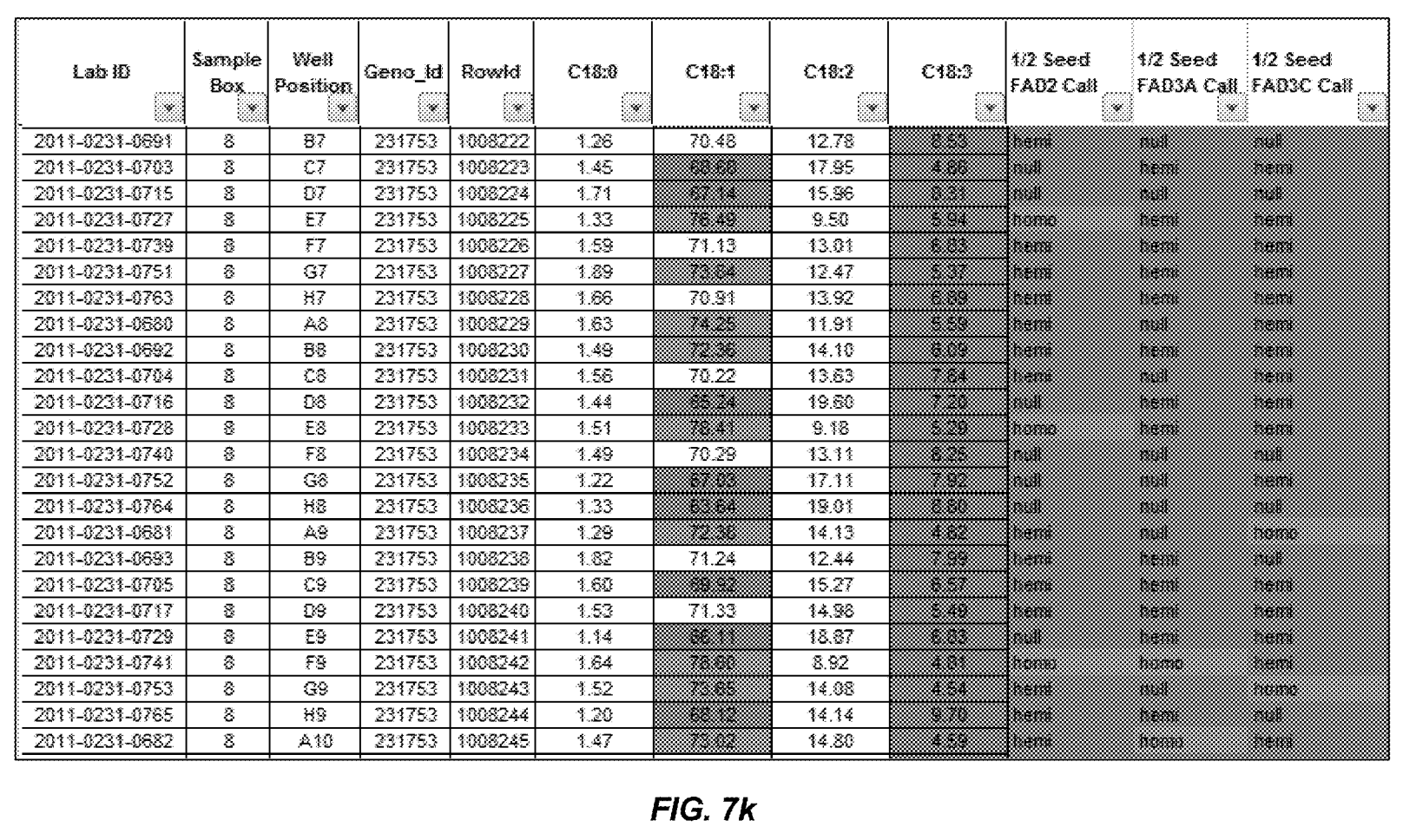

FIGS. 7a through 7l include comparisons of oil profiles determined from canola half-seed samples by FAME analysis, and genotypes determined in the defatted remnant samples.

Figure 9B:
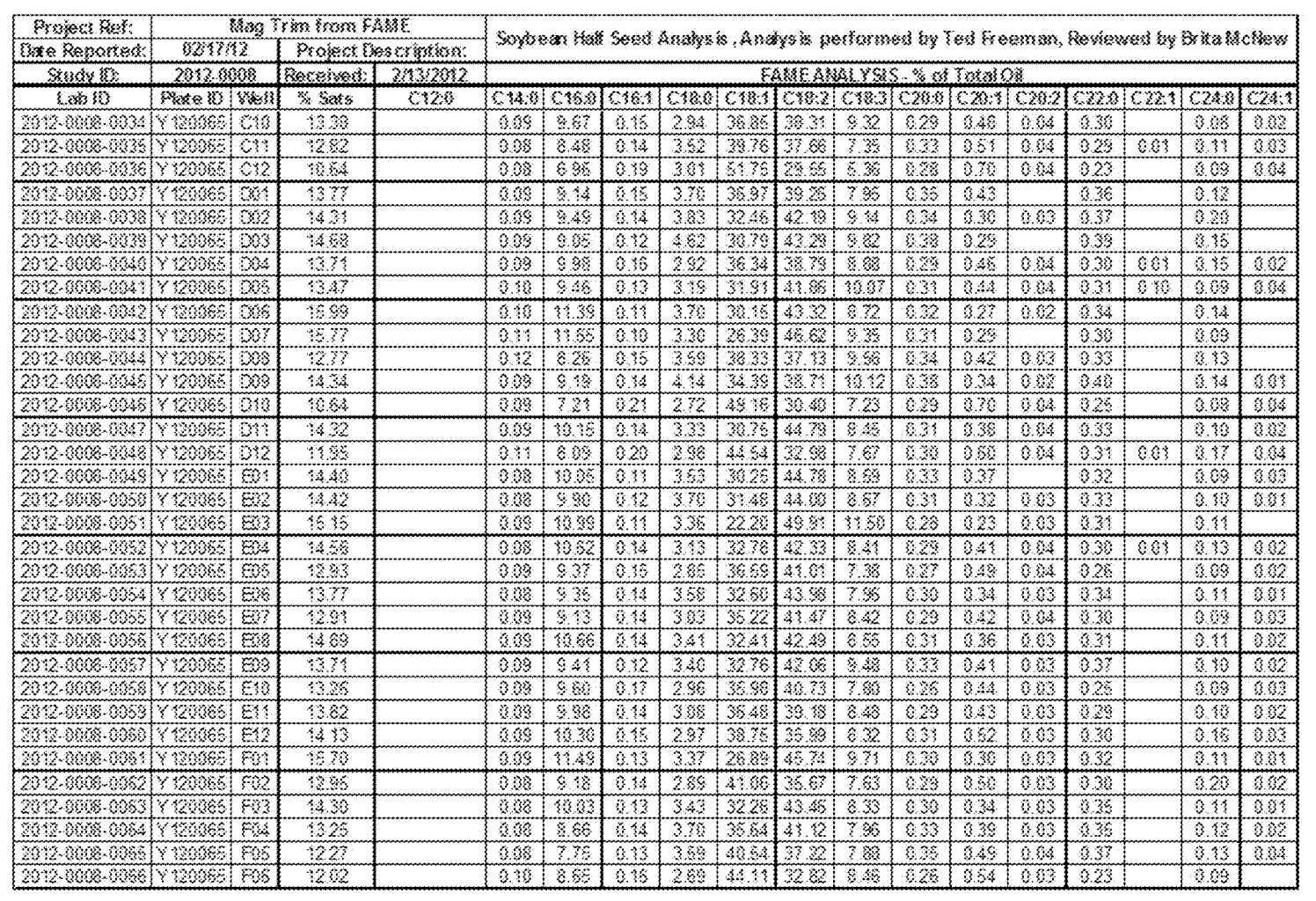
Figure 9E:
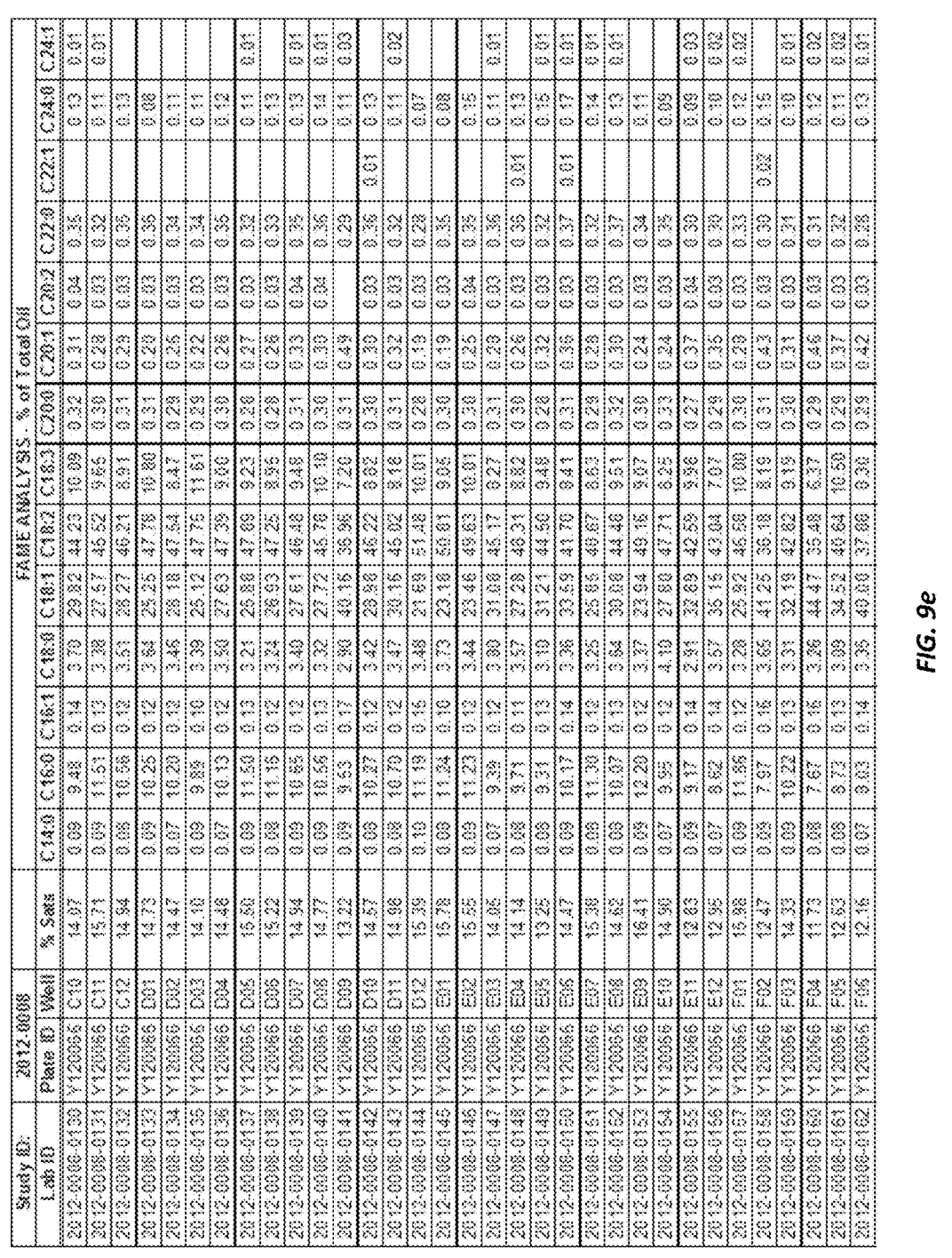

FIGS. 9a through 9i include oil profiles determined from soybean seed samples by FAME analysis.

FIGS. 14a and 14b include a description of exemplary sunflower seed populations used to evaluate systems and methods for isolating nucleic acids from defatted sunflower seed material.

FIGS. 15a through 15n include oil profiles determined from Group A2 sunflower ¼ seed portions (FIG. 15a) and from Group B sunflower ¼ seed portions (FIGS. 15b through 15n) by FAME analysis. Quality data was generated and all oleic values were within expected range. Standards and quality checks performed as expected.

FIGS. 16a through 16c include oil profiles determined from a population of sunflower ¼ seed portions by FAME analysis.

FIG. 19 includes data for KASPar analysis of 9 representative (Downey Mildew-specific) SNP markers from sunflower DNA recovered from seed material defatted by solvent extraction. Two micro liters of 2×-diluted dried down DNA was used per 4.0 µL KASPar reaction (384-well format). Samples of sufficient quality and yield clearly clustered as AA, AB, or BB genotype, represented by red, green, and blue clusters, respectively. Pink data points indicate a measurable signal was not generated and are identifiable as "fails." Black data points indicate "No Template Controls" (NTCs). Data for 4 of the markers tested is shown.

DETAILED DESCRIPTION

I. Overview of Several Embodiments

Figure 2:
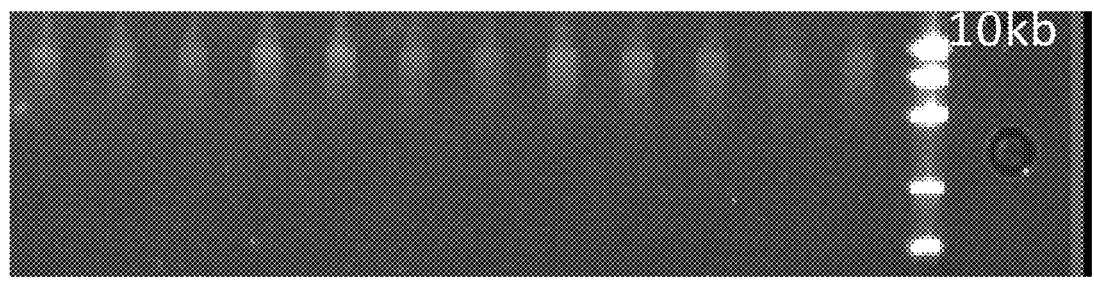
FIG. 2 includes an image showing gel electrophoresis of canola DNA isolated from seed material defatted by solvent extraction. A 10 kb high M.W. band is evident across all samples on the gel with some slight smearing.

Some embodiments of the invention provide systems and/or methods for genotyping and phenotyping a sample of a plant seed, wherein the remainder of the seed (containing the embryo) may be selected for growth and/or cultivation. In particular embodiments, a plant trait determined in such a seed is an oil trait.

The oil profile of a particular plant is a complex trait that results from the poorly understood interaction of multiple genes. Two plants with similar oil phenotypes may have very different genotypes that result in the phenotype through different mechanisms. When breeding plants for desirable oil traits, therefore, it may be desirable to determine the genotypes of individual plants, and use this information in correlation with phenotype information to make breeding selections.

For example, the omega-9 oil profile of certain canola germplasm depends upon the presence of mutations in the fad2, fad3a, and fad3c genes. Additionally, for male lines of the canola hybrid Ogura cytoplasmic male sterility system, the presence of the Rfo gene (restorer fertility) is required to restore male fertility to germplasm. Thus, in order to identify new omega-9 male breeding lines, the appropriate combination of variants for all 4 genes should be present. Due to the complex interaction between genes, it is possible that simple phenotypic selection will result in undesirable and undetected genetic changes in the selected plants, where the desired genotype is difficult to recover in subsequent breeding steps, if progeny plants are not also genotyped during selection.

In contrast to particular embodiments, the conventional approach used in breeding of oilseed plants identifies segregating populations that contain desired traits and genetics by, first, identifying the seed oil fatty acid profile of seeds through solvent extraction followed by transesterification and gas chromatographic analysis of the fatty acid methyl esters (FAME) from half-seed material (containing cotyledon), followed by growth of plants from the remaining half-seed (containing the embryo) and PCR analysis of leaf tissue DNA to identify the zygosity of genes of interest. Plants containing the desired genotype that were grown from a seed comprising the desired oil trait may then be selected for further breeding and/or cultivation. This conventional process is time-consuming and expensive when compared to embodiments herein, because the remaining half-seed from which the half-seed sample was taken for phenotypic analysis must be planted and allowed to grow before leaf tissue can be collected and genetic testing can be performed. This additional step is responsible for substantial resource costs during plant breeding. Van Deynze & Stoffel (2006) Seed Sci. & Technol. 34:741-5.

Examples presented herein involve systems and methods to isolate high-purity genomic DNA from remnant defatted (e.g., solvent-extracted) seed material (e.g., defatted seed material that does not comprise the seed embryo). In conventional systems and methods, such high-purity DNA, which is suitable for amplification and genotyping, is not recovered from the remnant seed material, and the material is discarded. Certain examples involve the automated isolation of genomic DNA from remnant defatted seed material from any of a variety of oilseed plants; e.g., canola half-seed material, sunflower seed material, and soybean seed material. Thus, embodiments of the invention have been shown to be broadly applicable across plant species, while DNA extraction from even unprocessed seed material has been unpredictable and often unsuccessful. Van Deynze & Stoffel (2006), supra. For example, the MAGATTRACT® bead-based DNA extraction protocol (Qiagen) has not been thought to be capable of extracting any DNA (let alone high-quality DNA) from *Brassica* seed material, nor has it been thought to be capable to retrieve DNA from remnant FAME material.

Some embodiments include systems and/or methods that may allow the provision of high-quality, amplifiable DNA from remnant defatted seed material, such that the DNA may be used, for example and without limitation, in PCR-based genotyping (e.g., TAQMAN® and KASPar SNP genotyping applications). Conventional methods do not utilize defatted seed material to produce high quality, pure, DNA for genetic applications such as genotyping. The isolation of such high purity DNA is not trivial, as sufficient amounts of large nucleic acids must be isolated, so as to make possible the analysis of the entire genome with a low error rate.

By obtaining oil and genetic profiles from a single seed source, the number of plants that are transplanted may be reduced by ensuring that only plants with a desired genotypic or phenotypic profile are advanced to the next generation. Thus, particular embodiments herein may result in significant time and resource savings by eliminating, or substantially reducing, tissue sampling requirements. Additional ability to conduct genome wide marker-assisted selection (MAS) utilizing high-purity DNA isolated utilizing a system and/or method herein will simplify and make more affordable the utilization of genotypic data for introgression and conversion projects that are not currently utilizing marker data.

Embodiments herein may have a significant impact on selective oilseed plant breeding. For example, the collection of a single half-seed can allow the determination of necessary fatty acid profile and genotypic (or zygosity) data for selection of advantageous germplasm prior to transplanting. Seed lacking the desired fatty acid profile and genotype may not be planted, or plants corresponding to such seed may be discarded, thus minimizing tissue sampling and transplanting efforts, and reducing greenhouse resources necessary to advance a plant breeding project.

In addition to the analysis of hybrid materials, genetic analysis of DNA isolated by systems and/or methods according to some embodiments herein may have any of many other potential applications. For example, a practitioner may analyze isolated DNA from a defatted seed sample to determine if an entity is illegally using proprietary germplasm. By way of further example, DNA isolated from a seed by systems and/or methods herein may be genotyped, such that new QTLs or linked markers corresponding to a phenotype (e.g., a complex phenotype) determined in the seed may be deduced or identified.

II. Abbreviations
CMS cytoplasmic male sterility
FAM carboxyfluorescein
FAME Fatty Acid Methyl Ester
KASPar KBioscience's Competitive Allele-Specific PCR SNP genotyping system
LIMS laboratory information management system
MAS marker-assisted selection
MW molecular weight
QTL quantitative trait locus
RS reduced saturate
SNP single nucleotide polymorphism
SSR simple sequence repeat
WOSR winter oilseed rape III. Terms In the description and tables which follow, a number of terms are used. In order to provide a clear and consistent understanding of the specification and claims, including the scope to be given such terms, the following definitions are provided:

Backcrossing: Backcrossing methods may be used to introduce a nucleic acid sequence into plants. The backcrossing technique has been widely used for decades to introduce new traits into plants. Jensen, N., Ed. Plant Breeding Methodology, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Cytoplasmic male sterility: Genetic male sterility is a method that may be used in hybrid seed production. In the absence of a fertility restorer gene, plants of a CMS inbred are male sterile as a result of factors resulting from the cytoplasmic, as opposed to the nuclear, genome. Therefore, the characteristic of male sterility is inherited exclusively through the female parent, since only the female provides cytoplasm to the fertilized seed. CMS plants are fertilized with pollen from another inbred that is not male-sterile. Pollen from the second inbred may or may not contribute genes that make the hybrid plants male-fertile.

High quality DNA refers to

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome).

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule," as used herein, is synonymous with "nucleic acid" and "polynucleotide." The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to the order of nucleobases occurring on both the sense and antisense strands of a nucleic acid, as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA5, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

A nucleic acid molecule may include naturally-occurring and/or modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially-duplexed, triplexed, hairpinned, circular, and padlocked conformations.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

Genome: As used herein, the term "genome" refers to chromosomal DNA found within the nucleus of a cell, and also refers to organelle DNA found within subcellular components of the cell.

Sequence identity: The term "sequence identity" or "identity," as used herein, in the context of two nucleic acid sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Infatuation (NCBI) Basic Local Alignment Search Tool (BLAST; Altschul et al. (1990)) is available from several sources, including the National Center for Biotechnology Information (Bethesda, Md.), and on the Internet, for use in connection with several sequence analysis programs. A description of how to determine sequence identity using this program is available on the Internet under the "help" section for BLAST. For comparisons of nucleic acid sequences, the "Blast 2 sequences" function of the BLAST (Blastn) program may be employed using default parameters. Nucleic acid sequences with even greater similarity to a reference sequence will show increasing percentage identity when assessed by this method.

Specifically hybridizable/specifically complementary: As used herein, the terms "Specifically hybridizable" and "specifically complementary" are tennis that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, $2^{nd}$ ed., vol. 1-3, Cold Spring Harbor Laboratory Press, Cold Spring Harbor, N.Y., 1989, chapters 9 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biology—Hybridization with Nucleic Acid Probes, Part I, Chapter 2, Elsevier, NY, 1993; and Ausubel et al., Eds., Current Protocols in Molecular Biology, Chapter 2, Greene Publishing and Wiley-Interscience, NY, 1995.

As used herein, "stringent conditions" encompass conditions under which hybridization will only occur if there is less than a 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence are those nucleic acid sequences that hybridize under stringent conditions (e.g., the Moderate Stringency conditions set forth, supra) to the reference nucleic acid sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, two nucleic acid sequence molecules are said to exhibit "complete complementarity" when every nucleotide of the sense strand read in the 5' to 3' direction is complementary to every nucleotide of the antisense strand when read in the 5' to 3' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Linked, tightly linked, and extremely tightly linked: As used herein, linkage between genes or markers may refer to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype. Because the proximity of two genes or markers on a chromosome is directly related to the probability that the genes or markers will be passed together to individuals in the next generation, the term "linked" may also refer herein to one or more genes or markers that are located proximate to one another on the same chromosome.

Linked genetic markers of a phenotype may be useful in marker-assisted breeding programs to identify plant varieties comprising the phenotype, and to breed the phenotype into other varieties.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" refers to the version of the marker that is present in a particular individual. The term marker, as used herein, may refer to a cloned segment of DNA and may also or alternatively refer to a DNA molecule that is complementary to a cloned segment of DNA.

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}P$. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait as the original marker.

A probe may be an exact copy of a marker to be detected. A probe may also be a nucleic acid molecule comprising, or consisting of, a nucleotide sequence which is substantially identical to a cloned segment of the subject organism's chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence. A probe may also be a nucleic acid molecule that is "specifically hybridizable" or "specifically complementary" to an exact copy of the marker to be detected ("DNA target").

Marker-assisted breeding: As used herein, the term "marker-assisted breeding" may refer to an approach to breeding directly for one or more traits. In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding. In marker-assisted breeding, the presence or absence of particular molecular markers is used to make selection decisions (marker-assisted selection (MAS)) in the breeding program.

Marker-assisted breeding provides a time- and cost-efficient process for improvement of plant varieties. Several examples of the application of marker-assisted breeding involve the use of isozyme markers. See, e.g., Tanksley and Orton, eds. (1983) Isozymes in Plant Breeding and Genetics, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electro-phoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, a marker used in marker-assisted plant breeding is an SNP marker comprised within the maternal DNA of the pericarp of a seed.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Seed sample: As used herein, the term "seed sample" may refer to one or more material(s) and/or substance(s) obtained from a seed. For example, a seed sample may comprise one or more half-seed(s) and/or seed fragments, sections, or portions(s) from a plant of interest. A seed sample may also comprise a collection of seed materials. In particular examples of embodiments herein, a seed sample may comprise all or part of a seed cotyledon, but may not comprise the seed embryo.

Trait or phenotype: The terms "trait" and "phenotype" are used interchangeably herein. For the purposes of the present disclosure, traits of particular interest include agronomically important traits (e.g., oil traits), as may be expressed, for example, in a crop plant.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers R. A. (ed.), Molecular Biology and Biotechnology: A Comprehensive Desk Reference, VCH Publishers, Inc., 1995 (ISBN 1-56081-569-8). All percentages are by weight and all solvent mixture proportions are by volume unless otherwise noted. All temperatures are in degrees Celsius.

IV. Automated Isolation of High Purity Nucleic Acids from Remnant Defatted Seed Material Embodiments herein include systems and/or methods to isolate a high-quality nucleic acid sample (e.g., genomic DNA) from defatted seed material. In some embodiments, the defatted seed material may be a remnant seed material produced by the solvent extraction (e.g., oil extraction for FAME analysis) of a seed sample, for example and without limitation, a small seed portion or half-seed material. While one of skill in the art will recognize that embodiments herein include isolation of nucleic acids from seed material of other plants, certain examples include isolation from *Brassica* (e.g., canola), sunflower, and/or soy. Particular embodiments include systems and/or methods that lead to the isolation of nucleic acids that are of such high purity (e.g., lacking contamination with less non-nucleic acid material) and which provide such complete genome coverage, that the nucleic acids may be utilized in an amplification-based genotyping process (e.g., a PCR-based analysis).

In some embodiments, a method for the isolation of nucleic acids may include cell disruption or cell lysis (e.g., by grinding or sonicating the seed material); removal of membrane lipids (e.g., with a detergent); and precipitation of DNA (e.g., with cold EtOH or IPA). A nucleic acid extraction method may also include removal of proteins from the sample; removal of salts from the sample; and/or removal of RNA molecules from the sample. In DNA isolation applications, a yield in certain embodiments may fluctuate between populations. In certain embodiments, the $A_{260}/A_{280}$ may be between about 1.7 and about 2.0 (i.e., a "pure" DNA sample). An $A_{260}/A_{280}$ value of less than 1.7 may indicate protein contamination of the sample, while a value above 2.0 may indicate carryover of residual RNA, phenol, salts, and/or alcohol.

As demonstrated by the several examples detailed below, DNA isolated from diverse defatted seed materials utilizing systems and methods according to some embodiments exhibited an average yield between about 0.5 and about 20.0 ng/µL, and a purity between about 1.7 and 2.0 ($A_{260}/A_{280}$). Furthermore, nucleic acids isolated by systems and methods herein may provide sufficient genome coverage to allow accurate genotype determinations of any source seed to be made. Thus, embodiments herein are suitable for extracting high-quality DNA from seed samples sourced from any of a wide variety of plants.

Accordingly, high-quality DNA isolated according to some embodiments may be obtained with a purity between about 1.7 and about 2.0 $A_{260}/A_{280}$. For example, DNA may be obtained with a purity of about 1.70; about 1.72; about 1.74; about 1.76; about 1.78; about 1.80; about 1.82; about 1.84; about 1.86; about 1.88; and about 2.0 $A_{260}/A_{280}$, or values and ranges including any of the foregoing. Moreover, high-quality DNA isolated according to some embodiments may be capable of serving as a substrate for amplification as an oligonucleotide of any and every genomic DNA sequence found within the source seed material.

In particular examples, nucleic acid molecules are isolated from a defatted seed material by DNA extraction using a MAGATTRACT® (Qiagen, Valencia, Calif.) bead-based chemistry. In particular examples, DNA extraction using a MAGATTRACT® bead-based chemistry may be performed in a fully-automated manner (for example, by utilizing a robot to transfer and process samples), thereby significantly reducing the time and expense involved in the procedure. For example and without limitation, DNA may be isolated using a fully-automated modified MAGATTRACT® DNA extraction process carried out on a robot (e.g., a BIOCEL® 1600 and 1800 robots (Agilent, Technologies, Inc., Santa Clara, Calif.).

In particular embodiments, a defatted seed material may be stored (e.g., at ambient temperature or at 4 degrees) prior to isolation of nucleic acids. This period of storage may be 24 hours, 48 hours, 72 hours, 96 hours, a week, ten days, or even longer. Surprisingly, even after extended storage of such seed materials, sufficient amounts of high-quality nucleic acids may be isolated from the material, such that amplification-based genetic analysis may be employed to determine genetic characteristics of the seed. In some examples, a defatted seed material may be stored at ambient temperature for days, weeks, and/or months. For example and without limitation, a defatted seed material may be stored for at least 1 day; at least 2 days; at least 3 days; at least 4 days; at least 5 days; at least 6 days; at least 1 week; at least 8 days; at least 9 days; at least 10 days; at least 11 days; at least 12 days; at least 13 days; at least about 2 weeks; or longer.

V. Determination of Plant Characteristics and Genetic Profile

In embodiments herein, it is possible to advantageously determine the characteristics of a plant through analysis of a seed sample, for example and without limitation, by utilizing a process comprising fatty acid extraction, and also determine from the same seed sample the genotype of the plant at one or more genetic loci.

In some embodiments, characteristics of the plant (e.g., an oil trait) are determined by subjecting the seed sample to fatty acid analysis. Solvent extraction, as well as other lipid extraction techniques, may be utilized to determine the composition of the oil from an oilseed. For example, FAME analysis may be used to determine the amounts of different fatty acids (e.g., oleic acid, stearic acid, palmitic acid) and classes thereof (e.g., saturated, unsaturated, and monounsaturated fatty acids). Particularly in the breeding of oilseed plants, such information may be used to make efficient decisions regarding the performance of new and/or uncharacterized varieties.

The removal of fatty acids from a seed sample produces a "defatted" seed sample, which has previously been only recognized as a waste product. Because it was not thought possible that high-quality DNA for genetic analysis could be extracted from such a defatted seed sample, conventional plant breeding methodologies included the extra and expensive step of growing the remainder of the seed to produce leaf material for DNA extraction and subsequent marker confirmation. It is a feature of some embodiments herein that the need for this step is eliminated, for example, such that only those seeds determined to have a desirable characteristic are advanced for growth and further analysis.

Accordingly, in some embodiments herein, high-quality nucleic acids that have been isolated from a defatted seed sample may be analyzed to determine at least a portion of the genotype of the seed from which the seed sample was obtained. In particular embodiments, the nucleic acids may be of sufficient quality and size to allow genome-wide genetic analysis via an amplification-based technique. For example, the zygosity of a seed may be determined at one or more loci; e.g., markers linked to a phenotype of interest, and candidate linked markers. Determination of the zygosity of a seed via analysis of a defatted sample thereof may be utilized to carry out marker-assisted selection. Such determinations may be essentially as accurate as those performed using DNA isolated from leaf material from a plant or plantlet by conventional means.

Analysis of high-quality DNA extracted from a defatted seed sample may in particular examples be performed utilizing any system or method of genetic analysis known in the art, for example and without limitation, PCR-based analysis techniques (e.g., a KASPar SNP genotyping platform (KBioscience Ltd., Hoddesdon, UK), and TAQMAN® analysis). Target DNA sequences used to design molecular markers for PCR-based genotyping may be identified from genome databases, or through independent sequencing. Oligonucleotide primers for use in DNA amplification may be synthesized accordingly.

A TAQMAN® genotyping assay utilizes oligonucleotide probes to detect amplified genetic markers from a sample. This method utilizes primers that are specific to a genetic marker (e.g., a marker linked to a gene or phenotype of interest), and fluorescent labeled probes configured to detect different marker alleles. The probe associated with one allele is labeled with a fluorescent dye, such as FAM, while the probe associated with the other allele is labeled with a different fluorescent dye, such as VIC® (Applied Biosystems). Hybridization data is analyzed as the presence or absence of a fluorescent dye signal. The detection system may be utilized in a high-throughput and convenient format.

KASPar is a commercially available homogeneous fluorescent system for determining SNP genotypes (KBiosciences Ltd., Hoddesdon, UK). A KASPar assay comprises an SNP-specific "assay mix," which contains three unlabeled primers, and a "reaction mix," which contains all the other required components; for example, a universal fluorescent reporting system. In addition to these mixes, the user provides, inter alia, a FRET-capable plate reader, microtitre plate(s), and DNA samples that contain about 5 ng/L high-quality DNA.

A typical KASPar assay comprises the steps of: allele-specific primer design (e.g., using Primer Picker, which is a free service available through the Internet at the KBiosciences website); preparation of reaction mix including the allele-specific primers; admixing the reaction mix to DNA samples in a microtitre plate; thermocycling; reading the plate in a fluorescent plate reader; and plotting and scoring the fluorescent data. Data from each sample are plotted together on a 2-D graph, where the x- and y-axes correspond to FAM and VIC fluorescence values. Samples having the same SNP genotype cluster together on the plot (i.e., A/A; A/a; and a/a). More technical information about the KASPar system, including a guide of solutions to common problems, is obtainable from KBiosciences Ltd. (e.g., the KASPar SNP Genotyping System Reagent Manual).

When utilized in particular embodiments, genetic analysis of DNA isolated from defatted seed material may be performed in a fully-automated manner. For example, defatted seed material corresponding to different seeds may be loaded into a plate fitted with discrete wells, such that the plate is processed without further manipulation by the practitioner to provide data used to make zygosity determinations and/or to provide such determinations themselves.

VI. Use of Isolated DNA in Plant Breeding

In some embodiments herein, genotypic information acquired utilizing a system and/or methods to isolate a high-quality nucleic acid sample (e.g., genomic DNA) from defatted seed material may be used to inform and/or guide plant breeding decisions, e.g., as may be made while selectively breeding a plant for one or more traits of interest.

For example, seed collected from a plant produced via a cross of parent genotypes may be sampled, wherein the sample is subjected to a phenotypic analysis including fatty acid extraction (e.g., an oil trait determination) and is then subsequently used as the source material for the isolation of the nucleic acid sample. Any phenotypic analysis that is measurable or otherwise ascertainable in a seed may be performed on the seed and/or seed sample. For example, analyses that do not include fatty acid extraction may be performed. The manner by which the seed sample is defatted prior to nucleic acid isolation varies in particular embodiments.

In some embodiments, a trait of interest in a plant from which a defatted seed sample is genotyped is an oil trait. For example, a trait of interest may be an oil trait in a plant produced during the execution of a strategy for the introgression of the oil trait into a new germplasm, and/or for the introgression of a different trait into a germplasm comprising the trait of interest, wherein preservation of the trait of interest in the plant is desired. In some examples, an oil trait of interest may be a trait that is being removed or altered via a plant breeding program.

A variety of genetic information may be determined in a high-quality nucleic acid sample from defatted seed material isolated by a system and/or method according to some embodiments herein. For example, a seed sample may be genotyped for one or more informative molecular markers (e.g., a marker linked to a gene and/or trait of interest). By way of further example, a seed sample may be genotyped for one or more polymorphic markers that do not have a known association with the gene and/or trait of interest, for example, to identify an informative marker from a pool of candidate markers. Depending on the particular breeding application, different genetic information may be useful in selecting seed, for example, to be grown into a plant or plantlet.

In some embodiments, seed produced by a generation of plants resulting from a cross in a plant breeding program may be screened by phenotypic analysis and genotypic analysis of a seed sample therefrom. For example, a sample may be taken from the seed, wherein the sample comprises cotyledon from the seed but not the seed embryo, and the seed sample may be phenotyped (e.g., for an oil trait, seed weight, protein composition, etc.). During phenotyping of the seed or separately therefrom, the seed sample may be defatted, and nucleic acids may subsequently be isolated from the defatted seed sample material according to a system and/or method herein. Such phenotypic and genetic screening of the seed sample, while reserving a viable seed material comprising the embryo and any amount of remaining cotyledon, allows selection of seed to be made without growing a plant or plantlet from the seed.

Particular illustrative examples involve selective breeding of plants for oil traits, including for example and without limitation, omega-9 oil traits (Dow AgroSciences, LLC), including high oleic acid content, low linolenic acid content, and low saturated fatty acid content. The introgression and maintenance of omega-9 oil traits in canola depends upon the presence of particular fad2, fad3a, and fad3c alleles, which may be determined in a seed by genetic screening for one or more linked markers. Furthermore, in the breeding of these and other traits, it may be desirable to simultaneously screen for an additional gene and/or trait of interest, for example and without limitation, a fertility restorer gene (e.g., the Rfo fertility restorer of the Ogura cytoplasmic male sterility system). In examples such as these, two analyses are utilized for selection of germplasm: the assessment of oil profile for fatty acid composition via fatty acid analysis of seed material; and zygosity analysis of the fad2, fad3a, and fad3c genes (and optionally Rfo to assess the presence of the fertility restorer). According to some systems and/or embodiments herein, these two analysis may both be conducted on the same seed sample from a seed. The oil profile is generated from a single seed (in the case of canola, from the outer cotyledon of a single seed), which process produces a remnant defatted seed material that is then subjected to genetic analysis. If comparison of the oil profile (and/or other traits determined in the seed) and the results of the genetic analysis is desirable, the remaining embryo and inner cotyledon may be planted for generation advancement and/or further zygosity testing.

The following examples are provided to illustrate certain particular features and/or embodiments. The examples should not be construed to limit the disclosure to the particular features or embodiments exemplified.

EXAMPLES

Example 1

Isolation of DNA from Defatted Canola Half-Seed Material for Use in Genotyping

The omega-9 oil profile of certain canola and winter oilseed rape (WOSR) germplasm depends upon the presence of mutations in the fad2, fad3a, and fad3c genes. Additionally, for male lines of the Ogura cytoplasmic male sterility hybrid system, the presence of the Rfo (restorer fertility) gene to restore male fertility is required. In order to identify new omega-9 male breeding lines, the appropriate combination of variants for all four genes should be present. To introduce significant time and cost savings in the production and identification of WOSR germplasm, a novel technique for the genetic and phenotypic analysis of seed material was developed, where planting and germination of seed may not be required to carry out the analysis.

Materials and Methods

Two groups of canola half-seed material were used. "Group A" was segregating for the Rfo gene, and "Group B" was segregating for the Rfo, Fad2a, Fad3a, and Fad3c genes. Table 1.

The half-seeding process for canola entailed soaking the seed in water for 1-2 days to separate the seed coat from the embryo and cotyledons. The seed coat was removed, the outer cotyledon was sent for analytical and genetic analyses, and the inner cotyledon/embryo portion of the seed was planted in a greenhouse. Leaf reference material was later collected at the fourth leaf stage, lyophilized, and shipped for genetic testing. Genomic DNA was recovered from both the seed and leaf reference material using the same bead-based extraction and isolation procedure. Homozygous, heterozygous, and null TAQMAN® PCR assay controls for the Fad2a, Fad3a, Fad3c, and Rfo genes were also extracted via the same bead-based chemistry.

TABLE 1

Canola $F_2$ seed populations used for testing. Group A was segregating for Rfo. Group B was segregating for Rfo, Fad2, Fad3a, and Fad3c.

| Geno ID of $F_2$ Population | Group |
| --- | --- |
| 231741 | A |
| 231743 | A |
| 200281 | A |
| 231761 | A |
| 231757 | B |
| 200278 | B |
| 231755 | B |
| 231753 | B |

An oil extraction followed by fatty acid methyl ester (FAME) analysis was performed on canola half-seed samples to identify the oil profile for each seed. FIGS. 1a through 1h. To pulverize the half-seed samples for solvent extraction, samples were ground with a ⅛" steel ball. Residual heptane from the extraction process was driven off using a CENTRIVAP®roto-evaporator (7810010, Labconco, Kansas City, Mo.) at 65° C. for 15 minutes, and the remnant seed material was prepared for DNA extraction.

Ground solvent-extracted canola half seed in a Matrix rack (RB tubes/Analytical steel bead) was incubated at ambient temp overnight to evaporate residual heptane. The following day, 300 µL Buffer RLT (79216, Qiagen) were added to each sample well, and racks were capped. Samples were ground for 5 minutes at 1500 rpm to initiate DNA release from the seed material, followed by a final spin at 6,000 rpm for 5 minutes to pellet suspended tissue debris. Racks were then loaded into an incubator below a BIO-CEL® 1800 robot. The rest of the protocol took place on the BIOCEL® 1800.

DNA was recovered using a fully-automated extraction procedure, initiated using Velocity11 software:

MAGATTRACT® Suspension G magnetic bead was resuspended by vigorous shaking or vortexing. 10 µL resuspended SuSPensin G bead was transferred into each sample well of a 1 mL AB-Gene Half Well plate. The Matrix microtube rack containing macerated tissue was centrifuged at 3000 rpm for 45 seconds. 200 µL sample supernatant from each microtube was transferred to the 1 mL AB-Gene Half Well plate containing Suspension G bead and binding buffer. The samples were tip-mixed and incubated for 90 seconds at room temperature to initiate DNA binding (15° C.-25° C.).

Samples were then placed on blocks on a titer shaker to mix thoroughly for 20 seconds, making sure that any visible clumps were broken apart. Samples were incubated for another 90 seconds at room temperature. Magnetic particles were separated for 15 seconds on a magnetic MAG-NARACK™. 200 µL sample supernatant was transferred back into the Matrix microtube rack. Wells were checked to verify that they contained only beads, and that all the liquid had been removed.

200 µL Buffer RPW (Qiagen) was added to each sample well, and the samples were then placed on the titer shaker to mix thoroughly for 20 seconds. Magnetic particles were separated for 15 seconds on the magnetic rack. 200 µL sample supernatant was transferred back into the 2D Matrix microtube rack. Wells were checked to verify that they contained only beads, and that all the liquid had been removed.

200 µL EtOH (96-100%) was added to each sample well of the block, which was then placed on the titer shaker and shaken for 20 seconds to ensure that the magnetic particles were suspended. Magnetic particles were separated for 15 seconds on the magnetic rack. 200 µL supernatant was transferred into the 2D Matrix microtube rack. Wells were checked to verify that all the liquid had been removed.

200 µL EtOH (96-100%) was added to each sample well of the block, which was then placed on the titer shaker and shaken for 20 seconds to ensure that the magnetic particles were evenly suspended. Magnetic particles were separated for 15 seconds on the magnetic rack. 200 µL supernatant was transferred into the 2D Matrix microtube rack. Wells were checked to verify that all the liquid had been removed.

Magnetic particles were incubated at room temperature for 5 minutes to ensure that all the EtOH was evaporated. 100 µL of Buffer AE (Qiagen) was added to each well of the block, which was then placed on the shaker for 1 minute to ensure that the magnetic particles were evenly suspended. Magnetic particles were separated on the magnetic rack for 30 seconds. 100 µL supernatant was transferred into a labeled 500 µL V-bottom collection plate. The collection plate was sealed with heat seal using a PLATELOC® set at 2.1 seconds at 175° C.

90 µL DNA was recovered for each sample and stored at 4° C.

Following bead-based DNA extraction, samples were quantified on a SYNERGY® 5 plate reader (BIOTEK, Winooski, Vt.) using PICOGREEN® reagent (P7581, Invitrogen, Carlsbad, Calif.) (an intercalating dsDNA dye). A dilution series (0 ng/µL, 2.5 ng/µL, 5.0 ng/ul, and 10 ng/µL) Lambda DNA was loaded to generate the standard curve. DNA purity ($A_{260}/A_{280}$ and $A_{260}/A_{230}$) was evaluated on a NANODROP® 8000 (Thermo Fisher) using 2 µL undiluted DNA. DNA quality (e.g., molecular weight) was also determined by visualizing 5 µL undiluted DNA on a 1.0% agarose E-GEL® (G5518-01, Life Technologies, Grand Island, N.Y.) against a 10 kB high M.W. DNA ladder DNA was screened for the presence and zygosity of the Rfo and/or FAD (Fad2, Fad3a, and Fad3c) genes using TAQMAN® PCR. 1 µL undiluted DNA was used per 10 µL reaction. For general genomic SNP testing, a KASPar chemistry was used. FAD zygosity results were compared to the FAME analysis data for each seed sample to select a high oleic oil profile.

For KASPar PCR validation, three dilution factors (1:2, 1:5, and 1:10) were tested on half-seed DNA, and compared to results obtained with reference leaf DNA (diluted 1:25). Sixteen markers were evaluated, with all DNA samples present on the same PCR plate. 2 µL diluted DNA were delivered to a 1536-well plate, and then dried at 65° C. for two hours. Once the DNA was dry, 1.3 µL prepared PCR cocktail mix (1× KASPar mix plus primers) was dispensed to each well using a MERIDIAN® (KBioSciences, UK). The plates were sealed, and thermocycled using a touch-down protocol on a HYDROCYCLER® (KbioSciences, UK), with a final annealing temperature of 55° C. Plates were read using a PHERASTAR® plate reader (BMG LabTech, Offensburg, Germany), and data were scored using the KRAKEN® software package (KbioSciences).

Evaluation of Canola Defatted Half-Seed DNA Yield, Purity, and Quality

Oil extraction and FAME analysis was performed on each group of canola half-seed samples and an oil profile was generated. FIGS. 1a through 1h. DNA was successfully recovered from the remnant solvent-extracted tissue of both groups using the bead-based automated BIOCEL® procedure. PICOGREEN® quantification revealed that concentrations were fairly consistent within a given group (Std. Devs. Pop (A): 0.24; Pop (B): 0.09). Tables 2-3. On average, 1.05 ng/µL DNA was recovered from Group A, and 0.4 ng/µL DNA was recovered from Group B.

DNA quality was evaluated by visualizing 5 µL genomic DNA from Group B on a 1.0% agarose E-GEL® w/EtBr. A representative set of DNA samples from Group B (Plate#673-768) was used for analysis. 10 µL HIGH-RANGE® high molecular weight genomic DNA ladder was added for reference. A high MW band (10 kb) with a slight smear was present. FIG. 2.

TABLE 2

DNA Yield (ng/µL) and Purity Metrics for Group A (Rfo).

| | 228658 | | | 228675 | | | 228676 | | | 286055 | | |
|---|---|---|---|---|---|---|---|---|---|---|---|---|
| | ng/µL | 260/280 | 260/230 | ng/µL | 260/280 | 260/230 | ng/µL | 260/280 | 260/230 | ng/µL | 260/280 | 260/230 |
| Pico Average | 1.33 | 2.10 | 0.60 | 1.06 | 1.88 | 0.50 | 0.76 | 2.75 | 0.62 | 1.08 | 2.03 | 0.53 |
| Min | 0.37 | 1.26 | 0.30 | 0.20 | 1.45 | 0.38 | 0.28 | 1.24 | 0.36 | 0.40 | 1.38 | 0.12 |
| Max | 2.67 | 3.59 | 0.85 | 3.10 | 2.48 | 0.72 | 3.24 | 9.52 | 0.80 | 6.23 | 7.34 | 0.79 |
| Std. Dev. | 0.37 | 3.59 | 0.85 | 0.45 | 0.17 | 0.06 | 0.45 | 1.25 | 0.08 | 0.41 | 0.76 | 0.09 |

TABLE 3

DNA Yield (ng/µL) and Purity Metrics for Group B (Rfo:Fad2a:Fad3a:Fad3b).

| | Grev 5 | | | Grev 6 | | | Grev 7 | | | Grev 8 | | |
|---|---|---|---|---|---|---|---|---|---|---|---|---|
| | ng/µL | 260/280 | 260/230 | ng/µL | 260/280 | 260/230 | ng/µL | 260/280 | 260/230 | ng/µL | 260/280 | 260/230 |
| Pico Average | 0.54 | 1.76 | 0.20 | 0.38 | 1.87 | 0.20 | 0.43 | 1.85 | 0.15 | 0.58 | 2.02 | 0.12 |
| Min | 0.16 | 1.07 | 0.14 | 0.07 | 1.39 | 0.11 | 0.13 | 1.41 | 0.04 | 0.22 | 1.73 | 0.10 |
| Max | 1.69 | 2.80 | 0.28 | 2.07 | 3.81 | 0.35 | 1.66 | 2.49 | 0.30 | 1.44 | 2.48 | 0.14 |
| Std. Dev. | 0.31 | 0.52 | 0.05 | 0.28 | 0.45 | 0.06 | 0.25 | 0.31 | 0.16 | 0.22 | 0.37 | 0.03 |

Evaluation of Canola Defatted Half-Seed DNA Efficacy in PCR Applications

Figure 3:
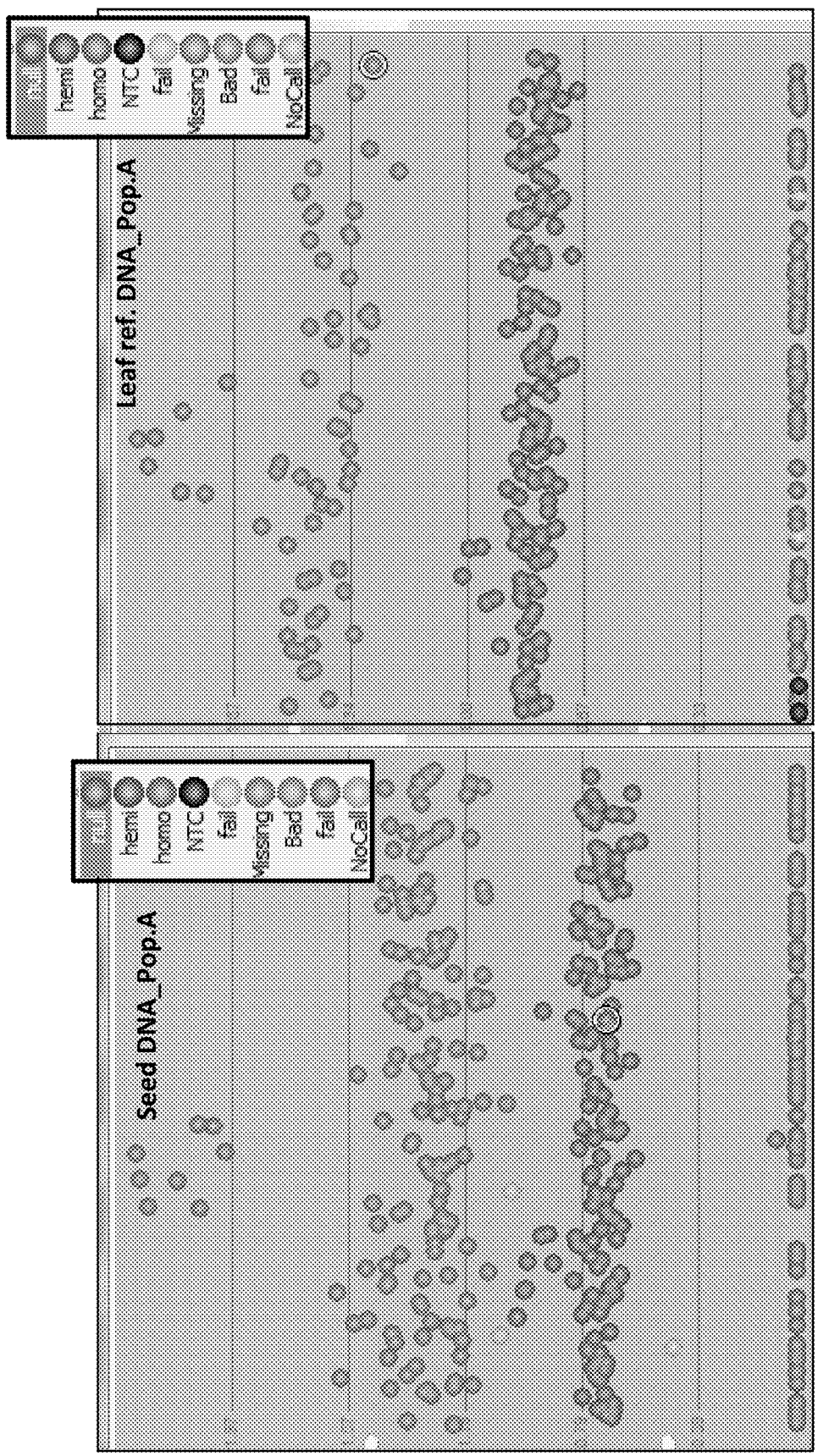
FIG. 3 includes data for Rfo Taqman analysis of canola DNA isolated from seed material (Rfo only) defatted by solvent extraction. Homozygous (blue), hemizygous (green), and null (red) MagAttract-extracted assay controls were included for zygosity reference. No template controls (NTC) are indicated in black.
Figure 4:
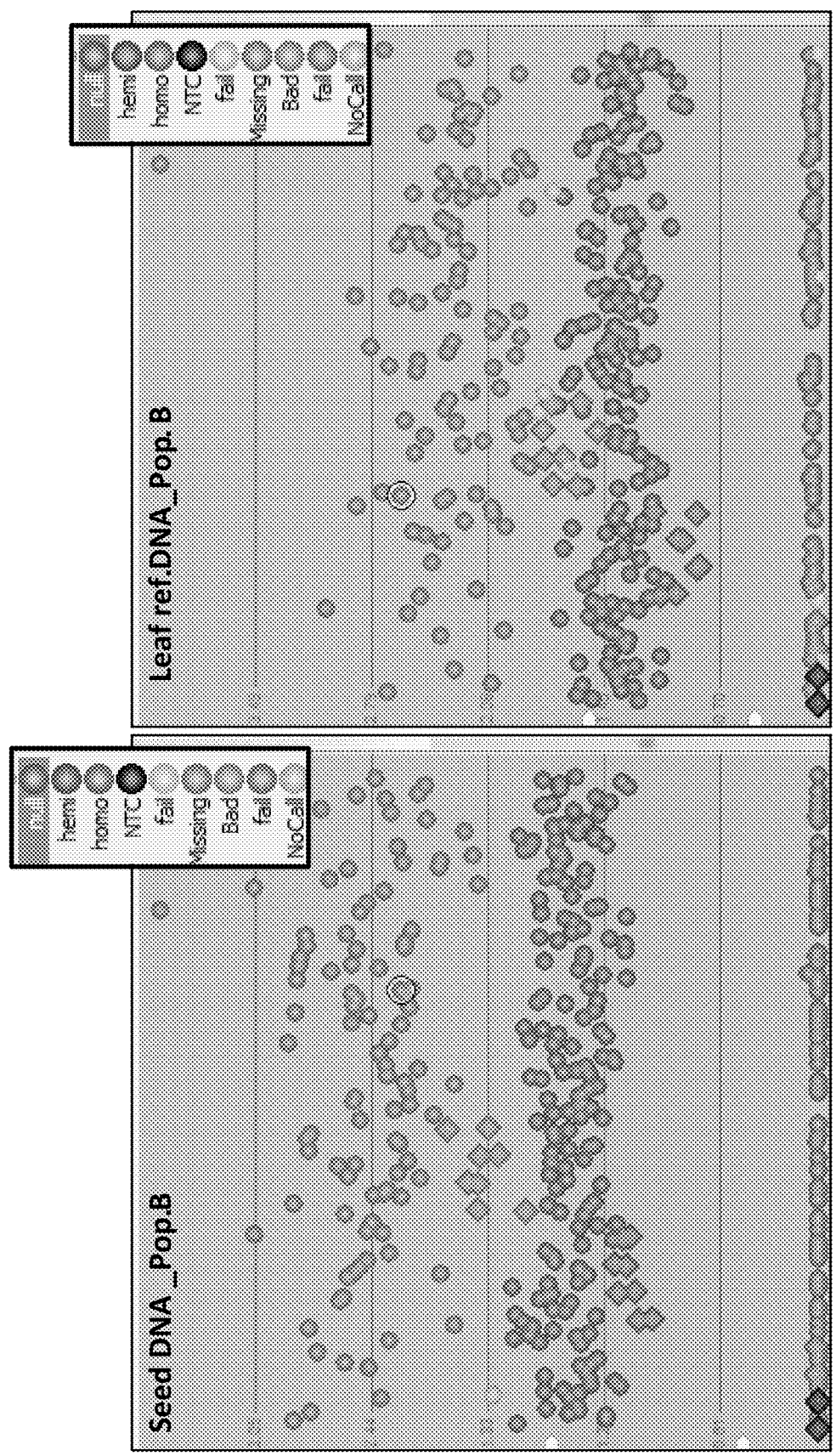
FIG. 4 includes data for Rfo Taqman analysis of canola DNA isolated from seed material (Rfo, Fad2a, Fad3a, and Fad3c) defatted by solvent extraction. Homozygous (blue), hemizygous (green), and null (red) assay controls (leaf DNA) are identifiable by their diamond shape (◇). The zygosity of samples indicated in orange could not be determined. NTCs are indicated in black.
Figure 5A:
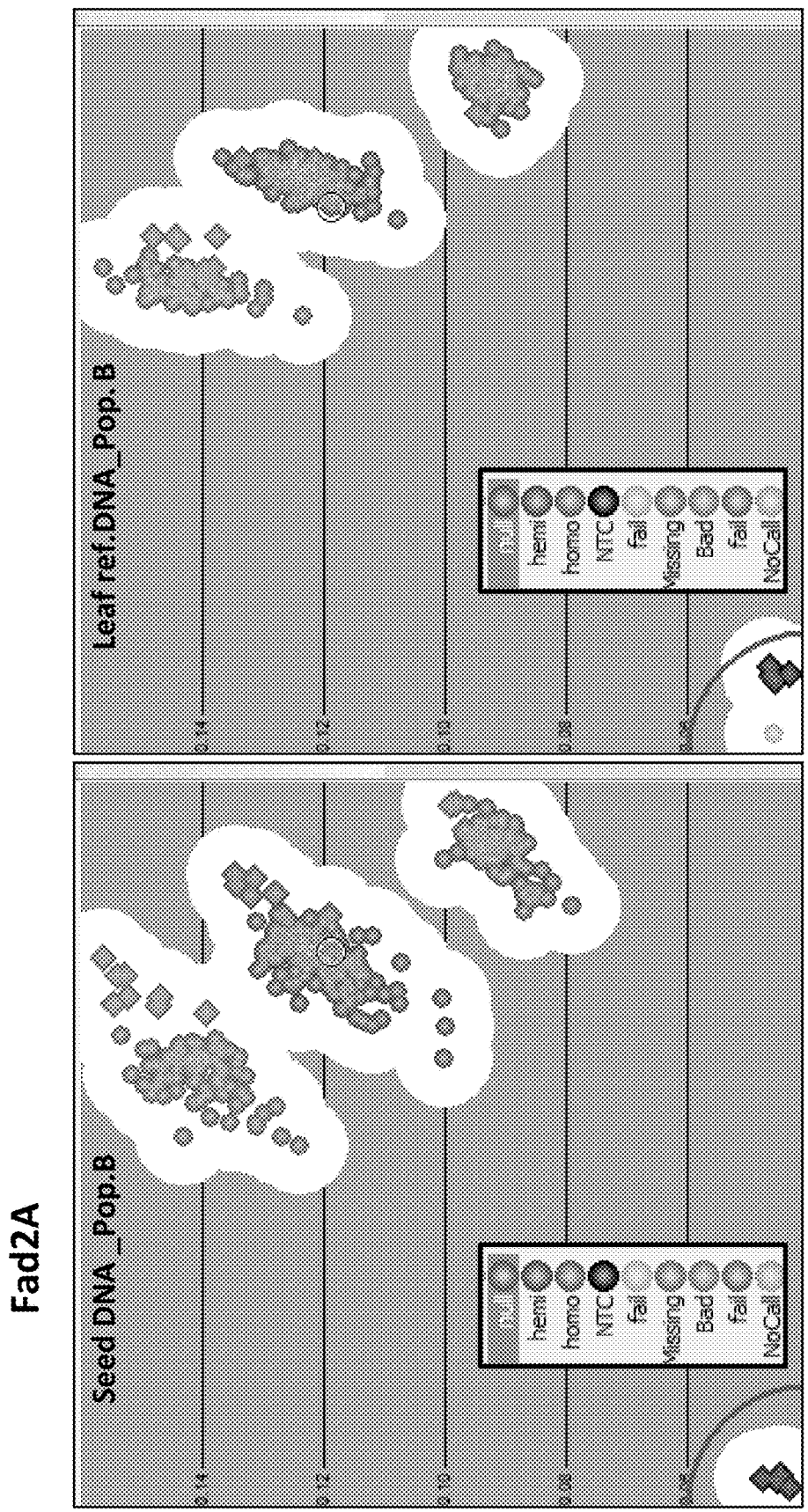
FIGS. 5a through 5c include data for Fad2a, Fad3a, and Fad3c Taqman analysis of canola DNA recovered from seed material (Rfo, Fad2a, Fad3a, and Fad3c) defatted by FAME extraction. Zygosity was determined using MagAttract-extracted controls (◇). Samples indicated in pink failed to produce a detectable signal.
Figure 5B:
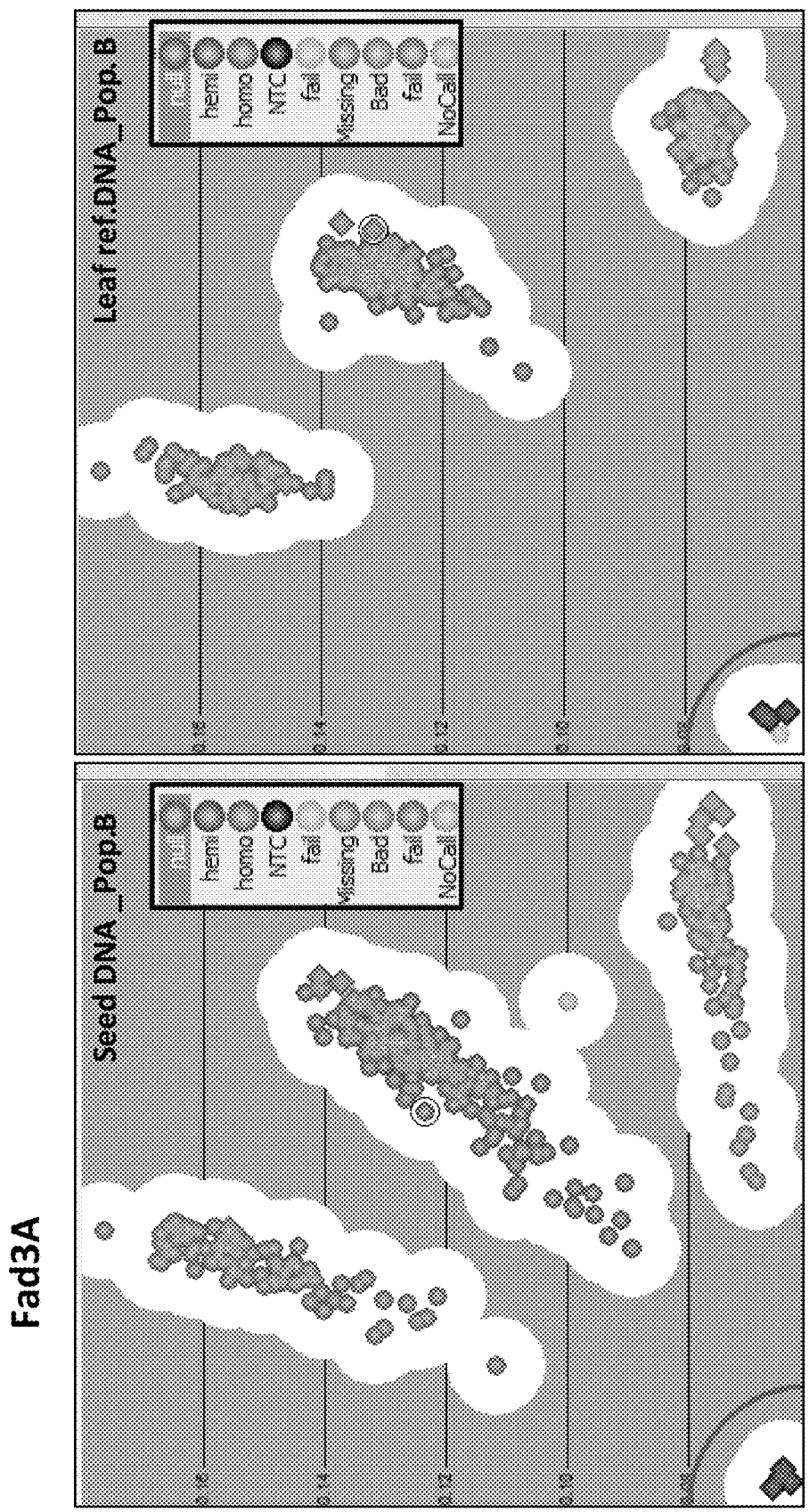
Figure 5C:
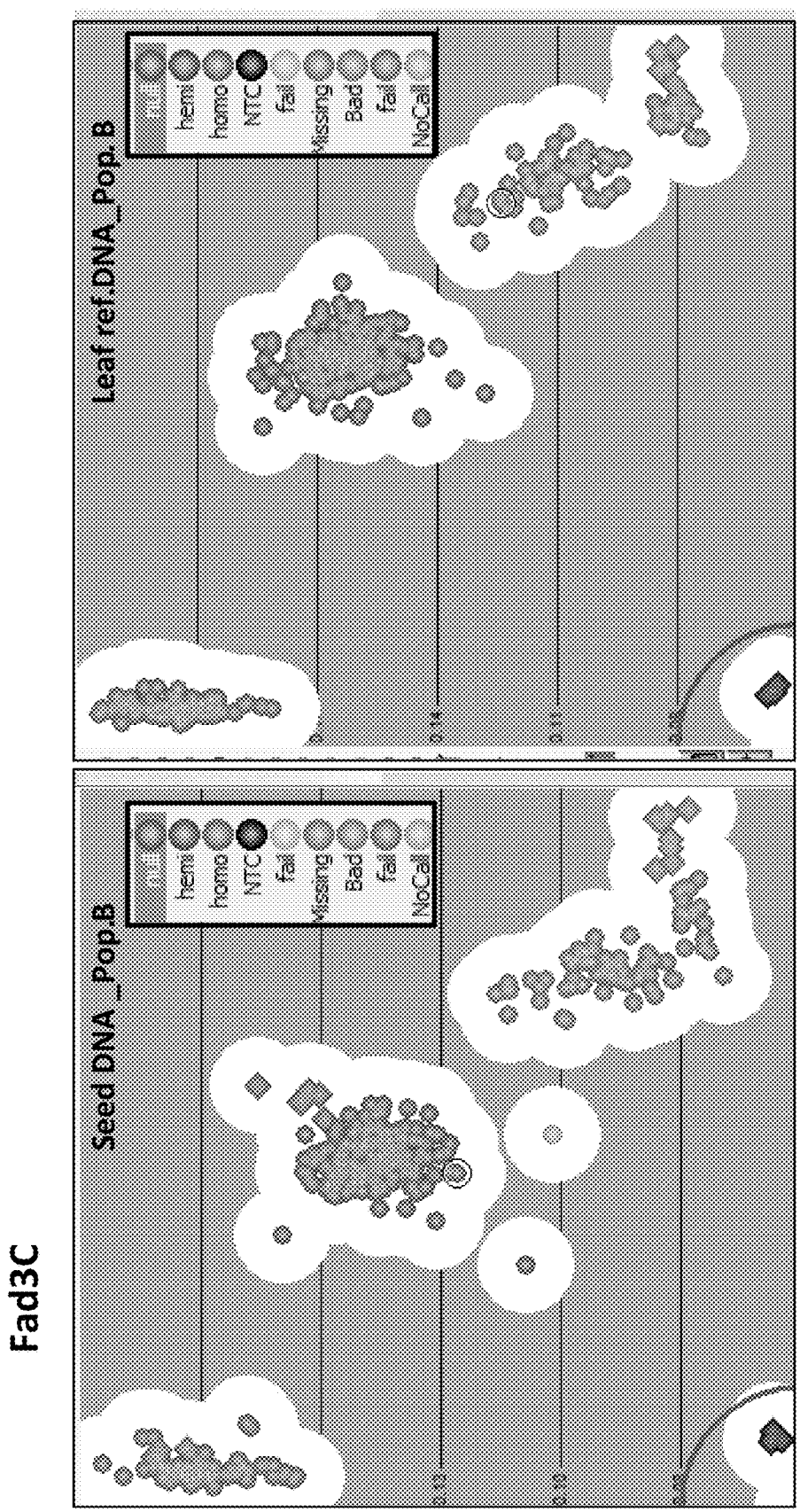

PCR assay performance was used to evaluate each group of DNA using trait-specific primers (Group A: Rfo, and Group B: Rfo, fad2a, fad3a, and fad3c). Real-time PCR was performed on 3 μL undiluted DNA isolated from the remnant solvent-extracted tissue to identify samples segregating for the Rfo gene. FIGS. 3-4. Leaf DNA extracted from the germinated portion of the seed was also screened to verify the accuracy of the determination of seed zygosity. FIGS. 3-4. Fad analyses were performed as endpoint Taqman assays. FIGS. 5a through 5c. Sample performance was measured by calculating percent data return, miss-call rate, no-call rate, and fail rate. Collectively, no-calls and fails were counted against the overall data return. DNA was not normalized prior to analysis.

High quality zygosity data was obtained across all assays with greater than 99% data return, and greater than 99% agreement between half-seed and leaf reference samples for the FAD genes. Table 4. There was also 97% agreement between leaf and seed samples for the Rfo gene. Table 4. Expected sample segregation patterns were found, and adequate separation between homozygous, hemizygous, and null clusters was seen. A total of 330 data points were generated for each assay. All zygosity validation criteria were satisfied.

The combination of oil profile and zygosity results will be used to select and advance the most promising omega-9 material. In application, the identification of both the oil and genetic profile from a single half-seed source will allow canola and WOSR breeding programs to select only those plants (grown from the embryo-containing portion of the seed) with the desired characteristics for transplantation based on a single sample, thereby reducing workload in the field and increasing breeding efficiency.

The chemistry has been automated for high-throughput extractions on a BIOCEL® 1800 robot, and the automated system is capable of processing up to seventy 96-well tissue plates (6,300 samples) per day. This method is robust. At a current cost of $0.62 for oil extraction/FAME analysis and $0.59 for DNA extraction, the ability to obtain oil and genetic profiles from a single seed source for less than $1.23 represents significant savings for the field and laboratory. Previous to this study, the genetic profile could only be attained by growing a population to at least the 4th leaf stage, and shipping leaf tissue punches for DNA extraction. Though little DNA is recovered from the remnant solvent-extracted material, it is of high molecular weight and high purity, allowing one to generate reliable SNP and zygosity data.

TABLE 4

PCR validation statistics for canola DNA isolated from defatted seed material.

| Group | Material | Rfo TAQMAN data return | Rfo TAQMAN call match | Fad2a TAQMAN data return | Fad2a TAQMAN call match | Fad3a TAQMAN data return | Fad3a TAQMAN call match | Fad3c TAQMAN data return | Fad3c TAQMAN call match |
|---|---|---|---|---|---|---|---|---|---|
| A | Leaf | 98.8% | 95.6% | | | Traits not segregating | | | |
|   | Defatted seed | 100.0% | | | | | | | |
| B | Leaf | 97.6% | 97.0% | 99.7% | 99.7% | 99.7% | 99.4% | 100.0% | 99.7% |
|   | Defatted seed | 99.7% | | 100.0% | | 99.7% | | 99.7% | |

Figure 6:
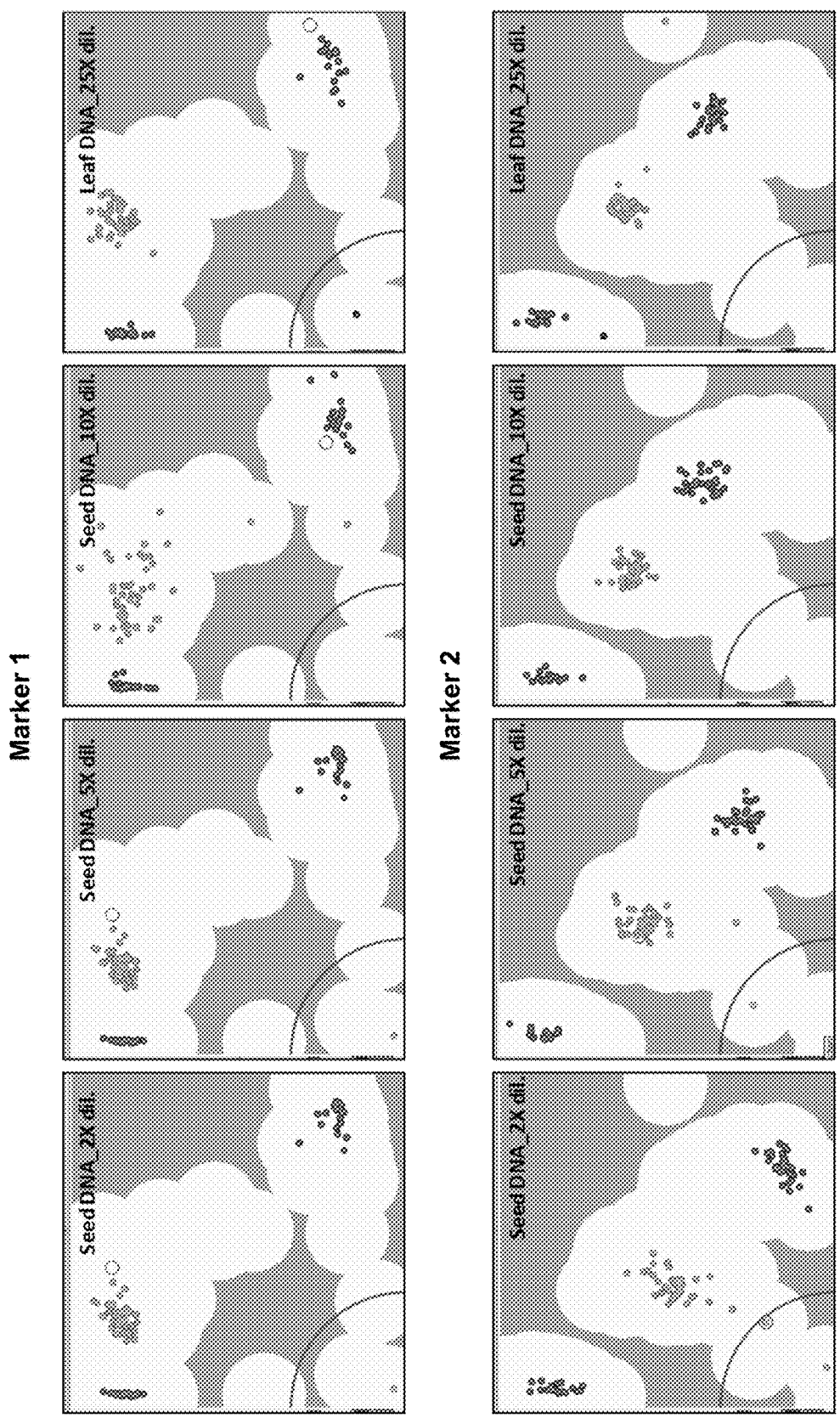
FIG. 6 includes data for KASPar analysis of two representative SNP markers (marker 1 (above) and marker 2 (below)) from canola DNA recovered from seed material (Rfo, Fad2a, Fad3a, and Fad3c) defatted by solvent extraction. Two micro liters of dried-down DNA was used per 1.3 µl KASPar wet reaction. Samples of sufficient quality and yield clearly clustered as AA, AB, or BB genotype, represented by red, green, and blue clusters, respectively. Pink data points indicate a measurable signal was not generated and are identified as "fails." Data for two of the markers tested (Marker 1=004-052 15792; Marker 2=040-0547 61844) with diluted DNA (2×, 5×, and 10×) is depicted. Leaf reference DNA images are included for comparison.

The performance of canola seed DNA isolated from defatted seed material was also evaluated using a panel of 16 SNP markers. A single plate of DNA from Group B was diluted 2×, 5×, and 10× with water prior to being analyzed. Reference leaf DNA was diluted 25×. Following PCR, each set of raw data was uploaded into KRAKEN® and plotted to visualize allelic segregation patterns. FIG. 6. Samples that were of insufficient quality would either appear as outliers or fails on the data plots.

Comparison of Oil Characteristics and Genotype

The oil profile for 18:1, 18:2 and 18:3 content was aligned with zygosity call data for the Fad2, Fad3a, and Fad3c genes across all samples. FIGS. 7a through 7l. Correspondence between 18:1 content and homozygous Fad2 was strong, with all homozygous individuals exceeding 70% oleic content. For linolenic acid content (18:3), Fad3a and Fad3c decrease levels (≤3.5%) when in the homozygous mutant state. We observed that some individuals homozygous for both genes had 18:3 content exceeding the expected 3.5%. The individuals with this profile all came from a single population, indicating that genes from the non-omega-9 parent are driving the 18:3 content higher than expected.

Example 2

Isolation of DNA from Defatted Soybean Seed Material for Use in Genotyping

Herein, we apply a similar automated procedure to that described in Example 1 to isolate high-quality genomic DNA from remnant solventextracted soybean seed material, followed by RR1, RR2, and AAD12 PCR analysis of the seed DNA to identify the zygosity of these genes of interest. Leaf reference samples, grown from the embryo-containing portion of the seed, were used to verify the accuracy of the zygosity determinations.

Materials and Methods

Two groups of soybean seed were used. "Group A" seed material consisted of individual populations of segregating RR1 and RR2 seed that were mixed prior to performing the experiment to create one "synthetic" population, while "Group B" material consisted of a single population of germplasm that was segregating for the AAD12 trait. Table 5.

All seed had been stored at ambient temperature for 1 year prior to performing this experiment. Due to the fact that ample RR1/RR2 seed was available for sampling, two plates of seed material were produced from that population (referred to as "Group A Population 1" and "Population 2"). Group B seed material was sampled only one time.

TABLE 5

Soybean F₂ seed populations used for testing.

| Group | Population | Source ID | Material Classification |
|---|---|---|---|
| A | Synthetic mix (1 & 2) | 09BIW057118 09B1X056130 | RR2 Segregating RR1 Segregating |
| B | 1 | GX08KX036929.008 | AAD12 Segregating |

Figure 8A:
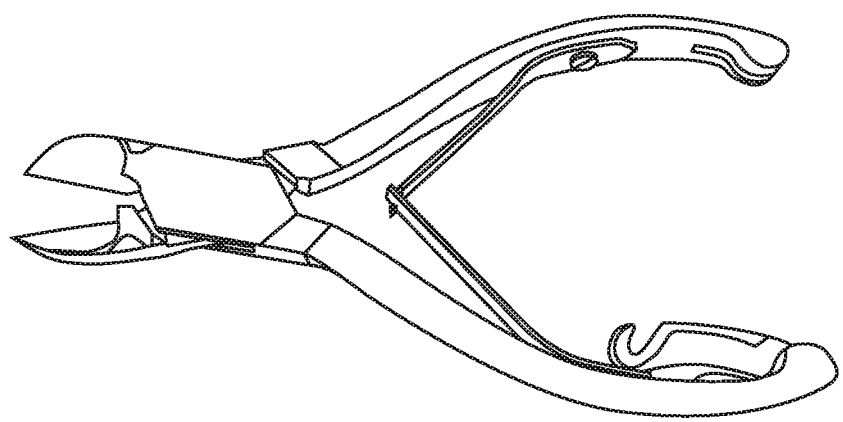
FIGS. 8a through 8b include a photograph of an exemplary device that may be used for seed "sectioning" to produce extractable seed material (FIG. 8a; top), and a photograph of a soybean with markers designating several features of the soybean (FIG. 8b; bottom).
Figure 8B:
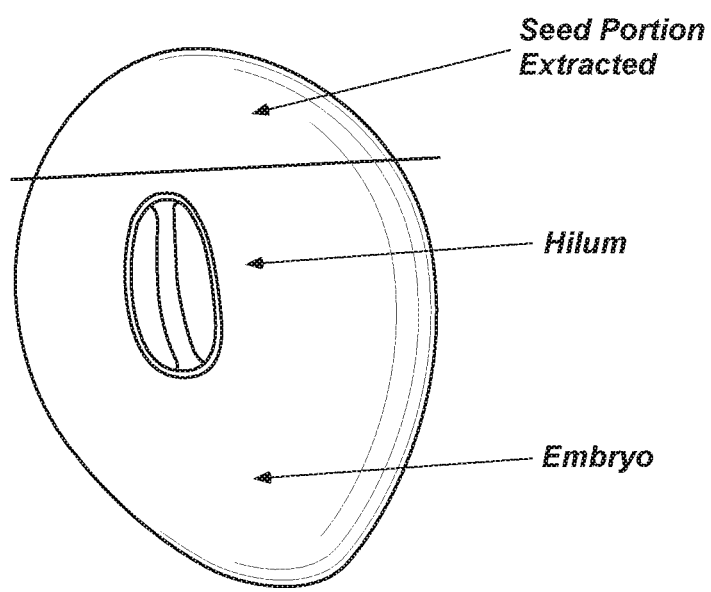

Whole seeds were imbibed for a period of 10 minutes in diH$_2$O prior to removing a small fragment, so that the endosperm would be more pliable. A toenail nipper (Top-Care) (FIG. 8a) was used to remove a portion of the cotyledon (i.e., from the side opposite the embryo, but not including the hilum) equaling approximately ⅓ of the total seed size (FIG. 8b). Each seed sample was then placed into a designated well of a 96-well assay plate, and the embryo-containing seed portion was placed into the corresponding well of another 96-well well assay plate.

All seed fragments were processed for oil extraction and fatty acid oil profile analysis, while the embryo-containing seed portions were planted in METRO-MIX® 360 soil, and grown in a mobile growth chamber on a diurnal cycle (day-16 hrs. 27° C.: night-8 hrs. 21° C.; 60% humidity) for a period of 2 weeks. At the 2-leaf stage of growth, a single 6 mm tissue punch was retrieved from each plant, and subjected to DNA extraction in order to obtain reference DNA for zygosity calls.

A fatty acid methyl ester (FAME) analysis was performed on the seed solvent extract to identify the fatty acid profile for each seed. FIGS. 9a through 9i. To pulverize the seed samples for solvent extraction, samples were ground with a ³⁄₁₆" steel ball. Residual heptane from the FAME process was evaporated using a CENTRIVAP® roto-evaporator (Labconco) at 65° C. for 15 minutes, and the remnant seed material was prepared for DNA extraction.

Within 24 hours, 350 µL Buffer RLT (Qiagen) was added to each sample well of a Matrix rack and capped. Samples were ground for 2 minutes at 1500 rpm to initiate DNA release from the seed material, followed by a final spin at 6,000 rpm for 5 minutes to pellet suspended tissue debris. Racks were then de-capped and loaded to onto a BIOMEK® NX to transfer 200 µL supernatant into a new pre-beaded (⅛" bead) Matrix rack, so that samples would balance against the centrifuge on a BIOCEL® 1800 robot. Racks were then loaded into an incubator below the robot, and DNA was recovered using the same fully-automated extraction procedure described in Example 1, initiated using Velocity11 software. 90 µL of DNA was recovered for each sample and stored at 4° C.

Following bead-based DNA extraction, DNA was characterized by PICOGREEN® quantification, NANODROP® quantification, and gel electrophoresis. For PICOGREEN® quantification, 50 µL PICOGREEN® dye was added to 10 mL 1×TE buffer and mixed (for each DNA plate to be quantified). 90 µL of the diluted PICOGREEN® reagent and 10 µL sample DNA were added to each well of a white NUNC® plate (236108, Nalge Nunc International, Rocheester, N.Y.) and mixed thoroughly. Absorbance was measured on a SYNERGY® 5 plate reader, and concentrations were adjusted for dilution factor.

To assess DNA purity, 2 µL undiluted soy seed DNA from each well was added directly to a pedestal of a NANO-DROP® 8000 reader (Thermo Scientific), and the A$_{260}$/A$_{280}$ purity ratio was recorded. A measurement of between about 1.8 and 2.0 is generally considered pure, while values outside of the range may indicate the presence of proteins, phenolics, salts, and other contaminants. DNA quality was also evaluated by visualizing 5 µL undiluted DNA on a 1.0% agarose E-GEL® (Life Technologies). The gel was visualized on a GELDOC® XR imager (170-8195, BioRad Laboratories, Hercules, Calif.).

After gathering DNA quality metrics for the half-seed samples, DNA was screened for the presence and zygosity of the RR1, RR2, and AAD12 genes using TAQMAN® PCR. A zygosity study was created in KRAKEN® LIMS system, so that assay data could be imported and viewed to identify sample segregation patterns.

The PCR master mix components and thermocycling conditions for the RR1/RR2 (Table 6) and AAD12 GS (Table 7) TAQMAN® assays are listed below. All PCR plates were analyzed on SYNERGY® 5 micro plate reader, and zygosity data was uploaded into KRAKEN® for analysis. Data from each sample plate was sorted according to the number of "no-calls," "miss-calls," or "fails." A "no-call" is defined as a data point that does not cluster with the homozygous, null, or heterozygous controls. A "miss-call" is a sample that does not match the reference (leaf) call. "Failed" samples that did not amplify (no signal produced) remained at the point of origin on the data plot.

TABLE 6 (a-b)

RR1 and RR2 TAQMAN® PCR reaction and thermocycling conditions used on seed DNA.

a. RR1 and RR2 TAQMAN® (endpoint) PCR Sample #: 100

| Reagents | Working Concentration | 1X volume (µL) | Total volume |
|---|---|---|---|
| H$_2$O | | 0.25 | 27.5 |
| GTExpress | 2X | 1.50 | 165 |
| Assay Mix | 8X | 0.25 | 27.5 |
| Total Mix vol. (µL) | | 2.00 | 220 |
| + | | | |
| DNA | | 1.00 | Each |
| Final PCR vol. (µL) | | 3.00 | | b. Endpoint TAQMAN® PCR conditions

| Step # | Temp. (° C.) | Time | Cycles |
|---|---|---|---|
| 1 | 50 | 2:00 min. | 1X |
| 2 | 95 | 10:00 | 1X |
| 3 | 95 64 −1° C./cycle | 0:15 1:00 | 10X |
| 4 | 95 | 0:15 | 30X |

TABLE 7 (a-b)

AAD12 TAQMAN® PCR reaction and thermocycling conditions used on seed DNA.

a. AAD12 gene-specific TAQMAN® PCR Sample #: 100

| Reagents | Working Conc. | Required Conc. | 1X vol. (µL) | Total vol. |
|---|---|---|---|---|
| PVP | 2.0% | 0.15% | 1.37 | 150.7 |
| Gene (Expression or -typing) MM | 2X | 1X | 5.00 | 550 |

TABLE 7 (a-b)-continued

AAD12 TAQMAN® PCR reaction and thermocycling conditions used on seed DNA.

| Assay Mix | 8X | 0.5X | 0.63 | 69.3 |
|---|---|---|---|---|
| H2O | | | 1.00 | 110 |
| Total Mix vol. (μL) | | | 8.00 | 880 |
| + | | | | |
| DNA | | | 2.00 | Each |
| Final PCR vol. (μL) | | | 10.00 | | b. Real-time TAQMAN® PCR

| Step # | Temp. (° C.) | Time | Cycles |
|---|---|---|---|
| 1 | 50 | 2:00 min. | 1X |
| 2 | 95 | 10:00 | 1X |
| 3 | 95 | 0:15 | 40X |
| | 60 | 1:00 | |
| 4 | 4 | Hold | |

Evaluation of Soybean Defatted Seed DNA Yield, Purity, and Quality

Figure 10:
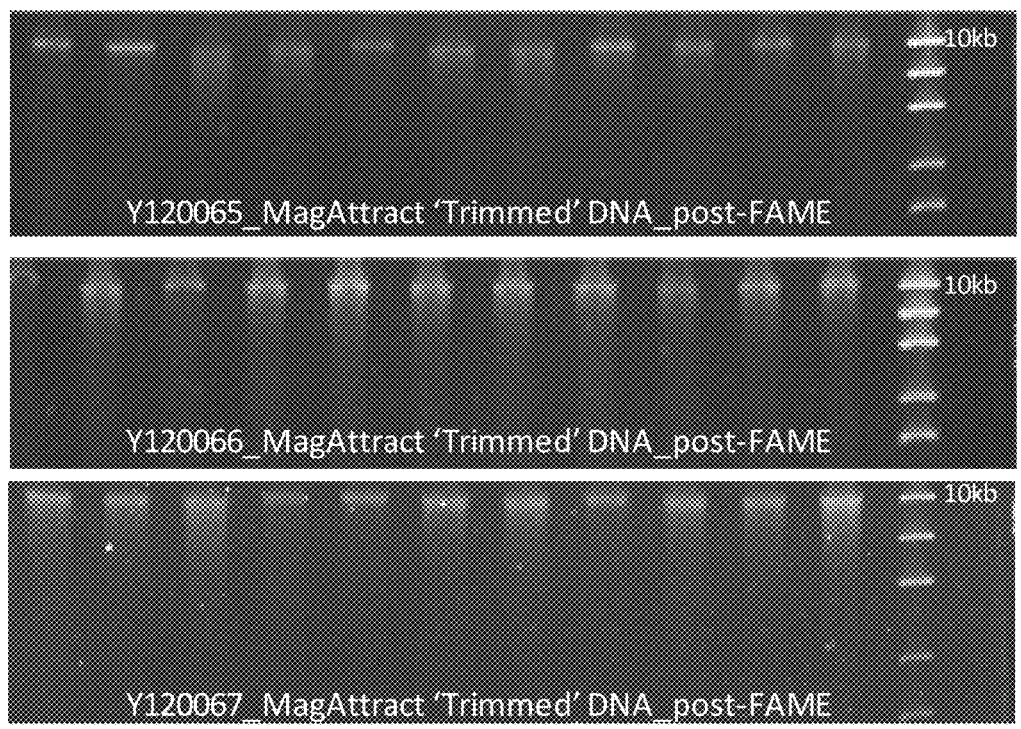
FIG. 10 includes an image showing gel electrophoresis of soybean DNA isolated from seed material defatted by solvent extraction. A 10 kb band is evident across all samples on the gel with some slight smearing.

DNA was successfully recovered from the remnant solvent-extracted Group A (Populations 1 and 2) and Group B soybean seed ship samples using the bead-based automated BIOCEL® procedure. PICOGREEN® quantification data revealed that the average DNA concentration among the plates ranged from 7.52 to 16.25 ng/μL, with a maximum recovery of 43 ng/μL recorded in a single well of plate #Y120067. Table 8. DNA quality was also evaluated by visualizing 5 μL genomic DNA from a representative row of each plate on an agarose E-GEL® w/EtBr. A high MW band (10 kb) with a slight smear was present, indicating that a portion of each DNA sample was fragmented. FIG. 10. DNA purity ($A_{260}/A_{280}$) was consistent among all the seed plates evaluated, and was well within the acceptable range of 1.7-2.0, indicating that carryover of contaminating compounds was unlikely.

TABLE 8

DNA yield (ng/μL) and purity for Groups A and B.

| | Group A | | | | Group B | |
|---|---|---|---|---|---|---|
| | Population 1 | | Population 2 | | Population 1 | |
| | Y120065 | | Y120066 | | Y120067 | |
| Well | Pico (ng/μL) | 260/280 | Pico (ng/μL) | 260/280 | Pico (ng/μL) | 260/280 |
| Average | 7.52 | 1.86 | 10.63 | 1.79 | 16.35 | 1.96 |
| Min. | 1.49 | 0.07 | 0.27 | 0.05 | 5.88 | 1.83 |
| Max. | 10.21 | 2.07 | 17.64 | 1.95 | 43.16 | 2.20 |
| Std. Dev. | 1.67 | 0.21 | 3.35 | 0.20 | 7.85 | 0.22 |

Evaluation of Soybean Defatted Seed DNA Efficacy in PCR Applications

Figure 11:
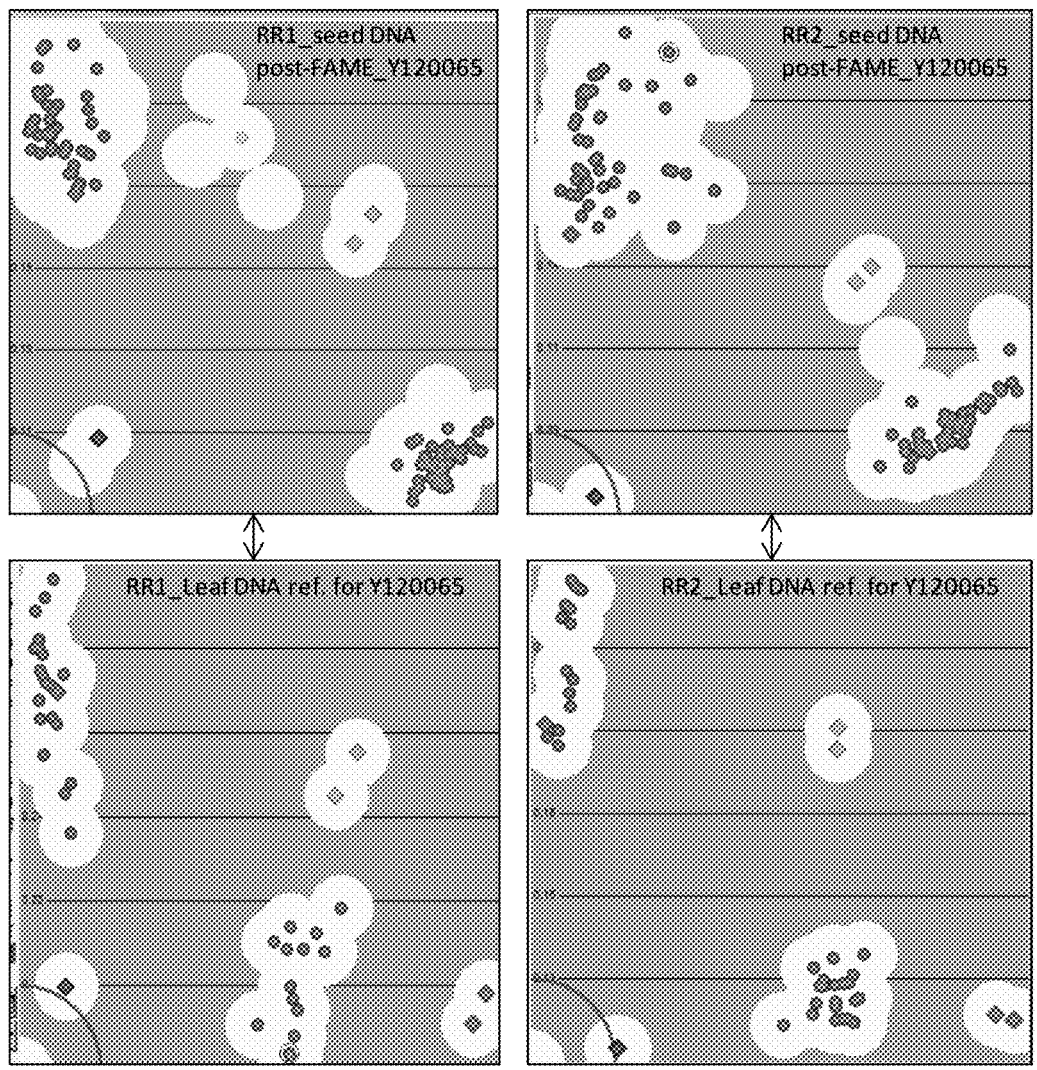
FIG. 11 includes data for RR1 and RR2Taqman analysis of soybean DNA isolated from seed material (Population 1) defatted by solvent extraction. Zygosity was determined using MagAttract-extracted homozygous (blue), hemizygous (green), and null (red) leaf controls, indicated by their (◇) shape. The zygosity of samples indicated in orange was undeterminable. No template controls (NTCs) are indicated in black.
Figure 12:
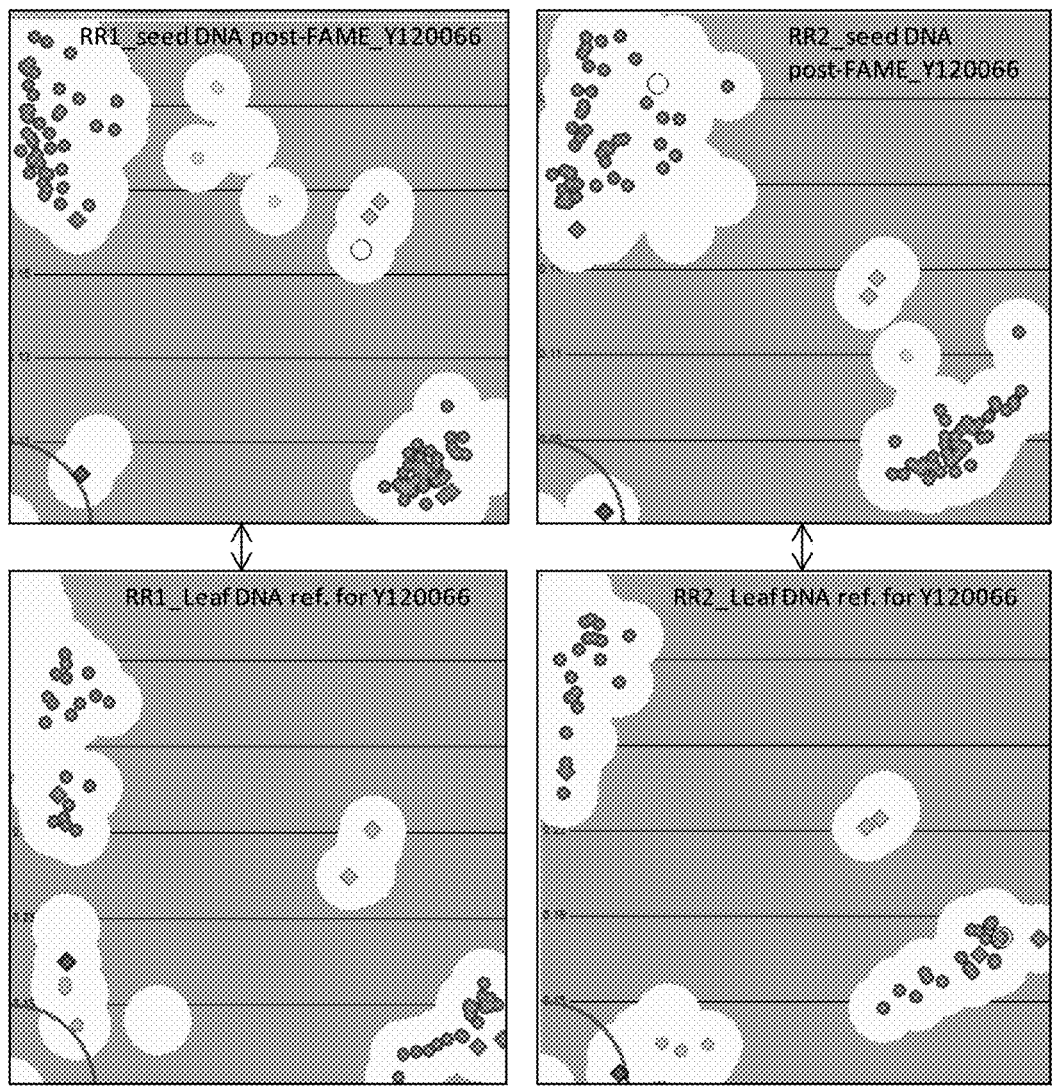
FIG. 12 includes data for RR1 and RR2Taqman analysis of soybean DNA isolated from seed material (Population 2) defatted by solvent extraction. Homozygous (blue), hemizygous (green), and null (red) assay controls are identifiable by their diamond shape. The zygosity of samples indicated in orange could not be determined. Samples indicated in pink failed to produce a detectable signal. NTCs are again indicated in black.
Figure 13:
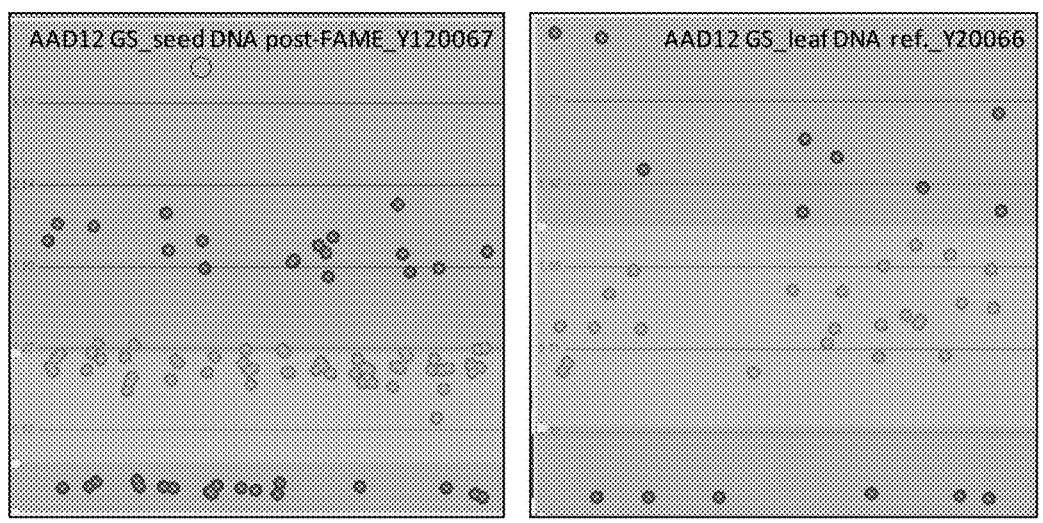
FIG. 13 includes data for real-time AAD12 Taqman analysis of soybean DNA isolated from seed material (Group B) defatted by solvent extraction. Leaf DNA extracted from the germinated portion of the seed was also screened to confirm the zygosity of the seed samples. Homozygous (blue), hemizygous (green), and null (red) MagAttract-extracted assay controls were included for zygosity reference. No template controls (NTCs) are indicated in black.

PCR assay performance was used to evaluate each group of seed DNA using trait-specific primers (Group A: RR1 and RR2; and Group B: AAD12). RR1 and RR2 PCR were performed in endpoint PCR format (FIGS. 11 and 12), while the AAD12 gene-specific TAQMAN® analysis was performed as a real-time PCR assay (FIG. 13). Sample performance was measured by calculating the percent of data return rate, miss-call rate, no-call rate, and fail rate. Collectively, no-calls and fails were counted against the overall data return. A total of 180 data points were generated amongst Group A seed DNA samples for the RR1 and RR2 assays and 90 data points were generated amongst Group B seed samples for the AAD12 assay. Expected sample segregation patterns were seen, and adequate separation between homozygous, hemizygous, and null clusters was observed.

High quality zygosity data was obtained for all seed DNA populations with a 98.4%, 99.5%, and 100% data return rate in the RR1, RR2, and AAD12 GS assays, respectively. Table 9. In turn, 100% agreement was seen between comparable seed and leaf reference samples in the RR1 and RR2 assays, and 92.3% agreement was seen between leaf and seed in the AAD12 GS assay. Table 9.

TABLE 9 (a-c)

PCR validation statistics for soybean DNA isolated from defatted seed material.

a.

| | RR1 endpoint TAQMAN | | | |
|---|---|---|---|---|
| | Population 1 | | Population 2 | |
| | Y120082 (leaf) | Y120065 (seed) | Y120064 (leaf) | Y120066 (seed) |
| Data Points | 33* | 90 | 39* | 90 |
| No-calls | 0 | 1 | 0 | 3 |
| Miss-calls | n/a | 0 | n/a | 0 |
| Fails | 0 | 0 | 3 | 0 |
| % Data return (factors in seed that didn't germinate*) | 36.7 | 100 | 40.0 | 96.7 |
| % Data return (of germinated samples) | 100 | | 92.3 | |
| Comparable data points (of germinated samples**) | 33** | | 39** | |
| Match rate (%) | 100 | | 100 | | b.

| | RR2 endpoint TAQMAN | | | |
|---|---|---|---|---|
| | Population 1 | | Population 2 | |
| | Y120082 (leaf) | Y120065 (seed) | Y120064 (leaf) | Y120066 (seed) |
| Data Points | 33* | 90 | 39* | 89 |
| No-calls | 0 | 0 | 0 | 1 |
| Miss-calls | n/a | 0 | n/a | 0 |
| Fails | 0 | 0 | 3 | 0 |
| % Data return (factors in seed that didn't germinate*) | 36.7 | 100 | 40.0 | 98.9 |
| % Data return (of germinated samples) | 100 | | 92.3 | |
| Comparable data points (of germinated samples**) | 33** | | 39** | |
| Match rate (%) | 100 | | 100 | | c.

| | AAD12 GS real-time TAQMAN Population 1 | |
|---|---|---|
| | Y20066 (leaf) | Y120067 (seed) |
| Data Points | 39* | 90 |
| No-calls | 1 | 0 |
| Miss-calls | n/a | 3 |
| Fails | 0 | 0 |
| % Data return (factors in seed that didn't germinate) | 42.2 | 100 |
| % Data return (of germinated samples) | 97.4 | |

TABLE 9 (a-c)-continued

PCR validation statistics for soybean DNA isolated from defatted seed material.

| | |
|---|---|
| Comparable data points | 39** |
| Match rate (%) | 92.3 |

*The embryo-containing portion of 90 sectioned seed were planted. The number that germinated is indicated by the asterisk.
**Only seed portions in which leaf reference calls were available were compared.

The foregoing system and method for extraction and amplification of seed DNA from remnant solvent-extracted tissue is robust. At a cost of $0.62 for oil extraction (FAME) and $0.61 for genomic DNA extraction, one can obtain the oil and genetic profiles from a single seed source for less than $1.23 per sample. In application, breeders are able to select only those seed that contain a desired oil and genetic profile for planting, and to simply discard unwanted germplasm, thereby reducing workload in the field and improving performance.

Example 3

Isolation of DNA from Defatted Sunflower Seed Material for Use in Genotyping

Herein, we apply a similar automated procedure to that described in Example 1 to isolate high-quality genomic DNA from remnant solvent-extracted sunflower seed material. Isolated DNA was used to genotype one group of half-seed solvent-extracted samples ("Group A") for 9 SNP markers previously identified to be linked to Downey Mildew resistance. DNA was isolated from a second group of solvent-extracted samples ("Group B"), segregating for Downey Mildew resistance and reduced saturated oil traits, and utilized in PCR analysis (for 14 SNP markers) to demonstrate that solvent-extract plates can be stored at ambient temperature for up to 11 days prior to DNA isolation, and that the procedure may be performed in a low volume to reduce cost, and to increase throughput. These features may be used to generate significant cost improvements when employed on a large scale.

Materials and Methods

Two groups of sunflower half-seed material were used. FIGS. 14a and 14b. Group A material (segregating for Downey Mildew resistance) was dissected into a cotyledon-containing seed portion (¼ seed) and embryo-containing seed portion (¾ seed). Seed portions were subjected to solvent extraction and DNA isolation processes. DNA was also isolated from an additional control set of ¼ seed material that had not been defatted. All DNA was diluted 2× prior to SNP analysis.

Group B seed material (¼ seed) was used to evaluate the stability of nucleic acids in remnant solvent-extracted seed material stored for an extended period (five or eleven days) prior to DNA isolation. Group B solvent-extracted material was processed with a modified version of the automated DNA isolation procedure (a.k.a LowVol) described in Example 1 to reduce procedure cost. Group B DNA samples were diluted 20× prior to SNP analysis, accommodating the use of a larger marker screening panel.

Unlike the canola and soybean half-seed material, sunflower seed material was not soaked, and the seed hull was not removed, prior to dissection. Extractable seed portions were manually removed with a scalpel. Because parent controls for Groups A and B had already been isolated using a similar procedure and catalogued in a marker library, no leaf tissue reference material was grown for this Example.

A solvent extraction was performed on ¼ seed and ¾ seed portions from Group A to identify the oil profile for each sample. FIGS. 15a through 15n. Group B material was ground utilizing a ⅜" steel bead and defatted. The oil profile of a supplemental solvent-extracted ¼ seed population was also determined. FIGS. 16a through 16c. Residual heptane from the solvent extraction process was evaporated using a CENTRIVAP® roto-evaporator (Labconco) at 65° C. for 15 minutes, and the remnant seed material was prepared for DNA extraction. After being defatted, solvent-extracted Group B material was stored under a fume hood for a period of 5 ("Group B1") or 11 ("Group B2") days at ambient temperature (~25° C.).

For solvent-extracted Group A seed material, 350 µL Buffer RLT (Qiagen) was added to each sample well of a Matrix rack within about 24 hours of extraction. Samples were ground utilizing a ⅜" steel bead for 2 minutes at 1500 rpm to initiate DNA release from the seed material, followed by a final spin at 6,000 rpm for 5 minutes to pellet suspended tissue debris. Racks were then loaded into a LICONIC® incubator below a BIOCEL® 1800 robot, and DNA was recovered using the same fully-automated extraction procedure described in Example 1, initiated using Velocity11 software. 90 µL of DNA was recovered for each sample and stored at 4° C.

The tissue preparation method varied slightly for the ¼ seed samples that were not defatted prior to DNA extraction ("Group A1"). An initial dry grind with a ⅛" steel bead was performed at 1500 rpm for 5 minutes to macerate the seed tissue. Then, 300 µL Buffer RLT was added to each sample well of the Matrix rack, and samples were capped. Samples were then ground for an additional 5 minutes at 1500 rpm to homogenize the sample and release DNA, followed by a final spin at 6,000 rpm for 5 minutes to pellet suspended tissue debris. As with the defatted samples, the rack was then de-capped and loaded into the incubator below the robotic platform for extraction using the automated process. 90 µL DNA was recovered for each Group A1 sample and stored at 4° C.

A "low volume" version of the automated DNA isolation procedure was used to extract Group B samples. The "low volume" method utilizes less magnetic bead for DNA binding, reduced wash buffers, and reduced elution buffer (concentrating the DNA).

In order to prepare the samples for DNA extraction, 300 µL Buffer RLT was added to each well of the Matrix rack. Samples were ground for 2 minutes at 1500 rpm to initiate DNA release from the seed material, followed by a final spin at 6,000 rpm for 5 minutes to pellet suspended tissue debris. Because sample wells still contained the ⅜" magnetic bead, the rack would not be compatible with the balance in the BIOCEL® centrifuge. Therefore, 200 µL sample supernatant was transferred into a new matrix rack containing a ⅛" bead using a BIOMEK® NX. The sample rack was uncapped and placed in the incubator. The automated "low volume" protocol was initiated using Velocity11 software, and 75 µL DNA was recovered for each sample and stored at 4° C.

"Low volume" procedure for DNA isolation from defatted seed material: Ground solvent-extracted sunflower half-seed in a Matrix rack was incubated at ambient temperature overnight to burn off residual heptane. The following day, 300 µL Buffer RLT was added to each tube. The rack was capped and ground for 20 seconds at 1500 rpm. The rack was then centrifuged at 6,000 rpm for 5 minutes. The Matrix rack was then transferred into a LICONIC® incubator on the BIOCEL® 1800. The rest of the protocol took place on the BIOCEL® 1800.

MAGATTRACT® Suspension G magnetic bead was resuspended by vigorous shaking or vortexing. 10 µL of resuspended Suspension G bead was transferred into each sample well of a 1 mL AB-Gene Half Well plate. The Matrix microtube rack containing macerated sample tissue was centrifuged at 3000 rpm for 45 seconds. 100 µL supernatant from each microtube was transferred to a corresponding well of 1 mL AB-Gene Half Well plate containing 10 µl of Suspension G. The samples were tip mixed and incubated for 90 seconds at room temperature to initiate DNA binding (15-25° C.).

Samples were then placed on blocks on a titer shaker to mix thoroughly for 20 seconds, making sure that any visible clumps were broken apart. Samples were incubated for another 90 seconds at room temperature. Magnetic particles were separated for 15 seconds on a magnetic MAGNARACK™. 150 µL sample supernatant was transferred back into the 2D Matrix microtube rack. Wells were checked to verify that they contained only beads, and that all the liquid had been removed.

100 µL Buffer RPW (Qiagen) was added to each sample well, and the samples were then placed on the titer shaker to mix thoroughly for 20 seconds. Magnetic particles were separated for 15 seconds on the magnetic rack. About 150 µL sample supernatant was transferred back into the 2D Matrix microtube rack. Wells were checked to verify that they contained only beads, and that all the liquid had been removed.

100 µL EtOH (96-100%) was added to each sample well of the block, which was then placed on the titer shaker and shaken for 20 seconds to ensure that the magnetic particles were suspended. Magnetic particles were separated for 15 seconds on the magnetic rack. About 150 µL supernatant was transferred into the 2D Matrix microtube rack. Wells were checked to verify that all the liquid had been removed.

200 µL EtOH (96-100%) was added to each sample well of the block, which was then placed on the titer shaker and shaken for 20 seconds to ensure that the magnetic particles were evenly suspended. Magnetic particles were separated for 15 seconds on the magnetic rack. 200 µL supernatant was transferred into the 2D Matrix microtube rack. Wells were checked to verify that all the liquid had been removed.

Magnetic particles were incubated at room temperature for 5 minutes to ensure that all the EtOH was evaporated. 75 µL of Buffer AE (Qiagen) was added to each well of the block, which was then placed on the shaker for 1 minute to ensure that the magnetic particles were evenly suspended. Magnetic particles were separated on the magnetic rack for 30 seconds. 75 µL supernatant was transferred into a labeled 500 µL V-bottom collection plate. The collection plate was sealed with heat seal using a PLATELOC® set at 2.1 seconds at 175° C.

75 µL DNA was recovered for each sample and stored at 4° C.

Following bead-based DNA extraction, DNA was characterized by PICOGREEN® quantification, NANODROP® quantification, and agarose gel electrophoresis. For PICOGREEN® quantification, 50 µL PICOGREEN® dye was added to 10 mL 1×TE buffer and mixed (for each DNA plate to be quantified). 90 µL of the diluted PICOGREEN™ reagent and 10 µL sample DNA were added to each well of a white NUNC® plate and mixed thoroughly. Absorbance was measured on a SYNERGY® 5 plate reader at 285/520 and 535/10 wavelengths. A serial dilution of 10.0, 5.0, 2.5, and 0 ng/µL Lambda DNA standard (N3011L, New England BioLabs, Ipswitch, Mass.) was added to adjacent wells to generate a standard curve, and concentrations were adjusted for the dilution factor.

To assess DNA purity, 2 µL undiluted ¼ seed from Group A, ¾ seed DNA from Group A, and undiluted ¼ seed DNA from Group B, were added directly to each pedestal of a NANODROP® 8000 reader (Thermo Scientific), and the $A_{260}/A_{280}$ purity ratio was recorded. A measurement of between about 1.8 and 2.0 is generally considered pure, while values outside of the range may indicate the presence of proteins, phenolics, salts, and other contaminants. The DNA quality of each sample was also evaluated by visualizing 5 µL undiluted DNA on a 1.0% E-GEL® (Life Technologies) containing EtBr. A 400-10,000 bp HIGH-RANGE™ molecular weight ladder was loaded on one end of the gel for comparison. The gel was visualized on a GELDOC® XR imager.

DNA samples isolated from the ¼ and ¾ seed samples that were defatted, and IA seed samples that were not defatted, were screened for zygosity of a SNP marker set utilizing a KASPar PCR-based protocol. 9 markers relevant to the Downey Mildew trait were evaluated using Group A material. Control DNA for both parents was obtained and diluted 20×.

2 µL 2×-diluted seed DNA was delivered into each well of a 384-well PCR plate, and dried down at 65° C. for 2 hours. At the end of the drying period, four 4 µL 1× KASPar PCR mix (with primers) (Table 10) was added to each well of the PCR plate using a MERIDIAN™ liquid hander (KBS-0002-001, KBioscience, Hertfordshire, UK), with addition of parent controls. Plates were sealed using a FLEXISEAL™ heat sealer (Kbioscience) and touchdown PCR (Table 10) was performed on a HYDROCYCLER™-16 (KBioscience), with a final annealing temperature of 55° C. Following PCR, the plates were centrifuged at 3000 rpm for 1 minute, and read using a PHERASTAR® (470-0268, BMG Labtech, Offenburg, Germany) plate reader.

SNP data analysis was completed using KRAKEN®.

TABLE 10(a-c)

KASPar PCR and cycling conditions for 384-well and 1536-well plates.

a. Assay mix preparation

| | Conc. in assay mix (µM) | Vol. in assay mix (uL) |
|---|---|---|
| Allele-specific primer 1 (100 µM) | 12 | 36 |
| Allele-specific primer 2 (100 µM) | 12 | 36 |
| Common (reverse) primer (100 µM) | 30 | 90 |
| Tris-HCl (100 µM, pH 8.3) | | 138 | b. KASPar PCR reaction set-up

| | KASPar PCR Bulk mix preparation (µL) | | | Per reaction volume (µL) | | |
|---|---|---|---|---|---|---|
| | | Vol. 1X | | | | |
| Dispense Template | Vol. SNP mix | KASPar PCR Master Mix | Tot. M.M. vol. | Wet DNA* | KASPar mix | Tot. rxn. vol. |
| 1536-well (96 samples, 16 assays) | 4 | 246 | 250 | 2.0 | 1.3 | 1.3 |
| 1536-well (192 samples, 8 assays) | 6 | 374 | 380 | 2.0 | 1.3 | 1.3 |

TABLE 10(a-c)-continued

KASPar PCR and cycling conditions
for 384-well and 1536-well plates.

| 384-well (48 samples, 8 assays) | 5 | 295 | 300 | 2.0 | 4.0 | 4.0 |
|---|---|---|---|---|---|---| c. PCR Thermocycling Parameters

| Step 1 | 94° C. | | 15 min. | 1 cycle |
|---|---|---|---|---|
| Step 2 | 94° C. | | 20 sec. | 10 cycles |
| | 65° C. to 57° C. | | 1 min. | |
| Step 3 | 94° C. | | 20 sec. | 29 cycles |
| | 57° C. | | 1 min. | |

*Dried prior to adding KASPar PCR Master Mix

Evaluation of Sunflower Defatted Seed DNA Yield, Purity, and Quality

DNA was successfully recovered from both the remnant solvent-extracted ¼ and ¾ seed tissue, and from intact ¼ seed tissue, using the bead-based isolation procedures. PICOGREEN® quantification data revealed that the average DNA concentration among the plates ranged from 4.87 (intact ¼ seed samples) to 19.50 ng/μL (defatted ¼ seed samples). Table 8. An average of 18.21 ng/μL DNA was recovered from defatted ¾ seed samples.

Figure 20:
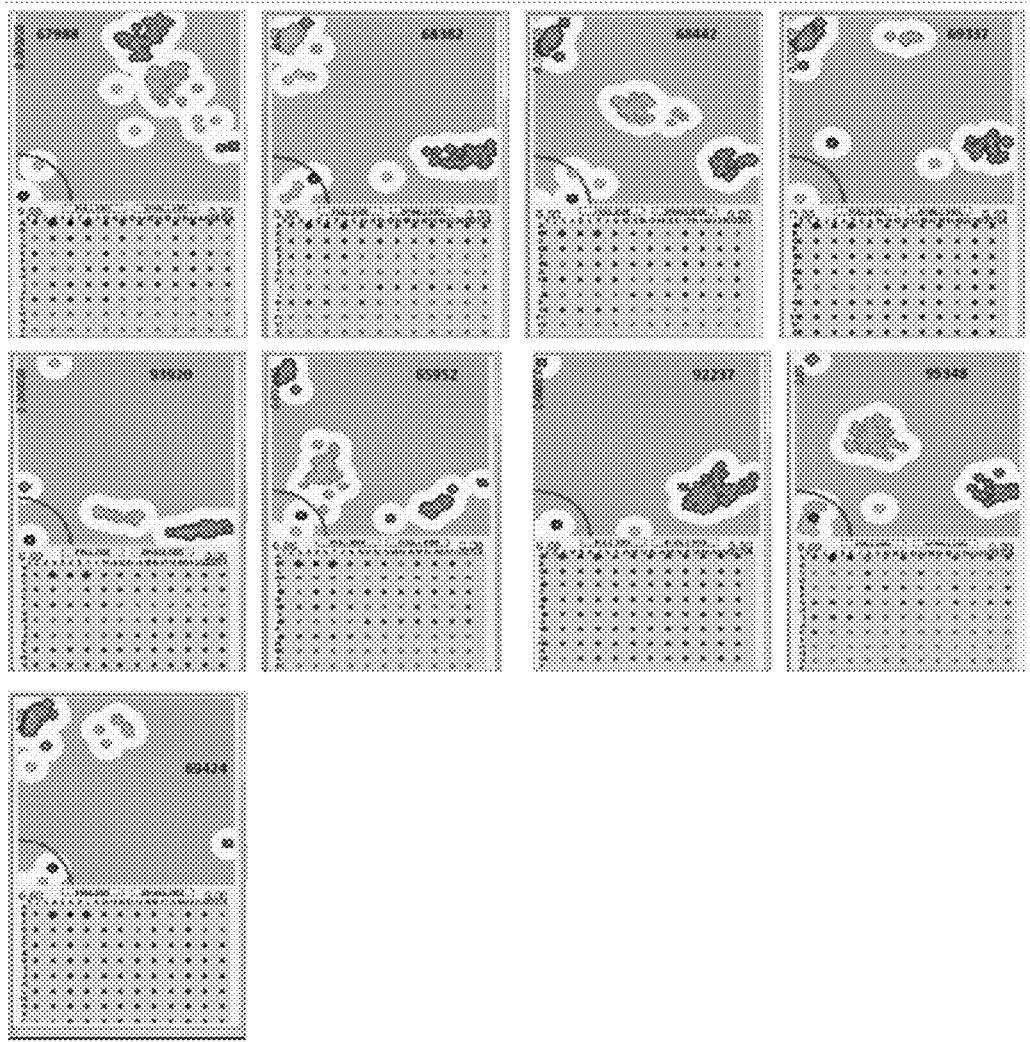
FIG. 20 includes data for KASPar analysis of the same 9 representative (Downey Mildew-specific) SNP markers as in FIG. 19 from sunflower DNA recovered from seed material defatted by solvent extraction.

The observed yield variation between the Group A1 and Group A2 ¼ seed plates appeared to be due to differences in seed fragment size, and was likely not a result of the FAME extraction process. Because FAME-extraction (when present) is performed before DNA extraction, the seed material was pulverized before DNA analysis, and it was impossible to confirm the seed fragment size at the DNA extraction step. Due to this uncertainty, an additional plate of ¼ seed samples (referred to as the "supplemental population") was used to gather additional oil composition (FIGS. 16a through 16c) and DNA data (FIG. 20). An average yield of 6.42 ng/μL DNA was obtained in this supplemental population, which is comparable to the DNA metrics gathered for the intact ¼ seed sample from Group A1.

Figure 17:
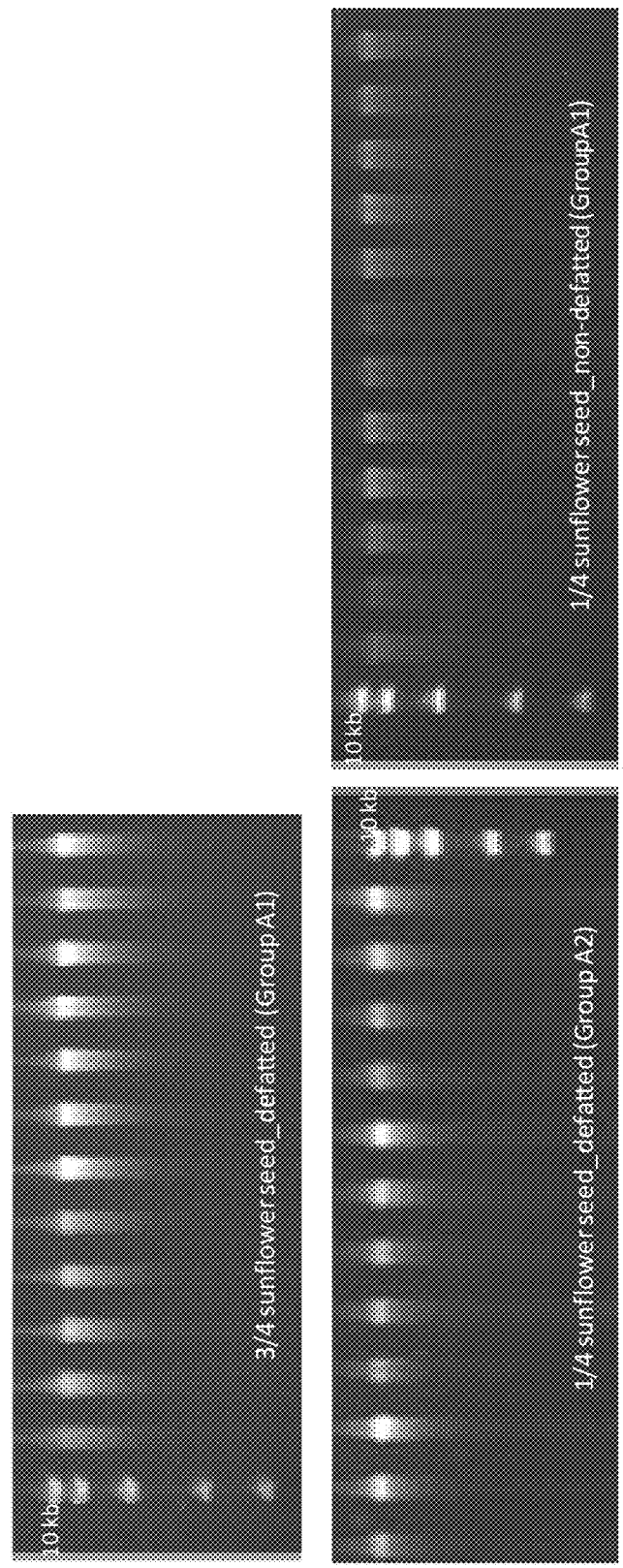
FIG. 17 includes images showing gel electrophoresis of sunflower DNA isolated from seed material defatted by FAME extraction. A 10 kb band is evident across all samples on the gel with some slight smearing, indicating high molecular weight and sheared DNA are present.

Gel electrophoresis of all Group A populations indicated that the band intensity for the ¼ seed DNA samples from Group A2 is most similar to the defatted ¾ seed samples from Group A1, which in turn indicates that the Group A2 ¼ seed samples were likely closer in size to the ¾ seed samples when received. FIG. 17. The gel also showed that a portion of each DNA sample was fragmented, by the presence of a slight smear.

TABLE 11

DNA Yield (ng/μL) and Purity Metrics for Group A
seed samples extracted with standard MagAttract method.

| | Population A1 | | | | Population A2 | |
|---|---|---|---|---|---|---|
| | ¾ seed portion (defatted) | | ¼ seed portion (intact) | | >¼ seed portion (defatted) | |
| | Conc. | 260/280 | Conc. | 260/280 | Conc. | 260/280 |
| Average | 18.21 | 1.61 | 4.87 | 2.67 | 19.50 | 1.75 |
| Min. | 3.16 | 1.39 | 1.64 | 1.44 | 5.56 | 1.61 |
| Max. | 33.90 | 1.74 | 10.47 | 3.95 | 25.63 | 1.86 |
| Std. Dev. | 7.00 | 0.09 | 2.10 | 0.41 | 4.58 | 0.01 |

NOTE:
Concentrations expressed in ng/μL; DNA eluted in 100 μL.

DNA was also successfully recovered from remnant solvent-extracted seed material using the "low volume" procedure. PICOGREEN® quantification data revealed that the average DNA concentration from these samples varied from 24.54 ng/μL to 30.49 ng/μL (defatted samples stored at ambient temperature for 11 days), and from 8.21 ng/μL to 19.87 ng/μL (defatted samples stored at ambient temperature for five days). Table 12. An average of 2.06 μg DNA was recovered from solvent-extracted material stored for eleven days, while 1.49 μg and 0.62 μg DNA was recovered from two solvent-extracted plates stored for five days.

DNA purity ($A_{260}/A_{280}$) was comparable for all samples tested, averaging between 1.72 and 1.75.

TABLE 12

DNA Yield (ng/μL) and Purity Metrics for DNA isolated
from stored defatted seed samples (Group B).

Group B sunflower MagAttract "Low Vol" seed DNA
(5 and 11 days post-extraction)

| | 2012-089_1 | | 2012-089_2 | | 2012-092_1 | | 2012-092_2 | |
|---|---|---|---|---|---|---|---|---|
| | Conc. | 260/280 | Conc. | 260/280 | Conc. | 260/280 | Conc. | 260/280 |
| Avg. | 30.49 | 1.74 | 24.54 | 1.75 | 19.87 | 1.72 | 8.21 | 1.72 |
| Min. | 2.40 | 1.67 | 16.36 | 1.62 | 1.13 | 1.56 | 0.37 | 1.54 |
| Max. | 51.12 | 1.82 | 36.41 | 1.85 | 50.49 | 1.84 | 23.26 | 2.27 |
| Std. Dev. | 7.98 | 0.03 | 4.20 | 0.06 | 13.53 | 0.06 | 5.34 | 0.12 |
| Days post-extraction | 11 | | | | 5 | | | |

NOTE:
Concentrations expressed in ng/μL; DNA eluted in 75 μL.

Figure 18:
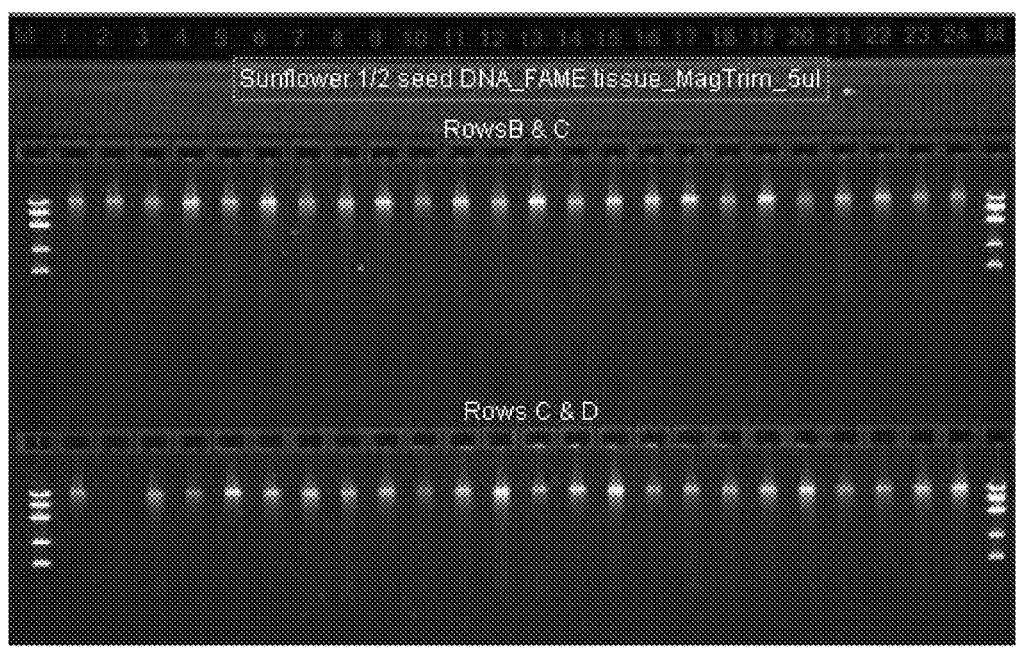
FIG. 18 includes an image showing gel electrophoresis of sunflower DNA isolated from seed material defatted by solvent extraction.

The DNA yield and purity of the supplemental solvent-extracted ¼ seed population was also determined. Table 13 and FIG. 18.

TABLE 13

DNA Yield (ng/μL) and Purity (A260/280) Metrics for DNA isolated
from a defatted ¼ sunflower seed "supplemental"
population using the MagAttract procedure.

| | Conc. (ng/μL in 100 μL) | 260/280 |
|---|---|---|
| Avg. | 6.42 | n/a |
| Min. | 2.58 | n/a |
| Max. | 13.11 | n/a |
| Std. Dev. | 1.91 | n/a |

Evaluation of Sunflower Defatted Seed DNA Efficacy in PCR Applications

PCR assay performance was used to evaluate each group of seed DNA samples for zygosity determination in a panel of 9 SNP markers (i.e., SNP IDs: 67988; 68382; 68442; 69337; 69424; 65952; 92237; 95348; and 89986). FIGS. 19-20. Each plate of defatted (Group A2) and non-defatted (Group A1) ¼ seed DNA samples was tested two times to ensure data reproducibility. In addition, the defatted ¾ seed DNA samples (embryo-containing) were evaluated with the same 9 markers to determine whether the presence of both male and female genetics would skew the marker data. All seed DNA was diluted 2× with water prior to being analyzed, and more concentrated parental leaf DNA controls were diluted 20×. Following PCR, each set of raw PCR data was uploaded into KRAKEN® and plotted to visualize allelic segregation patterns. Samples that were of insufficient quality would either appear as outliers or fails on the data plots.

Reliable SNP marker data was obtained across all the scenarios tested. In addition, comparison of marker data between the ¼ seed portions and corresponding ¾ seed portions revealed a high level of agreement between the calls.

The PCR assay performance of DNA recovered from the remnant solvent-extracted seed material that had been stored for five or eleven days prior to isolation was also evaluated. In these assays, DNA was diluted 20× with water prior to drying of 2 μL DNA and analysis in a 1.3 μL KASPar assay (1536-well format). A panel of 14 SNP markers (SNP IDs: 67988; 68382; 68442; 68862; 69337; 69424; 65952; 65992; 66345; 92237; 95348; 94512; 89986; and 93920) was used to genotype these samples. Following PCR, each set of raw data was uploaded into KRAKEN® and plotted to visualize allelic segregation patterns.

Figure 21:
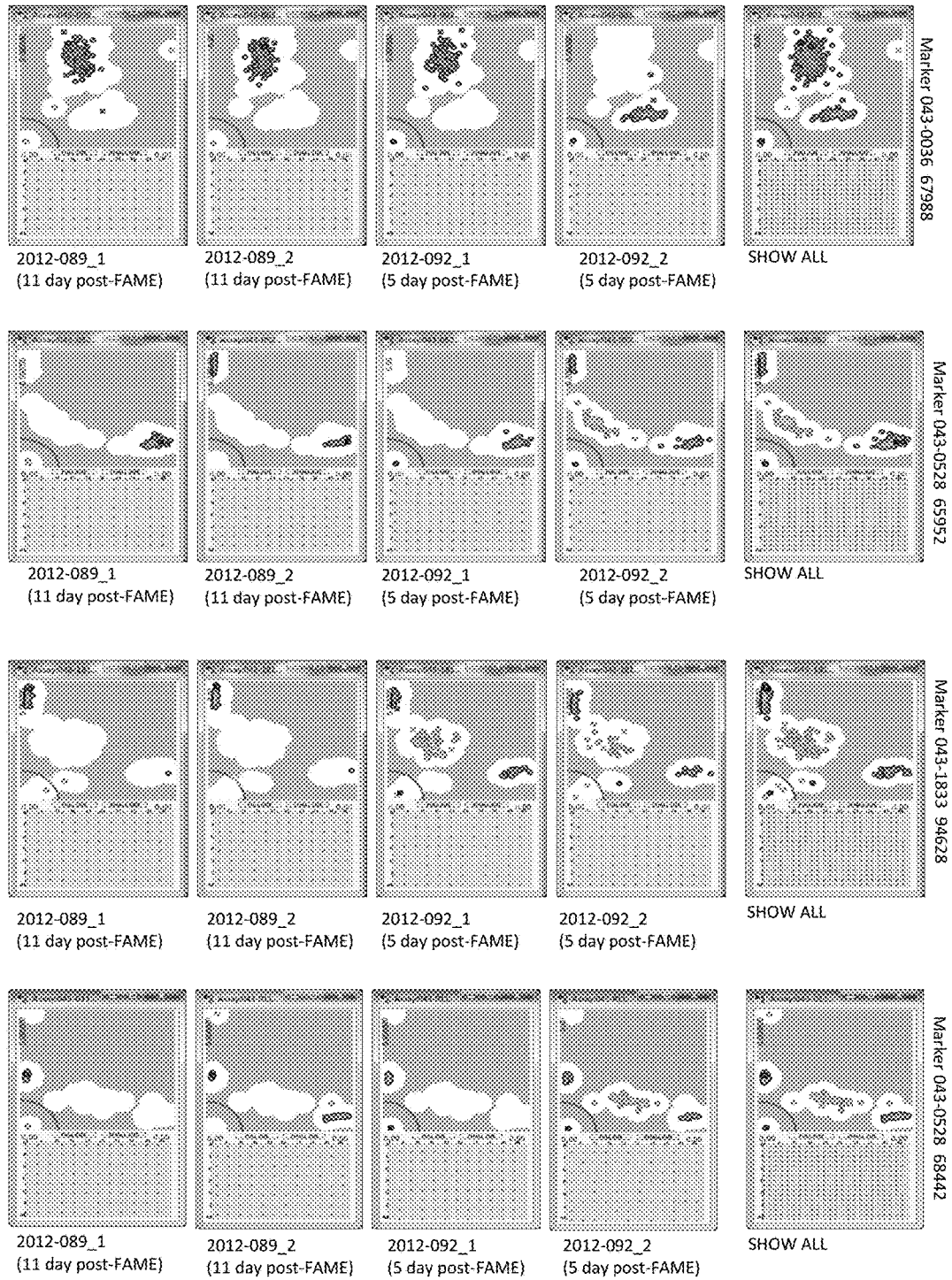
FIG. 21 includes data for KASPar analysis of representative SNP markers from sunflower DNA recovered from seed material defatted by FAME extraction, after extended storage at ambient temperature prior to DNA isolation. The same 9 Downey Mildew markers that were analyzed in FIGS. 19 and 20 were used again, in combination with 5 additional highly-polymorphic SNPs for the "Reduced Sat" trait (043-0186, 043-0568, 043-0916, 043-1231, and 043-1811). DNA was diluted 20× and KASPar PCR was set up in 1536-well format. PCR reaction volume was reduced to 1.3 µl (from 4 µl). Data for four of the 14 markers tested is included.

The data included samples tightly clustered with the expected parent, demonstrating the robustness of these samples in the PCR genotyping system. FIG. 21. For samples that did segregate across the marker panel (primarily Group B2 (Plates #2012-092_1 & 2)), adequate separation between AA, AB, and BB genotypes was seen. FIG. 21. Few fails or miss-calls were noted among either set of samples.

The "low volume" version of the DNA isolation procedure was validated, and it was determined that long-term storage of solvent-extracted seed material does not significantly impact DNA recovery and performance.

What may be claimed is:

1. A method for determining a genotype of interest at a locus in a plant, the method comprising:
   preparing from a single seed from an oilseed plant, wherein the oilseed plant is a Brassica spp., Glvcine max, or Helianthus annuus,
   (i) a seed sample comprising a portion of the single seed cotyledon, and
   (ii) a remaining seed portion comprising the single seed embryo;
   extracting oils from the seed sample by solvent extraction, thereby generating a defatted seed sample;
   converting the extracted oils to fatty acid methyl esters (FAMEs) by transesterification, and quantifying the FAMEs utilizing gas chromatography, thereby determining that the seed comprises an oil trait of interest;
   isolating nucleic acids from the defatted seed sample utilizing magnetic particles that bind nucleic acids in a bead-based DNA extraction;
   amplifying the nucleic acids at the locus of interest utilizing the polymerase chain reaction;
   identifying the allelic composition of the amplified nucleic acids from the seed comprising a genotype of interest at the locus;
   planting the remaining seed portion; and cultivating a plant from the planted seed portion.

2. The method of claim 1, wherein the locus is a gene.

3. The method according to claim 1, wherein identifying the allelic composition of the amplified nucleic acids comprises hybridizing an allele-specific probe to the amplified nucleic acids.

4. The method according to claim 1, wherein isolating the nucleic acids, amplifying the nucleic acids at the locus of interest, and identifying the allelic composition of the amplified nucleic acids are performed sequentially in an automated manner.

5. The method according to claim 1, wherein planting the remaining seed portion comprises placing the seed portion in soil.

6. The method according to claim 1, wherein planting the remaining seed portion comprises placing the seed portion in a growth-supporting medium.

7. A method for determining a genotype of interest at a locus in a plant, the method comprising:
   preparing from a single seed from an oilseed plant, wherein the oilseed plant is a Brassica spp.
   (i) a seed sample comprising a portion of the single seed cotyledon, and
   (ii) a remaining seed portion comprising the single seed embryo;
   extracting oils from the seed sample by solvent extraction, thereby generating a defatted seed sample;
   converting the extracted oils to fatty acid methyl esters (FAMEs) by transesterification, and quantifying the FAMEs utilizing gas chromatography, thereby determining that the seed comprises an oil trait of interest;
   isolating nucleic acids from the defatted seed sample utilizing magnetic particles that bind nucleic acids in a bead-based DNA extraction;
   amplifying the nucleic acids at the locus of interest utilizing the polymerase chain reaction;
   identifying the allelic composition of the amplified nucleic acids from the seed comprising a genotype of interest at the locus;
   planting the remaining seed portion; and
   cultivating a plant from the planted seed portion.

* * * * *